(12) United States Patent
Weismiller et al.

(10) Patent No.: US 8,413,274 B2
(45) Date of Patent: *Apr. 9, 2013

(54) HOSPITAL BED

(75) Inventors: Matthew W. Weismiller, Batesville, IN (US); Joseph A. Kummer, Cincinnati, OH (US); Peter M. Wukusick, Batesville, IN (US); Gregory W. Branson, Batesville, IN (US); Kenneth L. Kramer, Tai Po (HK); Stephen R. Schulte, Gibsonia, PA (US); Philip D. Palermo, Celina, OH (US); James M. C. Thomas, Mt. Pleasant, SC (US); Daniel F. Dlugos, Jr., West Chester, OH (US); Jay T. Butterbrodt, Lawrenceburg, IN (US); David J. Ulrich, Sunman, IN (US); David A. Albersmeyer, Hoagland, IN (US); Jason C. Brooke, Mount Pleasant, SC (US); Eric R. Meyer, Greensburg, IN (US); John D. Miller, Brookville, IN (US); John W. Ruehl, Shelbyville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/305,172

(22) Filed: Nov. 28, 2011

(65) Prior Publication Data

US 2012/0102647 A1    May 3, 2012

Related U.S. Application Data

(63) Continuation of application No. 12/859,978, filed on Aug. 20, 2010, now Pat. No. 8,065,764, which is a continuation of application No. 12/351,089, filed on Jan. 9, 2009, now Pat. No. 7,784,128, which is a continuation of application No. 11/734,954, filed on Apr. 13, 2007, now Pat. No. 7,480,951, which is a continuation of application No. 11/393,604, filed on Mar. 30, 2006, now Pat. No. 7,213,279, which is a (Continued)

(51) Int. Cl.
*A61G 7/057* (2006.01)
*A61G 7/10* (2006.01)

(52) U.S. Cl. .................................. 5/624; 5/662
(58) Field of Classification Search .................. 5/53.1, 5/53.3, 624, 662
See application file for complete search history.

(56) References Cited

U.S. PATENT DOCUMENTS

| RE10,906 E | 3/1888 | Case |
|---|---|---|
| 979,461 A | 12/1910 | Gale |

(Continued)

FOREIGN PATENT DOCUMENTS

| DE | 716981 (c) | 2/1942 |
|---|---|---|
| NL | 74802 | 5/1954 |

(Continued)

OTHER PUBLICATIONS

Jun. 1983 Prentke Romich Company, "Hospital Environmental Control System", 20 pages.

(Continued)

*Primary Examiner* — Michael Trettel
(74) *Attorney, Agent, or Firm* — Barnes & Thornburg LLP

(57) ABSTRACT

A bed having a frame and a deck is disclosed. The deck has at least a horizontal position and a chair position. The deck has an adjustable-length foot section.

18 Claims, 51 Drawing Sheets

Related U.S. Application Data continuation of application No. 11/353,743, filed on Feb. 13, 2006, now Pat. No. 7,237,287, which is a continuation of application No. 10/028,833, filed on Dec. 20, 2001, now Pat. No. 7,017,208, which is a continuation of application No. 09/655,127, filed on Sep. 5, 2000, now Pat. No. 6,336,235, which is a continuation of application No. 09/018,542, filed on Feb. 4, 1998, now Pat. No. 6,163,903, which is a continuation of application No. 08/511,711, filed on Aug. 4, 1995, now Pat. No. 5,715,548.

(56) References Cited

U.S. PATENT DOCUMENTS

| | | |
|---|---|---|
| 1,398,203 A | 11/1921 | Schmidt |
| 2,337,395 A | 12/1943 | Leland, Jr. |
| 2,452,366 A | 10/1948 | Freund |
| 2,747,919 A | 5/1956 | Ferneau et al. |
| 2,837,751 A | 6/1958 | McCall |
| 2,913,300 A | 11/1959 | Darnell et al. |
| 2,956,289 A | 10/1960 | Sullivan |
| 3,036,314 A | 5/1962 | Wetzler |
| 3,039,119 A | 6/1962 | Bourgraf et al. |
| 3,053,568 A | 9/1962 | Miller |
| 3,220,021 A | 11/1965 | Nelson |
| 3,220,022 A | 11/1965 | Nelson |
| 3,281,141 A | 10/1966 | Smiley et al. |
| 3,319,270 A | 5/1967 | Greiner |
| 3,336,606 A | 8/1967 | Beitzel |
| 3,353,193 A | 11/1967 | Greiner |
| 3,406,772 A | 10/1968 | Ahrent et al. |
| 3,593,350 A | 7/1971 | Knight et al. |
| 3,821,821 A | 7/1974 | Burst et al. |
| 3,913,153 A | 10/1975 | Adams et al. |
| 4,097,940 A | 7/1978 | Tekulve et al. |
| 4,127,906 A | 12/1978 | Zur |
| 4,139,917 A | 2/1979 | Fenwick |
| 4,183,015 A | 1/1980 | Drew et al. |
| 4,183,109 A | 1/1980 | Howell |
| 4,222,131 A | 9/1980 | Holdt et al. |
| 4,227,269 A | 10/1980 | Johnston |
| 4,312,500 A | 1/1982 | Janssen |
| 4,376,316 A | 3/1983 | Mercier et al. |
| 4,380,838 A | 4/1983 | Lutchansky |
| 4,409,695 A | 10/1983 | Johnston et al. |
| 4,411,035 A | 10/1983 | Fenwick |
| 4,435,862 A | 3/1984 | King et al. |
| 4,484,367 A | 11/1984 | Jenkins |
| 4,558,857 A | 12/1985 | Heller |
| 4,559,655 A | 12/1985 | Peck |
| 4,559,656 A | 12/1985 | Foster |
| 4,572,573 A | 2/1986 | Yoshikawa et al. |
| 4,592,104 A | 6/1986 | Foster et al. |
| 4,604,022 A | 8/1986 | Bourgraf |
| 4,612,679 A | 9/1986 | Mitchell |
| 4,637,652 A | 1/1987 | Bergenwall |
| 4,638,313 A | 1/1987 | Sherwood, Jr. et al. |
| 4,680,790 A | 7/1987 | Packard et al. |
| 4,685,159 A | 8/1987 | Oetiker |
| 4,711,486 A | 12/1987 | Fujiyama |
| 4,751,754 A | 6/1988 | Bailey et al. |
| 4,769,584 A | 9/1988 | Irigoyen et al. |
| 4,800,384 A | 1/1989 | Snijders |
| 4,847,929 A | 7/1989 | Pupovic |
| 4,862,529 A | 9/1989 | Peck |
| 4,894,876 A | 1/1990 | Fenwick |
| 4,910,816 A | 3/1990 | Lansing |
| 4,937,900 A | 7/1990 | Bridges |
| 4,944,055 A | 7/1990 | Shainfeld |
| 5,072,463 A | 12/1991 | Willis |
| 5,077,843 A | 1/1992 | Dale et al. |
| 5,097,550 A | 3/1992 | Marra, Jr. |
| 5,129,177 A | 7/1992 | Haigh et al. |
| 5,157,800 A | 10/1992 | Borders |
| 5,175,897 A | 1/1993 | Marra, Jr. |
| 5,181,762 A | 1/1993 | Beumer |
| 5,191,663 A | 3/1993 | Holder et al. |
| 5,235,258 A | 8/1993 | Schuerch |
| 5,239,300 A | 8/1993 | Berger et al. |
| 5,274,311 A | 12/1993 | Littlejohn et al. |
| 5,276,813 A | 1/1994 | Elliott et al. |
| 5,279,010 A | 1/1994 | Ferrand et al. |
| 5,283,781 A | 2/1994 | Buda et al. |
| 5,291,399 A | 3/1994 | Chaco |
| 5,335,313 A | 8/1994 | Douglas |
| 5,345,226 A | 9/1994 | Rice, Jr. et al. |
| 5,361,755 A | 11/1994 | Schraag et al. |
| 5,398,357 A | 3/1995 | Foster |
| 5,402,544 A | 4/1995 | Crawford et al. |
| 5,454,126 A | 10/1995 | Foster et al. |
| 5,465,082 A | 11/1995 | Chaco |
| 5,479,666 A | 1/1996 | Foster et al. |
| 5,537,701 A | 7/1996 | Elliott |
| 5,542,136 A | 8/1996 | Tappel |
| 5,542,138 A | 8/1996 | Williams et al. |
| 5,577,279 A | 11/1996 | Foster et al. |
| 5,588,167 A | 12/1996 | Pahno et al. |
| 5,592,153 A | 1/1997 | Welling et al. |
| 5,600,311 A | 2/1997 | Rice et al. |
| 5,630,238 A | 5/1997 | Weismiller et al. |
| 5,664,270 A | 9/1997 | Bell et al. |
| 5,678,264 A | 10/1997 | Walker |
| 5,699,038 A | 12/1997 | Ulrich et al. |
| 5,715,548 A | 2/1998 | Weismiller et al. |
| 5,732,423 A | 3/1998 | Weismiller et al. |
| 5,771,511 A | 6/1998 | Kummer et al. |
| 5,790,997 A | 8/1998 | Ruehl |
| 5,838,223 A | 11/1998 | Gallant et al. |
| 6,147,592 A | 11/2000 | Ulrich et al. |
| 6,163,903 A | 12/2000 | Weismiller et al. |
| 6,182,310 B1 | 2/2001 | Weismiller et al. |
| 6,279,183 B1 | 8/2001 | Kummer et al. |
| 6,336,235 B1 | 1/2002 | Ruehl |
| 7,213,279 B2 | 5/2007 | Weismiller et al. |
| 7,480,951 B2 | 1/2009 | Weismiller et al. |
| 7,784,128 B2 | 8/2010 | Kramer |
| 8,065,764 B2 | 11/2011 | Kramer |

FOREIGN PATENT DOCUMENTS

| | | |
|---|---|---|
| WO | 91/07157 | 5/1991 |
| WO | WO 94/27544 | 12/1994 |

OTHER PUBLICATIONS

HECS-1 Hospital/Home Environmental Control System Operational Manual; 41 pages.

Hill-Rom, "A Hill-Rom Solution TotalCare Bed System" brochure, 2000, 10 pages.

Hill-Rom, TotalCare Bed System Service Manual, pp. i through iii, pp. 1-18 through 1-69, pp. 3-44 through 3-51, pp. 4-11 though 4-16, pp. 4-80 through 4-81, p. 6-5, Nov. 1997-Jan. 2002.

Prentke Romich Company brochure entitled "Hospital Environmental Control System", 2 pages.

Prentke Romich Company, Operator's Manual for HECS-2 Hospital Environmental Control System, 8 pages.

Prentke Romich Company, Hospital/Home Environmetal Control System (HECS) Company, Jun. 1983, 15 pages.

Prentke Romich Company, Operational Guide for HECS-3 Hospital Environmental Control System, 29 pages.

Prentke Romich Company, Operational Guide for HECS-5 Hospital Environmental Control System, 28 pages.

Joerns Healthcare Inc.; A Sunrise Medical Company brochure entitled 670 Acute Care Hospital Bed; 6 pages.

Joerns Healthcare Inc.; A Sunrise Medical Company; Roomate Installation instructions for Joerns 670; Jun. 1987; 4 pages.

Joerns Healthcare Inc.; A Sunrise Medical Company brochure entitled Roomate 1986; 12 pages.

European Search Report dated Sep. 27, 2010 from EP 08021792.2.

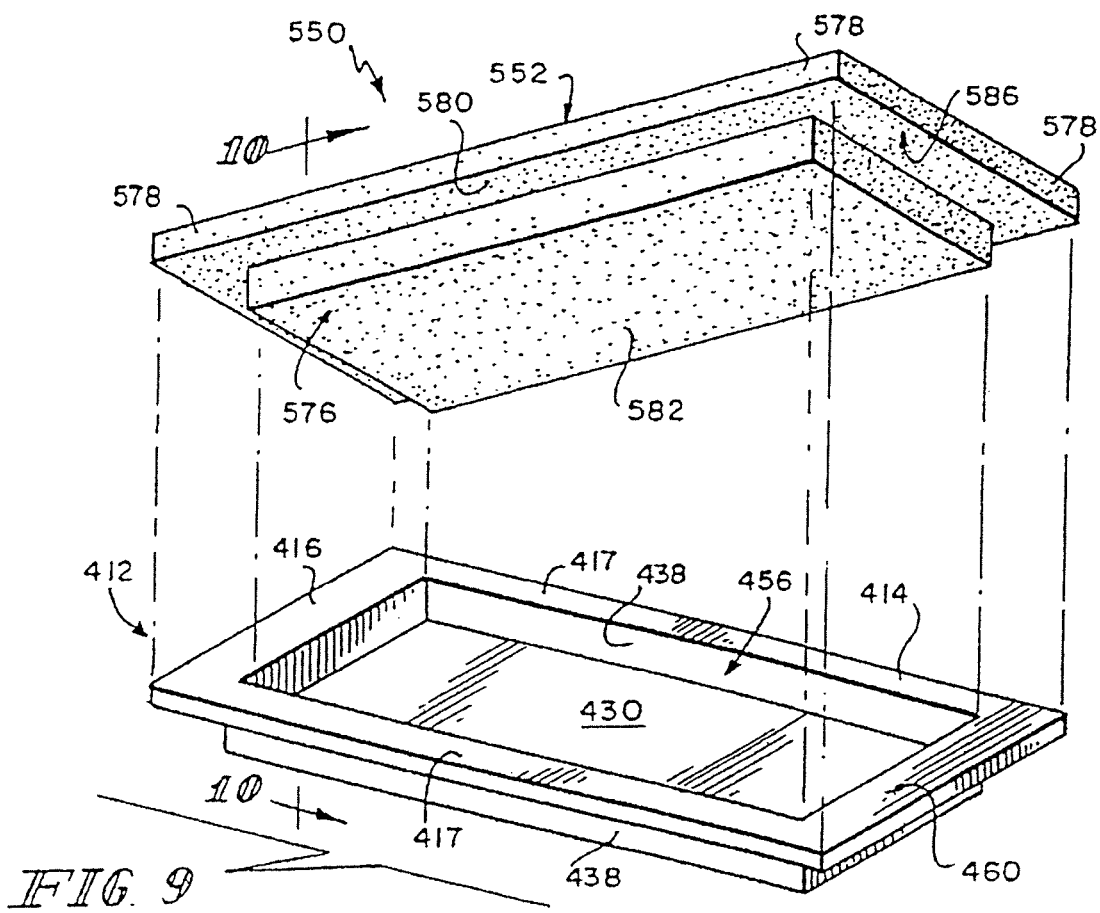
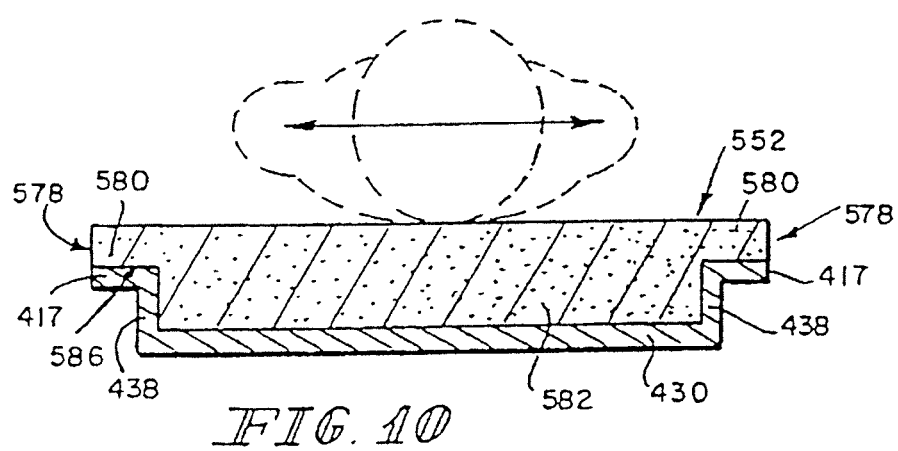

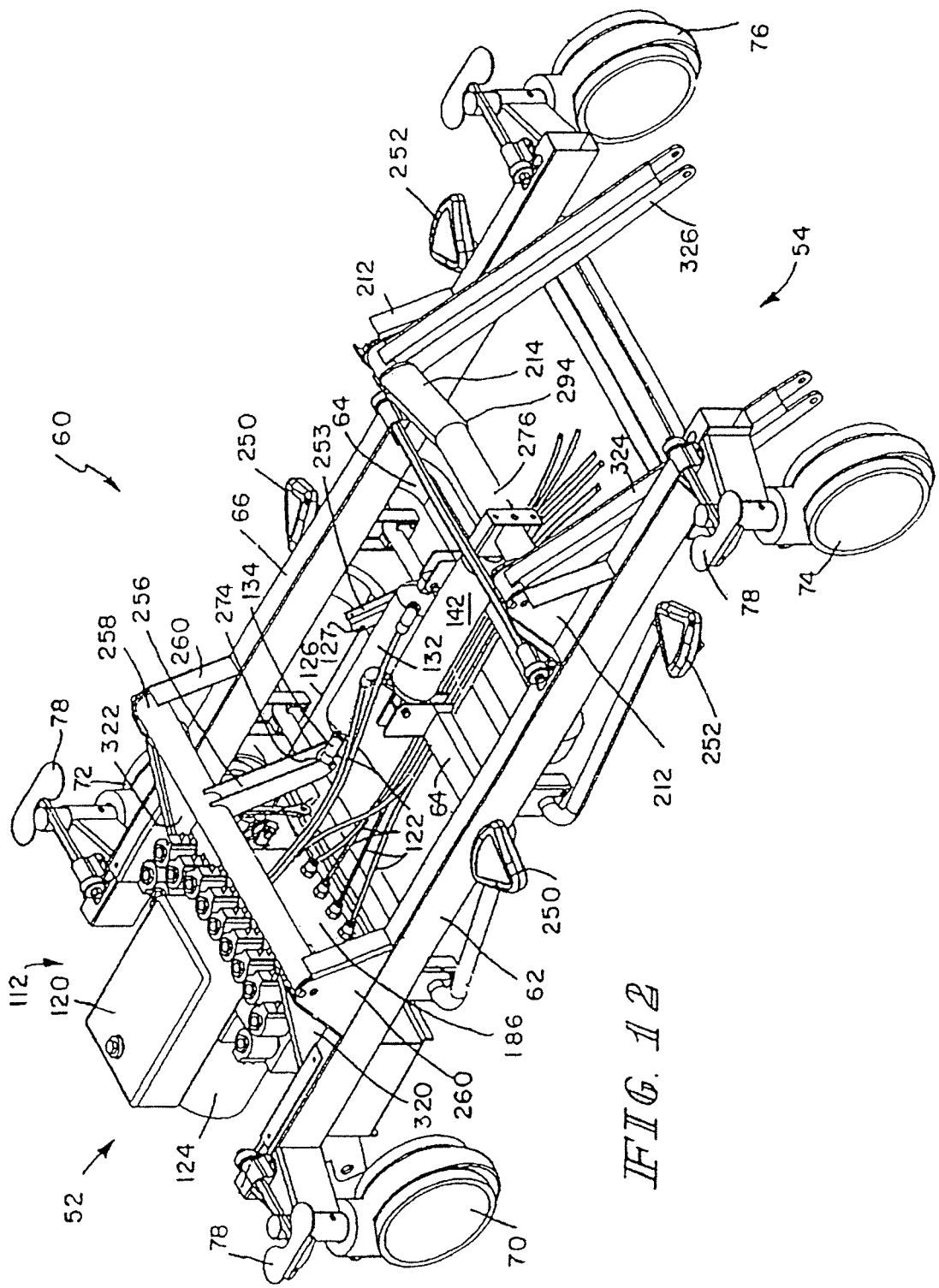

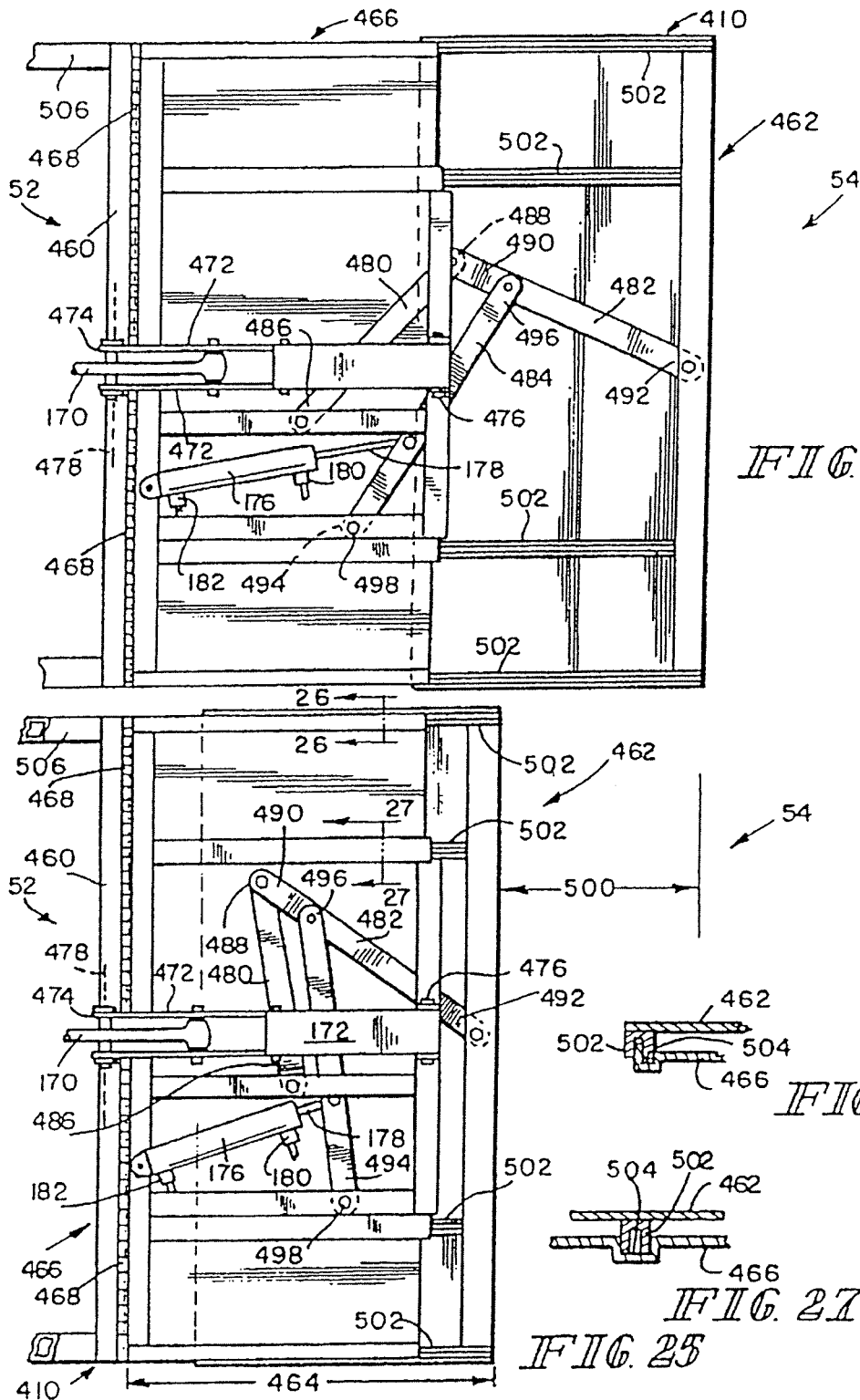

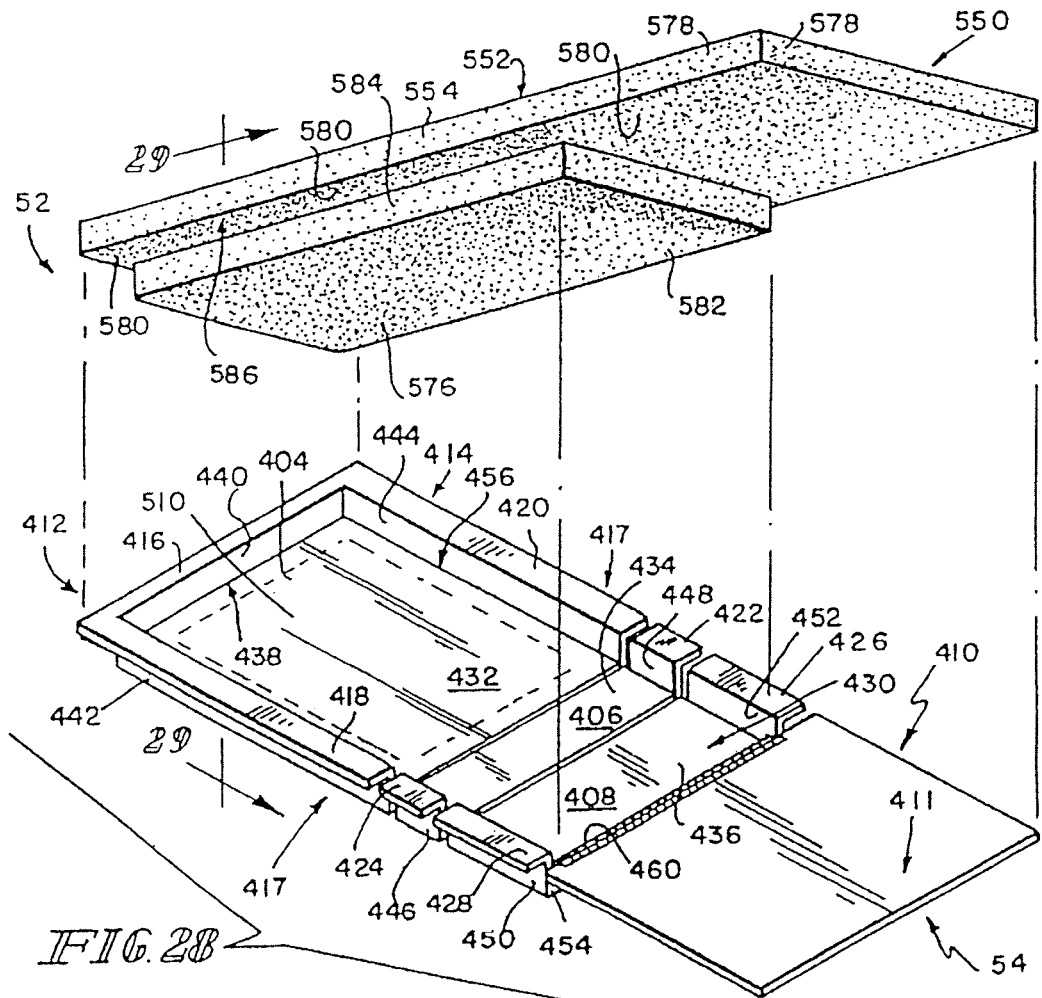
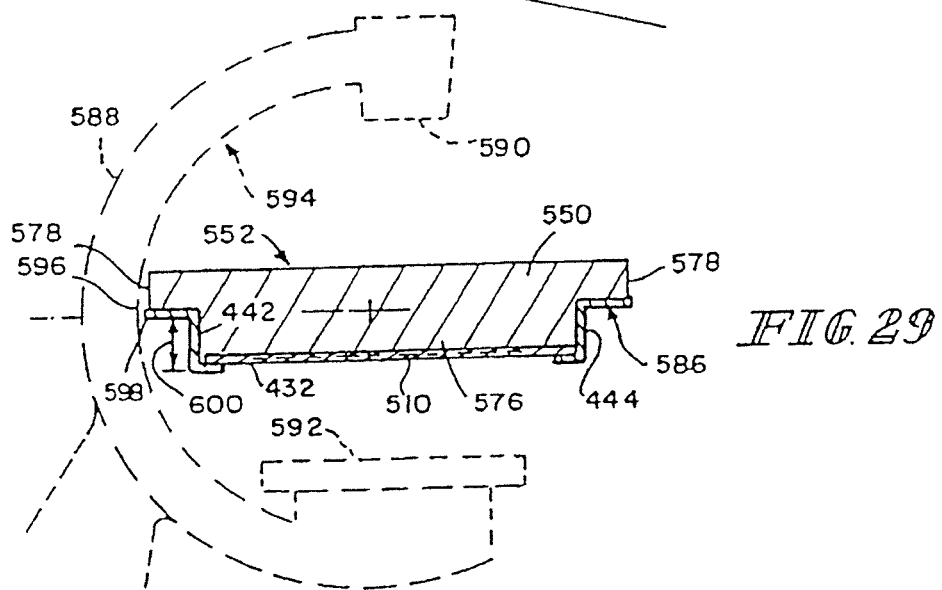

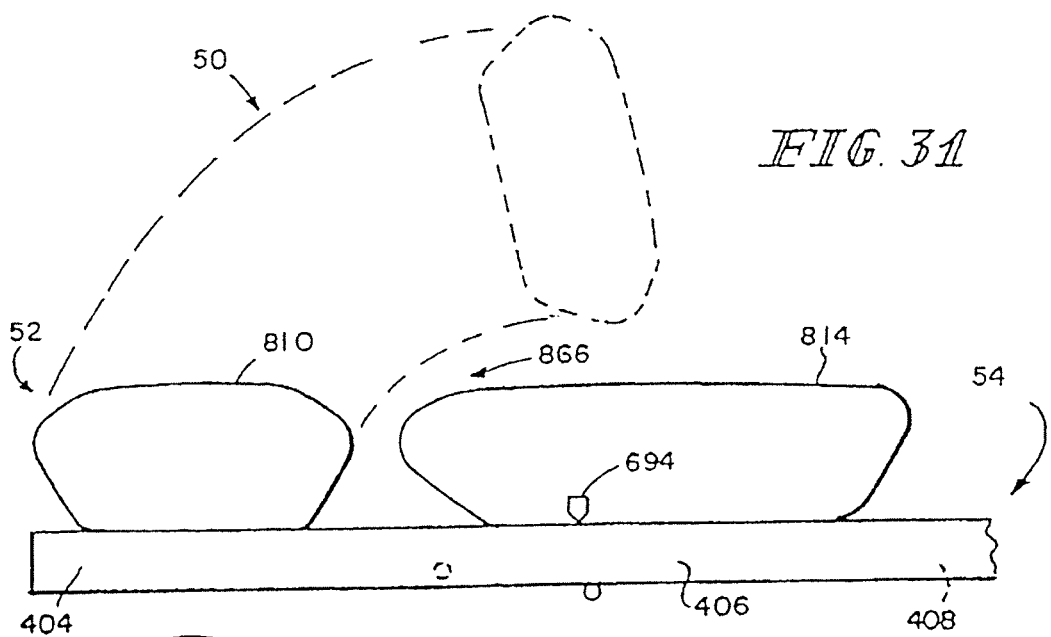
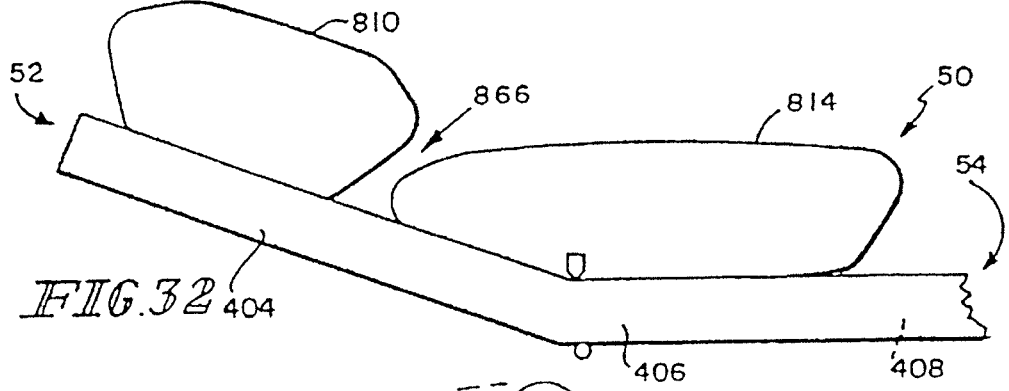
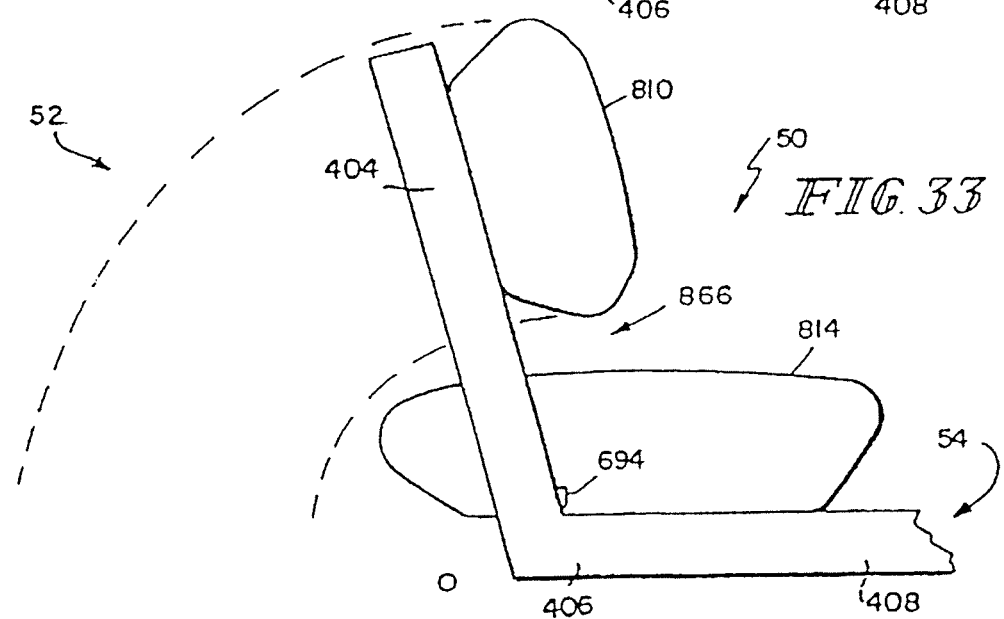

HOSPITAL BED

RELATED APPLICATIONS

This application is a continuation of U.S. application Ser. No. 12/859,978, filed Aug. 20, 2010, now U.S. Pat. No. 8,065,764, which is a continuation of U.S. application Ser. No. 12/351,089, filed Jan. 9, 2009, now U.S. Pat. No. 7,784,128, which is a continuation of U.S. patent application Ser. No. 11/734,954, filed Apr. 13, 2007, now U.S. Pat. No. 7,480,951, which is a continuation of U.S. patent application Ser. No. 11/393,604, filed Mar. 30, 2006, now U.S. Pat. No. 7,213,279, which is a continuation of U.S. patent application Ser. No. 11/353,743, filed Feb. 13, 2006, now U.S. Pat. No. 7,237,287, which is a continuation of U.S. patent application Ser. No. 10/028,833, filed Dec. 20, 2001, now U.S. Pat. No. 7,017,208, which is a continuation of U.S. patent application Ser. No. 09/655,127, filed Sep. 5, 2000, now U.S. Pat. No. 6,336,235, which is a continuation of U.S. patent application Ser. No. 09/018,542, filed Feb. 4, 1998, now U.S. Pat. No. 6,163,903, which is a continuation of U.S. patent application Ser. No. 08/511,711, filed Aug. 4, 1995, now U.S. Pat. No. 5,715,548, the disclosures of all of which are expressly incorporated by reference herein.

BACKGROUND AND SUMMARY OF THE INVENTION

The present invention relates to a bed, and particularly to a chair bed that can be manipulated to achieve both a conventional bed position having a horizontal sleeping surface upon which a person lies in a supine position and a sitting position having the feet of the person on or adjacent to the floor and the head and back of the person supported above a seat formed by the bed. More particularly, the present invention relates to a hospital bed or a patient-care bed which is convertible to a chair and which is configured to facilitate several activities that may be performed by a caregiver for a person on the sleeping surface of the bed.

Many hospital beds are positionable to a configuration having the sleeping surface of the bed at a predetermined height above the floor and having siderails positioned to restrain the movement of a person lying on the sleeping surface past sides of the sleeping surface and off of the bed. The sleeping surfaces of many such hospital beds can typically be lowered to reduce the distance between the sleeping surface and the floor, and the sleeping surfaces of such beds can often be manipulated to adjust the position of the person on the sleeping surface. In addition, the siderails of these hospital beds can typically be moved to a position away from the sleeping surface to facilitate movement of the person on the sleeping surface from the supine position on the sleeping surface to a standing position on the floor near the bed.

It may sometimes be desirable to have two caregivers assist a person trying to move from the supine position on the sleeping surface of such hospital bed to the standing position. After moving the siderails away from the sleeping surface, the caregivers may pivot the person so that the legs of the person hang over the side of the sleeping surface. The caregivers can then assist the person as the person slides past one side of the sleeping surface until the feet of the person touch the floor. The caregivers typically hold the person firmly while also bracing themselves to prevent a fall or other injury to the person as the person stands.

Beds and examination tables having articulating decks to adjust the position of the person on the surface are known in the art. See, for example, U.S. Pat. Nos. 5,077,843 to Foster L. Dale et al. and 4,751,754 to Baily et al., which are assigned to the assignee of the present invention, and U.S. Pat. No. 3,281,141 to Smiley et al. and German publication No. 716981. Each of these references discloses a bed or an examination table having a top surface that articulates to adjust the position of the person on the surface.

In addition, beds and examination tables that are convertible to chairs in order to simplify the task of moving a person on the sleeping surface from the supine position to the standing position are known in the art. See, for example, U.S. Pat. Nos. 5,157,800 to Borders, 5,129,177 to Celestina et al., and 4,862,529 to Peck, all of which are assigned to the assignee of the present invention, and U.S. Pat. Nos. 5,279,010 to Ferrand et al., 4,183,109 to Howell, 4,411,035 to Fenwick, and 3,220,022 to Nelson. Each of these references discloses a bed that can be converted to a chair-like configuration.

What is needed is a bed that can be converted to a chair and that can also facilitate activities that are typically performed by caregivers. For example, caregivers would welcome a bed that, in addition to being convertible to a chair, can be configured to weigh a person, to rapidly move the person from an upright position to a generally horizontal position when emergency procedures are initiated, and that can facilitate varied procedures that may be performed on a person carried by the bed, thereby reducing the number of times the person is transferred from one bed or surface to another.

According to the present invention, a chair bed for a person is provided, the bed having a head end, a foot end, and sides. The bed includes a base frame, an intermediate frame coupled to the base frame, a weigh frame coupled to the intermediate frame, and an articulating deck coupled to the weigh frame. A plurality of load cell supports couple the weigh frame to the intermediate frame. The load cell supports include means for determining the weight of objects supported by the weigh frame. Alternatively, the weigh frame and the intermediate frame may be fixed together to form a common frame or may be replaced by a single common frame.

In preferred embodiments, the articulating deck has longitudinally spaced head, seat, thigh, and foot sections. The head, thigh, and foot sections are movable relative to each other and are movable relative to the seat section which is fixed relative to the weigh frame. The head, thigh, and foot sections are infinitely adjustable to allow the bed to attain any desired position within the range of movement of the head, thigh, and foot sections, thus accommodating changes of position of a person on the bed. Of course, the articulating deck can provide a planar, horizontal sleeping surface, a planar sleeping surface that is tilted toward either the head end of the bed or the foot end of the bed, and a non-planar chair-shaped seating surface, in addition to the intermediate positions therebetween.

The bed can include a mechanism for raising and lowering the articulating deck and the sleeping surface between a low position and a raised position relative to the base of the bed. In addition, the bed can also include mechanisms for independently raising and lowering each of the head section, the thigh section, and the foot section so that the bed can assume many positions to suit the specific needs of individuals.

The sleeping surface of the chair bed can also be easily moved between a generally horizontal position and a Trendelenburg position. When in the Trendelenburg position, the intermediate frame is tilted such that the head end of the sleeping surface is higher than the foot end. The sleeping surface can also be moved to a reverse Trendelenburg position having the foot end above the head end.

The power required to raise and lower the sleeping surface and to move the head, thigh, and foot sections can be provided by a primary electrical power source such as the main AC power supply of a hospital in combination with a fluid system. In addition, a foot pedal can be pivotably mounted to the base frame and coupled to the bed to allow the caregiver to manually provide power to the bed for remote operation of the fluid system of the bed.

In one preferred embodiment of the bed, the articulating deck and the mechanism for raising and lowering the articulating deck are powered by a fluid system having a pump, valves, and actuators for positioning the intermediate frame relative to the base frame and for positioning the articulating deck sections. The actuators must be supplied with pressurized fluid to manipulate the bed and the valves control the flow of fluid to the actuators.

The bed is additionally provided with an electrical control system for operating a pump and controlling control valves. The electrical control system controls the operation of the bed when the bed is connected to an independent source of power. In addition, the electrical control system includes a battery source for operating the valves when the bed is not connected to an independent source of power.

The articulating deck can be a longitudinal step deck that includes upper deck side portions and a central, longitudinally extending recess between the side portions. The recess is defined by a lower deck and side walls connecting the lower deck and the upper portion of the deck.

A companion mattress is carried by the deck. The mattress has a planar, upwardly-facing sleeping surface, side portions resting on the side deck portions, and a projection beneath the sleeping surface. The projection extends downwardly into the recess and can engage at least a portion of the side wall of the deck. The varied thickness of the mattress provides the mattress with "zones" including a thick zone adjacent to the projection and a thin zone in areas away from the projection. The mattress includes a head mattress portion, a seat mattress portion, a thigh mattress portion, and a foot mattress portion. Each named mattress portion is associated respectively with the head, seat, thighs, and feet of the person resting on the sleeping surface of the bed as well as with the underlying head, seat, thigh, and foot sections of the deck.

A step deck and a mattress configured for use with a step deck can be used independently of the bed and the articulating deck. For example, a step deck can be provided for a stretcher. Such a stretcher, for example, can include a frame, a step deck mounted to the frame, the step deck having longitudinal upper side portions engaging the frame, and a mattress having a generally planar sleeping surface and a bottom surface including a projection configured so that the shape of the bottom surface generally conforms to the shape of the step deck. In the same manner, a step deck and associated mattress could be provided for a gurney. Such a gurney would be similar to the illustrative stretcher described above except that the frame would include wheels so that the gurney could be transported by rolling it from place to place.

Though there are many potential variations of step deck shapes and corresponding mattress shapes and numbers and types of mattress pieces that could be devised, any step deck having an upper deck portion and a recess defined by a bottom deck portion and walls connecting the bottom and the upper deck portions would achieve the desired results. Likewise, any mattress or combination of mattress pieces that provide a bottom surface generally conforming to the shape of the step deck would achieve the desired results.

The movable deck head section is coupled to the intermediate frame and is configured to pivot relative to the weigh frame about an effective pivot axis positioned to lie above the lower deck portion. Preferably, the effective pivot axis is located generally adjacent to a pivot axis defined by the hip of a person lying on the sleeping surface in order to minimize the shear between the sleeping surface and the back of the person in the bed as the head section moves between the down position and the back-support position. To achieve this "reduced-shear pivot," the head section is mounted to the weigh frame for both translational movement and pivoting movement relative to the weigh frame. The pivoting and translational movements combine to produce a motion in which the head portion pivots relative to the frame about the effective pivot axis.

The head section of the articulating deck can pivot relative to the intermediate frame between a down position generally parallel to the weigh frame and an upward back-support position. When a person on a sleeping surface moves from a flat position to a sitting position, the back and legs of the person engaging the sleeping surface lengthen. The reduced-shear pivot accommodates this lengthening to reduce the shear between the back and legs of the person and the sleeping surface as the head section pivots between the down position and the back-support position by expanding the deck and the sleeping surface. The reduced-shear pivot allows the upper body of the person on the sleeping surface to be tilted upwardly without moving the lower body of the person. This reduces the tendency of the person to slide relative to the sleeping surface during articulation of the head section, thereby reducing the shear between the back and legs of the person and the sleeping surface.

The step deck can also include an upper deck end portion adjacent to the foot end of the bed. The foot section can be coupled to the upper deck end portion for pivoting movement about a pivot axis that is positioned to lie above the lower deck. The foot section can also be configured to contract and expand to vary the length of the foot section as the foot section pivots about the pivot axis so that the foot section can pivot downwardly when the bed is in the low position to place the feet of the person supported on the sleeping surface on the floor. In addition, the foot portion of the mattress can be configured to shorten in conjunction with the contraction of the foot section. Also, the seat and foot portions of the mattress can automatically become thinner to maintain an appropriately sized seat area as the foot section pivots downwardly.

A pair of siderails can be provided on each side of the bed. Each pair of siderails includes a head section siderail that is movable with the pivoting head section of the deck and a body section siderail that is movable with the seat section. Each siderail is preferably maintained in a generally vertical orientation adjacent to the sides of the bed.

The siderails are each movable between an upward patient-restraining position restraining the movement of a person supported on the sleeping surface past the sides of the sleeping surface and a downward tucked position. When in the patient-restraining position, the bottoms of the siderails are positioned to lie above the upper deck side portions and the siderails abut the sides of the mattress. When in the tucked position, the tops of the siderails are positioned to lie beneath the upper deck side portions in a niche defined by the upper deck side portions and the side walls connecting the lower deck to the upper deck side portions.

When moving between the patient-restraining position and the tucked position, the siderails rotate outwardly and downwardly from the patient-restraining position away from the side of the bed, and then back inwardly and downwardly to the tucked position beneath the upper deck portion. The siderails trace the same path when moving from the tucked position to the patient-restraining position. The rotating mechanism, which holds the siderails in vertical orientations parallel to the side of the mattress through the entire range of movement, places the siderails against the sides of the mattress when the siderails are in the patient-restraining position, allowing for the provision of a narrower bed than would otherwise be provided, even though the mattress of the bed has a standard width.

The body section siderails are coupled to brackets that are fixed to the frame. The head section siderails are coupled to brackets fixed to the side wall of the deck. However, the bed may be provided with breakaway head section siderails, each head section siderail being mounted on a pivotable collateral deck section to move the siderail from the tucked position to a generally vertically downwardly extending down-out-of-the-way position, preferably extending downwardly along the head of the bed to provide clear access to space beneath the intermediate frame. Breakaway siderails provide the caregiver with even greater access to the space under the sleeping surface of the bed when the siderails are in the down-out-of-the-way position while also improving access across the sleeping surface for equipment that may be desired for use on a person on the sleeping surface.

The head section and body section siderails are configured to maintain a between-rail gap of approximately 2-3 inches as the head section siderail moves relative to the body section siderail. Also in preferred embodiments, the head section siderails are shorter than the body section siderails and shorter than typical siderails making it possible for a person to enter the bed from the side using the head section siderail as a support and to properly position their hip on the sleeping surface.

The bed can also be used to monitor the total weight of objects, including a person, carried by the bed. The bed is configured so that hospital equipment such as IV poles can be attached to the bed such that the weight of these items is not included in the weight monitored by the bed, thereby facilitating the convenient use of such equipment.

In this specification and in the claims, such terms as "chair bed," "hospital bed," "patient-care bed," and "examination table" are used in a general sense and not in a limiting sense. The bed of the present invention has wide application and may be used in a variety of situations. The improvements disclosed herein may be used on beds in general, on medical tables, stretchers, gurneys, and so forth as appropriate. However, the bed of the present invention provides significant improvements in caregiver productivity and patient outcomes. The following capabilities are included in the bed of the present invention:

1. Full chair capability as a built-in feature, enabling a single caregiver to execute an order from a physician to place the person in a chair by operating controls to convert the bed into a chair while the patent is on the bed.

2. Infinitely adjustable head, thigh, and foot section angles that allow any desired position of the head, thigh, and foot section with in the range of movement of those sections.

3. Foot egress capability, enabling a single caregiver to transfer a person from the bed to a wheelchair or ambulate the patient.

4. Modular surface capability, allowing a single caregiver to adapt the mattress surface to provide decubitus prevention and pulmonary treatment capability as the needs of the person change.

5. In-bed weighing capability, enabling a caregiver to monitor the weight of a person on the sleeping surface.

6. Electric or manual Trendelenburg capability, allowing the sleeping surface to assume the Trendelenburg position having the feet of the person carried by the bed slightly elevated above the head. In addition, the sleeping surface can assume a reverse Trendelenburg position having the head of the person slightly elevated above the feet.

7. Reduced-shear pivot capability, causing the articulating sections to minimize shear forces between the sections and the person so that the person does not slide appreciably relative to the sleeping surface of the mattress as the articulating sections pivot.

8. Siderails having a one-handed release mechanism and that rotate outwardly and rotate from the patient-restraining position to a tucked position underneath the patient-restraining position.

9. Breakaway siderail capability, having a pin that can be removed from the foot end of each head section siderail after the siderail has been rotated under to the tucked position so that the foot end of the head rail pivots downwardly and toward the head end of the bed, thereby providing a caregiver with additional access to the sleeping surface, additional clearance around the deck so that the caregiver has improved access to the patient, and allowing for the insertion of a C-arm laterally further across the person than may be achieved without the breakaway siderail capability.

10. CPR foot pedal capability, enabling rapid movement of the head section from the upward sitting position to the horizontal CPR position by activation of a CPR pedal so that the caregiver has instantaneous control with one-step operation that requires constant activation.

11. Manual pump articulation and a battery for controlling the valves, allowing the caregiver to raise or lower the sleeping surface or the head, thigh, and foot sections of the articulating deck and allowing movement of the sleeping surface to the Trendelenburg position during remote operation of the bed when the bed is disconnected from external power sources.

12. In-bed X-ray capability including a radiolucent window and head and abdomen access for a separate C-arm of X-ray equipment allowing the caregiver to obtain X-rays of the head, chest, and abdomen without removing the person from the sleeping surface of the bed.

13. Four wheel braking capability for braking four caster wheels mounted to the base, the braking capability being activated by a butterfly wheel pedal that can move between a braking position, a neutral position, and a steering position that allows for the steering of the caster wheels during movement of the bed.

14. Mattress including pressure-reducing capability in the seat section when in the sitting position to reduce the chance of skin breakdown.

15. Mattress including a modular design so that several surfaces/air therapies are driven by a common air source, a common graphical caregiver interface, and a common distributed network, and so that a caregiver can install and initiate an air therapy without moving the person off of the original sleeping surface.

The bed of the present invention includes a base frame or a main frame upon which several basic components are mounted such as the system displays and the air compressor for the various air-driven treatment technologies. The base frame provides various care modules which are mountable on the bed and usable with the control network, display, and air compressors built therein. Illustratively, a common air power source and handling unit is located on the main frame of the bed to supply air to all of several selected mattress surface therapies. Therapy frame header connectors including a plurality of air lines for coupling the air source to selected air surface modules is provided. A therapy surface control module is mounted on the bed. A microprocessor or microcontroller-based electronic module is configured to be electrically coupled to electronics residing in each of the separate treatment surface modules. The control module on the bed will control power, air distribution, and graphical display, and the control module contains valves and electronic controls to be described hereinafter. The control module is capable of recognizing the specific surface which is connected to the control module and will then control the air handling unit and display according to the selected surface.

The bed will primarily be powered from the main AC power input for the hospital or clinic in which it is installed. When disconnected from the main AC power input, a battery may be provided on the base frame for limited functionality.

The bed including the features described above meets the needs of multiple acute care areas including critical care, step down, medical/surgical, and subacute care. This flexibility results in reduced handling and transport of the person since mobility can be provided closer to the stretcher, and the person can stay on one bed for transport so that seamless care can be provided. In addition, convertibility of the bed to the sitting position provides benefits including that the upright position provides physiological benefits meeting M.D. orders, it minimizes handling of the person and minimizes the number of caregivers required for handling people, it speeds patient recovery, it minimizes the length of stay satisfying the critical pathway, and it enhances patient safety.

Bed with Deflatable Foot Section

It is an object of the present invention to provide a bed for supporting a person, the bed having a head end, a foot end, and sides, and the bed comprising a frame, and an articulating deck supported on the frame. The articulating deck comprises longitudinally spaced apart head, seat, and foot sections. The head, seat, and foot sections are all movable relative to each other to accommodate changes of the position of the person on the bed.

A mattress is supported on the deck and the mattress has head, seat, and foot mattress portions associated with or corresponding, respectively, to the head, seat, and foot sections of the deck. The words "corresponding" and "associated" are used in a general sense herein to associate portions of the mattress with sections of the articulating deck and/or with areas of the body of the person resting on the sleeping surface of the bed. In some cases, a mattress will be selected for a particular person and the mattress will have longitudinally spaced portions corresponding respectively to portions of the person.

The foot section of the deck is movable from a generally horizontal up position to a generally vertically downwardly extending down position to permit the lower legs and feet of the person to be lowered, for example, when the bed moves to a sitting position. This foot section may be selectively stopped in its various positions between the generally horizontal up position and the generally vertically downwardly extending down position to permit the lower legs of the person to be inclined in a conventional recliner fashion. The mattress foot portion is inflatable to serve as a sleeping surface when inflated and when the foot section of the deck is generally horizontal, and is declined downwardly and deflated when the foot section of the deck is in the down position to provide clearance for the lower legs and feet of the person.

The head section of the deck preferably translates toward the head end of the bed and pivots upwardly to provide a pivotable backrest or back-support portion for the person when the bed moves to the sitting position. In the illustrative and preferred embodiment, the seat section includes a thigh section that pivots upwardly relative to the frame. When the bed serves as a chair, the thigh section pivots upwardly to form an angle with the frame and cooperates with the head section to cradle the person on the bed thus providing a secure seat for the person.

The seat section of the articulating deck can be lowered to a low position at which the sleeping surface adjacent to the seat portion of the mattress is approximately 15 inches (38 cm) above the floor. The seat section is typically in the low position when the bed is in the sitting position. Thus, although the preferred and illustrative foot section of the articulating deck may be longer than 15 inches (38 cm) when the foot section is in the up position, the foot section preferably and illustratively can be manipulated to have a longitudinal dimension of 15 inches (38 cm) or less that will "clear" the floor when the bed is converted to the sitting position and the foot section moves to the down position.

Articulating Deck Having a Contracting Foot Section

It is still another object of the present invention to provide a bed having an articulating deck having a unique contracting foot section. The bed has an articulating deck on a frame and a mattress on the deck. The deck has longitudinally spaced head, seat, and foot sections that are movable relative to each other to accommodate changes of the position of the person on the mattress. The mattress has head, seat, and foot mattress portions corresponding, respectively, to the head, seat, and foot deck sections.

The foot section of the deck is movable from a generally horizontal up position to a generally vertically downwardly extending down position to permit the lower legs and feet of the person to be lowered. The foot section of the deck and the mattress foot portion have a first length when the foot section is in the up position and a second length shorter than the first length when the foot section is in the down position. This foot section may be selectively stopped in its various positions between the generally horizontal up position and the generally vertically downwardly extending down position to permit the lower legs of the person to be inclined in a conventional recliner fashion.

The seat section of the articulating deck can be lowered to a low position in which the sleeping surface adjacent to the seat portion of the mattress is approximately 15 inches (38 cm) above the floor. The seat section is typically in the low position when the bed is in the sitting position. Thus, although the preferred and illustrative foot section of the articulating deck may be longer than 15 inches (38 cm) when the foot section is in the up position, the foot section can contract so that the foot section has a longitudinal dimension that will "clear" the floor when the bed is converted to the sitting position and the foot section moves to the down position. Thus, the foot section can expand and contract so that the length of the foot section varies between a first length and a second length, the second length being greater than the first length.

Step Deck in Combination with a Reduced-Shear Pivot Assembly

It is also an object of the present invention to provide such a bed having a head, a foot, and sides, and including a unique combination of a step deck with a reduced-shear pivot feature. The bed includes a frame and a deck carried by the frame. The deck includes an upper deck portion and a central, longitudinal recess in the upper deck portion, the recess being defined by a lower deck portion and walls connecting the upper and lower deck portions. In addition, the bed includes a mattress having a planar, upwardly-facing support surface, side portions resting on the side deck portions, and a central projection extending downwardly into the recess. The bed also includes a first longitudinal deck section coupled to the deck to pivot about a pivot axis above the lower deck portion between a generally horizontal position and a tilted position.

The head section is coupled to the walls adjacent to the seat section and above the lower deck so that the head section is movable from a generally horizontal down position to a back-support position providing a pivotable backrest. Preferably, the head section simultaneously translates toward the head end of the bed and pivots upwardly when moving from the down position to the back-support position. The translation and the pivoting motions combine to produce a motion wherein the head section pivots relative to the seat section about an effective pivot axis positioned to lie above the lower deck.

The vertical distance between the support surface and the reduced-shear pivot assembly can be minimized when the bed includes a step deck having upper deck side portions and a corresponding thin mattress portion. Mounting the reduced-shear pivot assembly to the walls connecting the lower deck and the upper deck portion minimizes the extent that the reduced-shear pivot assembly is required to raise the effective pivot axis above the reduced-shear pivot assembly as compared to a reduced-shear pivot assembly mounted to the bottom of a deck.

Bed Base Frame, Intermediate Frame, and Power Package

It is still another object of the present invention to provide a bed for supporting a patient, the bed being convertible between a bed position and a sitting position and having a head end, a foot end, and opposite sides as well as a unique base frame and power unit arrangement. The bed comprises a base frame, casters for supporting the base frame for movement of the bed by a caregiver, and an intermediate frame mounted on the base frame for movement upwardly and downwardly to selected heights and orientations relative to the base frame. An articulated deck is mounted on the intermediate frame, the deck having head, foot, and seat sections that are movable relative to each other.

The bed also includes a fluid system including a pump, valves, and actuators for positioning the intermediate frame relative to the base frame and for articulating the deck sections. In addition, an electrical control system for operating the pump and controlling the valves of the fluid system when connected to an independent source of power and for operating only the valves using a battery source on the bed when not connected to an independent source of power is provided on the bed.

The deck has head, foot, and seat sections, the head section being movable between a down position generally parallel to the intermediate frame and an upward back-support position propping up the person and serving as a chair back. The seat section includes a thigh section that is movable between a generally horizontal down position and an up position to prop up the thighs of the patient. The foot section is movable between a generally horizontal up position and a generally vertically downwardly extending down position to lower the lower legs and feet of the patient.

First means are provided for raising and lowering the intermediate frame relative to the base frame to raise and lower the articulating deck. Second means are provided for raising and lowering the head section of the deck relative to the intermediate frame, third means are provided for raising and lowering the thigh section relative to the intermediate frame, and fourth means are provided for raising and lowering the foot section relative to the intermediate frame. In the illustrative and presently preferred embodiment, each of the first, second, third and fourth means comprises a hydraulic actuator such as a hydraulic piston and cylinder arrangement.

The intermediate frame and a weigh frame carried by the intermediate frame support the articulating deck sections for movement to their various positions. The seat section of the deck is illustratively and preferably fixed to the weigh frame. Power actuators act between the weigh frame and the articulating deck head, thigh, and foot sections. Additional power actuators act between the intermediate frame and the base frame to raise and lower the intermediate frame relative to the base frame.

Illustratively, the weigh frame is supported on the intermediate frame by a plurality of load beams which serve to weigh the person as will be described hereinafter. If a weighing capability is not provided, the weigh frame may be fixedly secured to the intermediate frame by "dummy" beams or members which are not load-cell members to provide a "non-scale" bed. In such a non-scale bed, the weigh frame and the intermediate frame are linked together such that they both may be considered as a common frame.

The bed further comprises a hydraulic power unit carried on the base frame to provide pressurized fluid for activating the actuators, conduit for connecting the power unit to the actuators, and a plurality of valves for controlling the flow of fluid between the hydraulic power unit and each actuator. While hydraulic actuators are shown in the illustrative embodiment, it will be appreciated that, in accordance with the present invention, various mechanical and electromechanical actuators and drivers may be used to raise and lower the intermediate frame on the base frame as well as to raise and lower individual deck sections relative to the intermediate frame.

It is well known in the hospital bed art that electric drive motors with various types of transmission elements including lead screw drives and various types of mechanical linkages may be used to cause relative movement of portions of hospital beds. It is also well known to use pneumatic actuators to actuate and/or move individual portions of hospital beds. As a result, the terms "means for raising and lowering" in the specification and in the claims, therefore, are intended to cover all types of mechanical, electromechanical, hydraulic and pneumatic mechanisms, including manual cranking mechanisms of all types, for raising and lowering portions of the hospital bed of the present invention.

It is an object of the present invention also to provide such a hydraulic power unit comprising electrically driven pump means for supplying hydraulic power when sufficient electrical power is available and connected to the bed, as well as manually driven pump means for supplying hydraulic power when sufficient electrical power is not available. The bed of the present invention may preferably comprise a battery power pack for supplying electrical power sufficient to operate the above-said valves, whereby, with the manually-driven pump means and the battery powered valves, the deck can be raised and lowered and the head, thigh, and foot sections can be raised and lowered when the bed is disconnected from the primary power source, for example, the main AC electrical source provided by a hospital.

The bed of the present invention may be lowered to a position such that the mattress supporting deck is 15 inches (38 cm) from the floor and raised to a work position such that the deck is 34 inches (86.4 cm) from the floor. The head section of the mattress-supporting deck is connected to the weigh frame of the bed by a reduced-shear pivot arrangement such that the head section, with the mattress thereon, travels toward the head of the bed and simultaneously pivots upwardly simulating the pivot of the hip of the human body. The head of the bed may have, for example, 85° of articulation.

The thigh section of the mattress-supporting deck is connected to the weigh frame of the bed for pivoting movement so that the end of the thigh section adjacent to the foot section may have, for example, 10° of articulation upwardly away from the weigh frame. The end of the foot section of the mattress-supporting deck nearest to the thigh section is connected to the weigh frame of the bed and may have, for example, 90° of articulation downwardly away from the weigh frame. In addition, the foot section may contract and expand so that the length of the foot section can vary, for example, between a first length when the foot section is in the up position and a second length when the foot section is in the down position, the first length being longer than the second length.

Emergency Trendelenburg Positioning

It is further an object of the present invention to provide a bed having an emergency Trendelenburg positioning feature. The bed is convertible between a bed position and a sitting position, and has a head end, a foot end, and opposing sides. The bed comprises a base frame and an intermediate frame mounted on the base frame for upward and downward movement to selected heights and orientations relative to the base frame. An articulated deck is mounted on the intermediate frame, the articulated deck having head, foot, and seat sections movable relative to each other.

The bed further comprises a fluid system including a pump, valves, and actuators for positioning the intermediate frame relative to the base frame and articulating deck sections and an electrical control system for operating the pump and controlling the valves of the fluid system. The fluid system includes a manual valve for operating an actuator to lower an end of the intermediate frame relative to the other end of the intermediate frame independent of the electrical control system.

The bed can alternatively comprise a mattress supported on the frame and having a support surface and a positioning system for positioning the intermediate frame relative to the base frame between a generally horizontal position and a Trendelenburg position having one end of the support surface inclined with respect to the other end of the support surface and including a first lock for locking and unlocking the intermediate frame in the horizontal position. A manual actuator can be coupled to a second lock in the positioning system for unlocking the intermediate frame independent of the first lock so that the positioning system can move the intermediate frame to the Trendelenburg position.

CPR Foot Pedal

It is further an object of the present invention to provide a bed having a unique CPR foot pedal feature. The bed has a head, a foot, and two sides, and includes a frame having a top and a bottom. The bed also includes an articulating deck coupled to the frame, the articulating deck having a head section that is movable relative to the frame. The head section can move between an upward back-support position providing a backrest and a generally horizontal bed position. The bed also includes locking means for securing the head section in the back-support position.

A CPR foot pedal is coupled to the locking means and is positioned to lie beneath the articulating deck so that the foot pedal is accessible to the foot of a caregiver. The foot pedal is movable between an up position and a downward releasing position releasing the locking means so that the head section can move downwardly to the bed position when the foot pedal is in the releasing position.

The head section of the articulating deck can quickly drop from the back-support position to the down position, for example, to allow a caregiver to quickly administer cardiopulmonary resuscitation to a person on the sleeping surface who experiences cardiac arrest when the bed is in the sitting position. The CPR foot pedal can be activated by a caregiver by pressing the pedal to cause the head section to rapidly pivot downwardly from the back-support position. Preferably, constant activation is required and the head section will continue to drop only so long as the pedal is activated, leaving the hands of the caregiver free to conduct other activities as the head section moves toward the down position.

Docking Site for Docking to the Bed when the Bed is in the Sitting Position

It is further an object of the present invention to provide a patient-care bed with a unique built-in docking capability. The bed has a head end, a foot end, and two opposing sides, and is convertible between a sitting position and a bed position. The bed includes a base and a frame coupled to the base. The frame is movable relative to the base between a low position having the frame a first distance from the floor and a high position having the frame a second distance from the floor, the first distance being less than the second distance.

An articulating deck is coupled to the frame. The articulating deck includes longitudinally spaced head and foot sections that are movable relative to the frame and movable relative to each other to accommodate changes of position of a person on the bed. The bed is movable to a sitting position having the frame in the low position, the head section in an upward back-support position providing a backrest, and the foot section in a generally vertically downwardly extending down position.

A latch-receiver post is appended to the frame and is configured to receive a latch connected to a portable equipment module so that the portable equipment module can dock with the bed when the bed is in the sitting position. The portable equipment module can include any equipment that is portable and that may be docked with the bed to maintain the relative position of the portable equipment module and the bed while taking advantage of the mobility of the bed and the stability of the bed when the bed is in the sitting position. For example, a mobile power module and a mobile toilet facility would each be portable equipment modules that could be docked to the bed when the bed is in the sitting position.

Bed with a Weigh Frame Supporting an Articulating Deck

It is further an object of the present invention to provide a patient-care bed with a built-in weighing feature. The bed has a head, a foot, and two sides. The patient-care bed includes a first frame, a weigh frame, and a plurality of load cell supports coupling the weigh frame to the first frame. In the context of the preferred embodiment, the "first frame" is the "intermediate frame." The load cell supports include means for determining the weight of objects supported by the weigh frame.

An articulating deck is coupled to the weigh frame. The articulating deck includes longitudinally spaced head, seat, thigh, and foot sections, the head, thigh, and foot sections being movable relative to the weigh frame and movable relative to each other. The movements of the sections of the deck accommodate changes of the position of the person on the bed.

Bed with Extended Frame

It is further an object of the present invention to provide a bed having a head, foot and opposite sides with a unique extended frame feature. The bed comprises a frame, a deck coupled to the frame, a mattress resting on the deck to cushion the patient, and an extended frame coupled to the frame at the foot of the bed. The extended frame comprises two gate assemblies, each gate assembly including a gate, a frame-extender member connected to the frame, and a swing member connecting the gate to the frame-extender member.

The gates have closed positions transverse to the bed sides. When in the closed position, the gates cooperate to close the foot of the bed. The frame-extender members are connected to the frame adjacent to the sides of the bed and extend in a direction outwardly and away from the head end of the bed.

A first swing member has a first end pivotably connected to the first frame extender member. The second end of the swing member swings between a storage position adjacent to the frame and a closed position adjacent to the deck near the foot of the bed. The first gate is rotatably coupled to the second end of the swing member. Likewise, a second swing member has a first end pivotably connected to the second frame-extender member and the second gate is rotatably coupled to the second end of the second frame-extender member. The gates have normal positions transverse to the bed sides acting together to close the foot of the bed, and the gates cooperate with the swing members to move to positions extending generally adjacent to the frame along the sides of the bed, thereby opening the foot of the bed.

The gates are configured to move with the sleeping surface as the sleeping surface is raised and lowered so that if the bed is in the sitting position, the person can grasp the gates for support. The sleeping surface can then be raised to assist the person as they stand and the gates will raise with the sleeping surface, providing support to the person as they stand.

Typically, the extended frame is carried by the weigh frame. For non-scale embodiments of the bed having the common frame configuration, the extended frame is carried by the common frame. Mounting the extended frame to the weigh frame or to the common frame causes the extended frame and foot gates to move with the weigh frame or the common frame and to remain stationary relative to the person supported on the sleeping surface. The gates of the extended frame can swing outwardly from the closed position to an open position having each gate positioned to lie adjacent to the swing member. When gates are in the open position, the caregiver has clear access to the foot section of the bed. When the bed is in the sitting position and the gates are in the open position, the person carried by the sleeping surface has clear path for egress from the foot end of the bed.

Additionally, the extended frame can fold like an accordion against the bed with the swing members swinging outwardly and around to the storage position and the gates swinging inwardly against the swing members to a side-grip position next to the swing members. In the side-grip position, the gates serve as a protective "crib-like" perimeter and provide hand supports for the person egres sing from the foot of the bed when the bed is in the sitting position. Additionally, the frame and gates can easily be removed entirely from the foot end of the bed by folding the frame back and folding the gates back.

Swing members in the extended frame minimize the radius of the arc of the gate as it swings between the side-grip position and the closed position. Also, use of the swing members allows the length of the frame-extender members to be minimized while providing the caregiver with satisfactory access to the person when the bed is in either the bed position or the sitting position.

The present invention includes several combinations of individual features disclosed herein. For example, the combination of the step deck with several features such as the reduced-shear pivot, the siderails, the pivoting foot section, the mattress having the projection, and the mattress having the deflatable foot portion are all combinations that are included in the bed in accordance with present invention.

The electronic system architecture for the hospital bed of the present invention includes a plurality of electronically controlled modules located on the bed which are interconnected in a peer-to-peer configuration. This peer-to-peer communication network configuration enables any of the plurality of modules to communicate directly with another module in the network without the need for a master controller. In the preferred embodiment, information flow between the electronic modules is primarily accomplished through the use of a twisted pair network channel, although other physical protocols would be acceptable.

One feature of the control system of the present invention is improved upgradeability. The peer-to-peer network configuration of the electronic control modules of the present invention facilitates adding or removing modules from the bed. In conventional bed control systems which use a master controller, the master controller must be initially designed or subsequently redesigned to accommodate additional modules. Since no master controller is required in the peer-to-peer network configuration, the electronic control system of the present invention does not have to be redesigned or reprogrammed each time a module is added or removed from the bed.

An open product architecture for the communication control network and air controls provides substantial flexibility for future additions of new modules. A graphic caregiver interface control module is provided for controlling the operation of various modules of the hospital bed. This control module is coupled to the peer-to-peer communication network. The control module includes a user input control panel and a display. The control module is programmed to recognize when a new module is added to the network automatically and to permit control of the new module from the user input control panel. The control module also displays specific control options for the added new module on the display automatically. Therefore, this new module recognition and control apparatus eliminates the need for separate controls on each individual module.

The network of the present invention also includes a bed status information charting feature. The network allows all data from each of the modules coupled to the network to be available at any time to the other modules. An optional module allows the network to supply information to a remote location through a data link. This information includes information from any of the modules communicating on the network. The peer-to-peer communication network of the present invention transmits electrical signals representing bed status variables that indicate the current position, status, and configuration of the bed. These variables include bed articulation angles, brakes, bed exit, scale, surface therapy attributes, as well as other variables. By detecting and storing changes in these bed status variables in the memory of a module or by transmitting these variables via the data link to a remote location, the present invention permits automatic charting of the bed status variables. Therefore, the hospital information system can monitor and record changes in the bed status variables continuously during the patient's stay for billing, legal, insurance, clinical/care plan studies, etc. The caregiver can also routinely check a nurse call bed status at a remote nurse master station rather than making bed check rounds. A history of the bed status for a particular patient can be displayed on the graphical user interface module, downloaded to a data file, and/or routed via the data link to a remote location.

The peer-to-peer communication network of the present invention is a distributed network. This distributed design allows for peer-to-peer communications between any of the nodes or modules connected to the network. Failure of a single module does not cause failure or impairment of the entire peer-to-peer communication network.

The peer-to-peer communication network of the present invention includes embedded self diagnostic capability. The network is capable of internally diagnosing hardware and software failures and recommending a corrective action. A signal for this corrective action can be supplied to a troubleshooting screen on the graphical user interface module, downloaded to a data file, and/or transmitted via a data link to a remote location.

Alternately, a service indicator can be lit to indicate the need for servicing of a specific system failure. Remote troubleshooting or diagnostics is also possible through a modem connected to an accessory module of the bed. A remote computer can run tests and interrogate other modules of the bed to indicate problems and suggest solutions.

This diagnostic capability also enhances serviceability of the bed. The lighted LEDs indicate a specific system failure. The graphic caregiver interface provides detailed information related to product failures on the bed. In addition, after diagnosis of the bed is performed from a remote location, a company service technician at the remote location can call an engineer at the hospital to help service the bed.

According to yet another aspect of the present invention, the bed includes a plurality of different air therapy and support surfaces, all of which can be connected to the bed to provide a complete therapy line that is rapidly installed or exchanged on demand as census or diagnostic population varies. In an acute care environment, a hospital typically needs decubitus prevention, decubitus treatment (stage one and two minimum), pulmonary therapies including rotation therapy and percussion and vibration therapy, and venous compression therapy capabilities.

The modular therapy and support surface design of the present invention allows several air support surfaces and air therapy devices to be driven by a common air source, a common graphical interactive display device, and a distributed communication network. The modular therapy and surface support system of the present invention is designed to provide a one bed solution for acute care including critical care, step down/progressive care, med-surg, high acuity subacute care, PACU, and sections of ED. The modular therapy and support surface system of the present invention provides therapies that benefit a large percentage of the patient population in an acute care hospital.

The bed of the present invention includes an air handling unit located on a bed frame which is capable of supplying air pressure and/or a vacuum to all the therapy and support surface modules. Typically, the air handling unit is mounted on the base frame of the bed. Preferably, the air handling unit drives two lines simultaneously for supplying both air pressure and vacuum to the air therapy modules. A header connector is coupled to the air handling unit by a plurality of air lines. The header connector is configured to couple the air handling unit to a selected modular air therapy device support surface.

The modular therapy and support surface components for the different therapies are contained within the sleep surface on the bed, enabling a caregiver to install, initiate, or remove a desired air therapy from the bed without moving the patient off the original support surface. The modular design of the present invention allows modules for air therapy to have reduced size. Therefore, the modules can be delivered after the bed and stored easily. The air handling unit of the present invention is coupled to therapy control modules that contain air distribution means such as adjustable valves and sensors by a simple connection of pneumatic lines to the control modules.

According to one aspect of the present invention, a bed includes a base frame, a deck coupled to the base frame, an electrical communication network, and an air handling unit mounted on the base frame. The bed also includes a plurality of air therapy devices located on the bed, and a plurality of control modules. Each control module includes a connector for coupling a corresponding air therapy device to the air handling unit and to the electrical communication network. Each control module also includes a controller for operating the corresponding air therapy device with the air handling unit based on command signals received from the electrical communication network.

The bed further includes a control unit coupled to the electrical communication network for transmitting command signals for the plurality of air therapy devices over the electrical communication network to control operation of the plurality of air therapy devices. The control unit includes a display and a user input. Each control module transmits display commands to the display related to the corresponding air therapy device. The display commands from the control modules provide a menu driven list of options to the display to permit selection of control options for the plurality of air therapy devices from the user input.

In the illustrated embodiment, one of the plurality of air therapy devices is a support surface air bladder located on the deck. The support surface air bladder includes a plurality of independently controlled air zones. One of the plurality of control modules is a decubitus prevention control module coupled to the support surface air bladder to control each of the plurality of air zones of the support surface with a common connection to the air handling unit. Another of the plurality of control modules is a decubitus treatment control module for independently coupling the plurality of air zones of the support surface air bladder to the air handling unit.

Another of the plurality of air therapy devices is a pulmonary rotation bladder located between the deck and the support surface air bladder. A pulmonary rotation control module is provided for coupling the pulmonary rotation air bladder to the air handling unit. The pulmonary rotation control module is coupled to the electrical communication network.

Yet another of the plurality of air therapy devices is a sequential compression therapy device. A sequential compression device air control module is provided for coupling the sequential compression device to the air handling unit. The sequential compression device air control module is coupled to the electrical communication network.

Still another of the plurality of air therapy devices is a pulmonary percussion and vibration bladder located on the deck for providing pulmonary percussion and vibration therapy. A pulmonary percussion and vibration control module is provided for coupling the percussion and vibration bladder to the air handling unit. The percussion and vibration module is coupled to the electrical communication network. Alternatively, the percussion and vibration control module is configured to couple a selected air zone of the support surface air bladder to the air handling unit to provide percussion and vibration therapy in the selected air zone.

An auxiliary air port control module is coupled to the air handling unit and to the electrical communication network. The air port control module provides an auxiliary air outlet on the bed.

According to another aspect of the present invention, a control module is provided for activating an air therapy device on a bed which includes a base frame, a deck coupled to the base frame, an electrical communication network, an air handling unit mounted on the base frame, a graphical interactive display coupled to the electrical communication network for transmitting and receiving command signals from the communication network, and a plurality of air therapy devices stored on the bed. The control module includes at least one electrically controlled valve having an input and an output, at least one pressure sensor having an input and an output, and an electronic controller coupled to and controlling the at least one electrically controlled valve and coupled to the output of the at least one pressure sensor. The control module also includes a connector for coupling the input of the valve to the air handling unit on the bed, for coupling the output of the valve to the selected air therapy device, for coupling the input of the pressure sensor to the selected air therapy device, and for coupling the controller to the electrical communication network on the bed so that the controller receives the command signals from the graphical interactive display to control the selected air therapy device.

The graphical interactive display includes a display and a user input. The controller transmits display command signals to the graphical interactive display to display information related to the selected air therapy device on the display. The display commands from the controller provide a menu driven list of control options for the selected air therapy device to the display to prompt selection of various control options for the selected air therapy device from the user input.

If the selected air therapy device includes a plurality of air zones, the control module includes an electrically controlled valve for each of the plurality of air zones to couple the plurality of air zones to the air handling unit on the bed independently. The control module also includes a separate pressure sensor for each of the plurality of air zones.

According to yet another aspect of the present invention, a bed includes a base frame, a deck coupled to the base frame, an electrical communication network, an air handling unit mounted on the base frame, and a header connector including an electrical connector coupled to the electrical communication network and a pneumatic connector coupled to the air handling unit. The bed also includes a plurality of exchangeable air therapy devices. Each of the air therapy devices includes at least one air zone, a therapy control module having a controller, a valve coupled to each air zone of the air therapy device, and a module connector configured to mate with the header connector to couple the valve to the air handling unit and to couple the controller to the electrical communication network so that each of the plurality of exchangeable air therapy devices use the same air handling unit and electrical communication network.

In the illustrated embodiment, the module connector includes a first connector coupled to an input of the valve and a second connector coupled to the controller, the first connector of the module connector being configured to mate with the pneumatic connector of the header connector on the bed to couple the air handling unit to the at least one air zone of the air therapy device through the corresponding valve and the second connector being configured to mate with the electrical connector of the header connector on the bed to couple the electrical communication network to the controller so that the controller receives commands from the electrical communication network to control air flow to the air therapy device through the valve.

According to still another aspect of the present invention, the modular support surface of the present invention includes an improved surface foot section specifically designed for use with a bed having an articulating deck movable from a normal bed position to a chair position. The surface foot section is configured to retract or shorten as the bed moves to the chair position to enable a patient's feet to be placed on the floor or on a foot prop. The foot section also collapses or thins to maintain an acceptable chair seat size which also enables the patient's feet to be placed on the floor or foot prop.

In the illustrated embodiment, a surface foot section apparatus is provided for a bed including a base frame, an articulating deck coupled to the base frame, the articulating deck including a generally planar foot deck section, the articulating deck being movable from a bed configuration to a chair configuration. The surface foot section apparatus includes a first set of air bladders configured to collapse in a first direction generally parallel to the foot deck section when the first set of air bladders is deflated, and a second set of air bladders located adjacent the first set of air bladders. The second set of air bladders is configured to collapse in a second direction normal to the foot deck section when the second set of air bladders is deflated so that the surface foot section has a substantially reduced thickness and a substantially reduced length when the first and second bladders are deflated. The surface foot section apparatus also includes a foot section control module for selectively inflating and deflating the first and second sets of air bladders. The foot section control module deflates the first and second sets of air bladders when the articulating deck is in the chair configuration, and the foot section control module inflates the first and second sets of air bladders when the articulating deck is in the bed configuration.

Preferably, the length of the surface foot section is reduced by at least 40% when the first and second air bladders are deflated and the thickness of the surface foot section is reduced by at least 80% when the first and second air bladders are deflated. This feature maintains an appropriate size for a seat section of the chair and permits a patient's feet to touch the floor when the bed is in the chair configuration. The foot deck section is movable from an extended position to a retracted position to shorten the foot deck section as the articulating deck moves to the chair configuration.

Also in the illustrated embodiment, each of the second air bladders is independently controlled as a separate air zone by the foot section control module. The foot section control module selectively inflates and deflates the second air bladders to provide a heel pressure relief in the surface foot section. The first set of air bladders is commonly controlled as a single air zone by the foot section control module.

According to a further aspect of the present invention, a pulmonary rotation therapy apparatus is provided for use on a bed having a base frame, a deck coupled to the base frame, and a support surface located on the deck. The pulmonary rotation therapy apparatus includes a normally deflated rotation air bladder located between the support surface and the deck. The rotation air bladder remains deflated during normal use of the bed. It is understood that the rotation air bladder can be normally inflated and used as a support surface for the bed, if desired. The pulmonary rotation therapy apparatus also includes a pulmonary rotation control module coupled to the rotation air bladder. The pulmonary rotation control module selectively inflates and deflates portions of the rotation air bladder to provide rotational therapy to a body located on the support surface.

In the illustrated embodiment, the rotation air bladder includes a plurality of elongated air bladders extending generally parallel to a longitudinal axis of the bed. The pulmonary rotation control module selectively inflates or deflates the plurality of air bladders to control rotation of the patient on the support surface. The rotation air bladders are divided into at least three separate air zones which are independently controlled by the pulmonary control module.

In an illustrated embodiment of the invention, the support surface includes a plurality of air bladders located on the deck. It is understood that any type fluid may be used. The air bladders are preferably divided into separately controlled air zones corresponding to the various deck sections of the articulating deck. Therefore, the support surface includes separately inflatable head, seat, thigh, and foot air zones.

Inflation and deflation of the various surface sections is controlled by a surface instrument control module and an air supply module, both of which are coupled to the electrical communication network on the bed. The surface instrument module and the air supply module both receive signals from the bed articulation control module and from a position sensing module as the bed begins moving from the bed position to the chair position. The surface instrument module and air supply module automatically partially deflate a seat air zone section of the support surface and the foot air zone section of the support surface as the bed moves to the chair position. For this purpose, the seat section includes not only the air zone overlying the seat portion of the deck, but also the air zone overlying the thigh portion of the deck. In the chair position, a person's weight is mostly supported by the thigh sections of the support surface and deck. Such partial deflation of the seat section of the bed is automatically controlled to distribute the person's weight as the bed moves to the chair position. In addition, the bed articulation control module automatically elevates an end or the thigh deck section closest to a foot end of the bed to maintain the patient in a seated position on the chair bed.

Additional objects, features, and advantages of the invention will become apparent to those skilled in the art upon consideration of the following detailed description of the preferred embodiments exemplifying the best mode of carrying out the invention as presently perceived.

BRIEF DESCRIPTION OF THE DRAWINGS

The detailed description particularly refers to the accompanying figures in which:

FIG. 9 is a perspective view of a first embodiment of a step deck and a mattress in accordance with the present invention;

FIG. 10 is a sectional view taken along line 10-10 of FIG. 9 showing the bottom of the step deck beneath the projection;

FIG. 12 is a perspective view of the base frame of the chair bed of FIG. 1 showing portions of the hydraulic system module mounted on the base frame;

FIG. 14a is a sectional view taken along line 14a-14a of FIG. 14 showing a load beam cantilevered to the intermediate frame;

FIG. 24 is a sectional view taken along line 24-24 of FIG. 1 showing the deck foot section in an expanded position;

FIG. 25 is a view similar to FIG. 24 showing the deck foot section and the pivoting member in the contracted position;

FIG. 26 is a view taken along line 26-26 of FIG. 25 showing a first tongue and groove connection between the pivoting member and the sliding member;

FIG. 27 is a view taken along line 27-27 of FIG. 25 showing a second tongue and groove connection between the pivoting member and the sliding member;

FIG. 28 is an exploded perspective view of a second embodiment of a step deck and the mattress of the chair bed;

FIG. 29 is a sectional view taken along line 29-29 of FIG. 28 of the step deck and the mattress and showing a C-arm (in phantom) for holding medical equipment such as fluoroscopic equipment;

FIG. 31 is a diagrammatic side elevation view of the chair bed of FIG. 1 showing the chair bed in the bed position of FIG. 3 and showing a head section siderail and a body section siderail;

FIG. 32 is a diagrammatic view similar to FIG. 31 showing the head section of the articulating deck of the chair bed raised to an intermediate position of FIG. 7;

FIG. 33 is a diagrammatic view similar to FIG. 31 showing the head section in the back-support position of FIG. 8;

DETAILED DESCRIPTION OF THE ILLUSTRATIVE AND PREFERRED EMBODIMENTS

Figure 1:
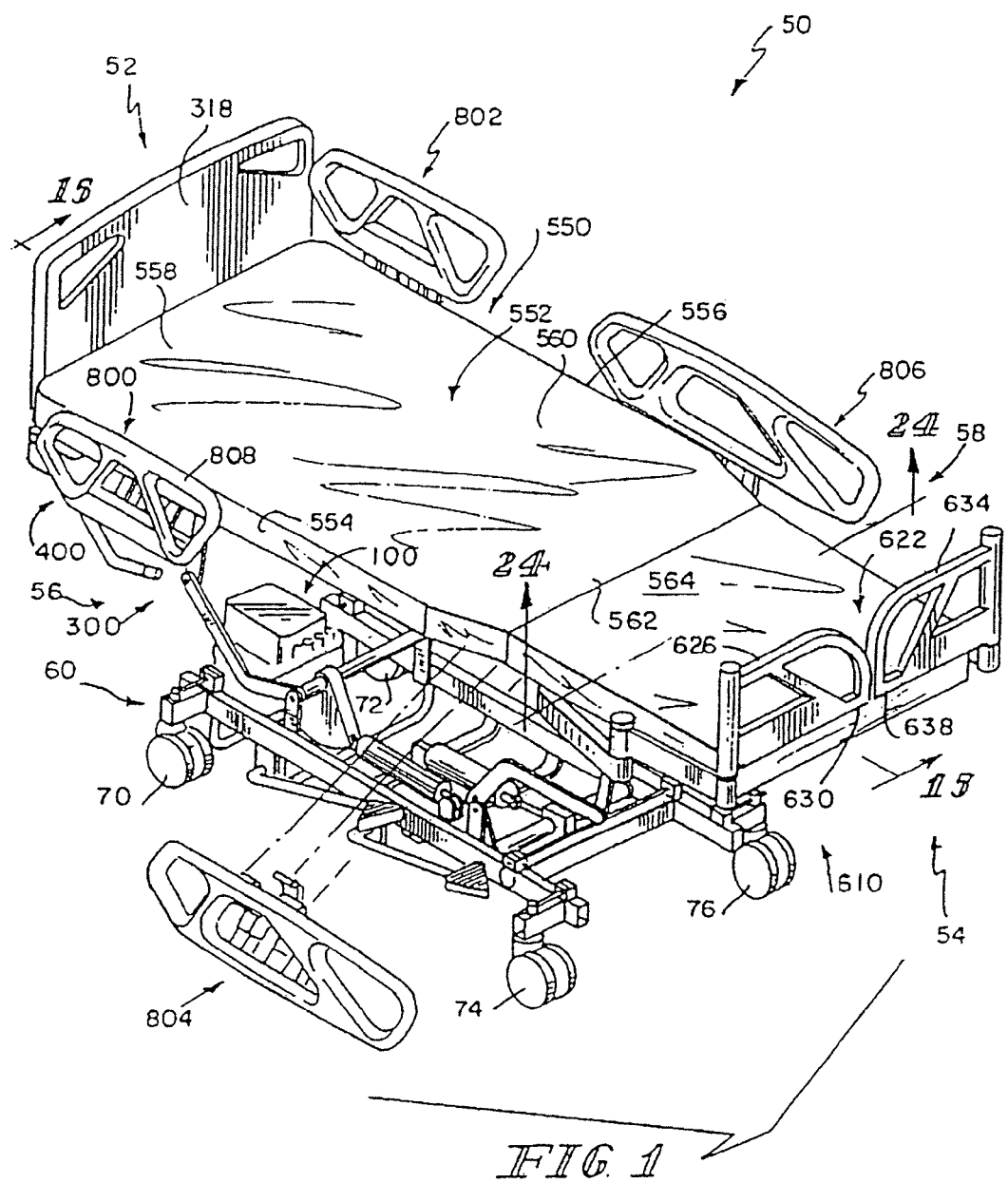
FIG. 1 is a perspective view of a chair bed in accordance with the present invention showing a siderail exploded away from the chair bed, head siderails and foot siderails positioned along longitudinal sides of the deck, and a swinging foot gate in a closed position.

A chair bed 50 in accordance with the present invention having a head end 52, a foot end 54, and sides 56, 58 is illustrated in FIG. 1. As used in this description, the phrase "head end 52" will be used to denote the end of any referred-to object that is positioned to lie nearest head end 52 of chair bed 50. Likewise, the phrase "foot end 54" will be used to denote the end of any referred-to object that is positioned to lie nearest foot end 54 of chair bed 50.

Figure 11:
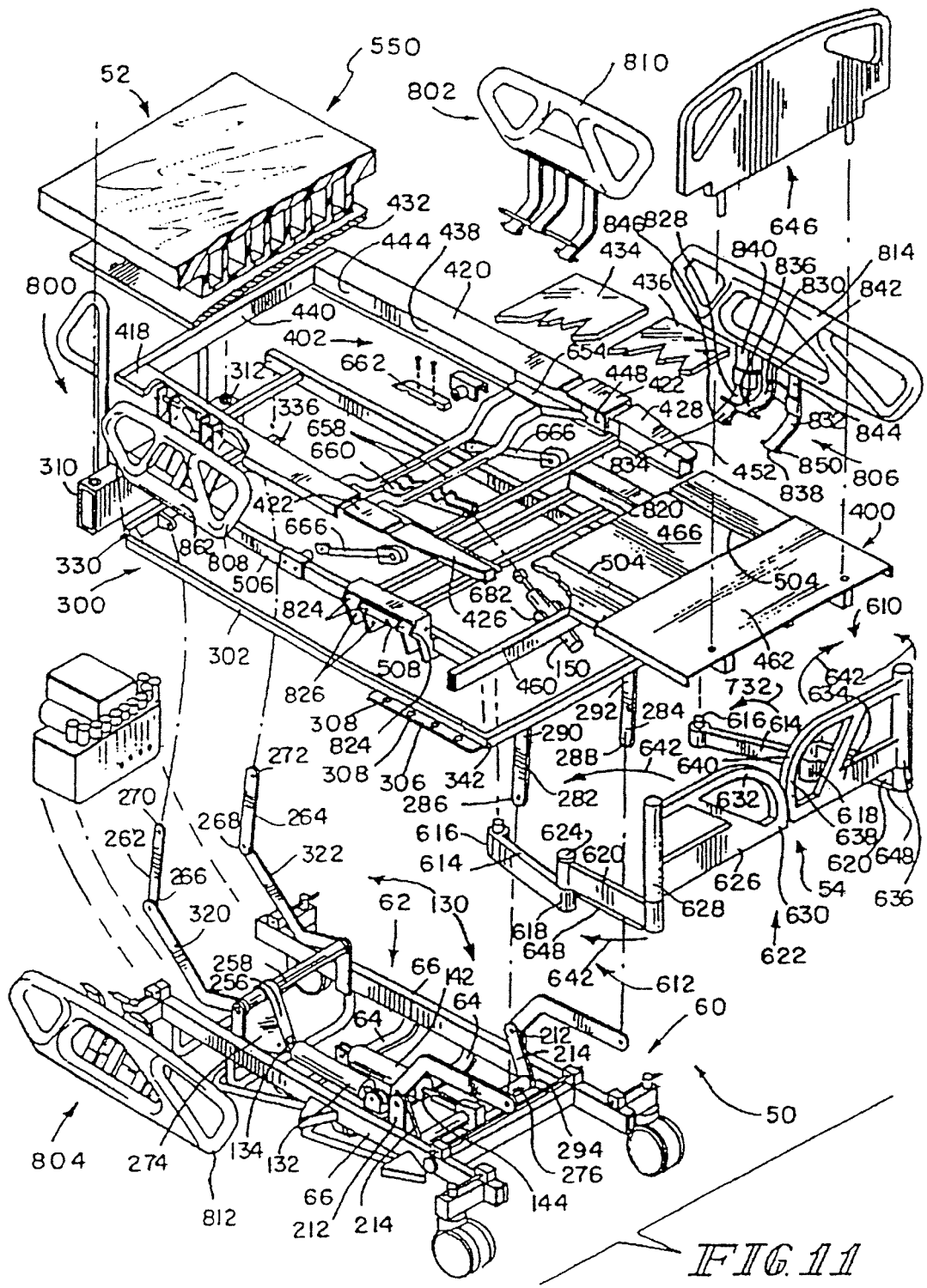
FIG. 11 is an exploded perspective view of the chair bed of FIG. 1 with portions broken away.
Figure 43:
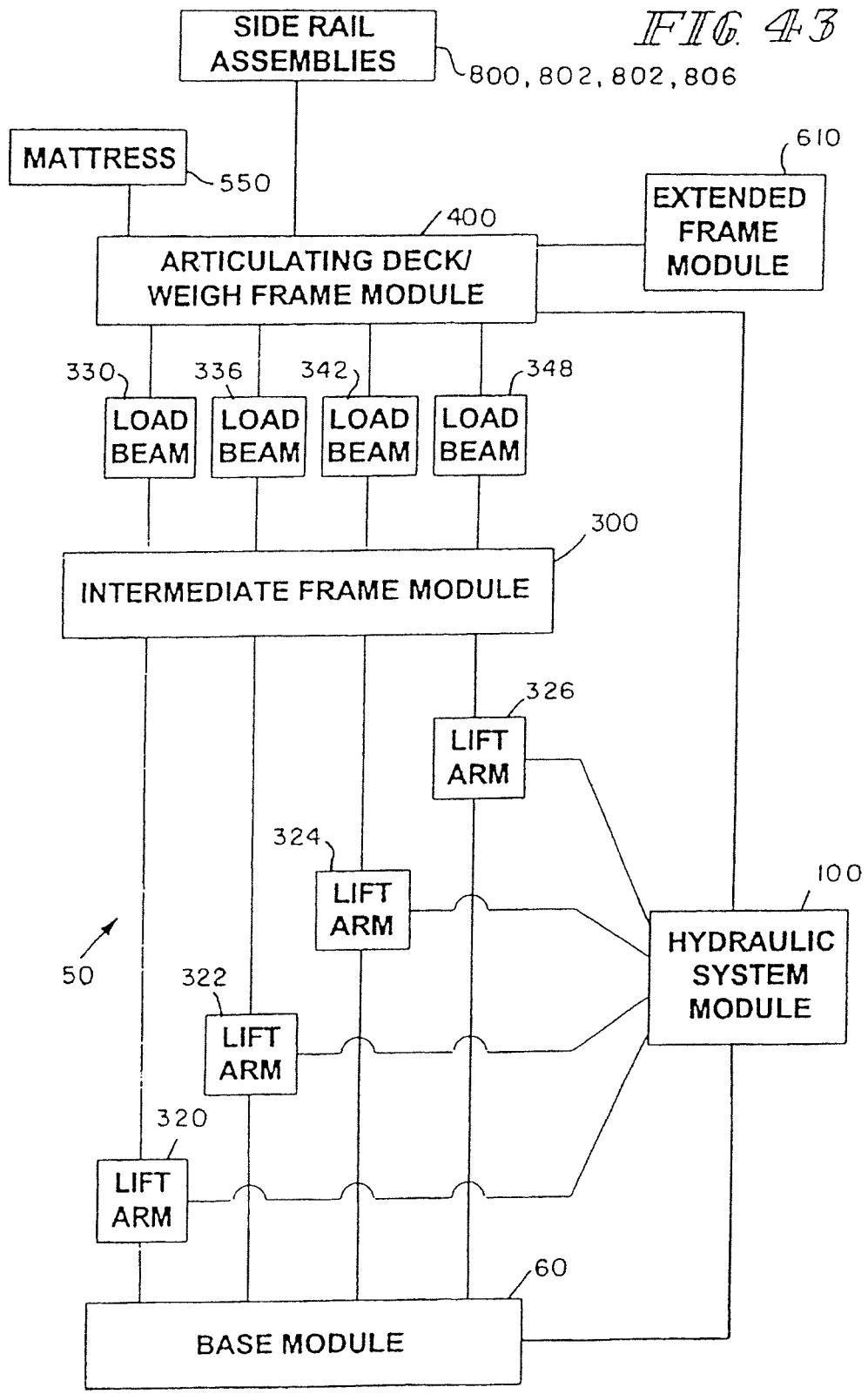
FIG. 43 is a block diagram illustratively showing major functional components of the chair bed and some of the mechanical and fluid connections therebetween.

Chair bed 50 includes a base module 60 having a base frame 62 connected to an intermediate frame module 300 by lift arms 320, 322, 324, 326 as shown in FIGS. 1, 11 and 43. An articulating deck/weigh frame module 400 is coupled to intermediate frame module 300 by load beams 330, 336, 342, 348. Siderail assemblies 800, 802, 804, 806 and an extended frame module 610 having a swinging foot gate 622 are coupled to articulating deck/weigh frame module 400. A mattress 550 is carried by articulating deck/weigh frame module 400 and provides a sleeping surface or support surface 552 configured to receive a person (not shown).

Chair bed 50 can be manipulated by a caregiver or by a person (not shown) on sleeping surface 552 using hydraulic system module 100 so that mattress 550, an intermediate frame 302 of intermediate frame module 300, and an articulating deck 402 of articulating deck/weigh frame module 400 assume a variety of positions, several of which are shown diagrammatically in FIGS. 3-7.

Articulating deck 402 includes a head section 404, a seat section 406, a thigh section 408, and a foot section 410. Mattress 550 rests on deck 402 and includes a head portion 558, a seat portion 560, a thigh portion 562, and a foot portion 564, each of which generally corresponds to the like-named portions of deck 402, and each of which is generally associated with the head, seat, thighs, and feet of the person on sleeping surface 552. Details of deck 402 and mattress 550 will be explained hereinafter.

Figure 3:
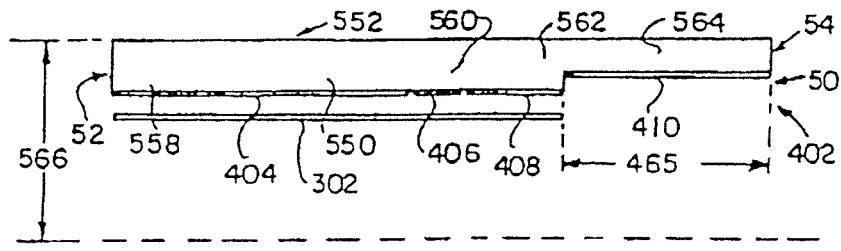
FIG. 3 is a diagrammatic view of the chair bed of FIG. 1 showing the chair bed in a bed position including a mattress having an upwardly-facing sleeping surface held a predetermined first distance above the floor, the deck being in an initial position supporting the sleeping surface in a generally planar configuration, and the foot section being a first length.
Figure 4:
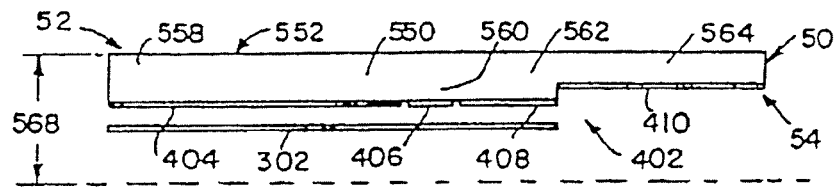
FIG. 4 is a diagrammatic view showing the chair bed in a low position.

Chair bed 50 can assume a bed position having deck 402 configured so that sleeping surface 552 is planar and horizontal, defining an initial position of deck 402 as shown in FIG. 1 and as shown diagrammatically in FIG. 3. In the bed position, sleeping surface 552 is a predetermined first distance 566 above the floor. Chair bed 50 can also be manipulated to assume a low position shown diagrammatically in FIG. 4 having deck 402 in the initial position and having sleeping surface 552 a predetermined second distance 568 above the floor, the second distance 568 being smaller than first distance 566. The foot section 410 of the articulating deck 402 has a first length 465 when the deck 402 is in the initial position.

Figure 5:
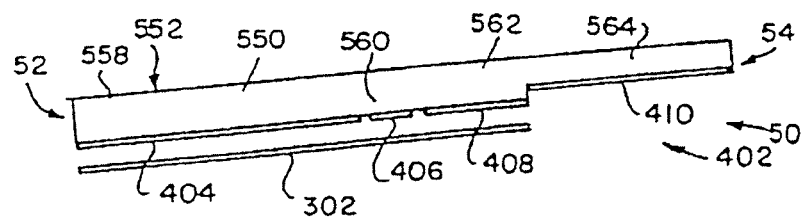
FIG. 5 is a diagrammatic view showing the chair bed in a Trendelenburg position.
Figure 6:
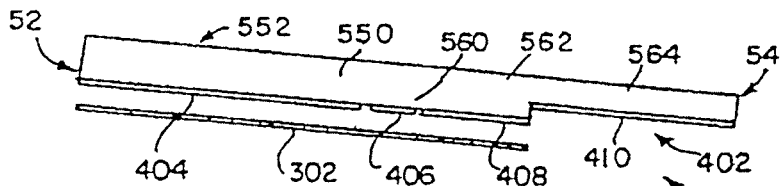
FIG. 6 is a diagrammatic view showing the chair bed in a reverse Trendelenburg position.

Chair bed 50 can be moved to a Trendelenburg position shown diagrammatically in FIG. 5 having deck 402 in a planar configuration and tilted so that head end 52 of sleeping surface 552 is positioned to lie closer to the floor than foot end 54 of sleeping surface 552. Chair bed 50 can also achieve a reverse Trendelenburg position shown diagrammatically in FIG. 6 having deck 402 in a planar configuration and tilted so that foot end 54 of sleeping surface 552 is positioned to lie closer to the floor than head end 52 of sleeping surface 552.

Figure 2:
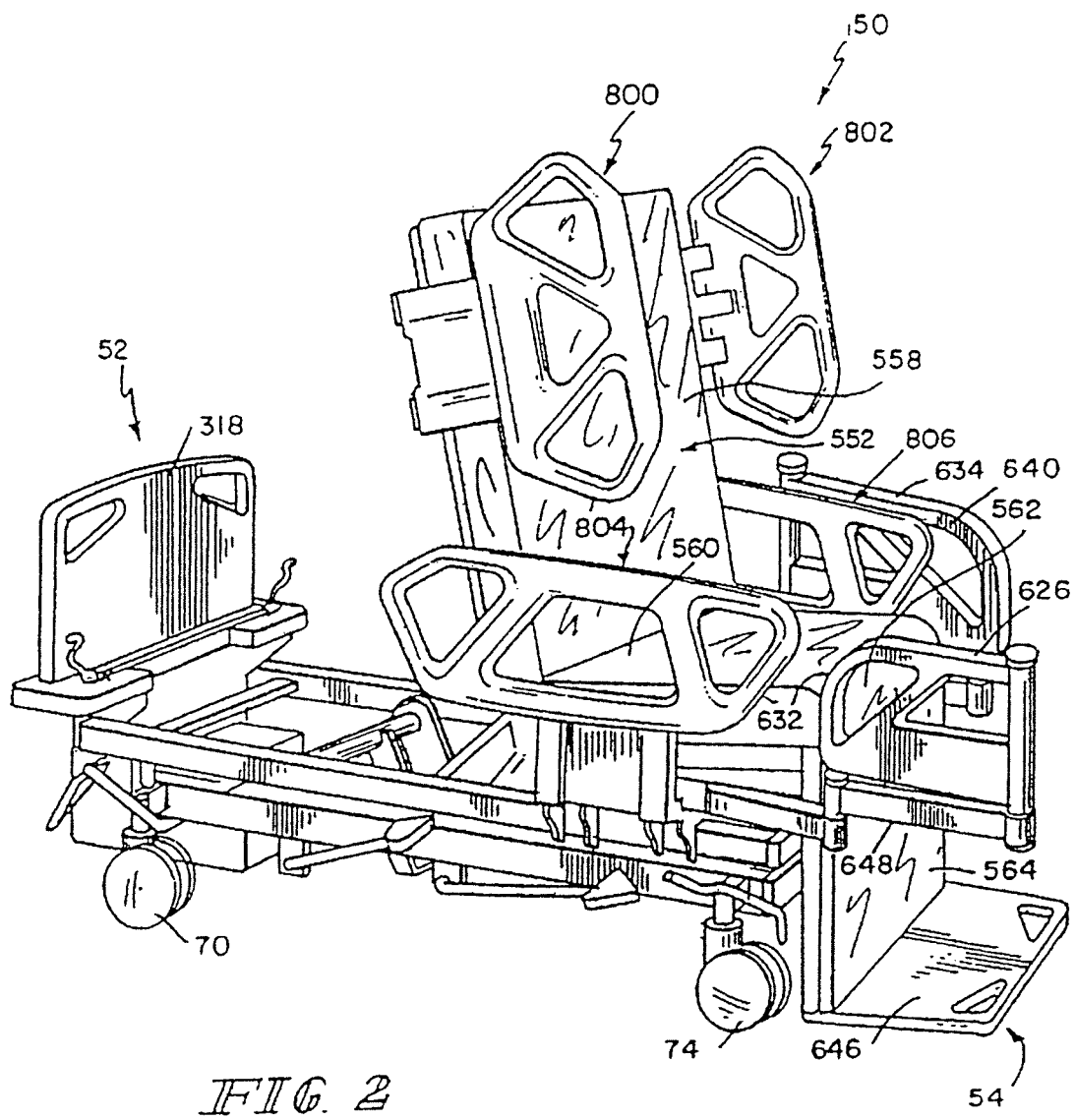
FIG. 2 is a view similar to FIG. 1 showing the chair bed in the sitting position having a head section of an articulating deck moved upwardly to a back-support position, a thigh section of the deck inclined slightly upwardly, a foot section of the deck moved to a generally vertical downwardly extending down position, a foot portion of the mattress being deflated, and swinging gates moved to an open position with one swinging gate folded next to the chair bed.
Figure 8:
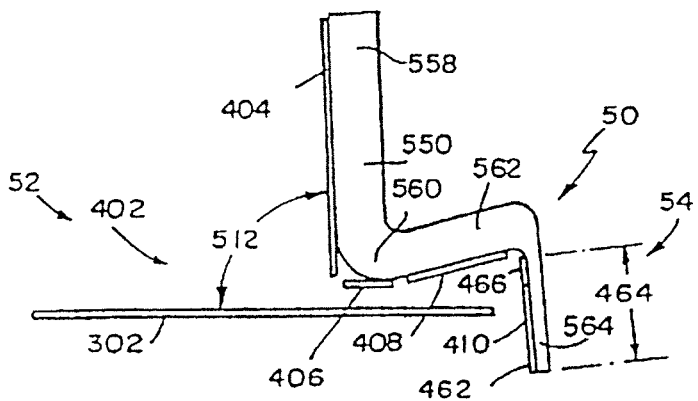
FIG. 8 is a diagrammatic view showing the chair bed in a sitting or chair position with the head end of the head section pivoted upwardly away from the seat section to a back-support position, the seat section lying generally horizontal as in the initial deck position, the thigh section being raised upwardly, the foot section extending downwardly from the thigh section and being a second shorter length, and the portion of the mattress over the foot section being deflated.

As described above, chair bed 50 is convertible to a sitting position shown in FIG. 2 and shown diagrammatically in FIG. 8. In the sitting position, head end 52 of head section 404 of deck 402 is pivoted upwardly away from intermediate frame 302 to a back-support position providing a pivotable backrest so that head section 404 and intermediate frame 302 form an angle 512 generally between 55 and 90 degrees. Seat section 406 of deck 402 is positioned to lie generally horizontally as in the initial position, foot end 54 of thigh section 408 is slightly upwardly inclined, and foot section 410 of deck 402 extends generally vertically downwardly from thigh section 408 and has a length 464 that is shorter than when deck 402 is in the initial position. Foot portion 564 of mattress 550 is inflatable and is in a deflated condition when chair bed 50 is in the sitting position. Foot portion 564 of mattress 550 is thinner and shorter when deflated than when inflated.

Chair bed 50 is capable of assuming positions in which head, thigh, and foot sections 404, 408, 410 of deck 402 are in positions intermediate to those shown in FIGS. 3 and 8. For example, chair bed 50 can assume an intermediate position shown diagrammatically in FIG. 7 and also shown in FIG. 15, having head end 52 of head section 404 of deck 402 pivoted slightly upwardly from the initial position, seat section 406 positioned to lie in the same generally horizontal plane as in the initial position, foot end 54 of thigh section 408 raised slightly upwardly from the initial position, and foot section 410 being inclined so that foot end 54 of foot section 410 lies below head end 52 of foot section 410.

Figure 30:
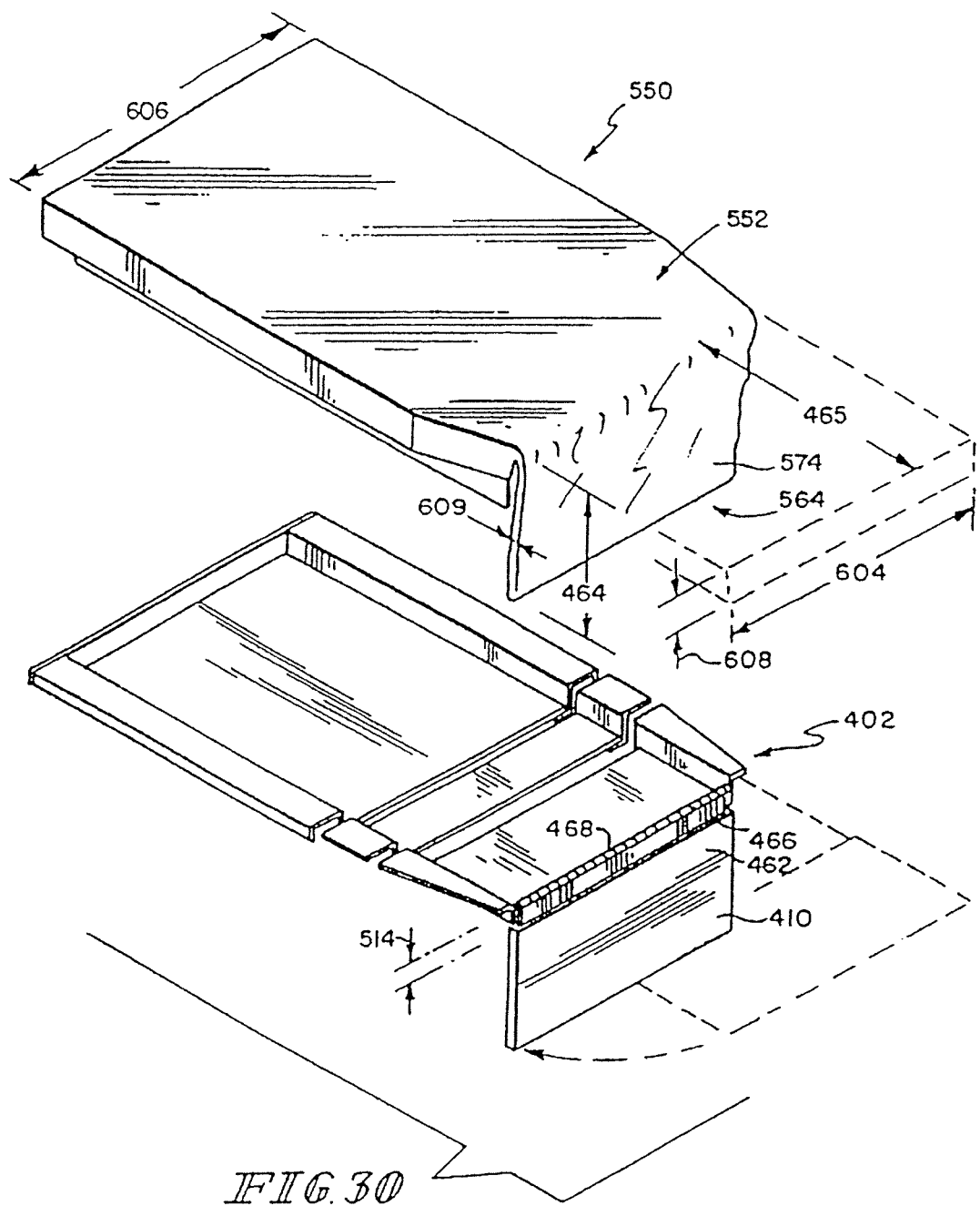
FIG. 30 is an exploded perspective view of a third embodiment of the mattress and the deck showing the foot section of the deck and the foot portion of the mattress in a minimized condition having the foot section of the deck contracted and the foot portion of the mattress contracted longitudinally and deflated so that the foot portion of the mattress is thinner and shorter than when foot portion is inflated.

Additionally, articulating deck 402 of chair bed 50 is configured as a step deck 412 as shown illustratively along with illustrative step mattress 550 in FIGS. 9, 10, and 28-30. The step deck and mattress of FIGS. 28-30 are those illustrated in FIGS. 3-8. Step deck 412 includes an upper deck 414 and a central, longitudinally extending recess 456 defined by a lower deck 430 of step deck 412 and a wall 438 surrounding recess 456 and connecting lower deck 430 to upper deck 414. Upper deck 414 includes longitudinally extending upper deck side portions 417, a head end upper deck end portion 416, and a foot end upper deck end portion 460.

Mattress 550 includes a generally upwardly-facing sleeping surface 552 and a bottom surface 586 that is generally parallel to sleeping surface 552 and that is positioned to lie beneath sleeping surface 552. A perimetral side 578 connects sleeping surface 552 and bottom surface 586. A projection 576 is appended to bottom surface 586 and extends downwardly therefrom. Preferably, projection 576 is spaced-apart from sides 578 of mattress 550 and nests in recess 456. Projection 576 may engage wall 438 of step deck 412 to prevent movement of mattress 550 relative to step deck 412 and to maintain the generally central position of mattress 550 on deck 412.

Preferably, mattress 550 is provided with a thick zone 582 adjacent to recess 456 and projection 576, and a thin zone 580 engaging upper deck 414 as shown in FIG. 10. For example, thick zone 582 can be one and one-half times the thickness of thin zone 580. In one preferred embodiment, the thick zone is approximately 7½ inches (19 cm) thick and the thin zone is 5 inches (12.7 cm) thick. Thick zone 582 is positioned to carry the majority of the weight of a person (shown in phantom) supported on sleeping surface 552 to maximize the comfort of the person. Having perimetral thin zone 580 provides a perimetral portion of mattress 550 that appears to the person on sleeping surface 552 to be firmer than thick zone 582, facilitating entry onto and exit from sleeping surface 552 along sides 578 of mattress 550.

As can be seen, step deck 414 and mattress 550 can be used in many applications requiring a support surface for supporting a person. For example, step deck 414 and mattress 500 can be configured for use as a stretcher to be carried by caregivers and as a gurney having step deck 414 mounted on a frame with wheels for transporting the person supported by the gurney.

A general overview of the system architecture will be followed by a description of the general operation of chair bed 50.

System Architecture

Base module 60, intermediate frame module 300, articulating deck/weigh frame module 400, and siderail assemblies 800, 802, 804, 806 are illustratively shown in FIG. 11 and are shown diagrammatically in FIGS. 43-47. The solid lines of FIGS. 43-47 represent mechanical connections, the thick short dashed lines represent fluid connections, the thin long dashed lines represent electrical connections, and the double lines represent connections to the electronic network. Base module 60, intermediate frame module 300, and articulating deck/weigh frame module 400 cooperate with a hydraulic system module 100 to manipulate mattress 550 in accordance with commands from the caregiver or from the person supported by sleeping surface 552. These modules and some connections therebetween are described below.

Base Module 60

Figure 44:
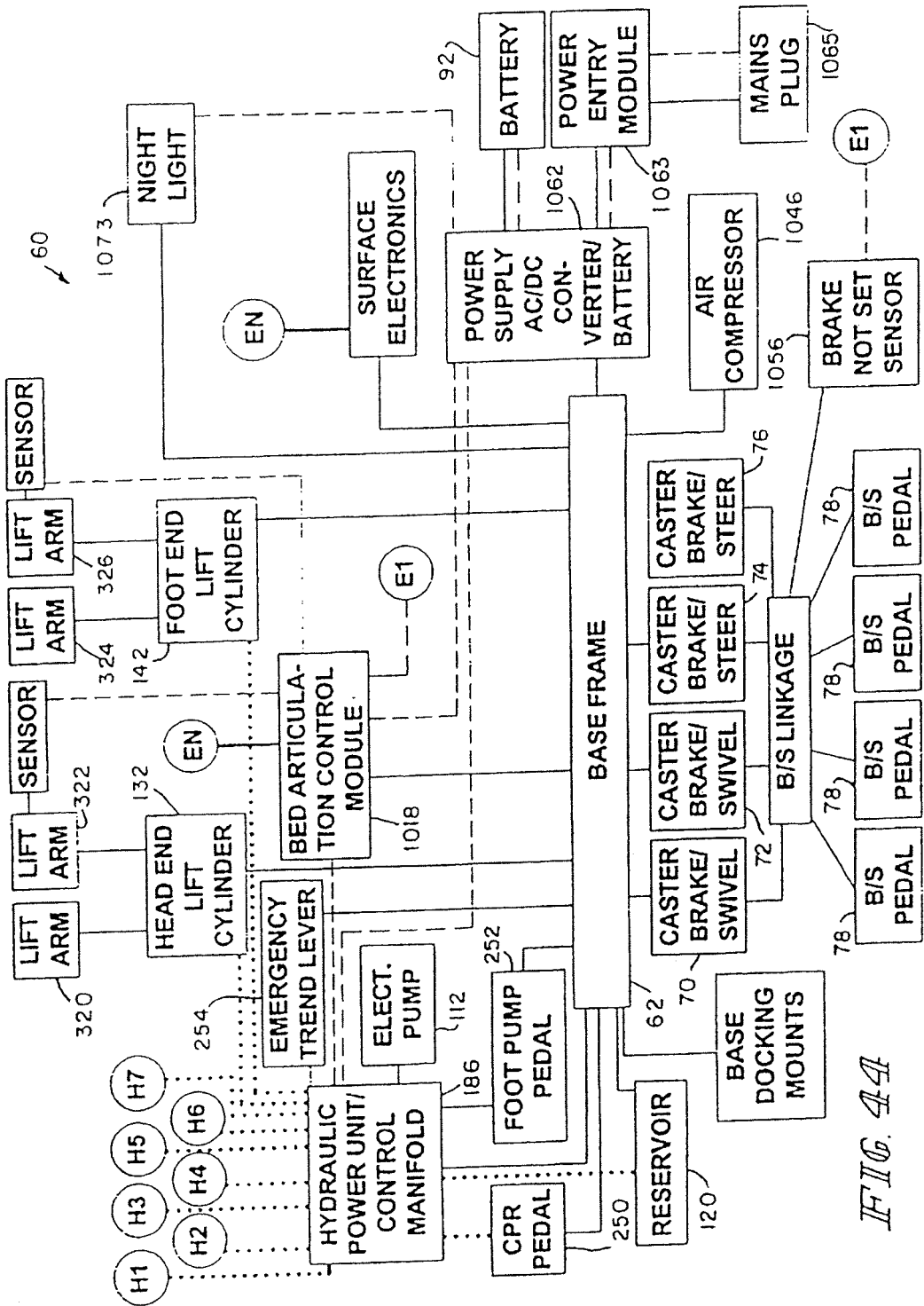
FIG. 44 is a block diagram of the base module and portions of the hydraulic module illustratively showing some components of the base module and illustrating some of the mechanical, fluid, and electrical interconnections therebetween.
Figure 45:
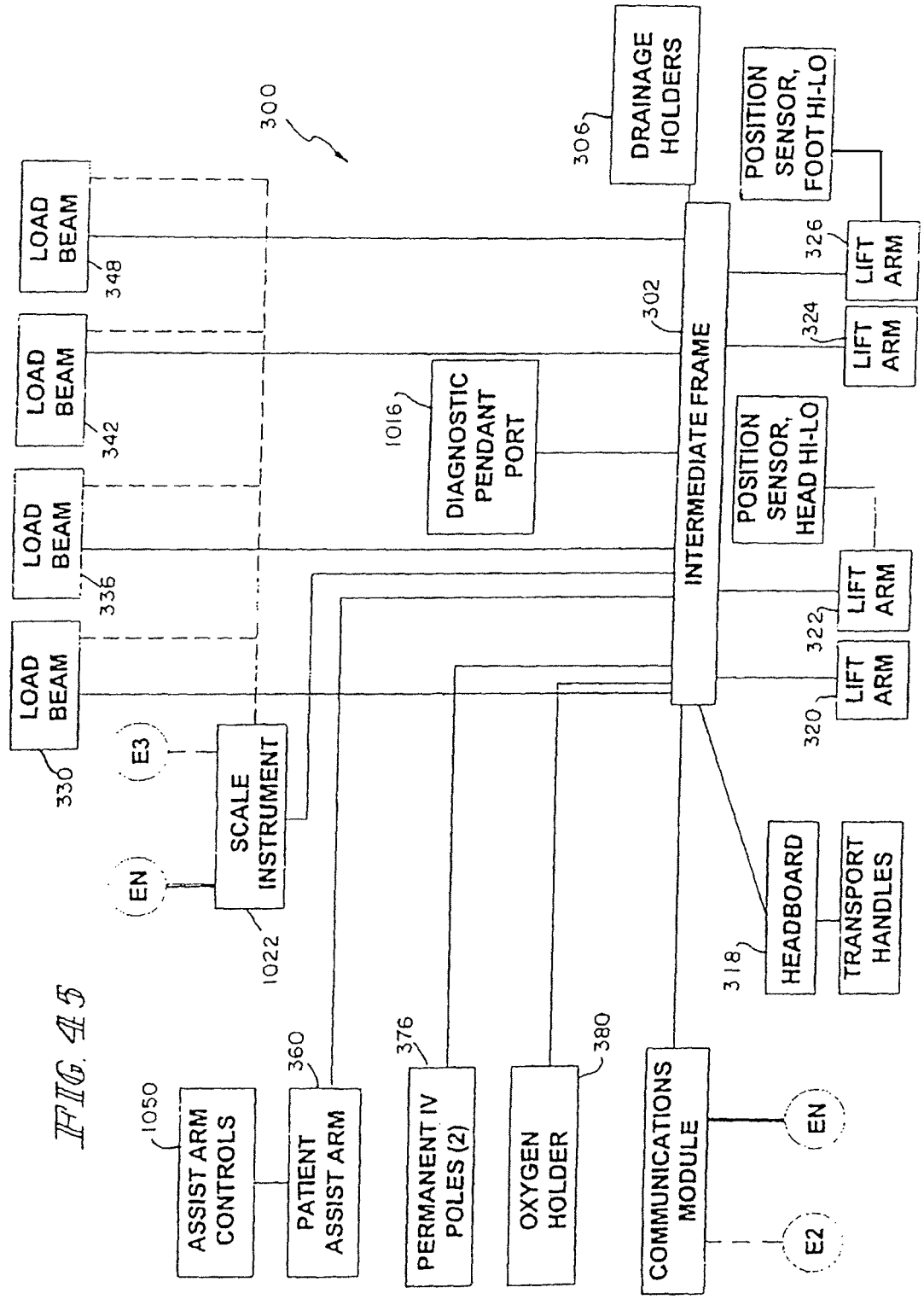
FIG. 45 is a block diagram of the intermediate frame module and portions of the hydraulic module illustratively showing some components of the intermediate frame module and illustrating some of the mechanical, fluid, and electrical interconnections therebetween.

Base Module 60 includes a base frame 62 on which the components of the chair bed 50 are mounted as shown in FIGS. 11 and 12, and diagrammatically in FIG. 44. Base module 60 includes a lifting mechanism 130 that raises and lowers sleeping surface 552 of chair bed 50 relative to base frame 62. Much of the electrical, air, and hydraulic components of chair bed 50 are located in or on base frame 62.

Head end casters 70, 72, and foot end casters 74, 76 coupled to the base frame 62. A brake/steer linkage 80 couples the casters 70, 72, 74, 76 to brake/steer pedals 78 that are connected to base frame 62. Brake/steer pedals 78 are butterfly wheel pedals that can move between a braking position locking casters 70, 72, 74, 76 so that casters 70, 72, 74, 76 do not rotate, a middle neutral position that allows casters 70, 72, 74, 76 to rotate freely, and a steering position having foot end casters 74, 76 locked into steer and head end casters 70, 72 free to swivel.

Figure 15:
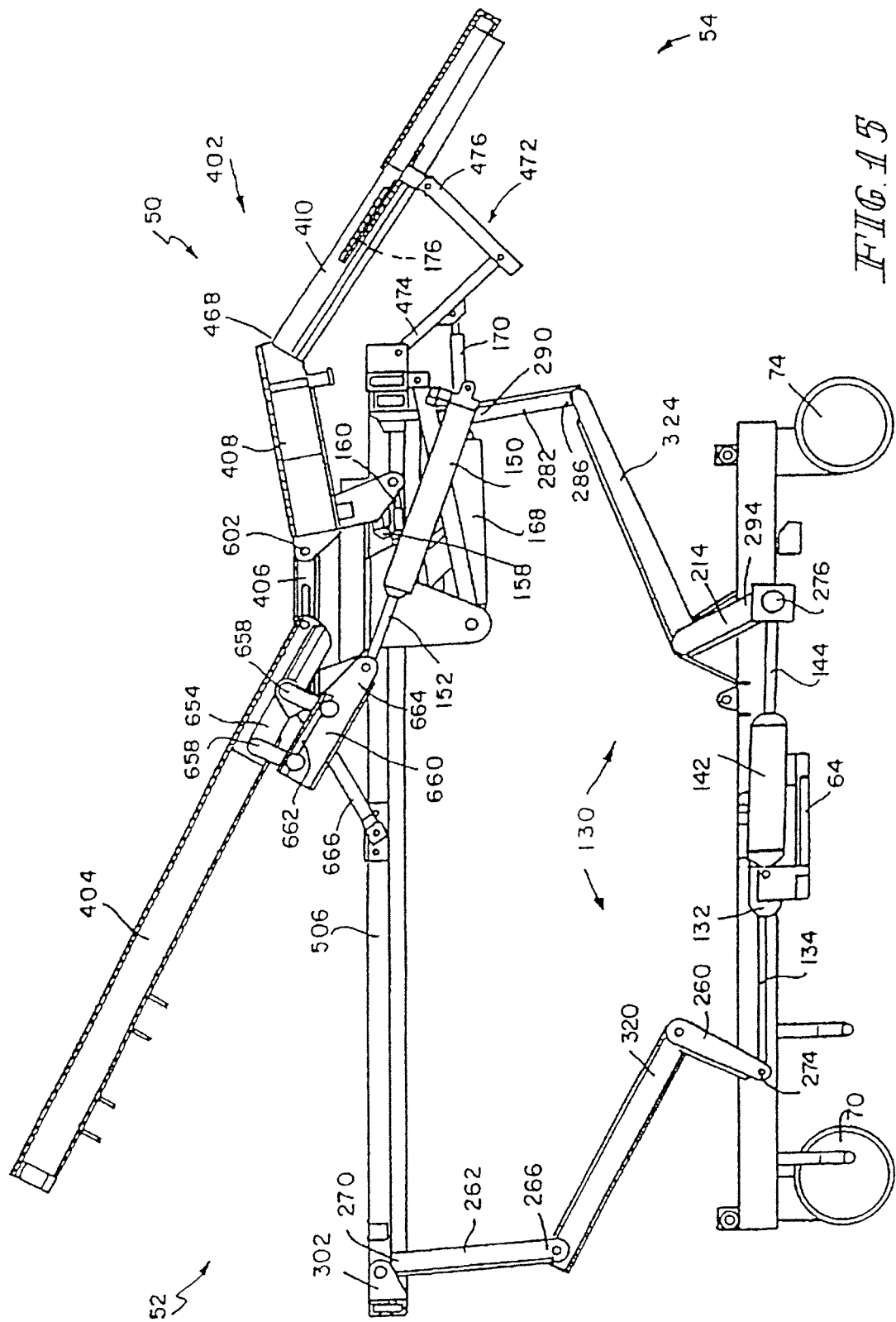
FIG. 15 is a sectional view taken along line 15-15 of FIG. 1 having the chair bed in the intermediate position similar to the position shown in FIG. 7.

Head end casters 70, 72 are positioned to lie adjacent to head end 52 of chair bed 50 and foot end casters 74, 76 are spaced-apart from foot end 54 of chair bed 50 as shown in FIGS. 11 and 15 to facilitate articulation of chair bed 50 to the sitting position. Additionally, this inward positioning of foot end casters 74, 76 closer to the center of gravity of chair bed 50 maximizes the maneuverability of chair bed 50 in the steering condition.

Figure 12A:
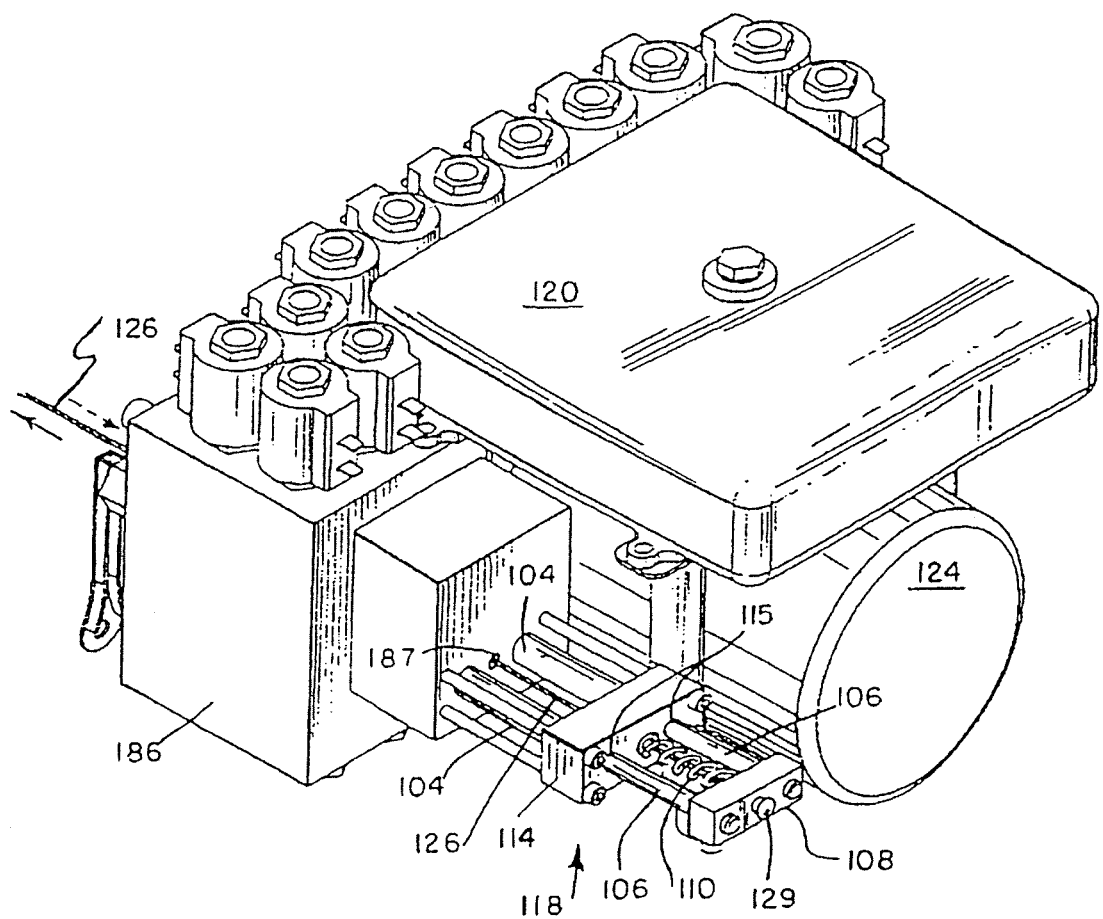
FIG. 12a is a perspective view of the power unit for supplying power to move the portions of the chair bed.
Figure 13:
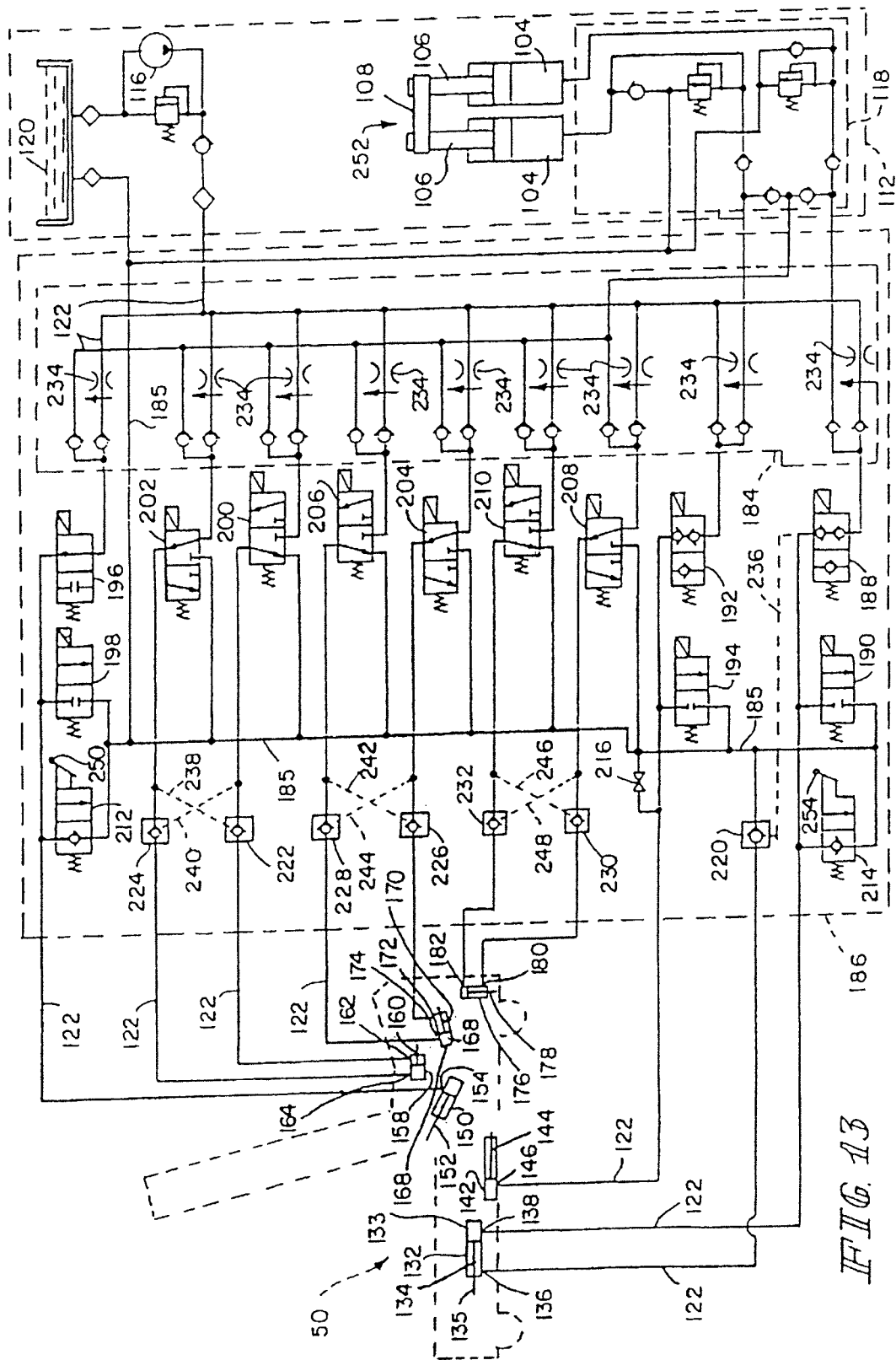
FIG. 13 is a fluid circuit diagram of a hydraulic system module of the chair bed of FIG. 1.

Struts 64 are appended to sides 66 of base frame 62 to provide mounting surfaces for portions of hydraulic system module 100 as shown in FIGS. 11-13 and 44. As shown best in FIGS. 12 and 13, illustrative hydraulic system module 100 includes lifting mechanism 130 having actuators 132 and 142 for individually raising and lowering head end 52 and foot end 54 of intermediate frame 302 relative to base frame 62, actuators 150, 158, 168, 176 for raising and lowering the head, thigh, and foot sections 404, 408, 410 of articulating deck 402 relative to intermediate frame 302, control manifold 186 for selectively controlling actuators 132, 142, 150, 158, 168, 176, power unit 112 for providing energy to drive actuators 132, 142, 150, 158, 168, 176, and conduit 122 for connecting power unit 112 and control manifold 186 to actuators 132, 142, 150, 158, 168, 176.

Power unit 112 is preferably a hydraulic power unit and actuators 132, 142, 150, 158, 168, 176 are preferably hydraulic cylinders. It will be appreciated, however, that in accordance with the present invention, various mechanical and electromechanical actuators and drivers may be used to raise and lower intermediate frame 302 on base frame 62 as well as to raise and lower individual deck sections 404, 406, 408, 410 relative to intermediate frame 302. As will be explained below, fluid actuators are preferred since they are capable of manual operation with a battery to provide power for electrical control.

It is well known in the hospital bed art that electric drive motors with various types of transmission elements including lead screw drives and various types of mechanical linkages may be used to cause relative movement of portions of hospital beds. It is also well known to use pneumatic actuators to actuate and/or move individual portions of hospital beds. The terms "means for raising or lowering" in the specification and in the claims, therefore, are intended to cover all types of mechanical, electromechanical, hydraulic, and pneumatic mechanisms, including manual cranking mechanisms of all types, for raising and lowering portions of chair bed 50 of the present invention.

The caregiver can adjust the height and angle of inclination of sleeping surface 552 as shown in FIGS. 3-6 by activating a hydraulically powered lifting mechanism 130 to control intermediate frame 302 by lift arms 320, 322, 324, 326 connected to cylinders 132, 142. A CPR foot pedal 250 and emergency Trendelenburg actuator 254 are mounted on base frame 62 to manually control manifold 186. In addition, CPR foot pedal 250 shown in FIG. 12 may be used as the emergency Trendelenburg actuator 254 when pivoted upwardly to a raised position.

If chair bed 50 is plugged into an AC outlet (not shown), the caregiver activates the lifting function with the push of a button. When not plugged in, the caregiver may raise chair bed 50 by pumping one of the hydraulic foot pump pedals 252 located on either side of the base frame 64. The caregiver may also place chair bed 50 in the Trendelenburg position when chair bed 50 is not plugged in or in an emergency by activating the emergency Trendelenburg actuator 254 located on base frame 62. If chair bed 50 is equipped with a battery 92, the caregiver may operate any functions of chair bed 50 by pumping the hydraulic foot pump pedal 252 and simultaneously pressing the desired function switch. The electrical control of the valves is supported by a battery 92 on base frame 62.

Base frame 62 also serves as a mounting location for other modules or components such as well as a bed articulation control module 1018, surface electronics, a bed-side communications interface, components of the electronic network, bed exit electronics, a night light 1073, a power supply AC/DC converter 1062, and a battery/charge circuit 88.

Hydraulic System Module 100

Hydraulic System Module 100 provides the mechanical power required to move articulating deck 402 and to raise and lower chair bed 50. Hydraulic system module 100 includes hydraulic cylinders 132, 142, 150, 158, 168, 176 that cooperate with linkages to provide these movements.

Movements of head, thigh, and foot sections 404, 408, 410 of articulating deck 402 and the raising and lowering of intermediate frame 302 of chair bed 50 illustratively shown in FIGS. 3-8 are accomplished with hydraulic system module 100. The illustrative system comprises a hydraulic power unit 112, conduit 122, a valve or control manifold 186, and cylinders 132, 142, 150, 158, 168, 176 as shown in FIG. 13. Hydraulic power unit 112 comprises an electric motor 124, a pump 116 driven by electric motor 124, a manual pump 118, and a reservoir 120 containing hydraulic oil.

Pump 116 pressurizes hydraulic oil when chair bed 50 is connected to AC power, which in turn moves piston rods 134, 144, 152, 160, 170, 178 inside of cylinders 132, 142, 150, 158, 168, 176 to articulate chair bed 50. When chair bed 50 is not connected to AC power, manual pump 118 can be used, via a foot pump pedal 250 mounted on base frame 62 and coupled to manual pump 118, to pressurize the hydraulic oil and cause piston rods 134, 144, 152, 160, 170, 178 to move. Manually activated valves 212, 214 in valve manifold 162 make it possible for the caregiver to rapidly lower head section 404 to a horizontal CPR position and to take advantage of a manual Trendelenburg feature to manually move chair bed 50 to the Trendelenburg position, illustratively shown in FIG. 5, when AC power is not available.

For chair beds 50 equipped with a battery 92, the caregiver may use any of the nurse control functions by pumping foot pump pedal 252 and simultaneously pressing the desired nurse control function on the siderail assemblies 800, 802, 804, 806. The caregiver supplies the hydraulic power via the foot pump pedal 252, and battery 92 supplies electrical power to open or close the valves on valve manifold 186 in illustrative chair bed 50.

Intermediate Frame Module 300

Intermediate Frame Module 300 includes intermediate frame 302 which is supported and positioned via lift arms 320, 322, 324, 326 of lifting mechanism 130 of base frame 62. Intermediate frame 302 in turn supports articulating deck/weigh frame module 400 and thus couples articulating deck/weigh frame module 400 to lifting mechanism 130 as shown in FIG. 11 and shown diagrammatically in FIG. 45.

Intermediate frame 302 includes four load beams 330, 336, 338, 342 that movably couple weigh frame 506 of articulating deck/weigh frame module 400 to intermediate frame 302. Each load beam 330, 336, 342, 348 includes a housing 334, 340, 346, 352 and a sensing end 332, 338, 344, 350 that is movable relative to housing 334, 340, 346, 352. The details of load beam 330 is discussed herein with reference to FIG. 14a. Each load beam 330, 336, 342, 348 additionally comprises a transducer (not shown) connected to sensing ends 332, 338, 344, 350 that provides an electrical signal in response to movement of sensing end 332, 338, 344, 350 relative to housing 334, 340, 346, 352. The extent of the movement of sensing ends 332, 338, 344, 350 depends upon the amount of weight supported by load beams 330, 336, 342, 348, so that the electrical signal provided by load beams 330, 336, 342, 348 varies in response to the weight supported by weigh frame 506.

Load beams 330, 336, 342, 348 can be replaced by dummy beams (not shown) that support weigh frame 506 on intermediate frame 302 but that do not provide for any movement of weigh frame 506 relative to intermediate frame and that do not provide any electrical signals. When chair bed 50 has dummy beams instead of load beams 330, 336, 342, 348, weigh frame 506 is fixed to intermediate frame 302 and cooperates therewith to provide a common frame (not shown). The common frame is used with chair beds 50 that do not include weigh scales 368 but that include other features of chair beds 50 described herein.

Figure 14:
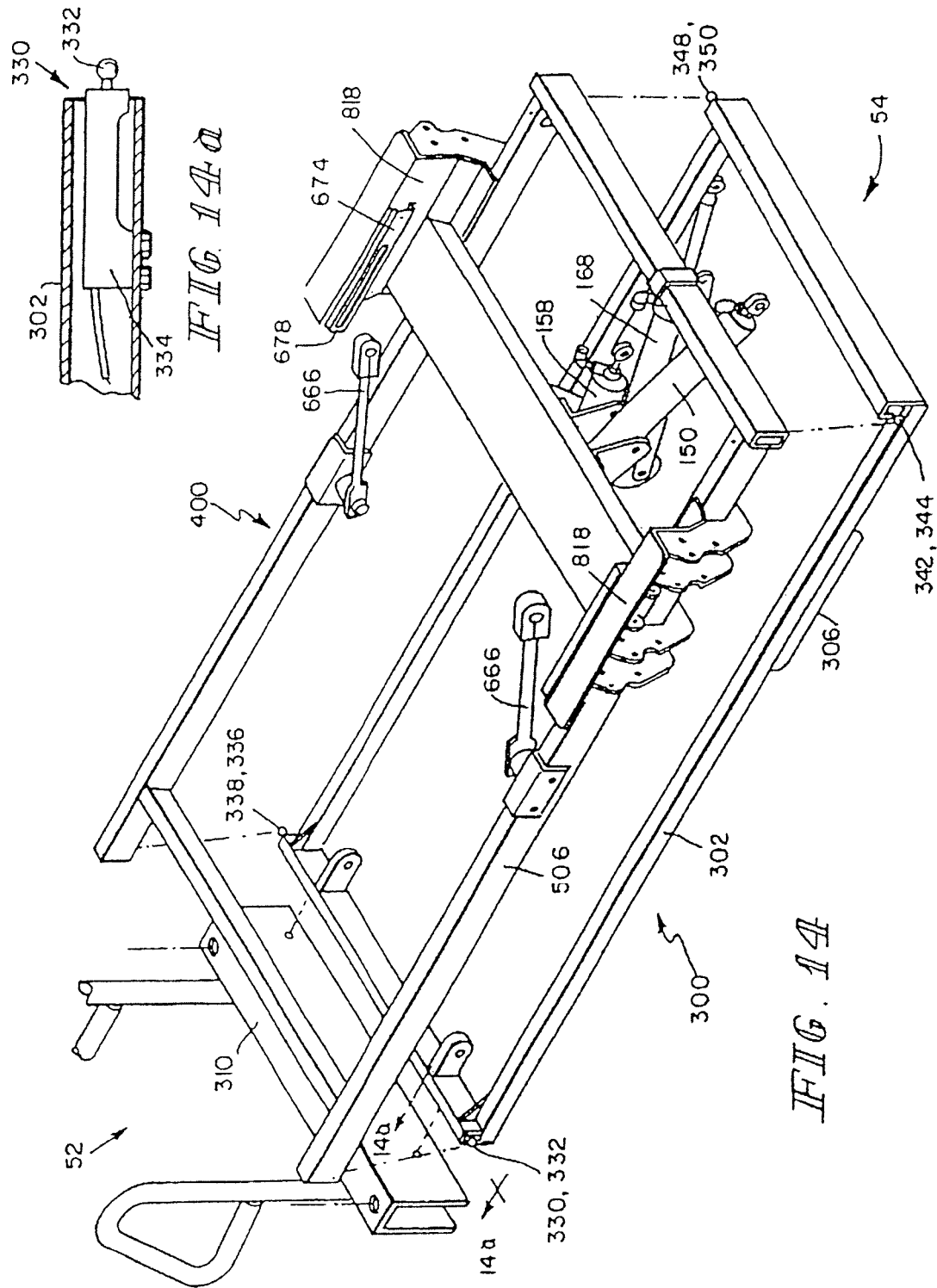
FIG. 14 is an exploded perspective view of the intermediate frame and the weigh frame of the chair bed of FIG. 1.

Intermediate frame 302, illustratively shown in FIG. 14, includes permanent IV poles 376, an oxygen tank holder 380, a mount 310 having openings 312 for caregivers to mount added-on IV poles (not shown), mounting locations 304 for bumpers, mounting locations 316 for headboard 318 adjacent to head end 52 of intermediate frame 302 as shown in FIG. 1, and a drainage bag mount 306 for holding drainage bags (not shown) adjacent to foot end 54 of intermediate frame 302 so that the weight of added-on oxygen tanks, IV poles, and drainage bags is not included in the weight measurement of the person (assuming the chair bed 50 is equipped with weigh scales 368). Intermediate frame 302 is the fixed platform on which load beams 330, 336, 342, 348, which are weight sensing components of the weigh scales 368, are mounted and weigh frame 506 is mounted to intermediate frame 302 by load beams 330, 336, 342, 348. Any equipment (not shown) mounted to the intermediate frame 302 will not be weighed.

Intermediate frame 302 moves upwardly and downwardly relative to base frame 62, so that weigh frame 506, articulating deck 402, mattress 550, and extended frame module 610 connected to weigh frame 506, which are supported thereon as shown in FIG. 11, also move upwardly and downwardly relative to base frame 62. The movable head, thigh, and foot sections 404, 408, 410 of articulating deck 402 move upwardly and downwardly relative to weigh frame 506, and seat section 406 is fixed relative to weigh frame 506.

Intermediate frame 302 provides a place off of weigh frame 506 for mounting equipment. For chair beds 50 equipped with weigh scales 368, the caregiver may wish to exclude the weights of added-on components such as IV bags (not shown) and drainage bags (not shown) from the weight of the patient. Mounting drainage bag mount 306 and IV pole mount 310 on intermediate frame 302 makes this possible.

Articulating Deck/Weigh Frame Module 400

Articulating Deck/Weigh Frame Module 400 includes mattress 550 that rests on four sections, head section 404, seat section 406, thigh section 408, and foot section 410 of articulating deck 402 as shown in FIGS. 11, 28-30, and 46. The sections 404, 406, 408, 410 of articulating deck 402 are movable to change the position of a person supported on sleeping surface 552 of mattress 550. For chair beds 50 equipped with weigh scales 368, deck 402 and a weigh frame 506, which supports deck 402 and is interposed between deck 402 and intermediate frame 302, are equivalent to a weigh platform of a platform scale, i.e., anything resting on deck 402 will be weighed when the weigh scales 368 are used. For chair beds 50 that are not equipped with weigh scales 368, deck 402 and weigh frame 506 are fixed together by dummy beams (not shown) to form a common frame (not shown).

Figure 16:
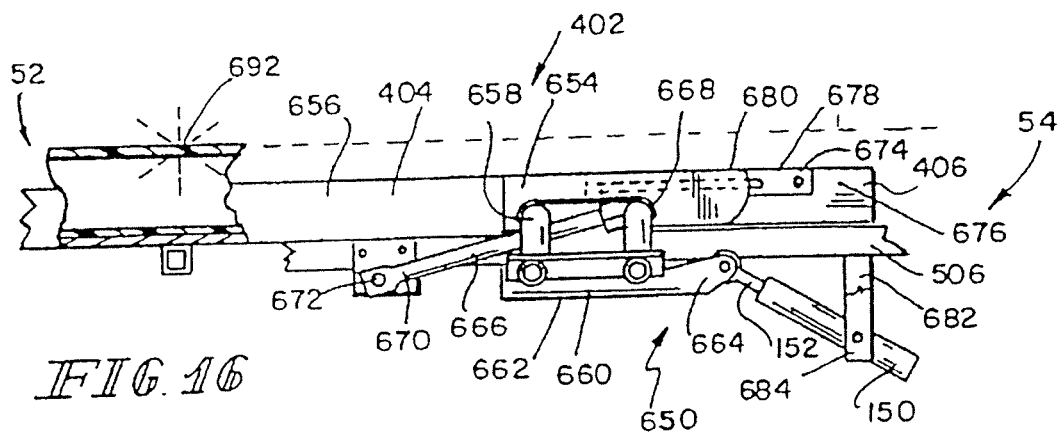
FIG. 16 is a view similar to FIG. 15 showing portions of the head section of the articulating deck and the reduced-shear pivot assembly in the down position shown in FIG. 3.
Figure 17:
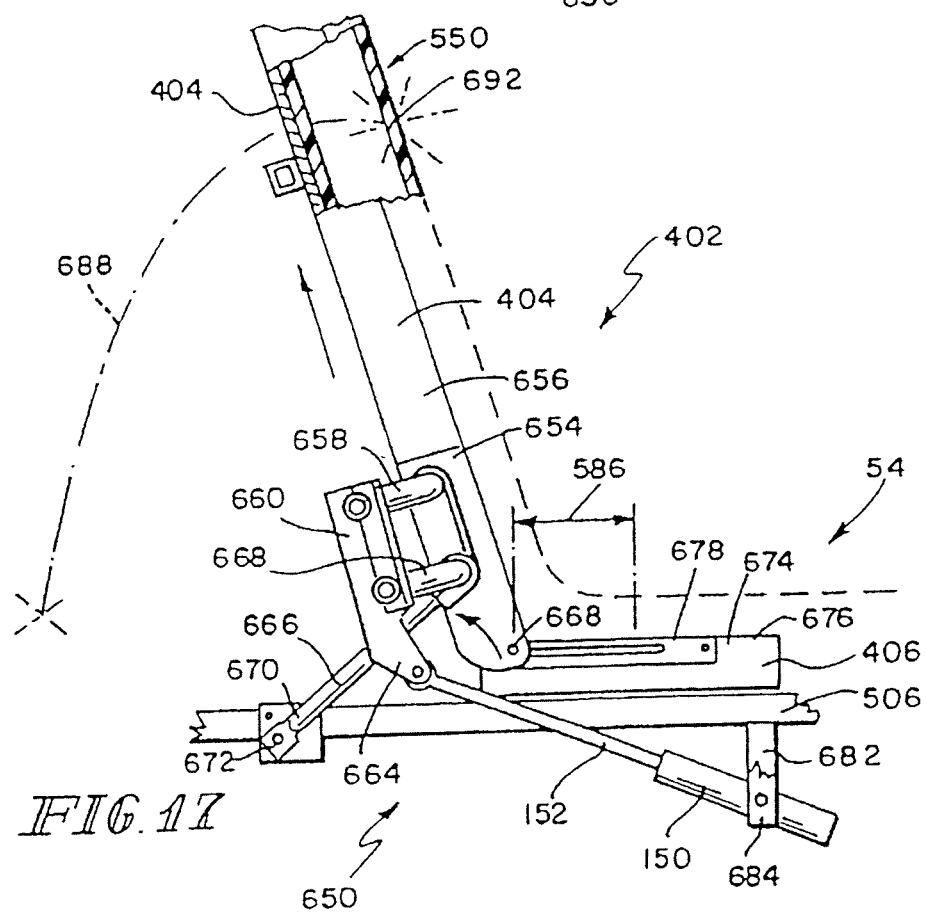
FIG. 17 is a view similar to FIG. 16 showing portions of the head section and the reduced-shear pivot assembly in the back-support position shown in FIG. 8.

Articulating deck 402 is the surface upon which the mattress 550 rests. Deck 402 is illustratively segmented into head, seat, thigh, and foot sections 404, 406, 408, 410, three of which, head section 404, thigh section 408, and foot section 410, may be rotated to change the angle of inclination of the back, thighs, and lower legs of the person (not shown) with respect to seat section 408. Head section 404 has a special "reduced-shear pivot" which is the movement produced by a reduced-shear pivot assembly 650 to be described hereinafter that causes head section 404 to pivot about an effective pivot axis 652 that is positioned to lie above lower deck section 510 and that is preferably at upper deck 414 as shown in FIGS. 16 and 17. Seat section 406 of deck 402 remains horizontal and the head, thigh, and foot sections 404, 408, 410 of deck 402 can move relative to the seat section 406 and relative to each other, thereby moving the head, thigh, and foot portions 558, 562, 564 of mattress 550 relative to seat portion 560 of mattress 550 and relative to each other.

Articulating deck 402 is mounted to weigh frame 506. Actuators or cylinders 150, 158, 168, 176, that power the movement of head, thigh, and foot sections 404, 408, 410 of deck 402, are also mounted to weigh frame 506 as shown in FIGS. 11, 14, and 15. Articulating deck/weigh frame module 400 is, in turn, supported by intermediate frame module 300. The interface between articulating deck/weigh frame module 400 and intermediate frame module 300 is illustratively limited to four attachments as shown in FIG. 14. For beds equipped with weigh scales 368, load beams 330, 336, 342, 348 are located at these points. For chair beds that are not equipped with weigh scales 368, or "non-scale chair beds," the modules are rigidly coupled.

Articulating deck/weigh frame module 400 may also carry other components of chair bed 50. For example, details 304 on the articulating deck 402, shown in FIG. 11, make it possible for caregivers to tie restraint straps (not shown) to deck 402 when required. While head section siderails 808, 810 are mounted to head section 404, body section siderails 812, 814 are mounted to weigh frame 506 by brackets 816, 818. In a preferred embodiment, head siderails 808, 810 are mounted to breakaway mounting brackets or collateral deck portions 922, 924. Other modules or components that may be attached to articulating deck/weigh frame module 400 include, for example, a removable foot prop 646 for supporting the feet of the person on sleeping surface 552 during movement between the bed position and the sitting position, a foot safety switch 648, and extended frame module 610.
Extended Frame Module 610

Figure 46:
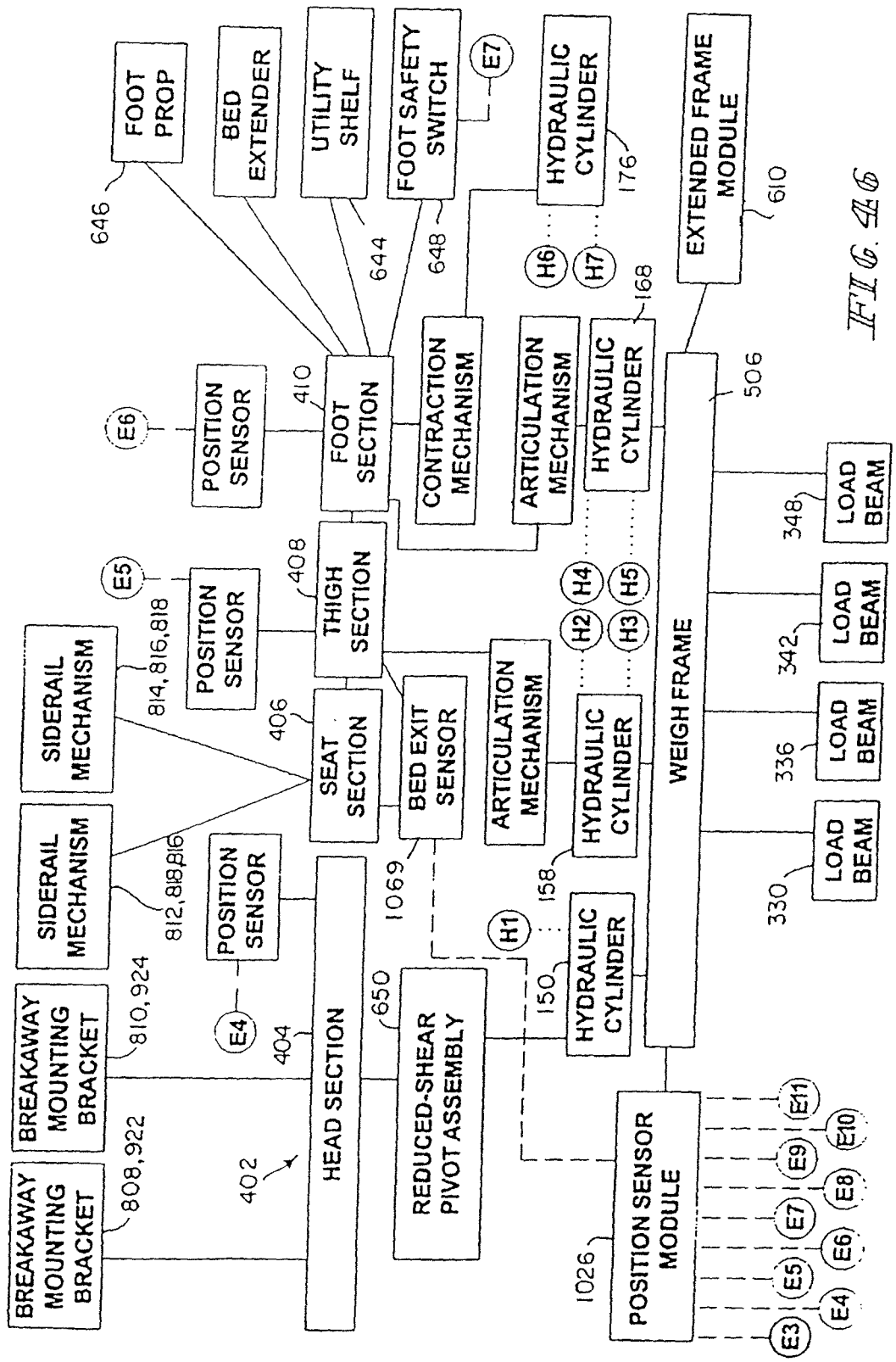
FIG. 46 is a block diagram of the articulating deck/weigh frame module and portions of the hydraulic module illustratively showing some components of the articulating deck/weigh frame module and illustrating some of the mechanical, fluid, and electrical interconnections therebetween.

Extended Frame Module 610, shown in FIG. 11 and shown diagrammatically in FIG. 46, includes an extended U-shaped frame 612 at the foot end 54 of the chair bed 50 and mounted to weigh frame 506, extended frame 612 providing a location for mounting caregiver controls, traction equipment (not shown), handles for transport (not shown), a utility shelf 644, and bumpering (not shown). The design of chair bed 50 provides for egress or ingress of the person at foot end 54 of chair bed 50, particularly when chair bed 50 is converted to the sitting position shown in Fig. and diagrammatically in FIG. 8.

Extended frame module 610 includes a foot gate 622 having swinging gates 626, 634, one swinging gate 626, 634 mounted on either side of chair bed 50 as shown in FIGS. 1, 2, and 11. Gates 626, 634 can swing outwardly away from chair bed 50 to provide the person a clear path out of chair bed 50 for easy egress from the sitting position while also providing the caregiver clear access to the patient. Foot section 410 of articulating deck 402 and foot portion 564 of mattress 550 rotate through the U-shaped extended frame 612 when foot section 410 moves between the up position and the down position.

Siderail Assemblies 800, 802, 804, 806

Figure 47:
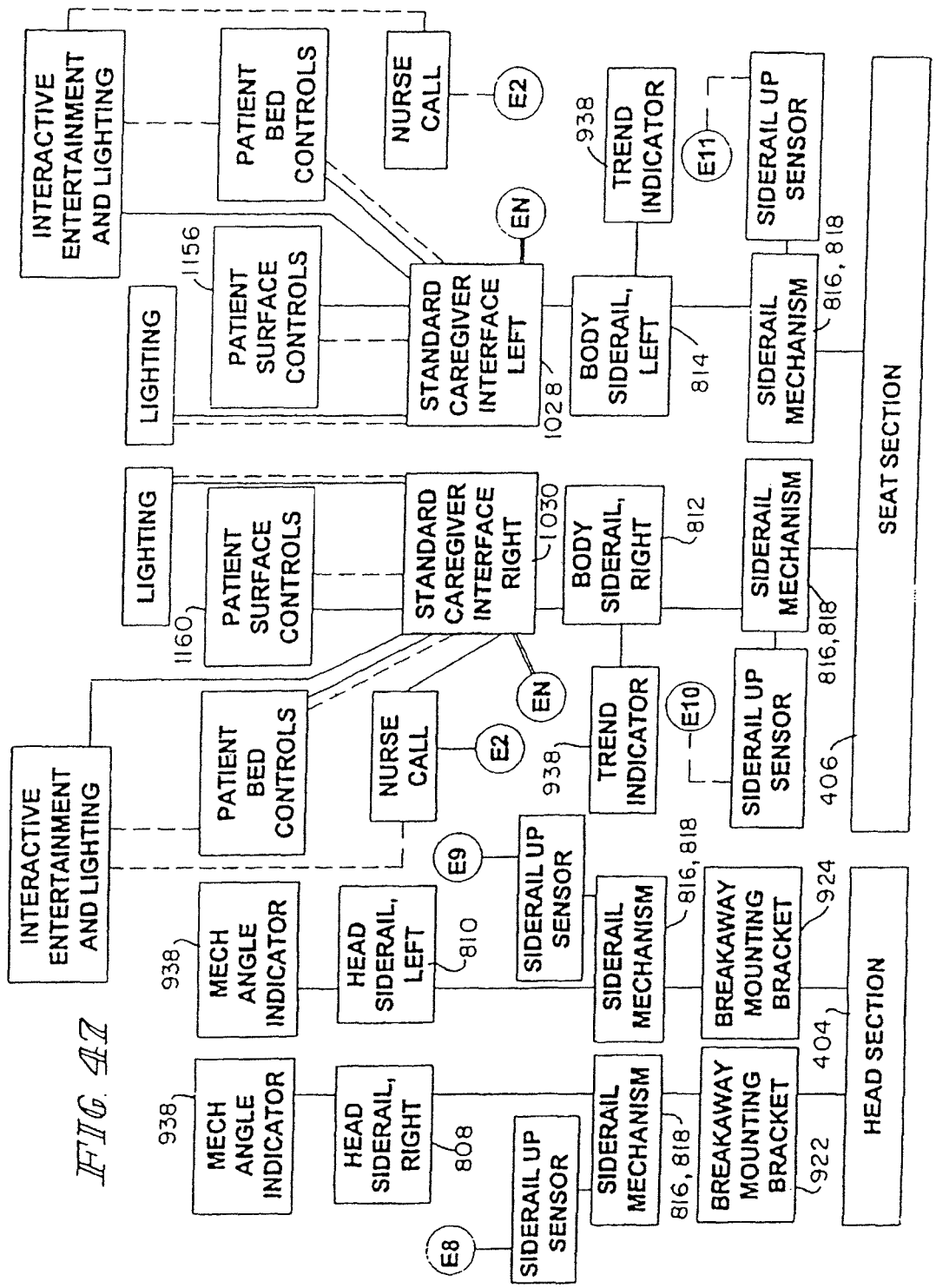
FIG. 47 is a block diagram of the siderail assemblies illustratively showing some components of the siderail assemblies and illustrating some of the mechanical, fluid, and electrical interconnections therebetween.

Siderail Assemblies 800, 802, 804, 806 include siderails 808, 810, 812, 814, which are passive restraint devices mounted on both sides of chair bed 50 as shown in FIGS. 1, 2, 11, 31-38, and diagrammatically in FIG. 47. In the upward patient-restraining position, siderails 808, 810, 812, 814 are vertical barriers extending above sleeping surface 552 to restrain movement of the person past sides 554, 556 of sleeping surface 552. Siderails 808, 810, 812, 814 may also be lowered below sleeping surface 552 of mattress 550 to permit the person to move past sides 554, 556 of sleeping surface 552 when entering and exiting chair bed 50 or to give the caregiver clear access to the patient.

Lowering each siderail 808, 810, 812, 814 is accomplished by pulling a release handle 862. After pulling release handle 862, the caregiver may let go of release handle 862 and allow siderail 808, 810, 812, 814 to rotate downwardly and tuck into the tucked position under deck 402. The rate at which each siderail 808, 810, 812, 814 rotates downwardly is preferably controlled by a mechanical damper 868. To raise siderails 808, 810, 812, 814, the caregiver pulls upwardly on siderails 808, 810, 812, 814 until they lock in the patient-restraining position.

Illustratively, there are four siderails 808, 810, 812, 814 on chair bed 50. Two head section siderails 808, 810 are mounted to head section 404 of articulating deck 402, and two body section siderails 812, 814 are mounted to move or stay with seat section 406 of deck 402, seat section 406 and siderails 812, 814 being fixed relative to weigh frame 506.

Siderails 808, 810, 812, 814 can be provided with mechanical angle indicators 938 that provide a visual indication of the angular orientation of siderails 808, 810, 812, 814 relative to the floor. Head section siderails 808, 810 move with head section 404 of deck 402 as head section 404 pivots between the down position and the back-support position, so that angle indicators 938 mounted to head section siderails 808, 810 generally indicate the angular orientation of head section 404. Likewise, body section siderails 812, 814 are generally fixed in an angular orientation relative to intermediate frame 302 so that angle indicators 938 mounted to body section siderails 812, 814 generally indicate the angular orientation of intermediate frame 302.

Body section siderails 812, 814 can also be provided with a hip pivot guide 694 shown in FIGS. 31-33 to help the caregiver to properly position the hip (not shown) of the person (not shown) on sleeping surface 552. Proper positioning of the hip operates to maximize the effectiveness of the reduced-shear pivot.

Besides serving as passive restraints, siderails 808, 810, 812, 814 also serve as a mounting location for nurse controls 1028, 1030, patient controls 1156, 1160 and entertainment modules. These modules are referred to as human interface control modules. These interface control modules output the occurrence of any switch activation into the electronic network. In addition, siderails 808, 810, 812, 814 may preferably contain the necessary hardware to allow patient-to-nurse communications (not shown) and entertainment audio output (not shown).
Detailed Description of Modules and Systems
Hydraulic System Module 100

Actuators 132, 142, 150, 158, 168, 176 are preferably hydraulic actuators. For example, head end actuator 132 is a lift cylinder as shown in FIG. 12 having an interior region 133 shown diagrammatically in FIG. 13 and a piston rod 134 slidably received by interior region 133. Head end lift cylinder 132 is formed to include a front port 136 and a rear port 138, each of which are in fluid communication with interior region 133. When pressurized fluid such as hydraulic oil is received by rear port 138, the pressurized fluid pushes piston rod 134 toward front port 136 and causes an end 135 of piston rod 134 to extend out of and move away from lift cylinder 132. At the same time, non-pressurized fluid escapes from front port 136 and is received by a return conduit 185 in fluid communication with a reservoir 120. Likewise, if pressurized fluid were to be received by front port 136, it would act on piston rod 136 to slide piston rod 136 toward rear port 138, thereby retracting end 135 into lift cylinder 132 and releasing non-pressurized fluid into return line 185 and reservoir 120. This allows actuators 132, 142, 150, 158, 168, 176 to be hydraulically locked.

Hydraulic power unit 112 is mounted on base frame 62 and includes reservoir 120, pump 116 which is driven by electric motor 124, and manual pump 118 which is driven by foot pump pedal 252 as shown in FIGS. 12, 12a, and 13. Hydraulic power unit 112 operates to pressurize a fluid such as hydraulic oil which is stored at atmospheric pressure in reservoir 120. The pressurized hydraulic oil is supplied to control manifold 186 which in turn selectively supplies the pressurized hydraulic oil to actuators 132, 142, 150, 158, 168, 176.

Pump 116 receives the hydraulic oil from reservoir 120, pressurizes the hydraulic oil, and supplies the pressurized hydraulic oil to a pressurized oil manifold 184 of control manifold 186 as shown in FIG. 13. Control valves of control manifold 186 receive the pressurized hydraulic oil and each control valve either supplies the pressurized hydraulic oil to the actuator or blocks the flow of the hydraulic oil to the actuator, depending upon the state of the control valve. The control valves are typically either three-way valves or they are two-way valves that cooperate with companion two-way valves to supply pressurized hydraulic oil to the actuators or to receive hydraulic oil from the actuators and divert the hydraulic oil from the actuators to return conduit 185 that returns non-pressurized hydraulic oil to reservoir 120. Thus, the control valves operate to control the flow of pressurized hydraulic oil between hydraulic power unit 112 and actuators 132, 142, 150, 158, 168, 176.

Lifting mechanism 130 includes head end actuator 132 to raise and lower head end 52 of intermediate frame 302 and foot end actuator 142 to raise and lower foot end 54 of intermediate frame 302 as shown in FIG. 13. A head end rear first valve 188, a head end rear second valve 190, and an emergency Trendelenburg valve 214 control the flow of fluid between rear port 138 of head end actuator 132 and hydraulic power unit 112. A head end front pilot operated check valve 220 controls the flow of fluid between front port 136 of head end actuator 132 and hydraulic power unit 112. The raising and lowering of head end 52 of intermediate frame 302 will provide the most satisfactory results when the operation of valves 188, 190, 214, 220 is coordinated as described below.

First valve 188 is a two-way valve interconnecting pressurized oil manifold 184 and conduit 122 that is in fluid communication with rear port 138 of head end lift cylinder 132 as shown in FIG. 13. In addition, a head end lift pilot line 236 is in fluid communication with rear port 138 so that when first valve 188 is activated, as shown in FIG. 13, first valve 188 blocks the flow of pressurized hydraulic oil from pressurized oil manifold 184 to both pilot line 236 and rear port 138. When first valve 188 is deactivated, fluid communication is restored between pressurized oil manifold 184 and both pilot line 236 and rear port 138 so that pressurized hydraulic oil can flow to both rear port 138 and pilot line 236.

Second valve 190 is a two-way valve coupled to return conduit 185 and coupled by conduit 122 to rear port 138 of head end lift cylinder 132. When second valve 190 is deactivated as shown in FIG. 13, second valve 190 blocks the flow of hydraulic oil between rear port 138 and return conduit 185. When second valve 190 is activated, fluid communication is restored between rear port 138 and return conduit 185 to allow hydraulic oil to flow from rear port 138 of head end lift cylinder 132 to reservoir 120. Typically when first valve 188 is deactivated to restore fluid communication between pressurized oil manifold 184 and rear port 138, second valve 190 is also deactivated to block fluid communication between rear port 138 and return conduit 185.

Emergency Trendelenburg valve 214 is a two-way valve coupled to return conduit 185 and coupled by conduit 122 to rear port 138 of head end lift cylinder 132. When emergency Trendelenburg valve 214 is deactivated as shown in FIG. 13, emergency Trendelenburg valve 214 blocks the flow of hydraulic oil from rear port 138 to return conduit 185. When emergency Trendelenburg valve 214 is activated, fluid communication between rear port 137 and return conduit 185 is restored so that hydraulic oil can flow from rear port 138 to reservoir 120 bypassing second valve 190. Unlike first and second valves 188, 190 which are typically electronically activated, emergency Trendelenburg valve 214 is activated by a manual actuator 254 such as an emergency Trendelenburg lever, shown diagrammatically in FIG. 13. Emergency Trendelenburg valve can also be activated by pulling CPR pedal 250 upwardly. Typically, when emergency Trendelenburg valve 214 is activated to restore fluid communication between rear port 138 and return conduit 185, first valve 188 is activated to block fluid communication between pressurized oil manifold 184 and rear port 138.

Pilot operated check valve 220 is a two-way valve coupled to return conduit 185 and coupled by conduit 122 to front port 136 of head end lift cylinder 132. Check valve 220 is deactivated when head end lift pilot line 236 is not in fluid communication with pressurized oil manifold 184 as shown in FIG. 13. When pilot line 236 is in fluid communication with pressurized oil manifold 184, pilot operated check valve 220 is activated. Thus, check valve 220 is activated when first valve 188 is deactivated to restore the fluid communication between pilot line 236 and pressurized oil manifold 184, and check valve 220 is deactivated when first valve 188 is activated to block the fluid communication between pilot line 236 and pressurized oil manifold 184.

When pilot operated check valve 220 is deactivated, hydraulic oil can flow through check valve 220 only in a direction from return conduit 185 to front port 136 as shown in FIG. 13. When check valve 220 is activated, hydraulic oil can flow through check valve 220 either from front port 136 to return conduit 185 or from return conduit 185 to front port 136. Thus, when first valve 188 is deactivated to restore fluid communication between pressurized oil manifold 184, pilot line 236, and rear port 138, hydraulic oil can flow from front port 136, through check valve 220, to return conduit 185 and reservoir 120.

To raise the head end 52 of intermediate frame 302, first valve 188 is deactivated to restore fluid communication between pressurized oil manifold 184, pilot line 236, and rear port 138, second valve 190 and emergency Trendelenburg valve 214 are deactivated to block fluid communication between rear port 138 and return conduit 185, and pilot operated check valve 220 is activated to allow the flow of hydraulic oil from front port 136 to return conduit 185. As pressurized hydraulic oil flows from pressurized oil manifold 184, through first valve 188, through rear port 138, and into interior region 133, piston rod 134 is pushed toward front port 136 and end 135 of piston rod 134 extends from lift cylinder 132 lifting head end 52 of intermediate frame 302 through linkages between head end 52 of intermediate frame 302 and end 135 of piston rod 134 described below. As piston rod 134 is pushed toward front port 136, hydraulic oil flows out of interior region 133 through front port 136, through check valve 220, through return conduit 185, to reservoir 120.

To lower head end 52 of intermediate frame 302, first valve 188 is activated to block the fluid communication between pressurized oil manifold 184 and both pilot line 236 and rear port 138. Blocking fluid communication between pressurized oil manifold 184 and pilot operated check valve 220 deactivates check valve 220 so that check valve 220 blocks the flow of hydraulic oil from front port 136 to return conduit 185 but allows the flow of hydraulic oil from return conduit 185 to front port 136. Either one or both of second valve 190 and emergency Trendelenburg valve 214 are activated to restore fluid communication between rear port 138 and return conduit 185. The weight of intermediate frame 302 and articulating deck/weigh frame module 400 is sufficient to push piston rod 134 toward rear port 138 to retract end 135 of piston rod 134 into head end lift cylinder 132 and to push hydraulic oil from interior region 133, through rear port 138, through either one or both of second valve 190 and emergency Trendelenburg valve 214, and to return conduit 185 and reservoir 120. The retraction of piston rod 134 into head end lift cylinder 132 lowers head end 52 of intermediate frame 302 through linkages between head end 52 of intermediate frame 302 and end 135 of piston rod 134 described below.

Lifting mechanism 130 also includes foot end actuator 142 to raise and lower foot end 54 of intermediate frame 302 as shown in FIG. 13. A foot end rear first valve 192, a foot end rear second valve 194, and a bleed-off valve 216 control the flow the fluid between rear port 146 of foot end actuator 142 and hydraulic power unit 112. Unlike head end actuator 132, foot end actuator 142 includes no front port.

First valve 192 is a two-way valve coupled to pressurized oil manifold 184 and coupled by conduit 122 to rear port 146 of foot end lift cylinder 142. When first valve 192 is activated, as shown in FIG. 13, first valve 192 blocks the flow of pressurized hydraulic oil from pressurized oil manifold 184 to rear port 146. When first valve 192 is deactivated, fluid communication is restored between pressurized oil manifold 184 and rear port 146 allowing pressurized hydraulic oil to flow thereto.

Second valve 194 is a two-way valve coupled to return conduit 185 and coupled by conduit 122 to rear port 146 of foot end lift cylinder 142. When second valve 194 is deactivated as shown in FIG. 13, second valve 194 blocks the flow of hydraulic oil from rear port 146 to return conduit 185. When second valve 194 is activated, fluid communication is restored between rear port 146 and return conduit 185 so that hydraulic oil can flow from rear port 146 of foot end lift cylinder 142 to return conduit 185 and to reservoir 120.

Bleed-off valve 216 is a two-way valve coupled to return conduit 185 and coupled by conduit 122 to rear port 146 of foot end lift cylinder 142 as shown in FIG. 13. When bleed-off valve 216 is closed the flow of hydraulic oil from rear port 146 to return conduit 185 through bleed-off valve 216 is blocked. When bleed-off valve 216 is open, fluid communication is restored between return conduit 185 and rear port 146 to allow hydraulic oil to flow from rear port 146 of foot end lift cylinder 142, through bleed-off valve 216, to return conduit 185 and to reservoir 120. Unlike first and second valves 192, 194 which are typically electronically activated, bleed-off valve 216 is activated manually such as by turning a member (not shown) of bleed-off valve 216 to move bleed-off valve 216 between the open and closed positions.

To raise the foot end 54 of intermediate frame 302, first valve 192 is deactivated to restore fluid communication between pressurized oil manifold 184 and rear port 146, and second valve 194 is deactivated and bleed-off valve 216 is closed to block fluid communication between rear port 146 and return conduit 185. As pressurized hydraulic oil flows into lift cylinder 142 from pressurized oil manifold 194, through first valve 192, and through rear port 146, piston rod 144 is pushed forward to extend therefrom and acts through linkages between foot end 54 of intermediate frame 302 and piston rod 144 described below to lift foot end 54 of intermediate frame 302.

To lower foot end 54 of intermediate frame 302, first valve 192 is activated to block the fluid communication between pressurized oil manifold 184 and rear port 146 of foot end lift cylinder 142. Either second valve 194 can be activated or bleed-off valve 216 can be opened to restore fluid communication between rear port 146 and return conduit 185. The weight of intermediate frame 302 and articulating deck/ weigh frame module 400 is sufficient to push piston rod 144 toward rear port 146 thereby retracting piston rod 144 into foot end lift cylinder 142, and to push hydraulic oil out of foot end lift cylinder 142, through rear port 146, and through either one or both of second valve 194 and bleed-off valve 216 to return conduit 185 and reservoir 120. The retraction of piston rod 144 into foot end lift cylinder 142 lowers foot end 54 of intermediate frame 302 through linkages between foot end 54 of intermediate frame 302 and piston rod 144 described below.

Head section 404 is movable between a generally horizontal down position and an upward back-support position providing a pivotable backrest. Head section pivot cylinder 150 is pivotably coupled to weigh frame 506 as shown in FIGS. 15-17 and has a piston rod 152 pivotably coupled to head section 404 as described below. A head section rear first valve 196, a head section rear second valve 198, and a CPR valve 212 shown in FIG. 13 control the flow of fluid between rear port 154 of head section pivot cylinder 150 and hydraulic power unit 112.

First valve 196 is a two-way valve coupled to pressurized oil manifold 184 and coupled by conduit 122 to rear port 154 of head section pivot cylinder 150. When first valve 196 is deactivated, as shown in FIG. 13, fluid communication is restored between pressurized oil manifold 184 and rear port 154 allowing pressurized hydraulic oil to flow thereto. When first valve 196 is activated, first valve 196 blocks fluid communication between pressurized oil manifold 184 and rear port 154.

Second valve 198 is a two-way valve coupled to return conduit 185 and coupled by conduit 122 to rear port 154 of head section pivot cylinder 150. When second valve 198 is deactivated, as shown in FIG. 13, second valve 198 blocks the flow of hydraulic oil between rear port 154 and return conduit 185. When second valve 198 is activated, fluid communication is restored between rear port 154 and return conduit 185 to allow hydraulic oil to flow from rear port 154 of head section pivot cylinder 150 to return line 185 and to reservoir 120. Typically, when first valve 196 is deactivated to restore fluid communication between pressurized oil manifold 185 and rear port 154, second valve 198 is also deactivated to block fluid communication between rear port 154 and return conduit 185.

CPR valve 212 is a two-way valve coupled to return conduit 185 and coupled by conduit 122 to rear port 154 of head section pivot cylinder 150. When CPR valve 212 is deactivated, as shown in FIG. 13, CPR valve 212 blocks the flow of hydraulic oil from rear port 154 to return conduit 185. When CPR valve 212 is activated, fluid communication between rear port 154 and return conduit 185 is restored so that hydraulic oil can flow from rear port 154 to reservoir 120. Unlike first and second valves 196, 198 which are typically electronically activated, CPR valve 212 is activated by a manual activator such as CPR foot pedal 250, shown in FIG. 12 and shown diagrammatically in FIG. 13. Typically when CPR valve 212 is activated to restore fluid communication between rear port 154 and return conduit 185, first valve 196 is activated to block fluid communication between pressurized oil manifold 184 and rear port 154. Preferably, conduit 122 coupling CPR valve 212 to return conduit 185 has a sufficiently large diameter to cause the hydraulic oil to drain rapidly from head section pivot cylinder 150 resulting in rapid movement of head section 404 from the back-support position to the down position when CPR valve 212 is activated.

To move head section 404 from the down position to the back-support position, first valve 196 is deactivated to restore fluid communication between pressurized oil manifold 184 and rear port 154 of head section pivot cylinder 150. Second valve 198 and CPR valve 212 are deactivated to block fluid communication between rear port 154 and return conduit 185. As pressurized hydraulic oil flows from pressurized oil manifold 184 through first valve 196 and then through rear port 154 into head section pivot cylinder 150, piston rod 152 is pushed outwardly to extend from head section pivot cylinder 150, thereby lifting head section 404 as the result of connections between piston rod 152 and head section 404 described below.

To lower head section 404, first valve 196 is activated to block the fluid communication between pressurized oil manifold 184 and rear port 154, and either one or both of second valve 198 and CPR valve 212 are activated to restore fluid communication between rear port 154 and return conduit 185. The weight of head section 404 is sufficient to push piston rod 152 toward rear port 154 thereby retracting piston rod 152 into head section pivot cylinder 150. As piston rod 152 retracts into head section pivot cylinder 150, hydraulic oil is pushed through rear port 154, through either one or both of second valve 198 and CPR valve 212, and to return conduit 185 and reservoir 120. The retraction of piston rod 152 into head section pivot cylinder 150 lowers head section 404 as the result of the linkages connecting piston rod 152 and head section 404 described below.

Figure 7:
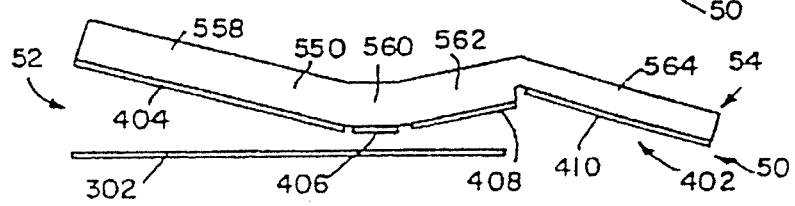
FIG. 7 is a diagrammatic view showing the chair bed in an intermediate position having a head end of a head section of the deck pivoted slightly upward from the initial position of the deck, a seat section positioned to lie in the horizontal plane defined by the seat section in the initial position of the deck, and the foot section being inclined slightly so that the foot end of the foot section lies below the position of the foot section when the deck is in the initial position of the deck.

Thigh section 408 of articulating deck 402 is movable between a generally horizontal down position and a slightly inclined up position shown diagrammatically in FIG. 7 and shown in FIGS. 2 and 15. Thigh section pivot cylinder 158 is coupled to thigh section 408 as shown in FIG. 13 to move thigh section 408 between the up position and the down position. A thigh section front valve 200 and a thigh section front pilot operated check valve 222 control the flow of fluid between a front port 162 and hydraulic power unit 112. A thigh section rear valve 202 and a thigh section rear pilot operated check valve 224 control the flow of fluid between a rear port 164 and hydraulic power unit 112. The raising and lowering of thigh section 408 of articulating deck 402 will provide the most satisfactory results when the operation of valves 200, 202, 222, 224 is coordinated as described below.

Rear valve 202 is a three-way valve coupling pressurized oil manifold 184 and return manifold 185 to rear port 164 of thigh section pivot cylinder 158. In addition, rear valve 202 couples a thigh section front pilot line 238 to pressurized oil manifold 184 so that when rear valve 202 is activated, as shown in FIG. 13, rear valve 202 restores the flow of pressurized hydraulic oil from pressurized oil manifold 184 to both rear port 164 and to pilot line 238, thus activating pilot operated check valve 222. When rear valve 202 is deactivated, fluid communication between pressurized oil manifold 184 and both rear port 164 and pilot line 238 is blocked, and fluid communication is restored between rear port 164 and return conduit 185 and reservoir 120 through check valve 224.

Front valve 200 is a three-way valve coupling front port 162 of thigh section pivot cylinder 158 to return conduit 185 when front valve 200 is in a deactivated position shown in FIG. 13, and to pressurized oil manifold 184 when front valve 200 is in an activated position. When front valve 200 is deactivated, front valve 200 blocks the fluid communication between front port 162 and pressurized oil manifold 184 while restoring the fluid communication between front port 162 and return conduit 185. When front valve 200 is activated, fluid communication is restored between front port 162 and pressurized oil manifold 184, while fluid communication between front port 162 and return conduit 185 is blocked. In addition, front valve 200 couples a thigh section rear pilot line 240 to pressurized oil manifold 184 so that when front valve 200 is activated fluid communication is restored between pressurized oil manifold 184 and pilot line 240 allowing pressurized hydraulic oil to flow to pilot operated check valve 224 to activate check valve 224.

Thigh section rear pilot operated check valve 224 is a two-way valve coupled to rear port 164 and rear valve 202. Check valve 224 is deactivated when fluid communication between thigh section rear pilot line 240 and pressurized oil manifold 184 is blocked as shown in FIG. 13. When pilot line 240 is in fluid communication with pressurized oil manifold 184, pilot operated check valve 224 is activated. Thus check valve 224 is activated when front valve 200 is activated and check valve 240 is deactivated when front valve 200 is deactivated as shown in FIG. 13.

When check valve 224 is deactivated, hydraulic oil can flow through check valve 224 only in a direction from rear valve 202 to rear port 164 as shown in FIG. 13. When check valve 224 is activated, hydraulic oil can flow through check valve 224 either from rear port 162 to rear valve 202 or from rear valve 202 to rear port 162. Thus, when front valve 200 is activated to restore fluid communication between pressurized oil manifold 184, pilot line 240, and front port 162 so that pressurized hydraulic oil flows from manifold 184 to front port 162, hydraulic oil can also flow from rear port 164, through check valve 224, to rear valve 202. If rear valve 202 is deactivated at the same time that front valve 202 is activated, then the hydraulic oil from rear port 264 can flow through rear valve 202 to return conduit 185 and reservoir 120.

Likewise, thigh section front pilot operated check valve 222 is a two-way valve coupled to front port 162 and to front valve 200. Check valve 222 is activated when rear valve 202 is activated so that thigh section front pilot line 238 is in fluid communication with pressurized oil manifold 184 as shown in FIG. 13. When rear valve 202 is deactivated, pilot line 238 is not in fluid communication with pressurized oil manifold 184 and pilot operated check valve 222 is deactivated. Thus, check valve 222 is activated when rear valve 202 is activated and check valve 222 is deactivated when front valve 202 is deactivated.

When pilot operated check valve 222 is deactivated, hydraulic oil can flow through check valve 222 only in a direction from front valve 200 to front port 162. When check valve 222 is activated, hydraulic oil can flow through check valve either from front port 162 to front valve 200 or from front valve 200 to front port 162. Thus, when rear valve 200 is activated to restore fluid communication between pressurized oil manifold 184, pilot line 238, and rear port 164 so that pressurized hydraulic oil flows from manifold 184 to rear port 164, hydraulic oil can also flow from front port 162, through check valve 222, to front valve 200. If front valve 200 is deactivated when rear valve 202 is activated, then hydraulic oil from front port 162 can pass through front valve 200 to return conduit 185 and reservoir 120.

To raise thigh section 408 of articulating deck 402, rear valve 202 is activated to restore fluid communication between pressurized oil manifold 184, pilot line 238, and rear port 164. Front valve 200 is deactivated to block fluid communication between pressurized oil manifold 184 and front port 162 and to restore fluid communication between front port 162 and return conduit 185. As pressurized hydraulic oil flows from pressurized oil manifold 184, through rear valve 282, through rear port 164, and into thigh section pivot cylinder 158, piston rod 160 is pushed toward front port 162 and extends from thigh section pivot cylinder 158 to lift thigh section 408 through linkages between thigh section 408 and piston rod 160 described below. As piston rod 160 is pushed toward front port 162, hydraulic oil flows through front port 162, through activated check valve 222, through front valve 200, and to return conduit 185 and reservoir 120.

To lower thigh section 408 of articulating deck 402, front valve 200 is activated to restore the fluid communication between pressurized oil manifold 184, pilot line 240, and front port 162 of thigh section pivot cylinder 158. Rear valve 202 is deactivated to block the fluid communication between pressurized oil manifold 184, pilot line 238, and rear port 164, and to restore fluid communication between rear port 164 and return conduit 185. As pressurized hydraulic oil flows from pressurized oil manifold 184, through front valve 200, through front port 162, and into thigh section pivot cylinder 158, piston rod 160 is pushed toward rear port 164 and is retracted into thigh section pivot cylinder 158, lowering thigh section 408 through linkages between piston rod 160 and thigh section 408 that are described below. As piston rod 160 is pushed toward rear port 164, hydraulic oil flows through rear port 164, through activated check valve 224, through rear valve 202, and to return conduit 185.

Foot section 410 of articulating deck 402 is movable between the generally horizontal up position shown in FIGS. 1, 11, and 24 and the generally vertically downwardly extending down position shown diagrammatically in FIG. 8 and shown in FIGS. 2 and 25. Foot section pivot cylinder 168 is coupled to foot section 410 as shown in FIG. 13 to move foot section 410 between the up position and the down position. A foot pivot front valve 204 and a foot pivot front pilot operated check valve 226 control the flow of fluid between a front port 172 and hydraulic power unit 112. A foot pivot rear valve 206 and a foot pivot rear pilot operated check valve 228 control the flow of fluid between a rear port 174 and hydraulic power unit 112. The raising and lowering of foot section 410 of articulating deck 402 provides the most satisfactory results when the operation of valves 204, 206, 226, 228 is coordinated as described below.

Rear valve 206 is a three-way valve coupling pressurized oil manifold 184 and return manifold 185 to rear port 174 of foot section pivot cylinder 168. In addition, rear valve 206 couples a foot pivot front pilot line 242 to pressurized oil manifold 184 so that when rear valve 206 is activated, as shown in FIG. 13, rear valve 206 restores the flow of pressurized hydraulic oil from pressurized oil manifold 184 to both rear port 174 and to pilot line 242, thus activating pilot operated check valve 226. When rear valve 206 is deactivated, fluid communication between pressurized oil manifold 184 and both rear port 174 and pilot line 242 is blocked, and fluid communication is restored between rear port 174 and return conduit 185 and reservoir 120 through check valve 228.

Front valve 204 is a three-way valve coupling front port 172 of foot section pivot cylinder 168 to return conduit 185 when front valve is in a deactivated position, and to pressurized oil manifold 184 when front valve 204 is in an activated position shown in FIG. 13. When front valve 204 is deactivated, front valve 204 blocks the fluid communication between front port 172 and pressurized oil manifold 184 while restoring the fluid communication between front port 172 and return conduit 185. When front valve 204 is activated, fluid communication is restored between front port 172 and pressurized oil manifold 184, while fluid communication between front port 172 and return conduit 185 is blocked. In addition, front valve 204 couples a foot pivot rear pilot line 244 to pressurized oil manifold 184 so that when front valve 204 is activated fluid communication is restored between pressurized oil manifold 184 and pilot line 244 allowing pressurized hydraulic oil to flow to pilot operated check valve 228 to activate check valve 228.

Foot pivot rear pilot operated check valve 228 is a two-way valve coupled to rear port 174 and rear valve 206. Check valve 228 is deactivated when fluid communication between foot pivot rear pilot line 244 and pressurized oil manifold 184 is blocked. When pilot line 244 is in fluid communication with pressurized oil manifold 184, pilot operated check valve 228 is activated as shown in FIG. 13. Thus check valve 228 is activated when front valve 204 is activated and check valve 228 is deactivated when front valve 204 is deactivated.

When check valve 228 is deactivated, hydraulic oil can flow through check valve 228 only in a direction from rear valve 206 to rear port 174 as shown in FIG. 13. When check valve 228 is activated, hydraulic oil can flow through check valve 228 either from rear port 174 to rear valve 206 or from rear valve 206 to rear port 174. Thus, when front valve 204 is activated to restore fluid communication between pressurized oil manifold 184, pilot line 244, and front port 172 so that pressurized hydraulic oil flows from manifold 184 to front port 172, hydraulic oil can also flow from rear port 174, through check valve 228, to rear valve 206. If rear valve 206 is deactivated at the same time that front valve 204 is activated, then the hydraulic oil from rear port 264 can flow through rear valve 206 to return conduit 185 and reservoir 120.

Likewise, foot pivot front pilot operated check valve 226 is a two-way valve coupled to front port 172 and to front valve 204. Check valve 226 is activated when rear valve 206 is activated and foot pivot front pilot line 242 is in fluid communication with pressurized oil manifold 184. When rear valve 206 is deactivated, pilot line 242 is not in fluid communication with pressurized oil manifold 184 and pilot operated check valve 226 is deactivated as shown in FIG. 13. Thus, check valve 226 is activated when rear valve 206 is activated and check valve 226 is deactivated when rear valve 206 is deactivated.

When pilot operated check valve 226 is deactivated, hydraulic oil can flow through check valve 226 only in a direction from front valve 204 to front port 172. When check valve 226 is activated, hydraulic oil can flow through check valve either from front port 172 to front valve 204 or from front valve 204 to front port 172. Thus, when rear valve 206 is activated to restore fluid communication between pressurized oil manifold 184, pilot line 242, and rear port 174 so that pressurized hydraulic oil flows from manifold 184 to rear port 174, hydraulic oil can also flow from front port 172, through check valve 226, to front valve 204. If front valve 204 is deactivated when rear valve 206 is activated, then hydraulic oil from front port 172 can pass through front valve 204 to return conduit 185 and reservoir 120.

To raise foot section 410 of articulating deck 402, rear valve 206 is activated to restore fluid communication between pressurized oil manifold 184, pilot line 242, and rear port 174. Front valve 204 is deactivated to block fluid communication between pressurized oil manifold 184 and front port 172, and to restore fluid communication between front port 172 and return conduit 185. As pressurized hydraulic oil flows from pressurized oil manifold 184, through rear valve 282, through rear port 174, and into foot section pivot cylinder 158, piston rod 160 is pushed toward front port 172 and extends from foot section pivot cylinder 158 to lift foot section 410 through linkages between foot section 410 and piston rod 160 described below. As piston rod 160 is pushed toward front port 172, hydraulic oil flows through front port 172, through activated check valve 226, through front valve 204, and to return conduit 185 and reservoir 120.

To lower foot section 410 of articulating deck 402, front valve 204 is activated to restore the fluid communication between pressurized oil manifold 184, pilot line 244, and front port 172 of foot section pivot cylinder 168 as shown in FIG. 13. Rear valve 206 is deactivated to block the fluid communication between pressurized oil manifold 184, pilot line 242, and rear port 174, and to restore fluid communication between rear port 174 and return conduit 185. As pressurized hydraulic oil flows from pressurized oil manifold 184, through front valve 204, through front port 172, and into foot section pivot cylinder 168, piston rod 160 is pushed toward rear port 174 and is retracted into foot section pivot cylinder 168, lowering foot section 410 through linkages between piston rod 160 and foot section 410 that are described below. As piston rod 160 is pushed toward rear port 174, hydraulic oil flows through rear port 174, through activated check valve 228, through rear valve 206, and to return conduit 185.

In addition to pivoting between the up and down positions, foot section 410 of articulating deck 402 is also movable between the expanded position, shown best in FIGS. 11 and 24, and the contracted position, shown best in FIG. 25. Foot section contracting cylinder 176 is coupled to foot section 410 to move foot section 410 between the expanded position and the contracted position. A foot contracting front valve 208 and a foot contracting front pilot operated check valve 230 control the flow of fluid between a front port 180 and hydraulic power unit 112 as shown in FIG. 13. A foot contracting rear valve 210 and a foot contracting rear pilot operated check valve 232 control the flow of fluid between a rear port 182 and hydraulic power unit 112. The raising and lowering of foot section 410 of articulating deck 402 will provide the most satisfactory results when the operation of valve 208, 210, 230, 232 is coordinated as described below.

Rear valve 210 is a three-way valve coupling pressurized oil manifold 184 and return manifold 185 to rear port 182 of foot section contracting cylinder 176. In addition, rear valve 210 couples a foot contracting front pilot line 246 to pressurized oil manifold 184 so that when rear valve 210 is activated the flow of pressurized hydraulic oil from pressurized oil manifold 184 is restored to both rear port 182 and to pilot line 246, thus activating pilot operated check valve 230. When rear valve 210 is deactivated, as shown in FIG. 13, fluid communication between pressurized oil manifold 184 and both rear port 182 and pilot line 246 is blocked, and fluid communication is restored between rear port 182 and return conduit 185 and reservoir 120 through check valve 232.

Front valve 208 is a three-way valve coupling front port 180 of foot section contracting cylinder 176 to return conduit 185 when front valve 208 is in a deactivated position and to pressurized oil manifold 184 when front valve 208 is in an activated position shown in FIG. 13. When front valve 208 is deactivated, front valve 208 blocks the fluid communication between front port 180 and pressurized oil manifold 184 while restoring the fluid communication between front port 180 and return conduit 185. When front valve 208 is activated, fluid communication is restored between front port 180 and pressurized oil manifold 184, while fluid communication between front port 180 and return conduit 185 is blocked. In addition, front valve 208 couples a foot contracting rear pilot line 248 to pressurized oil manifold 184 so that when front valve 208 is activated fluid communication is restored between pressurized oil manifold 184 and pilot line 248 allowing pressurized hydraulic oil to flow to pilot operated check valve 232 to activate check valve 232.

Foot contracting rear pilot operated check valve 232 is a two-way valve coupled to rear port 182 and rear valve 210. Check valve 232 is deactivated when fluid communication between foot contracting rear pilot line 248 and between pressurized oil manifold 184 is blocked. When pilot line 248 is in fluid communication with pressurized oil manifold 184 as shown in FIG. 13, pilot operated check valve 232 is activated. Thus check valve 232 is activated when front valve 208 is activated and check valve 232 is deactivated when front valve 208 is deactivated.

When check valve 232 is deactivated, hydraulic oil can flow through check valve 232 only in a direction from rear valve 210 to rear port 182 as shown in FIG. 13. When check valve 232 is activated, hydraulic oil can flow through check valve 232 either from rear port 182 to rear valve 210 or from rear valve 210 to rear port 182. Thus, when front valve 208 is activated to restore fluid communication between pressurized oil manifold 184, pilot line 248, and front port 180 so that pressurized hydraulic oil flows from manifold 184 to front port 180 so that pressurized hydraulic oil flows from manifold 184 to front port 180, hydraulic oil can also flow from rear port 182, through check valve 232, to rear valve 210. If rear valve 210 is deactivated at the same time that front valve 208 is activated, then the hydraulic oil from rear port 264 can flow through rear valve 210 to return conduit 185 and reservoir 120.

Likewise, foot contracting front pilot operated check valve 230 is a two-way valve coupled to front port 180 and to front valve 208. Check valve 230 is activated when rear valve 210 is activated so that foot contracting front pilot line 246 is in fluid communication with pressurized oil manifold 184. When rear valve 210 is deactivated as shown in FIG. 13, pilot line 246 is not in fluid communication with pressurized oil manifold 184 and pilot operated check valve 230 is deactivated. Thus, check valve 230 is activated when rear valve 210 is activated and check valve 230 is deactivated when front valve 208 is deactivated.

When pilot operated check valve 230 is deactivated, hydraulic oil can flow through check valve 230 only in a direction from front valve 208 to front port 180. When check valve 230 is activated, hydraulic oil can flow through check valve either from front port 180 to front valve 208 or from front valve 208 to front port 180. Thus, when rear valve 210 is activated to restore fluid communication between pressurized oil manifold 184, pilot line 246, and rear port 182 so that pressurized hydraulic oil flows from manifold 184 to rear port 182, hydraulic oil can also flow from front port 180, through check valve 230, to front valve 208. If front valve 208 is deactivated when rear valve 210 is activated, then hydraulic oil from front port 180 can pass through front valve 208 to return conduit 185 and reservoir 120.

To expand foot section 410 of articulating deck 402, rear valve 210 is activated to restore fluid communication between pressurized oil manifold 184, pilot line 246, and rear port 182. Front valve 208 is deactivated to block fluid communication between pressurized oil manifold 184 and front port 180, and to restore fluid communication between front port 180 and return conduit 185. As pressurized hydraulic oil flows from pressurized oil manifold 184, through rear valve 282, through rear port 182, and into foot section contracting cylinder 176, piston rod 160 is pushed toward front port 180 and extends from foot section contracting cylinder 176 to expand foot section 410 through linkages between foot section 410 and piston rod 160 described below. As piston rod 160 is pushed toward front port 180, hydraulic oil flows through front port 180, through activated check valve 230, through front valve 208, and to return conduit 185 and reservoir 120.

To contract foot section 410 of articulating deck 402, front valve 208 is activated to restore the fluid communication between pressurized oil manifold 184, pilot line 248, and front port 180 of foot section contracting cylinder 176. Rear valve 210 is deactivated to block the fluid communication between pressurized oil manifold 184, pilot line 246, and rear port 182, and to restore fluid communication between rear port 182 and return conduit 185. As pressurized hydraulic oil flows from pressurized oil manifold 184, through front valve 208, through front port 180, and into foot section contracting cylinder 176, piston rod 160 is pushed toward rear port 182 and is retracted into foot section contracting cylinder 176, contracting foot section 410 through linkages between piston rod 160 and foot section 410 that are described below. As piston rod 160 is pushed toward rear port 182, hydraulic oil flows through rear port 182, through activated check valve 232, through rear valve 210, and to return conduit 185.

Illustratively, the control valves can be configured to selectively operate actuators 132, 142, 150, 158, 168, 176 to move chair bed 50 to various positions including the sitting position shown diagrammatically in FIG. 13. To move chair bed 50 to the sitting position, the valves are configured so that piston rod 134 is retracted into head end lift cylinder 132, piston rod 144 is retracted into foot end lift cylinder 142, piston rod 152 is extended from head section pivot cylinder 150, piston rod 160 is extended from thigh section pivot cylinder 158, piston rod 170 is retracted into foot section pivot cylinder 168, and piston rod 178 is retracted into foot section contracting cylinder 176. As described above with respect to each individual actuator 132, 142, 150, 158, 168, 176 and as shown diagrammatically in FIG. 13, to attain the sitting position requires that head end rear first valve 188 is activated, foot end rear first valve 192 is activated, foot retractor front valve 208 is activated, foot section front valve 204 is activated, thigh section rear valve 202 is activated, and head section rear first valve 196 is activated. In addition, all other valves are maintained in the deactivated position. As can be seen, then, the positions of the head, thigh, foot sections 404, 408, 410 of articulating deck 402, and the position of intermediate frame 302 relative to base frame 62 can be manipulated by manipulating the control valves of control manifold 186.

Of note, in preferred embodiments, only two valves—head end rear first valve 188 and foot end rear first valve 192—are normally open, the other valves being normally closed as shown in FIG. 13, so that when all of the control valves are deactivated, pressurized hydraulic oil flows only through valve 188 and valve 192. When pressurized hydraulic oil flows through valve 188, piston rod 134 extends from head end lift cylinder 132 to lift head end 52 of intermediate frame 302. When pressurized hydraulic oil flows through valve 192, piston rod 144 extends from head end lift cylinder 142 to lift foot end 54 of intermediate frame 302. Therefore, if hydraulic oil is pressurized when all control valves are deactivated, intermediate frame 302 will move to the raised position.

In case of an emergency when intermediate frame 302 is in the low position, caregiver can simply pump foot pump pedal 252 to raise intermediate frame 302 even when chair bed 50 is away from an AC power source. If intermediate frame 302 is not level when caregiver starts pumping foot pump pedal 252, hydraulic system 100 will continue to raise intermediate frame as long as caregiver pumps foot pump pedal 252 until both head end 52 and foot end 54 of intermediate frame 302 are in the raised positions.

In addition, conduit 122 connecting pump 116 to each of the control valves includes a variable restrictive orifice 234 as shown in FIG. 13. Each restrictive orifice 234 widens and narrows to maintain the pressure drop across restrictive orifice 234 at a preselected value. This "pressure compensation" operates to cause uniform articulation of intermediate frame 302 and head, thigh, and foot sections 404, 408, 410 of deck 402 irrespective of the distribution of the weight load on deck 402. For example, pressure compensation will cause head end 52 and foot end 54 of intermediate frame 302 to raise or lower at the same rate even if the center of gravity of the person (not shown) on sleeping surface 552 is positioned to lie near one of the ends 52, 54 of intermediate frame 302.

Further, it can be seen that by bringing, for example, rear port 154 of head section pivot cylinder 150 into fluid communication with pressurized oil manifold 184, that head section 404 can be secured in the back-support position. In addition, by opening, for example, CPR valve 212, head section 404 can be released and can move downwardly toward the bed position. Additionally, by closing CPR valve 212 after head section 404 has moved away from the back-support position but before head section 404 has moved to the down position, head section 404 can be secured in an intermediate position between the back-support position and the down position. The ability to secure head section 404 in an intermediate position is a characteristic of actuator 150 that likewise holds true for actuators 132, 142, 158, 168, 176 so that when the actuators cooperate with lifting mechanism 130 and with the linkages connecting the actuators to the head, thigh, and foot sections 404, 408, 410 of articulating deck 402, chair bed 50 can be secured in many positions between the bed position and the sitting position providing a full range of positions of chair bed 50 to meet the needs of many different people.

Remote Operation of the Chair Bed (Away from an Electrical Power Source)

Foot pump pedal 252 shown in FIG. 12 can be pumped by the caregiver to operate manual pump 118, shown best in FIG. 12a, to pressurize the hydraulic oil. Foot pump pedal 252 can be used, for example, when electrical power is not available to electric motor 124 and pump 116 is, therefore, not operating to pressurize the hydraulic oil. Foot pump pedal 252 is pivotably coupled to base frame 62 for movement between an up position and a down position relative to base frame 62. A lever 253 is coupled to foot pump pedal 252 so that when foot pump pedal 252 is in the down position, lever 253 is pulled to a forward position toward foot end 54 of chair bed 50, and when foot pump pedal 252 is in the up position, lever 253 is pushed to a back position toward head end 52 of chair bed 50.

Manual pump 118 is mounted to control manifold 186 of hydraulic power unit 112 as shown in FIG. 12a. Manual pump 118 includes two cylinders 104, each cylinder 104 carrying a piston rod 106. Rods 106 are configured to pressurize hydraulic oil when rods 106 are pushed to a retracted position toward foot end 54 of chair bed 50, forcing pressurized hydraulic oil out of cylinders 104 and into pressurized oil manifold 184. As rods 106 move from the retracted position to an extended position toward head end 52 of chair bed 50, unpressurized hydraulic oil from reservoir 120 moves into cylinders 104.

Manual pump 118 also includes a bar 108 connecting head end 52 of rods 106 together as shown in FIG. 12a and a block 114 coupled to control manifold 186. Block 114 is formed to include guide openings 115 that are positioned to lie so that rods 106 are received by guide openings 115 and travel therethrough as rods 106 reciprocate between the retracted and extended positions. A cable 126 has a first end 127 connected to lever 253 as shown in FIG. 12 and a second end 129 connected through a third guide opening 115 formed in block 114 to bar 108 as shown in FIG. 13a.

Control manifold 186 is formed to include an opening 187 that extends through control manifold 186 so that cable 126 can be configured to lie in a generally straight line without having cable 126 between first and second ends 127, 129 engaging any portion of chair bed 50. Cable 126 runs from bar 108, through third guide opening 115 formed in block 114, through opening 187 formed in control manifold 186, and to lever 253 of foot pump pedal 252. Forming opening 187 through control manifold 186 additionally allows for compact placement of hydraulic power unit 112 and other components on base frame 62 of chair bed 50. A cylindrical return spring 110 is received by cable and is positioned to act against bar 108 and block 114 to yieldably bias bar 108 toward head end 52 of chair bed 50.

When foot pump pedal 252 is moved downwardly pulling lever 253 toward foot end of chair bed 50, lever 253 pulls cable 126 toward foot end 54 of chair bed and cable 126 pulls bar 108 and rods 106 toward foot end 54 of chair bed 50 so that rods 106 retract into cylinders 104 and pressurize hydraulic oil, forcing the hydraulic oil into pressurized oil manifold 184. When foot pump pedal 252 is released, return spring 110 pushes bar 108 toward head end 52 of chair bed 50, pulling rods 106 to their extended positions and drawing hydraulic oil from reservoir 120 into cylinders 104. At the same time, bar 108 pulls cable 126 through openings 115, 187, pulling lever 253 toward head end 52 of chair bed 50 and moving foot pump pedal 252 upwardly to the up position. Repeated pumping of foot pump pedal 252 causes manual pump 118 to pressurize the hydraulic oil so that the hydraulic oil can operate the head and foot end lift cylinders 132, 142, as well as head, thigh, and foot section pivot cylinders 150, 158, 168, and foot section contracting cylinder 176.

Typically, the control valves are moved between various configurations using electrical power. Chair bed 50 includes a battery 92 configured to provide electrical power to operate the control valves when electrical power is not available from a source outside of chair bed 50. Use of foot pump pedal 186 to pressurize the hydraulic oil and the availability of electrical power from battery 92 to operate the control valves allows a caregiver to manipulate lifting mechanism 130 and articulating deck 402 to move chair bed 50 to any desired position within its range of movement when there is no electrical power supplied to the chair bed 50.

In addition, depressing CPR foot pedal 250 manually moves head section 404 from the back-support position to the down position for performing CPR on a person on sleeping surface 552, and the emergency Trendelenburg lever 254 manually activates emergency Trendelenburg valve 214 to move sleeping surface 552 to the Trendelenburg position. Both of the CPR foot pedals 250 and the emergency Trendelenburg lever 254 operate to change the position of chair bed 50 when chair bed 50 is away from a power source, and both operate without the need to pump foot pump pedal 252.

Lifting Mechanism

Lifting mechanism 130 includes a head end axle 258 rotatably mounted to brackets 260 that are fixed to sides 66 of base frame 62 as shown in FIGS. 11 and 12. A lever 256, and lift arms 320, 322 are fixed to axle 258 and piston rod 134 of head end lift cylinder 132 is coupled to lever 256. Foot end 54 of base frame 62 carries levers 214 fixed to brackets 212, a foot end cross bar 276 fixed to distal ends 294 of levers 214, and piston rod 144 of foot end lift cylinder 142 coupled to foot end cross bar 276.

Head end connector members 262, 264 couple lift arms 320, 322 to intermediate frame 302. Each connector member 262, 264 has a first end 266, 268 that is pivotably connected to lift arms 320, 322. Second ends 270, 272 of head end connector members 262, 264 are pivotably coupled to intermediate frame 302. Foot end connector members 282, 284 each have a first end 286, 288 that is pivotably connected to lift arms 324, 326. Second ends 290, 292 of foot end connector members 262, 264 are fixed to intermediate frame 302.

Head end lift cylinder 132 and foot end lift cylinder 142 are each pivotably mounted to struts 64 of base frame 62 as shown in FIGS. 11 and 15. Piston rod 134 of head end lift cylinder 132 is pivotably coupled to distal end 274 of lever 256. When head end lift cylinder 132 is activated by supplying pressurized hydraulic oil to interior region 133 through rear port 138, the pressurized hydraulic oil pushes piston rod 134 so that piston rod 134 slides outwardly to extend from head end lift cylinder 132, pushing distal end 274 of lever 256 toward head end 52 of chair bed 50 and rotating head end axle 258 so that lift arms 320, 322 rotate upwardly. As lift arms 320, 322 rotate upwardly, connecting members 262, 264 push head end 52 of intermediate frame 302 upwardly relative to base frame 62.

Likewise, piston rod 144 of foot end lift cylinder 142 is pivotably coupled to foot end cross bar 276. When foot end lift cylinder 142 is activated by supplying pressurized hydraulic oil to foot end lift cylinder 142 through rear port 146, the pressurized hydraulic oil pushes piston rod 144 so that piston rod 144 slides outwardly to extend from foot end lift cylinder 142, pushing cross bar 276 and thus distal ends 294 of levers 214 toward foot end 54 of chair bed 50, thereby rotating lift arms 324, 326 upwardly. As lift arms 324, 326 rotate upwardly, connecting members 282, 284 push foot end 54 of intermediate frame 302 upwardly relative to base frame 62.

When chair bed 50 is in the standard bed position with articulating deck 402 configured to provide a planar sleeping surface 552, lifting mechanism 130 is in the raised position shown in FIG. 15 having lift cylinders 132, 142 activated and piston rods 134, 144 extended therefrom, axle 258 and lift arms 320, 322 rotated upwardly, and cross bar 276 pushed toward foot end 54 of chair bed 50 with lift arms 324, 326 rotated upwardly, so that lift arms 320, 322, 324, 326 and connecting members 262, 264, 282, 284 hold sleeping surface 552 first distance 566 above the floor as illustratively shown in FIG. 3. When chair bed 50 is in the low position, lifting mechanism 130 is in the low position shown in FIG. 12 having lift cylinders 132, 142 deactivated and piston rods 134, 144 retracted into lift cylinders 132, 142, axle 258 and lift arms 320, 322 rotated downwardly, and cross bar 276 pulled toward head end 52 of chair bed 50 with lift arms 324, 326 rotated downwardly, so that lift arms 320, 322, 324, 326 and connecting members 262, 264, 282, 284 hold sleeping surface 552 second distance 568 above the floor as illustratively shown in FIG. 4.

Lifting mechanism 130 can also be used when chair bed 50 is in the sitting position to help a person (not shown) on sleeping surface 552 to stand up. When chair bed 50 is in the sitting position, head section 404 of articulating deck 402 is in the back-support position, thigh section 408 is in the up position, foot section 410 is in the down position, and intermediate frame 302 is in the low position as shown in FIGS. 2 and 7. Typically, the person on sleeping surface 552 can place their feet (not shown) on the floor when chair bed 50 is in the sitting position. after the feet of the person are on the floor, lifting mechanism 130 can be moved from the low position to the raised position to help the person to stand up. Additionally, chair bed 50 can be provided with grip handles 632, 640, described below and shown in FIG. 2, that are mounted to move with intermediate frame 302 to provide additional support for the person standing up with the aid of chair bed 50.

Reduced-Shear Pivot

Head section 404 is coupled to weigh frame 506 by reduced-shear pivot assembly 650 shown in FIGS. 11 and 14-17. Reduced-shear pivot assembly 650 mounts head section 404 to weigh frame 506 for both translational movement and pivoting movement of head section 404 relative to seat section 406 of deck 402 and relative to weigh frame 506. The pivoting and translational movements combine to produce a motion in which head section 404 pivots relative to weigh frame 506 about an effective pivot axis positioned to lie above lower deck 430 and immediately adjacent upper deck 414. The shear between the back of the person and the sleeping surface 552 caused by movement of head section 404 is reduced, thereby reducing scrubbing of the sleeping surface 552 against the person.

Reduced-shear pivot assembly 650 includes brackets 654 mounted to each side 656 of head section 404 as shown in FIGS. 11 and 15-17. Brackets 654 connect flattened U-shaped struts 658 that span head section 404 to sides 656 as shown in FIG. 11. A lever arm 660 having a cap 662 is fixed to struts 658 and extends longitudinally in a direction parallel to the sides 656 of head section 404 toward foot end 54 of chair bed 50, terminating in a tip 664 as shown best in FIGS. 15-17. Two spacer rods 666 each have a first end 668 pivotably coupled to struts 658 adjacent to brackets 654 and a second end 670 pivotably connected to weigh frame 506 so that spacer rods 666 pivot about a spacer pivot axis 672. Spacer rods 666 maintain the separation between spacer pivot axis 672 and struts 658 as head section 404 moves between the back-support position of FIG. 15 and the down position of FIG. 16.

Slotted brackets 674 are fixed to sides 676 of seat section 406 adjacent to foot end 54 of head section 404 as shown in FIGS. 15-17. Each slotted bracket 674 is formed to include a horizontal longitudinal slot 678. Foot end 54 of head section 404 includes pins 680 that are received by slots 678. Pins 680 and slots 678 cooperate to guide the movement of foot end 54 of head section 404 so that foot end 54 of head section 404 translates horizontally or longitudinally toward head end 52 of chair bed 50 when head section 404 pivots upwardly to the back-support position.

Head section pivot cylinder 150 operates to pivot head section 404 between the down position and the back-support position as shown in FIGS. 11 and 15-17. A bracket 682 having a distal end 684 is fixed to an upper deck end portion 460 of thigh section 408. Bracket 682 is generally centrally located along weigh frame end portion 460. Head section pivot cylinder 150 is pivotably coupled to distal end 684 of bracket 682 and piston rod 152 of head section pivot cylinder 150 is pivotably coupled to tip 664 of lever arm 660 so that head section pivot cylinder 138 and lever arm 660 act between struts 658 of head section 404 and weigh frame 506.

When head section 404 is in the down position shown, for example, in FIG. 16, head end pivot cylinder 150 is in a deactivated configuration having piston rod 152 in the retracted position. Head section 404 and lever arm 660 are generally parallel to weigh frame 506 when head section 404 is in the down position.

When head end pivot cylinder 150 moves to the extended position, piston rod 152 pushes tip 664 of lever arm 660 toward head end 52 of chair bed 50. Lever arm 660 pushes against struts 658 to pivot head section 404 upwardly to the back-support position as shown in FIG. 17. Pins 680 cooperate with slots 678 so that foot end 54 of head section 404 moves longitudinally toward head end 52 of chair bed 50 a distance 686. At the same time, spacer rods 666 swing upwardly forcing head section 404 to engage in the motion illustratively shown by arc 688 in FIG. 17 combining the pivoting movement of head section 404 and the translating movement of head section 404 to provide the reduced-shear pivot. Since pivot pins 680 are located immediately adjacent the top of side walls 438 of step deck 412, the pivot is between sleeping surface 552 and bottom 586 of mattress 550. This reduces the travel required to reduce shear between the person (not shown) and sleeping surface 552.

The longitudinal displacement of the pivot is selected to prevent a crease in mattress 550 between head and seat portions 558, 560. The effective point of contact on mattress back portion 558 extends as it pivots upwardly as does the corresponding point on the person on sleeping surface 552 as the person pivots about his or her hip. As a result of the reduced-shear pivot assembly 650, the point of contact on mattress back portion 558 and the corresponding point on the person move together, thus reducing the sliding of the person relative to sleeping surface 552.

Although the surface of the person's back expands when the person pivots upwardly to a sitting position, the surface of the back legs of the person contract as the back legs pivot downwardly. As will be explained with respect to FIGS. 24-28 and 30, foot section 410 of deck 402 and foot portion 564 of mattress 550 are mounted and constructed to shorten in length and mattress 550 thins and shortens in length when pivoting to the sitting position to effect a reduced-shear pivot.

Chair bed 50 can be provided with hip pivot guide 694 shown in FIGS. 31-33 to help the caregiver accurately position the hip (not shown) of the person (not shown) on sleeping surface 552. Hip pivot guide 694 indicates the position of the hip of the person that will minimize the distance between effective pivot axis and the axis (not shown) about which the person's hip pivots, thereby maximizing the effectiveness of the reduced-shear pivot. Caregivers providing care to people using conventional beds having movable head sections typically attempt to place the hip of the person at the pivot joint of the head section to the bed. Typically, the only available method for the caregiver to estimate this placement is by viewing the distance between the top of the person's head and the head end of the mattress. Providing hip pivot guide 694 on body section siderails 804, 806 of chair bed 50 maximizes the ability of the caregiver to properly locate the hip of the person on sleeping surface 552.

Figure 18:
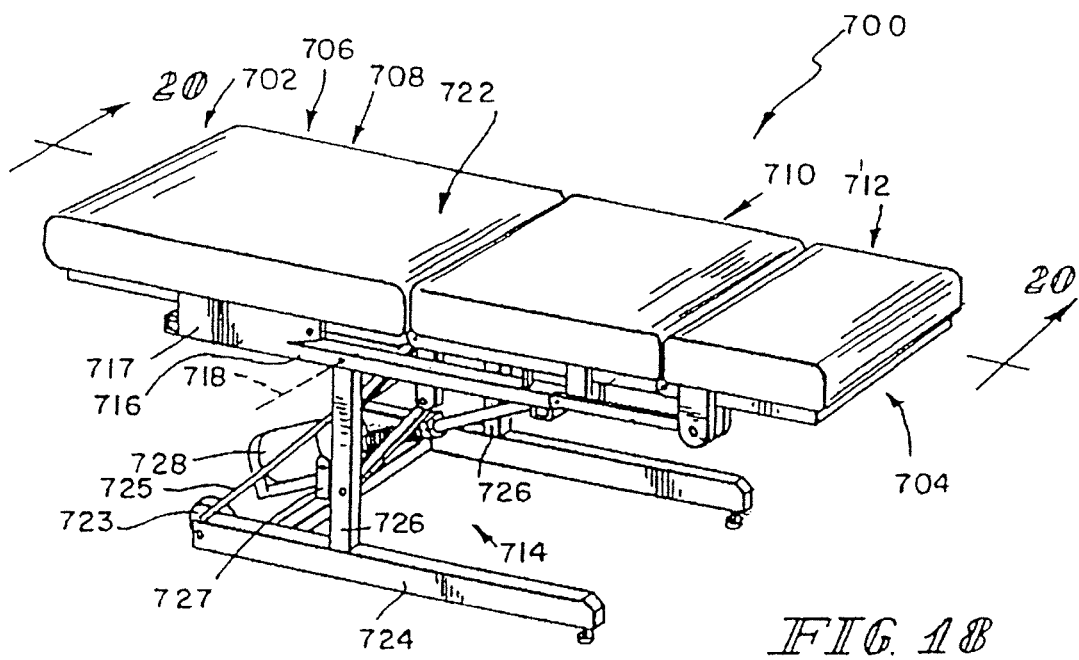
FIG. 18 is a perspective view of a second embodiment of a chair bed in a generally horizontal bed position.
Figure 19:
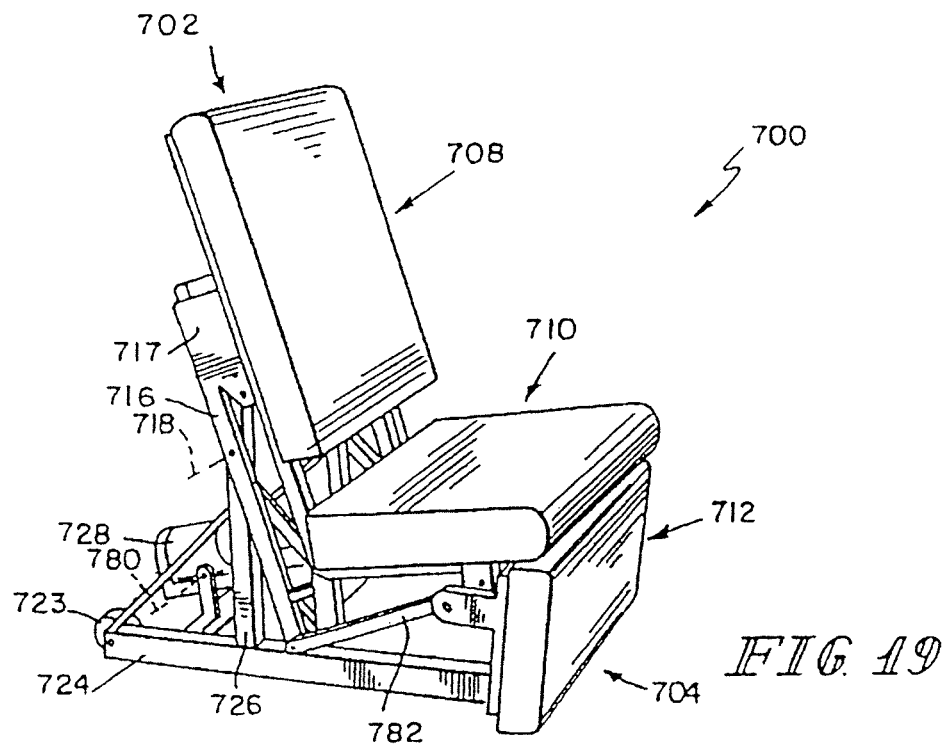
FIG. 19 is a perspective view of chair bed of FIG. 18 showing the chair bed in a sitting position.
Figure 20:
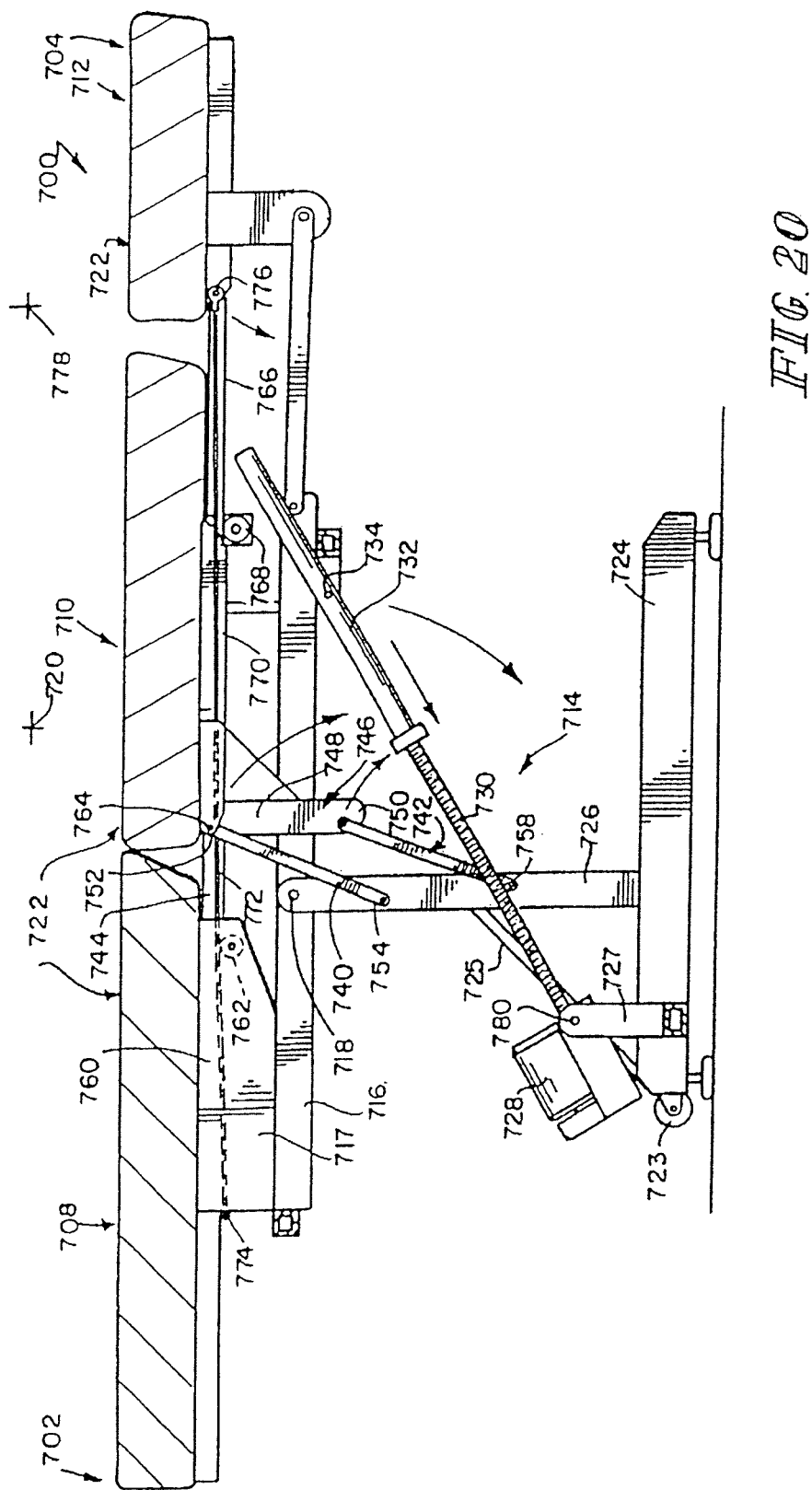
FIG. 20 is a sectional view taken along line 20-20 of FIG. 18 showing the chair bed of FIG. 18 in the bed position.
Figure 21:
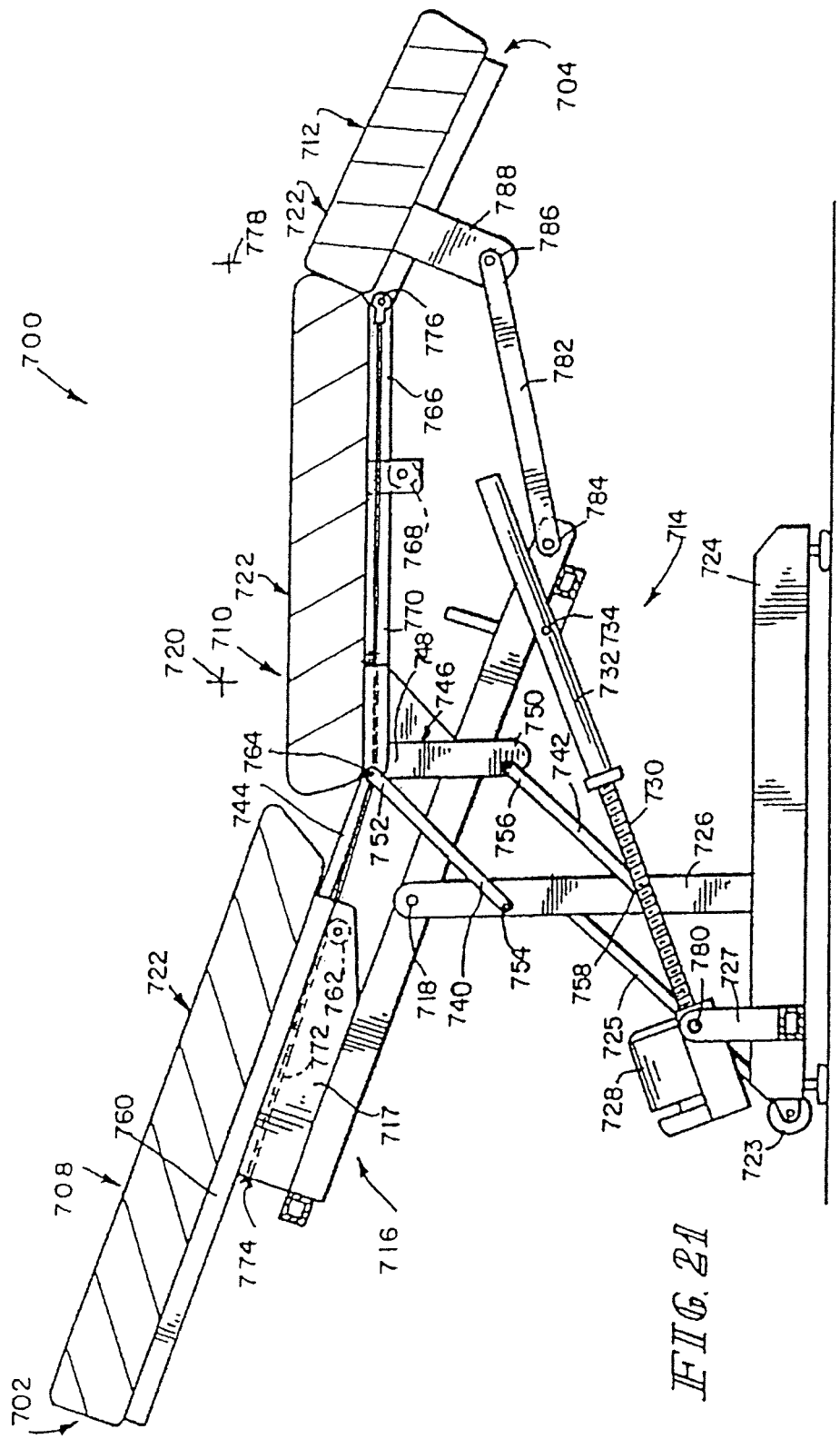
FIG. 21 is a view similar to FIG. 20 showing the chair bed in an intermediate position.
Figure 22:
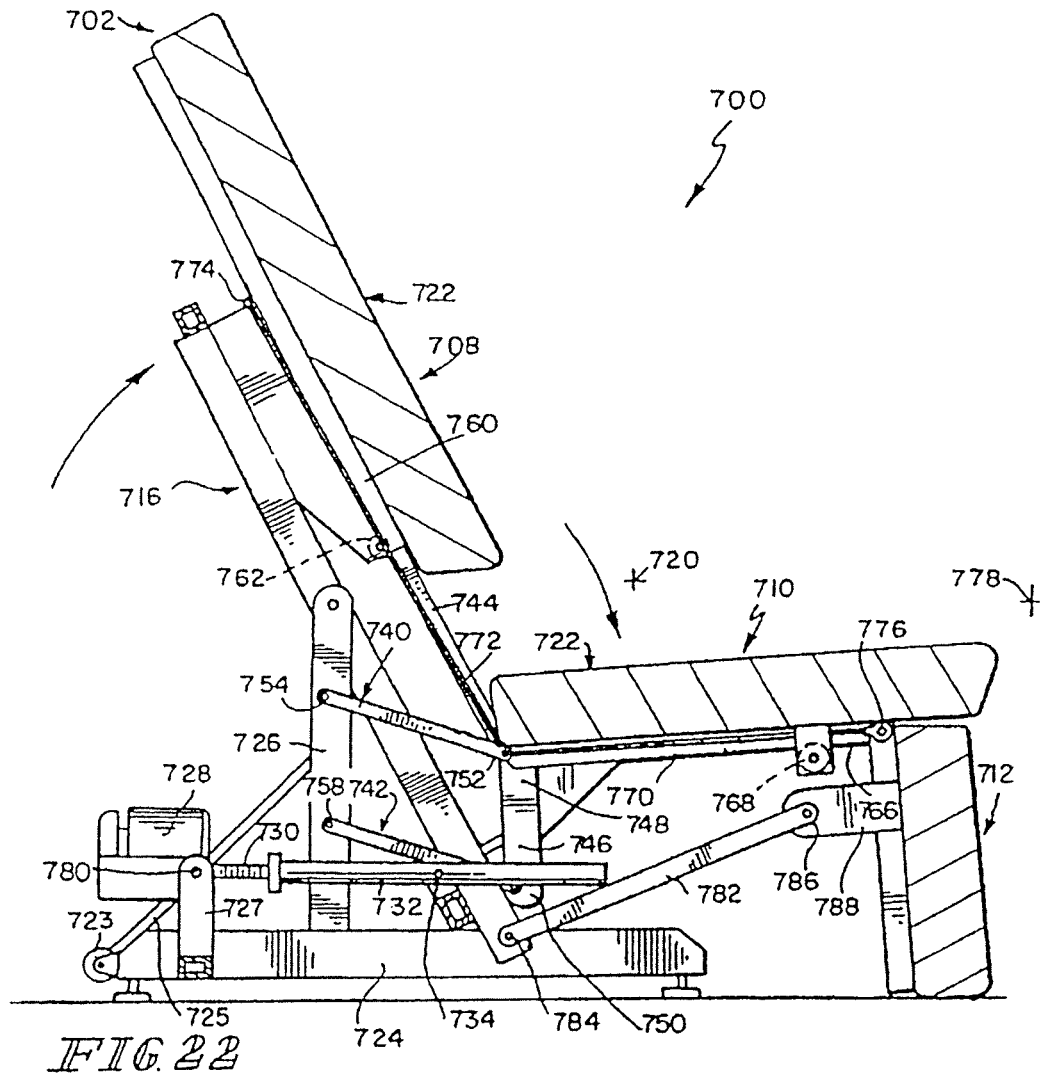
FIG. 22 is a view similar to FIG. 21 showing the chair bed in the sitting position.

A reduced-shear pivot assembly 714 is shown included on an examination table 700 having a head end 702, a foot end 704, and an articulating deck 706, including a head section 708, a seat section 710, and a foot section 712 as shown in FIGS. 18-23. Examination table 700 is convertible between an examination position having deck 6 in a generally planar configuration as shown in FIGS. 18, 20 and a sitting position as shown in FIGS. 19, 22. Head section 708 moves between a generally horizontal down position shown in FIG. 18 and an upward back-support position shown in FIG. 19, and foot section 712 moves between a generally horizontal up position shown in FIG. 18 and a generally vertically downwardly extending down position shown in FIG. 19.

Head section 708 and foot section 712 are both provided with a reduced shear pivot assembly 714, shown best in FIGS. 20-23, that operates to pivot head section 708 relative to seat section 710 about an effective pivot axis 720 that is positioned to lie above an examination or support surface 722 and that also operates to pivot foot section 712 relative to seat section 710 about an effective pivot axis 778 that is positioned to lie above examination or support surface 722.

Although the reduced shear pivot assembly 714 is described with respect to an examination table, it can also be used in a bed, a chair bed, a stretcher, a gurney or any other device having an articulated deck including one or more articulated deck sections wherein the pivot corresponds to the pivoting of a person on the deck.

Examination table 700 includes a base platform 724 having upstanding posts 726 fixed thereto and extending upwardly therefrom. The upstanding posts 726 are secured to the base 724 by diagonal braces 725. The base platform 724 is shown resting on the ground. Wheels 723 are provided at the back end of the base 724 displaced from the ground when the base 724 is in its horizontal position. To move the table, the table is rotated up such that the base 724 pivots back onto the wheel 723. Then, the table can be moved to any desired location. This movement is preferable when in the chair position of FIG. 19 with an occupant therein. It is not recommended to transport of the table in its supine position of FIG. 18 on wheel 723 with an occupant thereon. Alternatively, wheels may be provided at the four ends of the base 724 so as to make the table portable without tilting. This will allow the table to be used as a gurney in an emergency department wherein the patient is brought in from the ambulance, moved into an emergency bay, then moved out to a room or surgery center without moving from one conveyance to another.

Reduced-shear pivot assembly 714 includes a frame 716 pivotably attached to a pair of spaced upstanding posts 726 for pivoting movement relative thereto about a pivot axis 718. A drive motor 728 is pivotably attached to base platform 724 by bracket 727 for pivoting movement about a pivot axis 780. Drive motor 728 is configured to rotatably drive a lead screw 730 that angles upwardly from drive motor 728 to a sheath 732 that is coupled to frame 716 for pivoting movement about a pivot axis 734.

Sheath 732 is formed to include an interior region (not shown) that threadably receives lead screw 730 as shown in FIG. 20. Extension of lead screw 730 from sheath 732 by rotating causes frame 716 to pivot relative to base platform 724 about pivot axis 718 with foot end 704 of frame 716 pivoting upwardly and head end 702 of frame 716 pivoting downwardly. Likewise, retraction of lead screw 730 into sheath 732 cause frame 716 to pivot about pivot axis 718 with foot end 704 of frame 716 pivoting downwardly and head end 702 of frame 716 pivoting upwardly.

Head section 708 of articulating deck 706 is fixed to frame 716 by flanges 717 as shown in FIGS. 20-23. As frame 716 pivots from a generally horizontal initial position shown in FIG. 20 to an inclined position shown in FIG. 22 having head end 702 of frame 716 positioned above foot end 704 of frame 716, head section 708 pivots from a generally horizontal down position of FIG. 18 to an upward back-support position of FIG. 19.

The head end of seat section 710 is connected to upstanding posts 726 by transverse upper struts 740, transverse lower struts 742, and bracket 746. Bracket 746 includes a first end 748 fixed to head end of seat section 710 and extends downward to terminate at a second end 750. Each upper strut 740 has a first end 752 pivotably coupled to seat section 710 adjacent to first end 748 of bracket 746 and a second end 754 pivotably coupled to one of upstanding posts 726. Each lower strut 742 has a first end 756 pivotably coupled to second end 750 of bracket 746 and a second end 758 pivotably coupled to one of upstanding posts 726 beneath second end 754 of upper strut 740.

As can best be seen in FIGS. 20 and 22, the connection of the struts 740 and 742 at ends 754 and 758 respectfully to the upstanding post 726 are offset with respect to a vertical. The connection of the strut 740 and 742 at ends 752 and 756 to the bracket 746 are aligned vertically. The lengths of the struts 740 and 742 are substantially equal. As an alternative, the strut 740 and 742 may be of unequal length and their connection to the outstanding post 26 may be aligned vertically. As a further alternative, the connections may be offset and the struts lengths different. The lengths of the struts 740 and 742 and their connections to the upstanding posts 726 and to the bracket 726 are selected such that the seat section 710 is horizontal in the planar or horizontal position of the articulate deck 6 as shown in FIGS. 18 and 20 and the foot end of seat section 710 is raised with respect to the head end of seat section 710 in the chair position as illustrated in FIGS. 19 and 22. Thus, the struts 740, 742 do not form a true parallelogram with the upstanding post 726 and bracket 746. The raising of the knee with respect to the hip secures the occupant to the chair and prevents sliding out.

Figure 23:
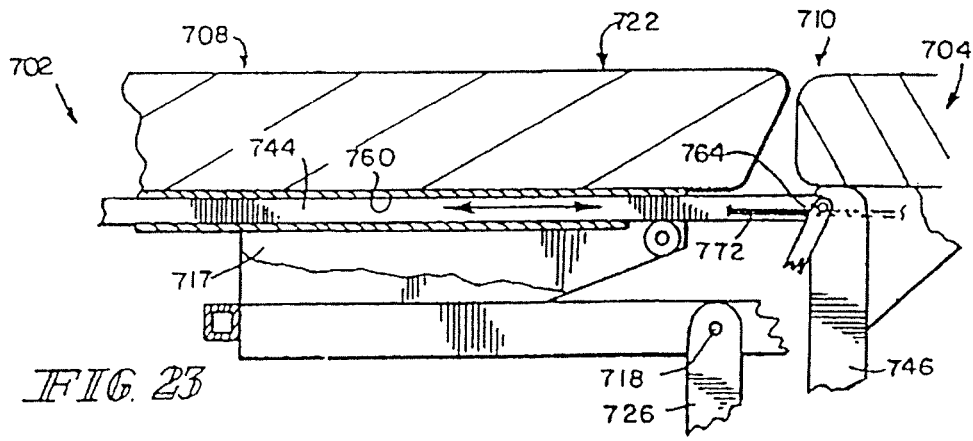
FIG. 23 is an enlarged view similar to FIG. 20 of the second embodiment of the chair bed showing a telescoping member received by a sheath and riding on a roller while in the fully retracted position.

First telescoping members 744 are slidably received by a sheath 760 appended to head section 708 and flange 717 of frame 716 as shown best in FIG. 23 for movement over rollers 762 between a retracted position shown in FIGS. 20 and 23, and an extended position shown in FIGS. 21 and 22. Each first telescoping member 744 includes a foot end 764 that is pivotably coupled to seat section 710 adjacent to first end 748 of bracket 746 and a head end (not shown) received by sheath 760. As first telescoping members 744 move between the retracted position and the extended position, seat section and head section translates relative to each other. Thus, the pivot point 764 of the seat and head sections moves alone a plane parallel to the frame 716.

Foot section 712 is pivotably coupled at head end 702 of foot section 712 to second telescoping members 766 at 776 as shown in FIGS. 20-22. Seat section 770 is formed to include sheaths 770 and each second telescoping member 766 is slidably received by a sheath 770 of the seat section 710 for movement over rollers 768 between an extended position shown in FIG. 20 and a retracted position shown in FIG. 22. As second telescoping members 766 move between the retracted position and the extended position, foot section 712 translates relative to seat section 710. Thus, the pivotal connection of the foot section 712 to the seat section 710 moves in a plane parallel to the seat section transfers to the plane of the frame 716. A link 782 is pivotably connected at a first end 784 to frame 716 and at a second end 786 to a bracket 788 extending from foot section 720 pivoting of the frame 716 pivots the foot section 712.

A cable 772 has a first end 776 fixed to head end of foot section 712 and a second end 774 fixed to flange 717 of head section 708. The length of cable 772 is fixed so that second telescoping members 766 move from the extended position to the retracted position when first telescoping members 744 move from the retracted position to the extended position. Consequently, cable 772, frame 716 and link 782 act to coordinate the movement of head section 708 and foot section 712 relative to seat section 710 so that as head section 708 translates and pivots upwardly relative to seat section 710, foot section 712 simultaneously translates and pivots downwardly relative to seat section 710.

Seat section 710 translates relative to head section 708 as head section 708 pivots from the down position to the back-support position as shown in FIGS. 19-22. The pivoting movement of head section 708 and the translational movement of seat section 710 combine to produce a motion in which head section 8 pivots relative to seat section 710 about effective pivot axis 720 positioned to lie above support surface 722 and coincident with a hip (not shown) of a person on the support surface 722.

Likewise, seat section 710 translates relative to foot section 712 as foot section 712 pivots from the up position to the down position as shown in FIGS. 19-22. The pivoting movement of foot section 712 and the translational movement of seat section 710 combine to produce a motion in which foot section 712 pivots relative to seat section 710 about a second effective pivot axis 778 positioned to lie above support surface 722 and coincident with a knee (not shown) of a person (not shown) on support surface 722.

The head section 708 is fixed to the frame 716 which pivots about a fixed pivot point 718 adjacent the foot end of head section 708 fixed to the base platform 724 and the seat section 710 moves relative to the head section 722 and frame 716. Thus, when the frame 716 pivots from the planar position of FIG. 18 to the sixty degree position of FIG. 19, the seat 722 is moved closer to the ground. This allows easy egress.

As can be seen both in bed/chair 50 and table 700, head section 404, 708 translates relative to seat section 406, 710 when head section 404, 708 pivots from the down position to the back-support position. This relative translation effectively expands the length of deck 402, 706 and support surface 552, 722 at the junction of the head and seat sections 404, 708 and 406, 710, during the articulation of deck 402, 706. The effective expansion of deck 402, 706 and support surface 552, 722 at the seat and head juncture conforms to the lengthening of the back of the person to minimize the shear that could take place between the person and surface 552, 722. For the foot-seat juncture, the surface 552, 722 contracts when moving from a lying position to a sitting position which corresponds to the concentration of the back of the legs.

In other words, the expansion of deck 402, 706 and surface 552, 722 at the back and contraction of the foot allows the lower body of the person to remain stationary relative to surface 552, 722 when tilting the upper body of the person, which also remains stationary relative to surface 552, 722, in order to minimize the scrubbing between the person and surface 552, 722 during articulation of deck 402, 706.

Thus, the translational movement of seat section 710 of examination table 700 illustratively shown in FIGS. 18-23 relative to head and foot sections 708, 712 and contemporaneous with the pivoting movement of head and foot sections 708, 712 results in a reduced-shear pivoting movement of head and foot sections 708, 712. The effective pivot axes 720, 778 of head and foot sections 708, 712 to lie above support surface 722. If effective pivot axes 720, 778 are approximately co-linear with axis of rotation of hip and knee respectively, then the scrubbing of support surface 722 against the person (not shown) supported by support surface 722 will be minimized.

As can be seen in both chair bed 50 and examination table 700, head section 404, 708 translates relative to seat section 406, 710 when head section 404, 708 pivots from the down position to the back-support position. This relative translation effectively expands the length of deck 402, 706 at the junction of the back and seat during the articulation of deck 402, 706.

When the upwardly-facing person (not shown) supported by surface 552, 722 moves from a lying position to a sitting position, the back (not shown) of the person lengthen. The effective expansion of deck 402, 706 at the juncture of seat section 406, 710 and head section 404, 708 and the consequent expansion of surface 552, 722 conforms to the lengthening of the back of the person to reduce the shear that could take place between the person and surface 552, 722. For the foot-seat juncture, surface 552, 722 contracts when moving from a lying position to a sitting position.

In other words, the expansion of deck 402, 706 and surface 552, 722 at the back and contraction at the foot allows the lower body of the person to remain stationary relative to surface 552, 722 when tilting the upper body of the person, which also remains stationary relative to surface 552, 722, in order to minimize the scrubbing between the person and surface 552, 722 during articulation of deck 402, 706. The reduced-shear pivot also minimizes the migration of the person on sleeping surface 552 toward foot end 54 of chair bed 50 as head section 404 is repeatedly raised and lowered and minimizes "bunching" of mattress 550 and the potential corresponding pressure on the hip and shoulder of the person.

CPR Foot Pedal

CPR foot pedals 250 are coupled to hydraulic system module 100 as shown in FIGS. 11 and 12 and are positioned to be operable by the foot of the caregiver. As described above, hydraulic system module 100 includes CPR valve 212 shown in FIG. 13 that can be activated to restore fluid communication between rear port 154 of head section pivot cylinder 150 and return conduit 185 so that hydraulic oil can be released from cylinder 150 and head section 404 can move from the back-support position to the down position. CPR foot pedals 250 are movable between an up position and a downward releasing position. When CPR foot pedals 250 are in the releasing position, CPR valve 212 is activated and head section 404 moves from the back-support position to the down position.

CPR foot pedals 250 and CPR valve 212 are configured so that CPR foot pedals 250 can be moved from the releasing position to the up position when head section 404 is in an intermediate position after head section 404 has moved away from the back-support position but before head section 404 has reached the down position. CPR valve 212 can thus be deactivated when head section 404 is in the intermediate position to block the fluid communication between rear port 154 of head section pivot cylinder 150 and return conduit 185. Blocking the fluid communication locks head section 404 in the intermediate position. CPR foot pedals 250 can thereafter be moved back to the releasing position so that CPR valve is once again activated to restore fluid communication between rear port 154 and return conduit 185 allowing movement of head section 404 toward the down position. Providing this capability to the caregiver in an actuator designed as a foot pedal keeps the hands of the caregiver free to conduct other activities while CPR foot pedals 250 are depressed and head section 404 moves to the down position.

Thigh Section

The first embodiment of a chair bed 50 in accordance with the present invention additionally includes thigh section 408 of articulating deck 402 which is configured to pivot relative to weigh frame 506 as shown in FIG. 15. Thigh section 408 pivots about a pivot axis 602 adjacent to head end 52 of thigh section 408 between a down position in which thigh section 408 is generally horizontal and parallel to weigh frame 506 and an upward position in which foot end 54 of thigh section 408 is elevated above weigh frame 506. Thigh section pivot cylinder 158 is connected to weigh frame 506 as shown in FIGS. 14 and 15. Although thigh section 408 can move independently of the head and foot sections 404, 410, thigh section 408 preferably moves to the upward position when head section 404 moves to the back-support position so that the head and thigh sections 404, 408 cooperate to cradle the person (not shown) on sleeping surface 552 therebetween. Thigh section 408 preferably moves to the down position when head section 404 moves to the down position.

Foot Section

Foot section 410 of articulating deck 402 is movable from a generally horizontal up position parallel to intermediate frame 302 as shown in FIGS. 1 and 3 to a generally vertically downwardly extending down position to permit the lower legs and feet of the person (not shown) to be lowered to the sitting position as shown in FIGS. 2 and 8. Foot section 410 can also be contracted from an expanded position having a longitudinal length 465 as shown in FIGS. 3, 24, and 30 to a contracted position having foot end 54 of foot section 410 drawn inwardly toward head end 52 of chair bed 50 so that foot section 410 has a longitudinal length 464 that will "clear" the floor when foot section 410 moves to the down position as shown in FIGS. 8 and 25. Preferably, length 464 of foot section 410 when foot section 410 is contracted is such that foot end 54 of foot section 410 clears the floor and is spaced-apart therefrom sufficiently to permit a base (not shown) of an over bed table (not shown) to fit therebetween.

Foot section 410 is pivotably coupled to an upper deck end portion 460 of thigh section 408 by hinge 468 as shown in FIGS. 12, 15, 24, 25, and 30. Consequently, foot section 410, when in the down position, can be longer by an amount equal to a vertical offset 514 between lower deck 430 and upper deck 414 than it could be if there were no step deck 412, and foot section 410 were instead connected to lower deck 430. Thus, for foot section 410 to clear the floor when foot section 410 pivots from the up position to the down position, foot section 410 can contract a lesser amount than would be required if there were no step deck 412.

Foot section 410 includes a pivoting member 466 that is pivotably coupled to thigh section 408 and a contracting member 462 that can be drawn inwardly toward head end 52 of foot section 410 from an expanded position to the contracted position. Foot section pivot cylinder 168 and foot section contracting cylinder 176 cooperate to move pivoting member 466 between the up position and the down position and to move contracting member 462 between the expanded position shown in FIG. 24 and the contracted position shown in FIG. 25.

Contracting member 462 is positioned to slide across top surface 470 of pivoting member 466 as shown in FIGS. 11 and 15. A folding bracket 472 has a first end 474 pivotably coupled to weigh frame 506 and a second end 476 pivotably coupled to pivoting member 466 as shown in FIGS. 15, 24, and 25. Piston rod 170 of foot section pivot cylinder 168 is pivotably coupled to bracket 472. Piston rod 170 pushes against bracket 472 as piston rod 170 extends from foot section pivot cylinder 168 causing bracket 472 to pivot upwardly from a folded position about a pivot axis 478 adjacent to weigh frame 506 and to push pivoting member 466 upwardly to the up position. When piston rod 170 is in the extended position, bracket 472 is generally unfolded, horizontal, and parallel to pivoting member 466.

Foot section 410 further includes first and second linkages 480, 482 and a thruster strut 484 as shown in FIGS. 24 and 25. First linkage 480 has a first end 486 pivotably coupled to pivoting member 466. A second end 488 of first linkage 480 is pivotably coupled to a first end 490 of second linkage 482 and a second end 492 of second linkage 482 is pivotably coupled to foot end 54 of contracting member 462. Thus, first and second linkages 480, 482 couple pivoting member 466 and contracting member 462.

Thruster strut 484 has a first end 494 that is pivotably coupled to pivoting member 466 and a second end 496 that is pivotably coupled to second linkage 482 between the first and second ends 490, 492 of second linkage 482 as shown in FIGS. 24 and 25. Foot section contracting cylinder 176 is pivotably coupled to pivoting member 466 near head end 52 of pivoting member 466 and piston rod 178 is pivotably coupled to thruster strut 484 between the first and second ends 494, 496 of thruster strut 484. First and second linkages 480, 482, thruster strut 484, and foot section contracting cylinder 176 are generally coplanar and generally operate in a plane that is parallel to foot section 410.

As piston rod 178 moves from the retracted position, shown in FIG. 25, to the extended position, shown in FIG. 24, thruster strut 484 pivots about a pivot axis 498 so that second end 496 of thruster strut 484 swings toward foot end 54 of chair bed 50. As thruster strut 484 swings toward foot end 54 of chair bed 50, second linkage 482 is pushed by thruster strut 484 toward foot end 54 of chair bed 50 and second linkage 482 pulls second end 488 of first linkage 480 toward foot end 54 of chair bed 50.

Second end 492 of second linkage 482 pushes contracting member 462 toward foot end 54 of chair bed 50 when thruster strut 484 pushes second linkage 482 toward foot end 54 of chair bed 50 as shown in FIGS. 24 and 25. Likewise, when piston rod 178 moves from the extended position shown in FIG. 24 to the retracted position shown in FIG. 25, thruster strut 484 pulls second linkage 482 toward head end 52 of chair bed 50 and second linkage 482 pulls foot end 54 of contracting member 462 toward head end 52 of chair bed 50, causing contracting member 462 to contract and reducing the length of foot section 410 by a distance 500 as shown in FIG. 25.

Contracting member 462 is formed to include downwardly extending longitudinal tabs 502 and pivoting member is formed to include longitudinal channels 504 as shown in FIGS. 24-27. Longitudinal tabs 502 are received by longitudinal channels 504 as shown best in FIGS. 26 and 27. Tabs 502 cooperate with channels 504 to maintain the transverse position of contracting member 462 relative to pivoting member 466 as contracting member 462 slides longitudinally relative to pivoting member 466.

As foot section 410 pivots from the up position to the down position, inflatable foot portion 564 of mattress 550 deflates as shown in FIG. 30 and shown diagrammatically in FIG. 8 so that foot section 410 of articulating deck 402 can move to the down position without interference from foot portion 564 of mattress 550. Deflating foot portion 564 also allows the person (not shown) carried by chair bed 50 to sit on chair bed 50 when chair bed 50 moves to the sitting position without having the thickness of foot portion 564 of mattress 550 pull the knees and shins of the person forward as foot section 410 of articulating deck 402 pivots to the down position. In addition, the deflating action of deflating foot portion 564 prevents scrubbing between sleeping surface 552 and the legs (not shown) of the person (not shown) on sleeping surface 552 by allowing sleeping surface 552 adjacent foot portion 564 to move with the legs of the person.

Figure 25A:
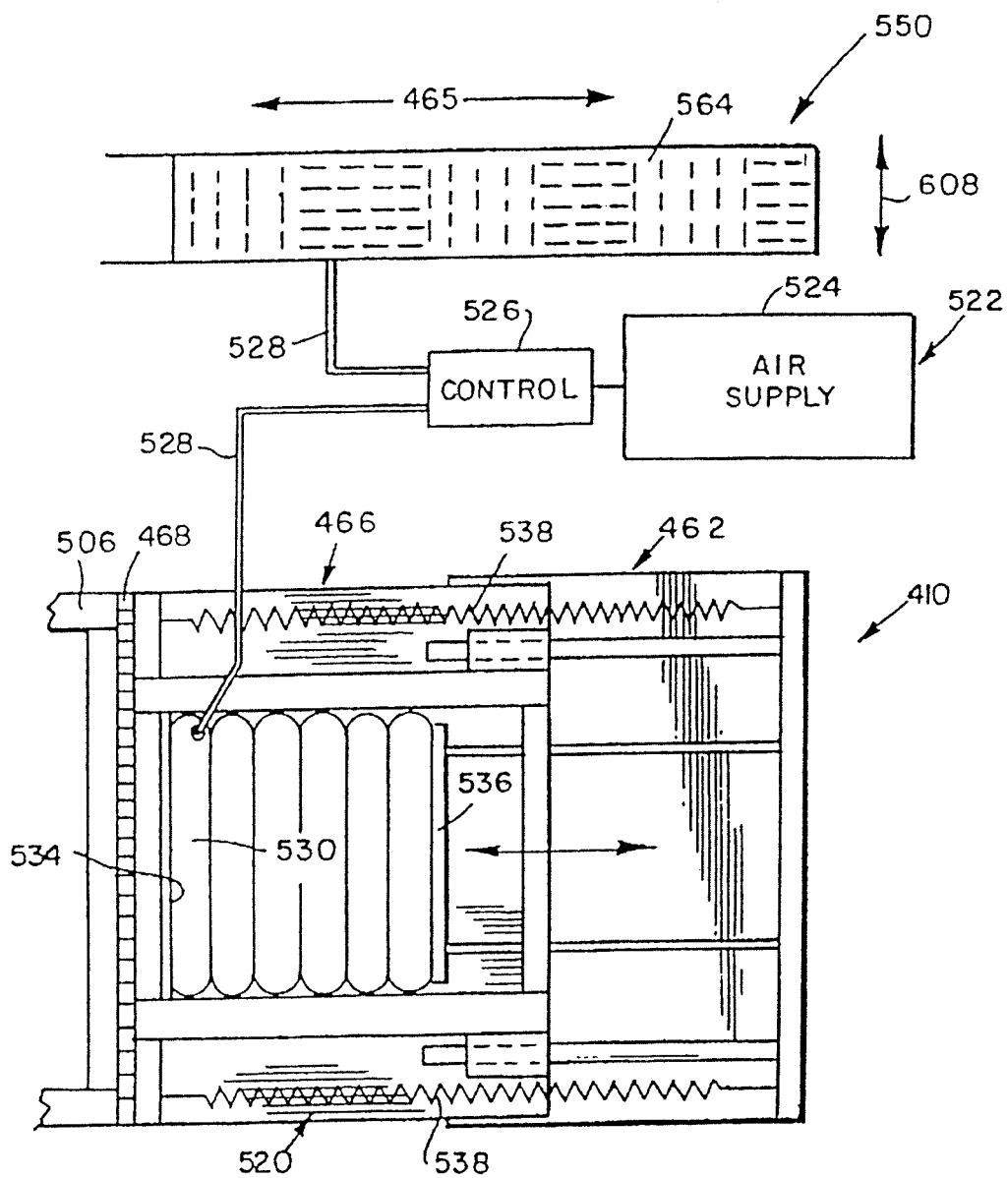
FIG. 25a is a view similar to FIG. 24 of a second embodiment of a deck foot section in an expanded position.

A second embodiment of a contracting mechanism 520 for expanding and contracting the length of foot section 410 can illustratively be operated using an air control system 522 that also operates to inflate and deflate foot portion 564 of mattress 550 as shown in FIG. 25a. Air control system 522 includes an air supply 524 for supplying pressurized air and a controller 526 for controlling the flow of air through conduit 528 to inflatable foot portion 564 and to contracting mechanism 520.

Contracting mechanism 520 includes a bellows 530 that is received between a first wall 534 that is fixed to pivoting member 466 and a second wall 536 that is fixed to contracting member 462 as shown in FIG. 25a. Contracting member 462 is slidably connected to pivoting member so that second wall 536 can slide relative to first wall 534. As second wall 536 moves toward first wall 534, contracting member is drawn inwardly to contract foot section 410. As second wall is pushed away from first wall 534, contracting member extends from foot section 410 and expands the length of foot section 410. Contracting mechanism 520 also includes two extension springs 538 connected to pivoting member 466 and contracting member 462 to yieldably bias contracting member 462 to the contracted position.

As air control system 522 supplies pressurized air to bellows 530, bellows expands and pushes against first and second walls 534, 536 moving second wall 536 away from first wall 534 and causing contracting member to extend from foot section 410 thereby expanding the length of foot section 410. As air control system 522 withdraws air from bellows 530, bellows stops pushing against first and second walls 534, 536, and springs 538 pull contracting member 462 inwardly toward pivoting member 466, thus contracting the length of foot section 410.

As described above, illustrative air control system 522 operate to control both the inflation of foot portion 564 and the inflation of bellows 530 as shown in FIG. 25a. The illustrative system provides a satisfactory method for coordinating the inflation and deflation of foot portion 564 with the contraction and expansion of the length of foot section 410.

Step Deck and Mattress

The head, seat, thigh, and foot sections 404, 406, 408, 410 of articulating deck 402 cooperate to define a step deck 412 as shown best in FIGS. 11, and 28-30. Step deck 412 includes an upper deck 414 having a head end upper deck portion 416 appended to head end 52 of head section 404, side upper deck portions 418, 420, 422, 424, 426, 428 appended to sides of the head, seat, and thigh sections 404, 406, 408, and a foot end upper deck portion 460 appended to foot end 54 of weigh frame 506 adjacent to thigh section 408. The upper deck portions 416, 418, 420, 422, 424, 426, 428, 460 and a top surface 411 of foot section 410 are coplanar when articulating deck 402 is in the initial position and cooperate to form upper deck 414 which is generally parallel to weigh frame 506.

Step deck 412 also includes a lower deck 430 having a head slat 432, a seat slat 434, and a thigh slat 436. Head, seat, and thigh slats 432, 434, 436, are coplanar when articulating deck 402 is in the initial position and they cooperate to form lower deck 430 which is generally parallel to weigh frame 506 and to upper deck 414 when articulating deck 402 is in the initial position.

Lower deck 430 is connected to upper deck 414 by a wall 438 including a head end wall 440 connecting head slat 432 to head end upper deck portion 416, side walls 442, 444, 446, 448, 450, 452 connecting head, seat, and thigh slats 432, 434, 436 to side upper deck portions 418, 420, 422, 424, 426, 428, and a foot end wall 454 connecting thigh slat 436 to foot end upper deck portion 460 as shown in FIGS. 11 and 28.

Step deck 412, then, comprises upper deck 414 and is formed to include a central, longitudinally extending recess 456 defined by lower deck 430 and by wall 438 connecting lower deck 430 to upper deck 414. In the preferred embodiment, foot section 410 of step deck 412 is displaced from recess 456 and forms part of upper deck 414, as shown in FIGS. 28 and 30.

In preferred embodiments, head section 404 of articulating deck 402 is coupled to weigh frame 506 by reduced-shear pivot assembly 650 immediately adjacent upper deck 414 which causes head section 404 of articulating deck 402 to pivot relative to weigh frame 506 between the down position and the back-support position.

Combining step deck 412 and reduced-shear pivot assembly 650 in chair bed 50 allows reduced-shear pivot assembly 650 to be mounted to wall 438 rather than to a bottom of a conventional deck. Consequently, the vertical distance between sleeping surface 552 and reduced-shear pivot assembly 650 is minimized. This minimizing the extent that reduced-shear pivot assembly 650 is required to raise effective pivot axis above reduced-shear pivot assembly 650.

Mattress 550 is received by articulating deck 402 and includes a projection 576 sized to be received by recess 456 as shown in FIGS. 28 and 29. Consequently, mattress 550 is thinner along sides 580 of mattress 550 where mattress 550 engages upper deck 414 of step deck 412. Conversely, mattress 550 is thicker in portions adjacent to projection 576. Preferably, projection 576 is positioned directly beneath portions of mattress 550 carrying a majority of the weight of the person on sleeping surface 552. The thick portion of mattress 550 including the thickness of mattress 550 between sleeping surface 552 and a bottom surface 586 engaging upper deck 414 plus the thickness of projection 576 provides greater comfort for the person on sleeping surface 552. Mattress 550, then, has a thinner perimetral zone 580 and a thicker body-support zone 582 adjacent to projection 576. Preferably, body support zone is 1½ times the thickness of perimetral zone 580. For example, perimetral zone can be 5 inches (12.7 cm) thick and body-support zone 582 can be 7½ inches (19 cm) thick.

Thinner perimetral zone 580 and upper deck side portions 417 cooperate to define "rammed" edges that provide greater firmness around the edges of sleeping surface 552 as the result of sleeping surface 552 being in close proximity to upper deck 414. This increased firmness is advantageous when the person enters and exits the bed along the sides of the bed.

Figure 34:
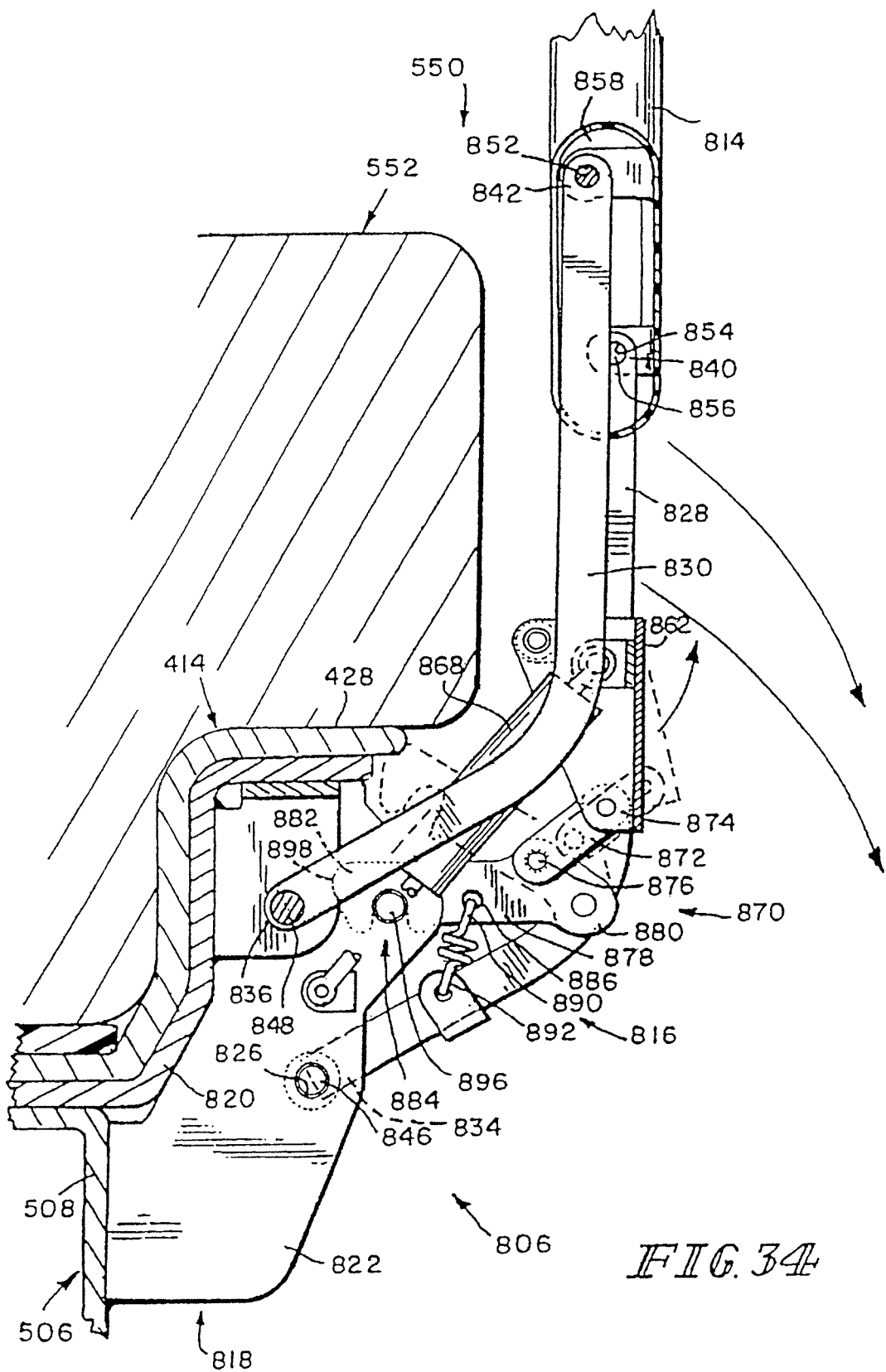
FIG. 34 is a sectional view taken along line 34-34 of FIG. 31 of a siderail in a patient-restraining position.
Figure 35:
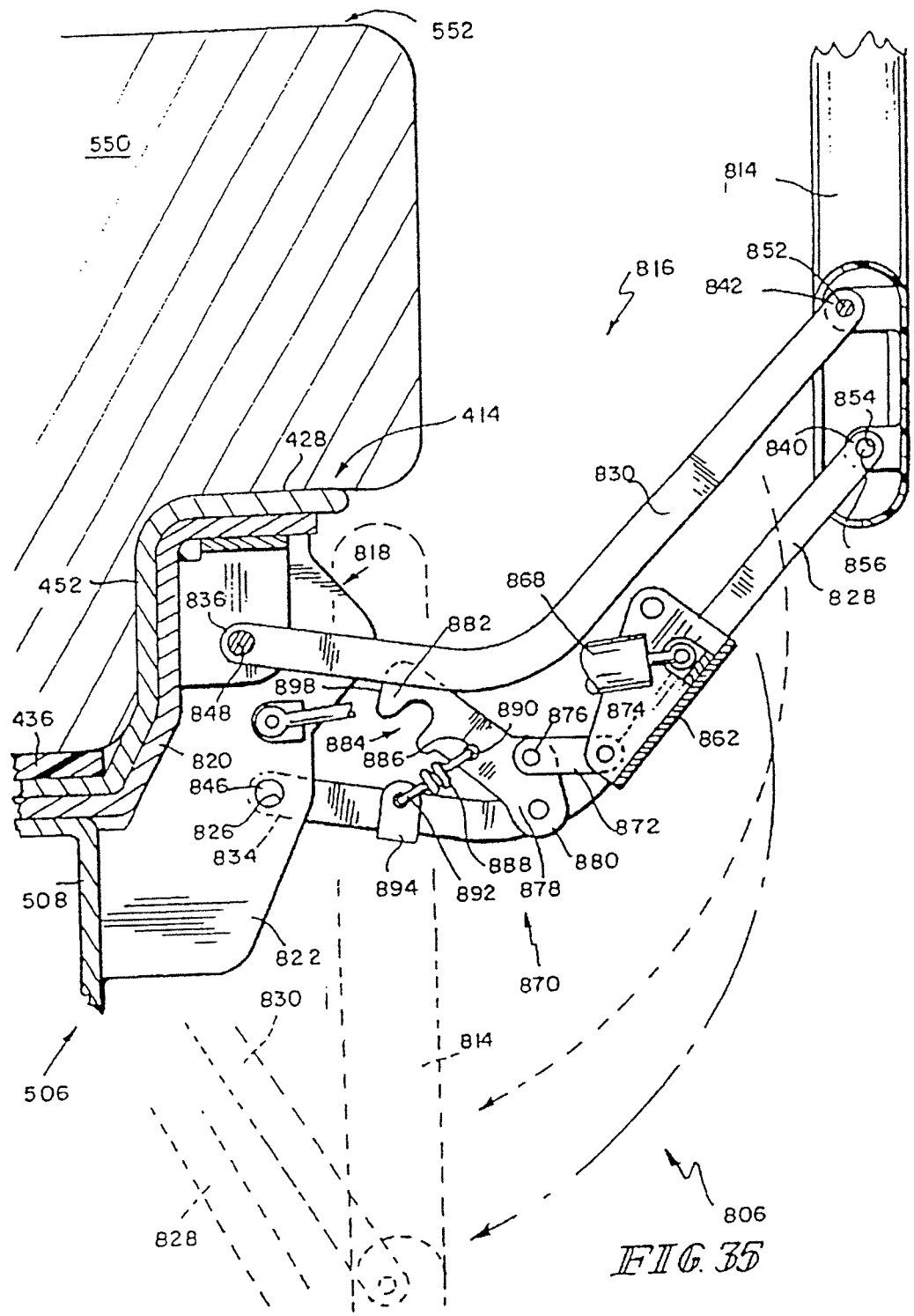
FIG. 35 is a view similar to FIG. 34 of the siderail intermediate the patient-restraining position of FIG. 34 and a down-out-of-the-way position (in phantom) having a top of the siderail beneath the sleeping surface.

Additionally, the rammed edges provide a firm edge that cooperates with siderail assemblies 800, 802, 804, 806 to minimize the potential for siderail entrapment, in which an object becomes wedged between sleeping surface 552 and one of siderails 808, 810, 812, 814. Also, step deck 412 cooperates with siderail assemblies 800, 802, 804, 806 to maximize the height relative to sleeping surface 552 at which siderails 808, 810, 812, 814 are mounted as shown in FIGS. 34 and 35. Tops of siderails 808, 810, 812, 814 can be higher when in the patient-restraining position for improved coverage and protection of the person (not shown) on sleeping surface 552 and bottoms 814 can be higher when in the tucked position for improved access to base frame 62 and to the space beneath intermediate frame 302.

Projection 576 includes a side wall 584 that can be configured to engage at least portions of the wall 438 of step deck 412 as shown in FIG. 29, thereby preventing lateral and longitudinal sliding of mattress 550 relative to step deck 412. Also, mattress 550 includes sides 578 connecting sleeping surface 552 and bottom surface 586. Mattress 550 and step deck 412 are configured so that sides 578 of mattress 550 are exposed above deck 402 as shown in FIGS. 28 and 29 providing the caregiver greater and easier access to mattress 550, rather than engaging a portion of a frame or upstanding walls of a deck as is found with conventional mattress and deck systems.

In preferred embodiments, sleeping surface 550 is generally planar and projection 576 is centrally located beneath sleeping surface 550 to form thick body support zone 582 of mattress 550 surrounded by perimetral zone 580 engaging upper deck 414. Mattress 550 may be provided in more than one piece, for example, mattress 550 may comprise a first mattress piece fit into recess 456 and a second mattress piece surrounding and abutting sides of the first mattress piece and engaging upper deck 414, or a first mattress piece could fit into recess 456 and a second mattress piece having a planar bottom surface could fit over the first mattress piece so that the bottom of the second mattress piece engages the first mattress piece and upper deck 414. However, a one-piece mattress 550 including both body-support zone 582 and perimetral zone 580 is preferred.

Inflatable Mattress Portion—Minimizing the Foot Section

Additionally, mattress 550 can include an inflatable portion 574 that can assume both an inflated position and a deflated position. Preferably, inflatable portion 574 is positioned to lie in foot portion 564 as shown in FIG. 30 so that inflatable portion 574 can be inflated to serve as sleeping surface 552 when foot section 410 of deck 402 is in the up position and so that inflatable portion 574 can be deflated and inclined downwardly when the foot section 410 is lowered to the down position to provide room for the lower legs of the person when chair bed 50 is in the sitting position. Foot portion 564 is thinner and shorter when deflated than when foot portion 564 is inflated.

Foot portion 564 of mattress 550 and foot section 410 of articulating deck 402 cooperate to minimize the length of the foot of chair bed 50 as shown in FIG. 30. Foot section 410 and foot portion 564 are a first length 465 when foot section 410 is in the up position and a second length 464 when foot section 410 is in the down position, first length 465 being greater than second length 464. Also, foot portion 564 is a first thickness 608 when foot section 410 is in the up position and a second thickness 609 when foot section 410 is in the down position, first thickness 608 being greater than second thickness 609.

In addition, the width 604 of foot portion 564 of mattress 550 is less than the width 606 of head portion 558 of mattress 550, the width 606 of head portion 558 typically being a standard mattress width as shown in FIGS. 28 and 30. This difference between the widths 604, 606 permits a standard fitted sheet (not shown) to be tightly installed onto mattress 550 while remaining loose adjacent to foot portion 564 so that pressure relief can be maintained in the section of foot portion 564 receiving the heels (not shown) of the person (not shown) supported on sleeping surface 552. The smaller width 604 of foot portion 564, the contraction of foot section 410 and the corresponding contraction of foot portion 564, and the deflation of inflatable portion 574 when inflatable portion 574 is positioned to lie in foot portion 564, all act to minimize the foot of chair bed 50 when the foot section 410 moves from the up position to the down position so that the feet of the person supported on the sleeping surface 552 can reach the floor (not shown) or foot prop 646. The narrow foot section 410 of deck 402 and foot portion 564 of mattress 550 minimizes the width of foot end 54 of deck 402 so that the width of bed 50 adjacent to extended frame 610 is no greater than the width of bed 50 adjacent to body section siderails 812, 814.

C-Arm Access

Use of step deck 412 can additionally improve access of equipment to portions of chair bed 50 as shown in FIG. 29. A C-arm 588 carrying equipment 590, 592 and having equipment 590 positioned to lie above sleeping surface 552 and equipment 592 positioned to lie below step deck 412 can be positioned near chair bed 50. C-arm 588 is C-shaped having an inner surface 594 and a point 596 on inner surface 594 that is the maximum lateral distance on inner surface 594 away from equipment 590, 592. An edge 598 of upper deck 414 is positioned to lie a distance 600 above lower deck 430 of step deck 412. While a conventional deck bottom (not shown) would have an edge (not shown) engaging C-arm 588 away from point 596, edge 598 of step deck 412 engages C-arm adjacent to point 596, thereby maximizing the area of sleeping surface 552 across which equipment 590, 592 can be located.

Additionally, head slat 432 can have a radiolucent portion 510 made from a radiolucent material that is transparent to X-rays thereby permitting X-rays to pass therethrough as shown in FIGS. 28 and 29. Equipment 590, 592 can be radiography equipment used to produce images such as X-ray images or photographs of the person (not shown) on sleeping surface 552. Having step deck 412 arranged to engage point 596 of C-arm 588 maximizes the area of sleeping surface 552 away from edge 598 that equipment 590, 592 can be positioned, thereby maximizing the area of sleeping surface 552 on which the person can be positioned to lie while fluoroscopic procedures are performed on the person.

Extended Frame

An extended frame module 610 can be provided for chair bed 50. Extended frame module 610 includes an extended frame 612 at foot end 54 of chair bed 50 as shown in FIG. 11. Extended frame 612 comprises frame-extender members 614, each frame-extender member 614 having a first end 616 fixed to foot end 54 of weigh frame 506 on each side of chair bed 50. Frame-extender members 614 each extend outwardly away from head end 52 of chair bed 50 and terminate in a second end 618 positioned to lie longitudinally between thigh section 408 and foot end 54 of foot section 410 and along sides 508 of foot section 410.

Extended frame 612 further comprises swing members 620, each swing member 620 having a first end 624 pivotably coupled to second end 618 of frame-extender members 614. Swing members 620 can swing between a tucked position beside frame-extender members 614 and an extended position beside foot section 410 of articulating deck 402 as shown in FIG. 2. Each swing member 620 is preferably provided with a foot safety switch 648 as shown in FIGS. 2 and 11 to prevent entrapment of objects under swing members 620 during movement of intermediate frame 302.

Extended frame 612 additionally comprises a foot gate 622 including swinging gates 626, 634, each swinging gate 626, 634 having a first end 628, 636 rotatably coupled to swing members 620 as shown in FIG. 11. Gates 626, 634 can rotate a full 360 degrees relative to swing members 620. Gates 626, 634 cooperate with swing members 620 to move gates 626, 634 to several positions relative to weigh frame 506. For example, gates 626, 634 can "close" foot end 54 of chair bed 50 as shown in FIG. 1 by moving to a closed position in which gates 626, 634 are positioned to lie transversely across foot end 54 of chair bed 50 having second ends 630, 638 of gates 626, 634 in juxtaposition. Gates 626, 634 provide a protective "crib-like" perimeter when gates 626, 634 are closed and chair bed 50 is in the sitting position.

Foot gate 622 can also be moved to a side-grip position shown in FIG. 2 by first swinging gates 626, 634 inwardly along arc 642 as shown in FIG. 11 so that gates 626, 634 are positioned to lie directly above swing members 620 and then swinging swing members 620 along arc 732 so that swing members 620 and gates 626, 634 are positioned to lie beside frame-extender members 614. Including both fixed frame-extender members 614 and swing members 620 in extended frame 612 allows gates 626, 634 to both close foot end 54 of chair bed 50 while at the same time reducing the radius through which swing members 620 swing when moving from the closed position to the side-grip position. As a result, the space required around chair bed 50 to permit the movement of gates 626, 634 is minimized. Gates 626, 634 are provided with grip handles 632, 640 that provide support for a person on sleeping surface 552 moving from a seated position to a standing position when chair bed 50 is in the sitting position and foot gate 622 is in the side-grip position as shown in FIG. 2.

Gates 626, 634 perform the function of a conventional footboard when gates 626, 634 are closed and chair bed 50 is in the bed position. Gates 626, 634 can swing outwardly from the closed position to an open position having each gate 626, 634 positioned to lie away from foot end 54 of chair bed 50. When gates 626, 634 are in the open position, the caregiver has clear access to foot section 410 of chair bed 50. Additionally, gates 626, 634 act as support aids for the person (not shown) supported by sleeping surface 552 when the person stands or is transferred to a wheelchair (not shown) or other equipment (not shown) when chair bed 50 is in the sitting position, swing members 620 are extended, and gates 626, 634 are angled back toward the person. Also, gates 626, 634 can be removed entirely from foot end 54 of chair bed 50 to clear foot end 54 of chair bed 50 for caregivers and equipment (not shown) when swing members 620 are folded back and gates 626, 634 are folded back. Safety switches (not shown) can be included to limit the articulation of deck 402 and intermediate frame 302 when gates 626, 634 are in selected positions to prevent limb entrapment between gates 626, 634 and either deck 402 or intermediate frame 302.

Typically, extended frame 612 is carried by weigh frame 506. For embodiments of chair bed 50 that do not include weighing capability, extended frame 612 is carried by the common frame, which typically includes intermediate frame 302 and weigh frame 506 fixed together. Weigh frame 506 and the common frame also carry articulating deck 402. Carrying extended frame 612 on weigh frame 506 or the common frame causes extended frame 612 to move with articulating deck 402 when intermediate frame 302 is raised and lowered relative to base frame 62. Consequently, extended frame 612 and gates 626, 634 remain stationary relative to the person (not shown) supported by sleeping surface 552. For example, when chair bed 50 is in the sitting position and extended frame 612 is in the side-grip position, intermediate frame 302 can be raised from the low position to the raised position to help the person to stand. Extended frame 612 is stationary relative to sleeping surface 552 so that the person can use grip handles 632, 640 for support.

Siderail Assemblies

Chair bed 50 is typically provided with siderail assemblies 800, 802, 804, 806 as shown in FIGS. 11 and 31-38 and shown diagrammatically in FIG. 47. Siderail assemblies 800, 802, 804, 806 include head section siderails 808, 810 mounted to head section 404 of articulating deck 402, and body section siderails 812, 814 mounted to weigh frame 506 adjacent to thigh section 408 of deck 402.

Head section siderails 808, 810 are mounted to move with head section 404 as head section 404 pivots relative to weigh frame 506 between the down position and the back-support position as shown in FIGS. 11 and 31-33. Body section siderails 812, 814 are mounted to weigh frame 506 and do not move relative to weigh frame 506 and seat section 406 when head, thigh, and foot sections 404, 408, 410 of articulating deck 402 move. Head section siderails 808, 810 are shorter than body section siderails 812, 814 and extend only adjacent head section 404, whereas body section siderails 812, 814 extend adjacent head and body (seat and thigh) sections 404, 406, 408. Both of the head section and body section siderails 808, 810, 812, 814 are configured to maintain a between-rail gap 866 of approximately 2-3 inches as head section 404 moves between the back-support position and the down position.

In addition, having short head section siderails 808, 810 ideally positions head section siderails 808, 810 to provide support to a person (not shown) entering or exiting chair bed 50 on one of sides 554, 556 when appropriate head section siderail 808, 810 is in the patient-restraining position and body section siderail 812, 814 is in the tucked position. This configuration allows the person to enter and exit by sitting on sleeping surface 552 while holding head section siderail 808, 810 for support, and pivoting off of or onto sleeping surface 552 so that the person does not have to "scoot" along sleeping surface 552. Also, a hip pivot guide 694 on body section siderails 812, 814 helps to optimize the positioning of the hip (not shown) of the person on chair bed 50 after entering chair bed 50 from one of sides 554, 556.

Siderails 808, 810, 812, 814, are passive restraint devices mounted on both sides of chair bed 50 as shown in FIGS. 11, 34, and 35. In the upward patient-restraining position shown in FIGS. 31-34, siderails 808, 810, 812, 814 are vertical barriers that can abut sides 554, 556 of mattress 550 and extending above sleeping surface 552 to restrain movement of the person past sides 554, 556 of sleeping surface 552. Siderails 808, 810, 812, 814 may also be lowered below sleeping surface 552 of mattress 550 to a tucked position shown in phantom in FIG. 35 beneath side portions 418, 420, 422, 424, 426, 428 of upper deck 414 to permit the person to move past sides 554, 556 of sleeping surface 552 when entering or exiting chair bed 50. Lowering siderails 808, 810, 812, 814 also provides the caregiver with clear access to the patient.

Lowering each siderail 808, 810, 812, 814 is accomplished by pulling release handle 862 as shown in FIGS. 34 and 35. After pulling release handle 862, the caregiver may let go of release handle 862 and allow siderail 808, 810, 812, 814 to rotate downwardly into the tucked position. The rate at which each siderail 808, 810, 812, 814 rotates downwardly is preferably controlled by a mechanical damper 868. To raise siderails 808, 810, 812, 814, the caregiver pulls up on siderails 808, 810, 812, 814 until they lock in the patient-restraining position. Siderail assemblies 800, 802, 804, 806 are configured so that siderails 808, 810, 812, 814 are generally vertical and generally parallel to the sides of chair bed 50 at all positions between the tucked position and the patient-restraining position as shown in FIGS. 34 and 35.

Siderail assemblies 800, 802, 804, 806 are of similar construction. The principles discussed below with respect to body section siderail assembly 806 pertains to each siderail assembly 800, 802, 804, 806 unless the description herein specifically states otherwise.

Siderail assembly 806 includes body section siderail 814, a siderail mounting mechanism 816, and a mounting bracket 818 connecting mounting mechanism 816 to sides 508 of weigh frame 506 as shown in FIGS. 34 and 35. Mounting bracket 818 is positioned to lie beneath upper deck 414 and is attached to weigh frame 506 as shown in FIGS. 34 and 35. Similarly, head section siderail assemblies 800, 802 are connected to walls 442, 444 of head section 404, and body siderail assembly 804 is connected to side 508 of weigh frame 506 as shown in FIG. 11.

Mounting bracket 818 includes an upstanding support wall 820 attached to wall 508 of weigh frame 506 and outwardly extending walls 822 attached thereto and attached to weigh frame 506 as shown in FIGS. 34 and 35. Walls 822 of mounting bracket 818 are formed to include upper openings 824 and lower openings 826. Siderail mounting mechanism 816 is a parallelogram connecting mechanism that connects siderail 814 to mounting bracket 818 for movement between the patient-restraining position and the tucked position while maintaining siderail 814 in a generally vertical orientation. Siderail mounting mechanism 816 includes three curved parallel bars 828, 830, 832 having first ends 834, 836, 838, and second ends 840, 842, 844. Curved bar 830 is laterally positioned to lie between curved bars 828, 832 and vertically positioned to lie above curved bars 828, 832. Bracket mounting pins 848 are appended to a first end 836 of curved bar 830 and are rotatably received by upper openings 824 of walls 822. Bracket mounting pins 846, 850 are appended to first ends 834, 838 of curved bars 828, 832 and are rotatably received by lower openings 826 of walls 822. Curved bars 828, 830, 832 are mounted to pivot relative to weigh frame 506.

Curved bars 828, 830, 832 each include a first section extending perpendicular to and above upper deck section 428 and a second section extending transverse to the first bar section below upper deck section 428 when siderail 814 is in the patient-restraining position as shown in FIG. 34. This curved structure in combination with the raised pivot connection to step deck 412 allows siderail 814 to be raised above bottom surface 586 of mattress 550 while being immediately adjacent sides 578 with minimum gap.

Siderail 814 is also formed to include upper openings 852 and lower openings 854 as shown in FIGS. 34 and 35. Siderail mounting pins 858 are appended to second end 842 of curved bar 830 and are received by upper openings 852 of siderail 814. Siderail mounting pins 856, 860 are appended to second ends 840, 844 of curved bars 828, 832 and are received by lower openings 854 of siderail 814. Curved bars 828, 830, 832 are mounted to pivot relative to siderail 814. Upper and lower openings 824, 826 of mounting bracket 818 are spaced apart and upper and lower openings 852, 854 of siderail 814 are spaced apart an equal amount so that curved bars 828, 830, 832 are positioned in parallel relation between siderail 814 and mounting bracket 818.

Siderail 814 can thus rotate between an upper patient-restraining position abutting side 556 of mattress 550 as shown in FIG. 34 to a tucked position beneath section 428 of upper deck 414 shown in FIG. 35 (in phantom). Parallel curved bars 828, 830, 832 cooperate with upper and lower openings 824, 826 of mounting bracket 818 and upper and lower openings 852, 854 of siderail 814 to keep siderail 814 generally parallel to wall 452 of step deck 412 and generally perpendicular to sleeping surface 552 as siderail 814 rotates between the patient-restraining position and the tucked position.

Siderail assembly 806 also includes a latching mechanism 870 including a release handle 862 rotatably mounted to curved bars 828, 832 for movement between a forward latched position shown in FIG. 34 and a rearward released position shown in FIG. 34 (in phantom). Latching mechanism additionally includes links 872 and latches 878, each link having a first end 874 pivotably connected to release handle 862 and a second end 876 that is pivotably connected to a latch 878. Each latch 878 is formed to include a first end 880 that is pivotably connected to curved bars 828, 832, a second end 882 spaced apart from first end 880, a rod-gripper recess 884 adjacent to second end 882, and a spring-receiving opening 886 spaced apart from both ends 880, 882 of latch 878.

Tension springs 888 each have a first end 890 connected to spring-receiving openings 886 of latches 878 and a second end 892 connected to brackets 894 fixed to curved bars 828, 832 as shown in FIG. 34. As release handle 862 is pulled outwardly by the caregiver, release handle 862 pulls links 872 outwardly and upwardly which in turn pull latches 878 upwardly to pivot latches 878 against the bias of springs 888.

A rod 896 is connected to walls 822 of mounting bracket 818 and is arranged to be received by rod-gripper recesses 884 when siderail 814 is in the patient-restraining position shown in FIG. 34 so that rod 896 and latches 878 cooperate to retain siderail 814 in the patient-retraining position. When release handle 862 is pulled outwardly, as shown in phantom in FIG. 34, latches 878 disengage from rod 896, thereby allowing siderail 814 to rotate downwardly as shown in FIG. 35 until siderail 814 reaches the tucked position beneath upper deck 414 of articulating deck 402, as shown for siderail 808 in FIG. 1 and siderail 814 in FIG. 35 (in phantom).

To raise siderail 814, the caregiver simply lifts siderail 814 to rotate siderail 814 upwardly to the patient-restraining position. Each latch 878 has second end 882 having a camming surface 898 as shown in FIGS. 34 and 35 that engages rod 896. As siderail 814 advances toward the patient-restraining position, camming engagement of camming surfaces 898 and rod 896 forces latches 878 to pivot upwardly against the bias of springs 888. Latches 878 ride over rod 896 as siderail 814 advances to the patient-restraining position until rod 896 is adjacent to rod-gripper recesses 884. Springs 888 then pull latches 878 downwardly to capture rod 896 in rod-gripper recesses 884, thereby holding siderail 814 in the patient-restraining position.

Siderail 814 cooperates with siderail mounting mechanism 816 to control the gap between mattress 550 and siderail 814. Because siderail 814 rotates upwardly from the tucked position to the patient-restraining position toward side 556 to abut side 556 of mattress 550, a gap that could form between mattress 550 and siderail 814 is minimized. Additionally, siderail 814 cooperates with step deck 412 to minimize the distance between a bottom 864 of siderail 814 and section 428 of upper deck 414, further maximizing the effectiveness of siderail 814 as a passive restraint. In addition, siderail mounting mechanism 816 provides a one-step release and auto-tuck movement as siderail 814 rotates from the patient-restraining position to the tucked position.

Each siderail assembly 800, 802, 804, 806 operates in a manner similar to siderail assembly 806 described above to move siderails 808, 810, 812, 814 between the tucked position and the patient-restraining position. Head section siderails 808, 810 can additionally be provided with breakaway siderails 920 that move from the tucked position to a generally vertically downwardly extending down-out-of-the-way position described below.

Breakaway Siderails

Figure 36:
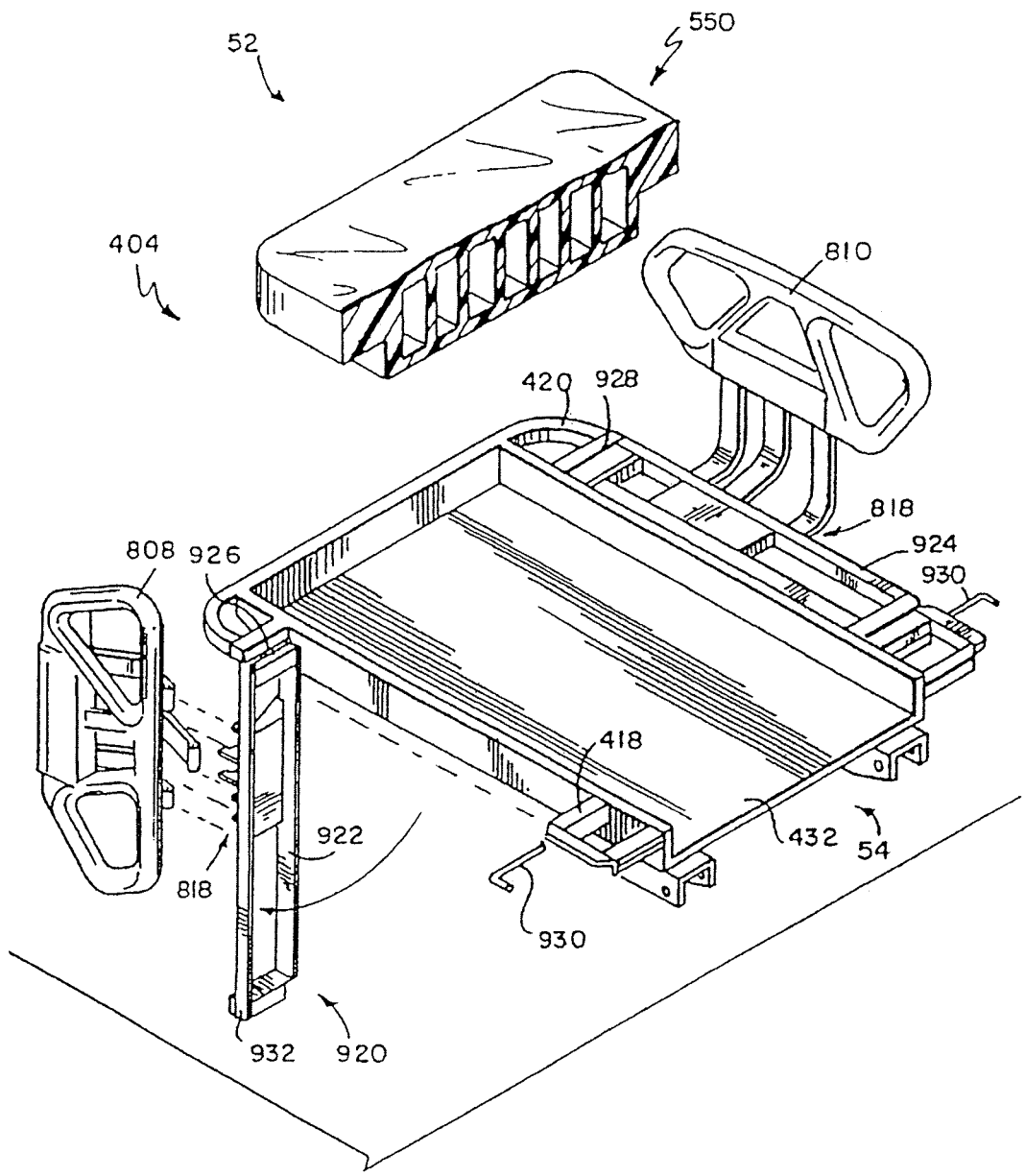
FIG. 36 is an exploded view of a head section of an articulating deck of the chair bed of FIG. 1 including a breakaway siderail.

Breakaway siderails 920 allow the caregiver to move the siderail assemblies from the generally horizontal tucked position to a generally vertically downwardly extending down-out-of-the-way position to provide clear access to chair bed 50 beneath intermediate frame 302 as shown in FIG. 36 and also to provide clear access beneath intermediate frame 302 for equipment mounted on a C-arm. Breakaway siderails 920 accomplish this by moving the siderail to a down-out-of-the-way position away from the side of chair bed 50 and by narrowing the width of the section of chair bed 50 adjacent to the siderail for deeper C-arm insertion.

When chair bed 50 is provided with breakaway siderails 920, head section upper deck side portions 418, 420 include collateral head frames 922, 924 as shown in FIG. 36. Each collateral head frame 922, 924 is pivotably mounted to upper deck side portion 418, 420 by a hinge 926, 928. Each collateral head frame 922, 924 can swing between an up position, as shown, for example, by collateral head frame 924 in FIG. 36, and a generally vertically downwardly extending down-outof-the-way position, as shown, for example, by collateral head frame 922 in FIG. 36. Preferably, hinges 926, 928 are connected to head end 52 of collateral head frames 922, 924 so that collateral head frames 922, 924 are adjacent to head end 52 of chair bed 50 when collateral head frames 922, 924 are in the down-out-of-the-way position. Each collateral head frame 922, 924 can be locked into the up position by a pin 930 configured to be received by an opening (not shown) in upper deck side portion 418, 420 and an opening 932 in collateral head frame 922, 924.

Mounting brackets 818 are fixed to collateral head frame 922, 924 and are configured to move with collateral head frames 922, 924 so that siderails 808, 810 swing between the generally horizontal tucked position and the generally vertically downwardly extending down-out-of-the-way position when collateral head frames 922, 924 move between the up position and the down-out-of-the-way position as shown in FIG. 36. When a caregiver wishes to move head section siderails 808, 810 to the down-out-of-the-way position, such as when preparing chair bed 50 for use during a procedure including the use of equipment mounted on a C-arm, the caregiver can raise intermediate frame 302 to the raised position, rotate the appropriate head section siderail 808, 810 to the tucked position, remove pin 930 from opening 932 in collateral head frame 922, 924 and from the opening (not shown) in upper deck side portions 418, 420, and swing siderail 808, 810 from the tucked position to the down-out-of-the-way position.

Mechanical Angle Indicators

Figure 37:
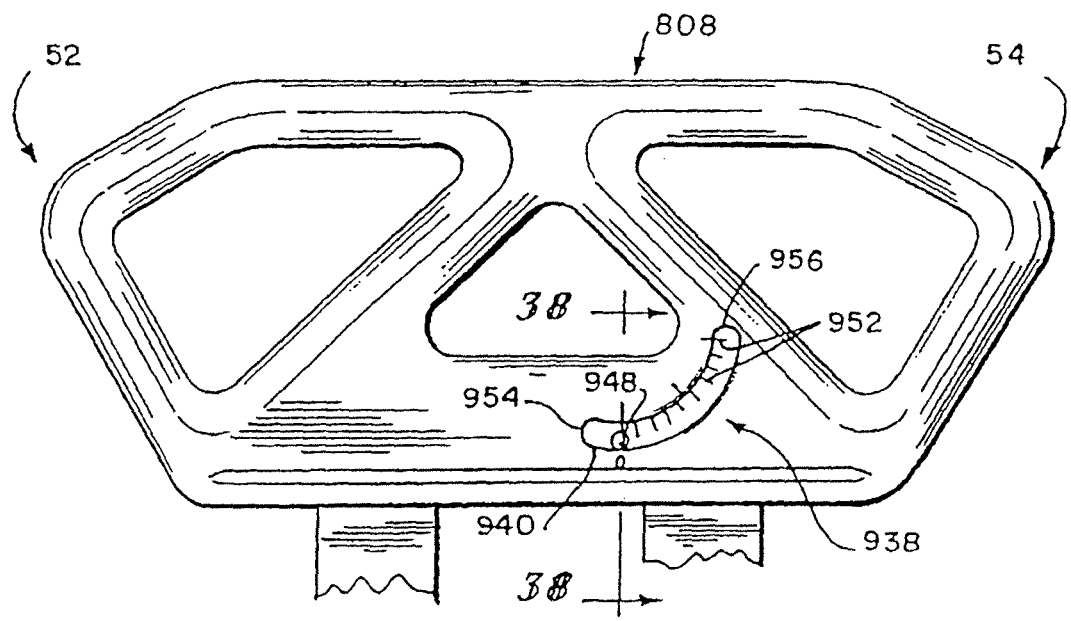
FIG. 37 is a front elevation view from outside of the bed of a head section siderail in accordance with the present invention having a mechanical angle indicator.
Figure 38:
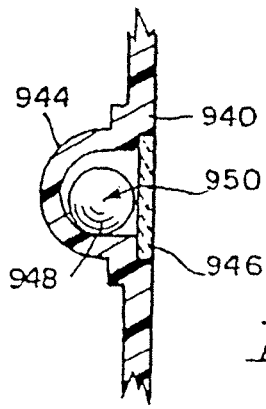
FIG. 38 is a sectional view taken along line 38-38 of FIG. 37 showing the mechanical angle indicator.
Figure 39:
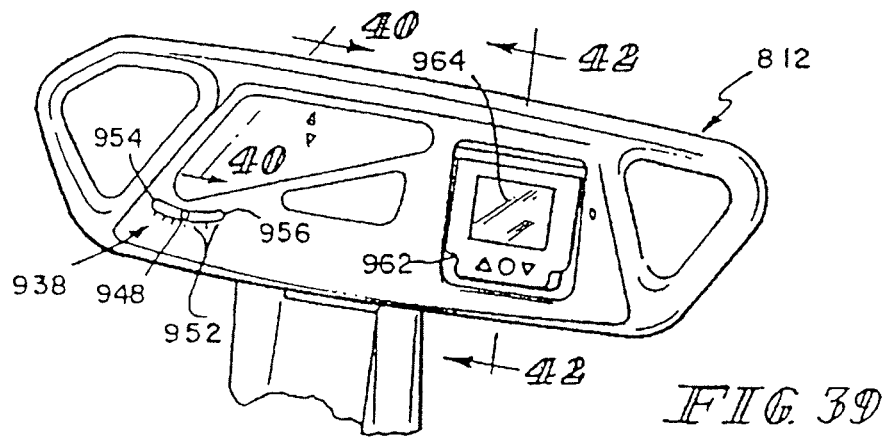
FIG. 39 is a perspective view from outside of the bed of a body section siderail in accordance with the present invention having a mechanical angle indicator and a pivotable display.

Siderails 808, 810, 812, 814 can additionally be provided with angle indicators 938 as shown, for example, in FIGS. 37-39. Head section siderails 808, 810 include indicators 938 as shown in FIG. 37 that generally indicate the angular orientation of head section 404 of deck 402, and body section siderails include angle indicators 938 as shown in FIG. 39 that generally indicate the angular orientation of intermediate frame 302 relative to base frame 62. Thus, angle indicators 938 on body section siderails 812, 814 are sometimes referred to as Trendelenburg indicators or Trend indicators. Mounting angle indicators 938 on siderails 808, 810, 812, 814 prominently displays angle indicators 938 so that the caregiver can quickly and easily judge the status of chair bed 50.

Each angle indicator 938 includes a housing 940 having an interior region 942 defined by a rear wall 944 formed in siderail 808, 810, 812, 814 and a front wall 946 connected to siderail 808, 810, 812, 814 as shown in FIG. 38. An indicator member 948 is received by interior region 942 for movement therein relative to housing 940 as the angular orientation of siderail 808, 810, 812, 814 and angle indicator 938 changes. The position of indicator member 948 relative to housing 940 indicates the angular orientation of angle indicator 938. Housing 940 can be formed so that rear wall 944 is arcuate across the face of siderail 808, 810, 812, 814 as shown in FIG. 37 and indicator member 948 can be spherical and can be positioned to lie on and to roll along arcuate rear wall 944 as the angular orientation of angle indicator 938 changes.

Preferably, indicator member 948 includes an indicator surface 950 that is visible through front wall 946 of housing 940. Markings 952 that are stationary relative to housing 940 can be positioned to lie adjacent to front wall 946 so that markings 952 and indicator member 948 cooperate to indicate the position of indicator member 948 relative to housing 940, thus indicating the angular orientation of siderails 808, 810, 812, 814.

Angle indicator 938 mounted to head section siderail 808, 810 includes a first end 954 positioned to lie toward head end 52 of siderail 808, 810 and a second end 956 positioned to lie toward foot end 54 of siderail 808, 810 and positioned vertically higher than first end 954 as shown in FIG. 37. When head section 404 is in the down position, shown in FIG. 37, indicator member 948 is toward first end 954. When head section 404 moves from the down position to the back-support position, indicator member 948 moves from first end 954 toward second end 956. Indicator member 948 is infinitely positionable relative to housing 940 between first end 954 and second end 956 and the positions of indicator member 948 correspond to positions of head section 404 between the down position and the back-support position.

Angle indicator 938 mounted to body section siderail 812, 814 is substantially identical to angle indicator 938 on head section siderail 808, 760, except that first and second ends 954, 956 are positioned to lie on generally the same horizontal plane as shown in FIG. 39. When intermediate frame 302 is generally horizontal, body section siderail 812, 814 is generally horizontal and indicator member 948 is positioned to lie generally half-way between first end 954 and second end 956. When intermediate frame 302 moves to the Trendelenburg position, intermediate frame 302, body section siderail 812, 814, and angle indicator 938 move so that indicator member moves toward first end 954 of housing 940. When intermediate frame 302 moves to the reverse Trendelenburg position, body section siderail 812, 814 and angle indicator 938 move so that indicator member moves toward second end 956 of housing 940. Indicator member 948 is infinitely positionable relative to housing 940 between first end 954 and second end 956 and the positions of indicator member 948 correspond to positions of intermediate frame 302 between the Trendelenburg position and the reverse Trendelenburg position.

Alternatively, an angle indicator can be a spirit level having a housing filled with a fluid to form a liquid-filled bulb type bubble spirit level. In such a spirit level, the position of the bubble relative to the housing changes as the angular orientation of the spirit level changes, the position of the bubble relative to the housing indicating the angular orientation of the spirit level.

Controls on Siderails

Figure 40:
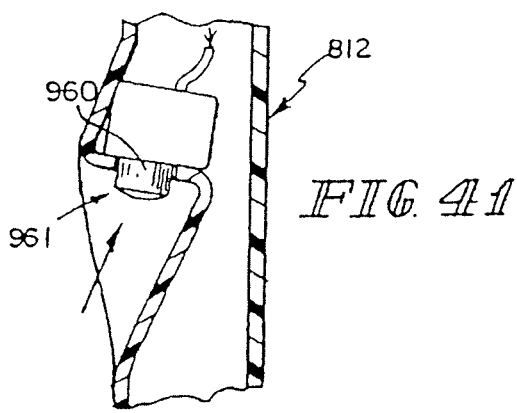
FIG. 40 is a sectional view taken along line 40-40 of FIG. 39 showing the pivotable display.
Figure 41:
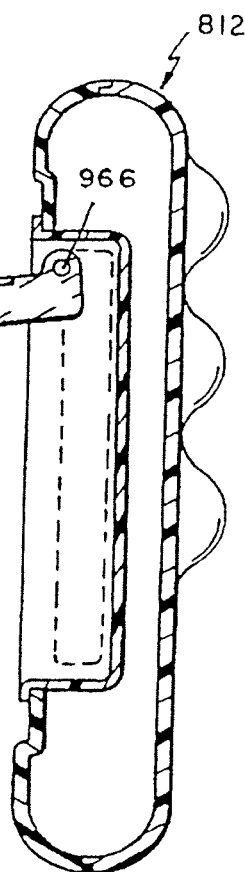
FIG. 41 is a sectional view taken along line 41-41 of FIG. 39 showing the patient control buttons on the inside of the siderail.

Siderails 808, 810, 812, 814 can additionally be provided with controls for operating bed 50 and moving bed 50 to various positions. Controls can include control buttons 960 on a bed side of the siderail 960 for use by a person (not shown) on sleeping surface 550 as shown in FIGS. 40 and 41. Typically, the person's head will rest on head end 52 of sleeping surface 550. To accommodate the person on sleeping surface and allow the person to easily locate and view control buttons 960, control buttons 960 can be angled toward head end 52 of deck 402 as shown in FIGS. 40 and 41 so that faces 961 of buttons 960 are toward head end 52 of deck 402. Bed 50 can also be provided with a second plurality of control buttons (not shown) on an outside of the siderail for use by a person outside of bed 50 as described below.

Figure 42:
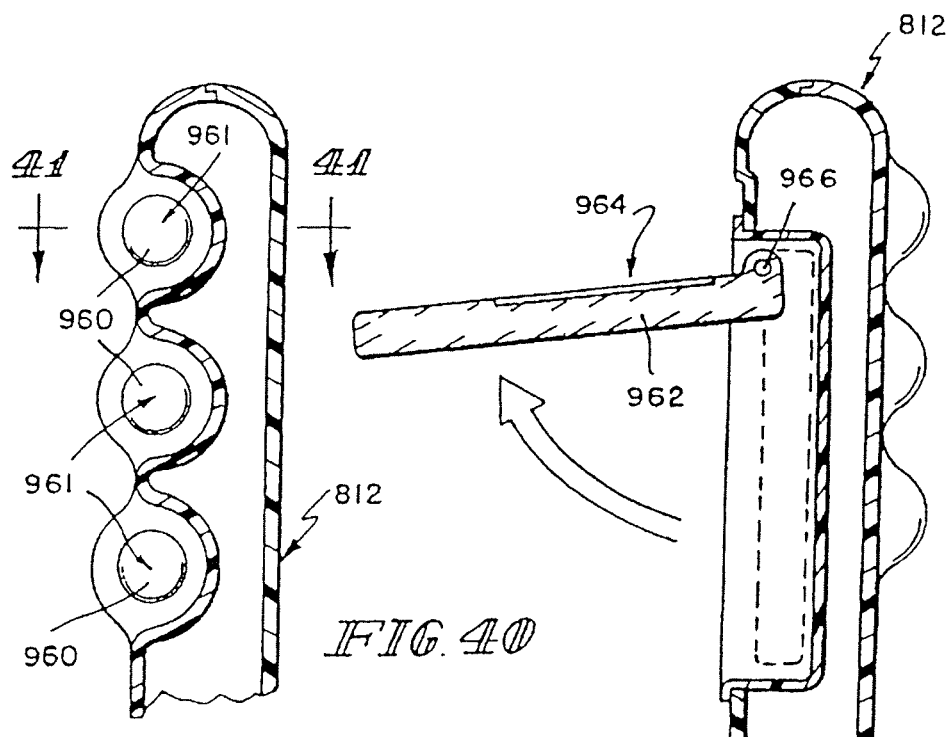
FIG. 42 is a sectional view taken along line 42-42 of FIG. 41 showing the patient control buttons.

Siderail 812 is coupled to the side of deck 402 for movement between the patient-restraining position and the tucked position. A pad 962 having a display screen 964 can be provided on a side of siderail 812 outside of bed 50 as shown in FIGS. 39 and 42 for use by the caregiver. Preferably, pad 962 is mounted to siderail 812 to pivot outwardly for easy viewing of display screen 964 as shown in FIG. 42. For example, pad 962 can be mounted to the outside of siderail 812 and can be configured to pivot upwardly about a pivot axis 966 adjacent to the top of pad 962. This movement of pad 962 particularly allows for easy viewing of display screen 964 by a person standing next to the bed 50 even when siderail 812 is in the tucked position.

Figure 48:
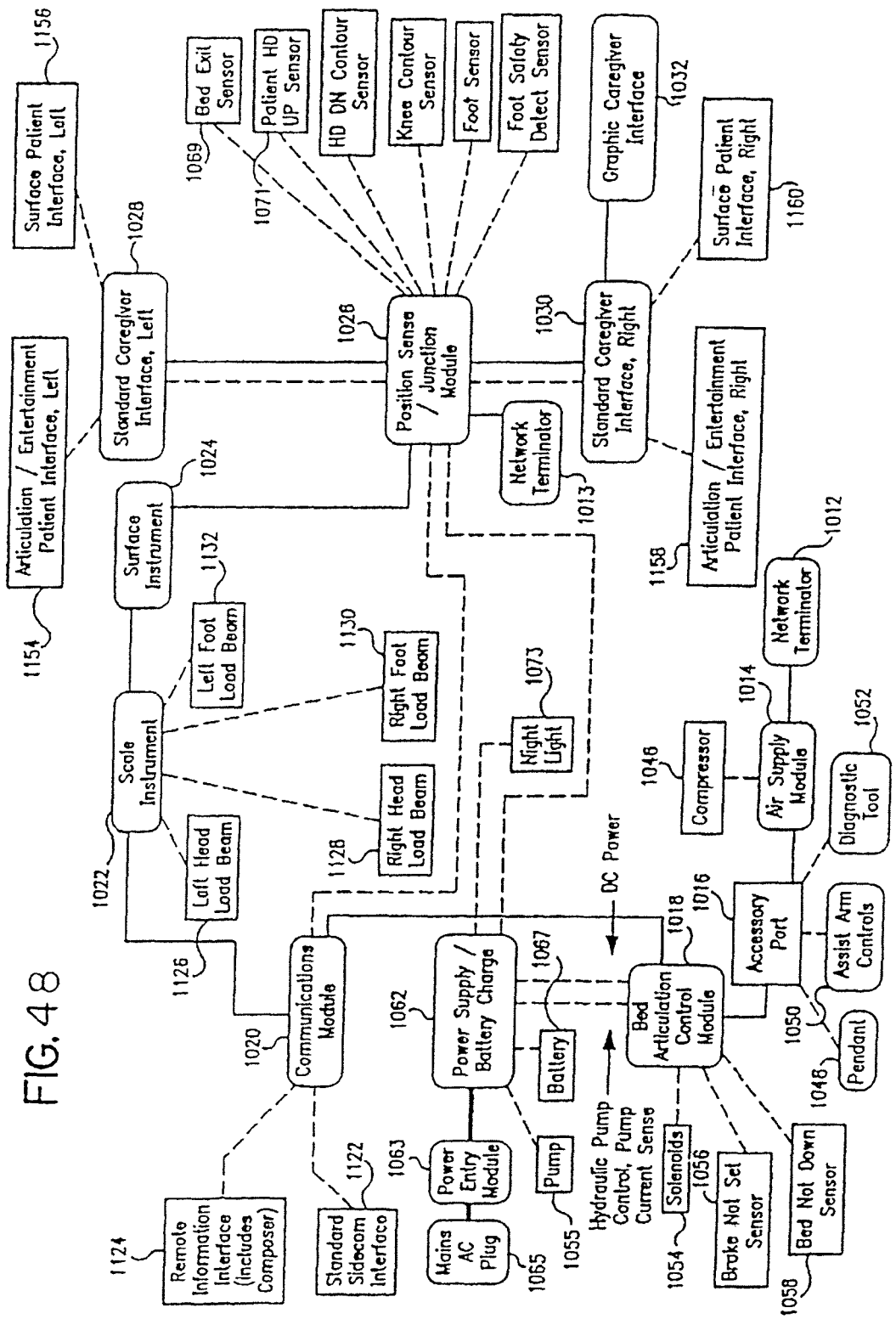
FIG. 48 is a block diagram illustrating the electronic control modules of the present invention connected in a peer-to-peer network configuration and illustrating the additional system components which are coupled to the various modules by discrete electrical connections.

FIG. 48 is a block diagram illustrating the plurality of electronic control modules for controlling operation of the hospital bed. As discussed above, the plurality of modules are electrically coupled to each other using a twisted pair network channel in a peer-to-peer configuration. The peer-to-peer network extends between first and second network terminators 1012 and 1013. The network connections are illustrated by the solid black lines in FIG. 48. Discrete connections to each of the modules are illustrated by the dotted lines in FIG. 48. The bold line of FIG. 48 illustrates an AC power connection.

Network terminator 1012 is coupled to an air supply module 1014. Air supply module 1014 is coupled via the network cable to accessory port module 1016. Accessory port module 1016 is coupled to the bed articulation control module (BACM) 1018. BACM 1018 is coupled to a communications module 1020. Communications module 1020 is coupled to scale instrument module 1022. Scale instrument module 1022 is coupled to surface instrument control module 1024. Surface instrument module 1024 is coupled to position sense and junction module 1026. Position sense module 1026 is coupled to the network terminator 1013. A left side standard caregiver interface module 1028 is also coupled to the network by a connection in position sense module 1026. The right side standard caregiver interface module 1030 and the graphic caregiver interface module 1032 are also coupled to the network using a connection in the position sense module 1026.

It is understood that the modules can be rearranged into a different position within the peer-to-peer network. The modules are configured to communicate with each other over the network cable without the requirement of a master controller. Therefore, modules can be added or removed from the network without the requirement of reprogramming or redesigning a master controller. The network recognizes when a module is added to the network and automatically enables a control interface such as graphic caregiver interface module 1032 to display specific module controls for the added module. This eliminates the requirement for controls on individual modules. The module recognition feature is discussed in detail below.

Each module is connected to its appropriate sensors and actuators so that it can perform its dedicated function. The following is a brief description of each electronic module:

Power for the communication network is supplied by a power supply and battery charge module 1062. Power supply 1062 is coupled to a power entry module 1063 and an AC main plug 1065. Power Supply/Battery charge module (PSB) 1062 converts the AC Mains input 1065 to DC levels to be used by the electronic modules. PSB 1062 contains filtering for the AC Mains 1065 at the Mains entry point 1063. The PSB 1062 also provides power for limited bed functionality upon removal of the AC Mains power input via a battery 1067. The PSB 1062 contains an automatic battery charging circuit with output to indicate battery status (i.e., battery dead, battery low, battery OK). PSB 1062 also controls the hydraulic pump 1055.

Bed Articulation Control Module (BACM) 1018—The BACM 1018 primarily controls the hydraulic system used to articulate the bed. BACM 1018 accepts inputs from various user interfaces located throughout the bed to control bed articulations. This control input is qualified with a position sensing input representing the actual locations of the bed deck sections, along with patient lockout controls, to determine whether the bed should articulate. The BACM 1018 is present in every bed. BACM includes a real time clock circuit to set the time for various other modules.

Position Sense module 1026 detects the angles of all the appropriate bed deck sections. In addition, it interfaces to the bed exit detect, and the four (4) siderail UP sensors. The position sense module 1026 outputs this information to the network. These functions may be incorporated into the BACM 1018 and Bed-Side Communications Interface module 1020. The position sense module 1026 also provides the interconnections of the bed network and hospital communications links to the siderail standard caregiver interface 1028 and 1030 modules.

Siderails (SIDE)—The siderails will contain standard caregiver interface modules 1028 and 1030 consisting of input switch controls, output status indicators, and an audio channel. The standard caregiver interface modules 1028 and 1030 are coupled to patient control mechanisms for bed articulations, entertainment, surface, lighting, Bed Exit, and Nurse Call.

Scale Instrument Module 1022 translates the signals from the embedded load beams into actual weight measured on the weigh frame. Scale module 1022 outputs this weight to the Graphic Caregiver Interface Module (GCI) 1032 for display purposes. This weight is also available to the communications module 1020 for transmittal to the hospital information network. Scale module 1022 includes Bed Exit and weight gain/loss alarm detection capability.

Surface Instrument Module 1024 controls the dynamic air surface. It will accept input from the GCI 1032 to dictate system performance characteristics. Surface module 1024 uses the GCI 1032 to display outgoing system information. Surface instrument module 1024 also interfaces with the air supply module 1014 to control the air handling unit 1046.

Sequential Compression Device (SCD)—This module will control the optional compression boots. It will use the GCI 1032 for interfacing to the caregiver.

Graphic Caregiver Interface Module (GCI) 1032 controls the scale 1022 and surface module 1024 (including SCDs). In addition, GCI 1032 provides control input and text and graphic output capability for future design considerations. GCI 1032 utilizes a graphic display along with a software menu structure to provide for full caregiver interaction.

Communications module 1022 is the gateway between the patient's environment controls and bed status information residing on the bed, and the hospital information/control network.

Bed Exit Sensor (BES) 1069 exists on non-scale beds. The BES connects to the position sense module 1026 to detect a patient bed exit.

Brake-Not-Set Sensor (BNS) 1056 detects the state of the Brake/Steer Pedal. It is connected to the BACM 1018.

Bed-Not-Down Sensor (BND) 1058 detects if the bed is fully down (both Head and Foot Hilo). It is connected to the BACM 1018.

Siderail Up Detect Sensors (SUD) 1071 consists of four switches to detect the secure UP position of the siderails. The SUD 1071 is connected to the position sense module 1026.

Night Light 1073 is a stand alone unit providing the night light function. It is powered by low voltage AC coming from the Power Supply/Battery module 1062.

Pendant 1048 provides for bed articulation control input through accessory port module 1016.

Patient Assist Arm Control 1050 is a functional equivalent of the standard caregiver interface modules 1028 and 1030 controls in a different physical embodiment. The assist arm includes a control pad coupled to the accessory module 1016.

The air supply module 1014, the bed articulation control module 1018, the power supply module 1062, and the power entry module 1063 are all coupled to the base frame of the hospital bed. The communications module 1020, the scale instrument 1022, and the remote information interface 1124 are all coupled to the intermediate frame. The left standard caregiver interface 1028 and patient interfaces 1154 and 1156 are all coupled to the left siderail. The right standard caregiver interface 1030 and patient interfaces 1158 and 1160 are all coupled to the right siderail. Graphical caregiver interface module 1032 may either be coupled to the left siderail or the right siderail. The position sense module 1026 and surface module 1024 are each coupled to the weigh frame. It is understood that the position of each module can be changed.

Figure 49:
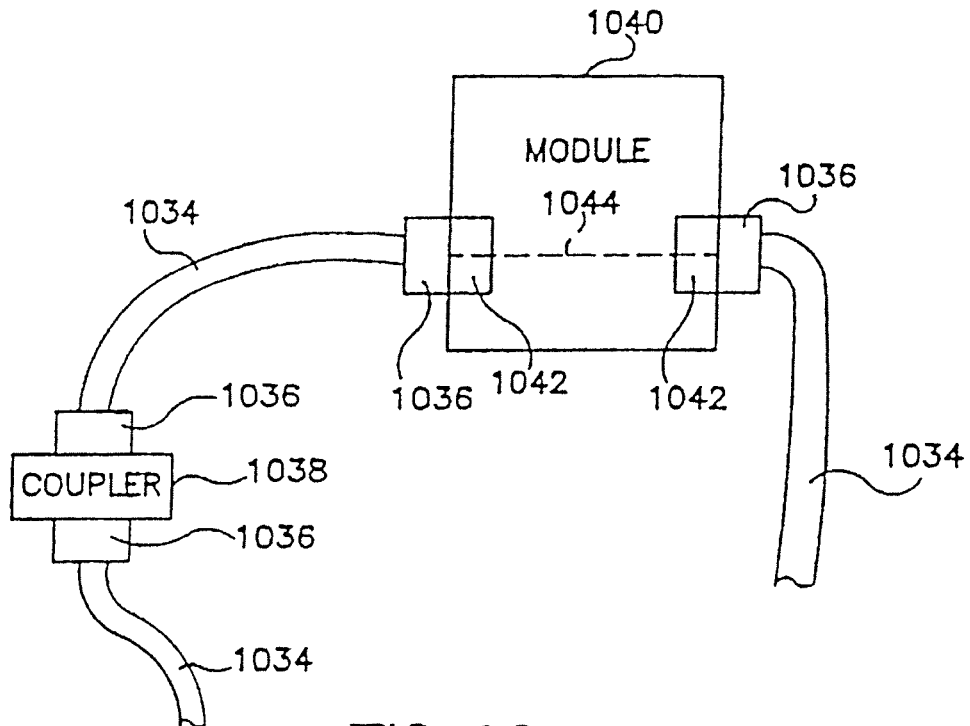
FIG. 49 is a diagrammatical view illustrating the electrical connection from the communication network cable to a selected module and illustrating a coupler between a pair of network connectors to facilitate adding another module to the network.

FIG. 49 diagrammatically illustrates how the various modules are added and removed from the network. The electronic network uses an Echelon LonTalk serial communications protocol for module to module communication in the bed. The cable 1034 illustrated in FIG. 49 contains power and a twisted pair connection. The preferred protocol is RS-485 with a transmission speed of 78 kbs. The cable 1034 is provided with connectors 1036. Extra connectors 1036 are provided for module additions. When the connectors 1036 are not coupled to a module, a coupler 1038 is provided to interconnect adjacent connectors 1036. In order to connect a particular module 1040 to the network, the coupler 1038 is removed and connectors 1036 are coupled to mating connectors 1042 of the module 1040. Connectors 1042 are electrically coupled within the module 1040 as illustrated by dotted line 1044.

Referring again to FIG. 48, air supply module 1014 is coupled to an air handling unit 1046 by a discrete electrical connection. Air supply module 1014 controls compressor 1046 to inflate and deflate the mattress surface of the bed as discussed in detail below (or in main application).

The accessory port module 1016 provides connections to the network for a pendant 1048, an assist arm control 1050, or a diagnostic tool 1052. Pendant 1048 is a hand held control unit which is movable from bed to bed. Therefore, pendant 1048 may be coupled and uncoupled from accessory port module 1016 to control various functions of the bed. For example, the accessory port module 1016 can communicate with BACM 1018 to control movement of the bed. Assist arm controls 1050 provide input to accessory port module 1016 from a control pad coupled to an assist arm extending out over the patient support surface of the bed. The assist arm 1050 can be used to control movement of the bed, as well as for other desired functions. The pendant 1048 and assist arm control 1050 may include all the controls of the right and left standard caregiver interface modules discussed below.

Diagnostic tool 1052 is used for servicing the bed, either at the bed site or from a remote location. A modem is coupled to accessory port module 1016 to provide a telephone line connection to the hospital bed. This permits information related to the bed from any module to be retrieved from the peer-to-peer network at a remote location. For instance, the amount of time that the surface of the bed is in use may be detected at the remote location through the modem for billing purposes. The diagnostic tool 1052 permits a remote operator to interrogate every module of the electrical control network. The diagnostic tool 1052 checks application dependent parameters, runs each of the modules through a test procedure, and fully accesses all network information. Diagnostic tool 1052 may be a hand held tool such as a lap top computer which is coupled directly to accessory port module 1016. In addition, a remote computer can be coupled to accessory port 1016 with the modem link to provide a data link to the network. A Voice Mate™ control system available from Hill Rom, Inc. may also be coupled to accessory port module 1016 to control the bed.

The bed articulation control module (BACM) 1018 is the module that controls movement of the bed. BACM 1018 controls actuation of a plurality of solenoids 1054 which open and close valves coupled to hydraulic cylinders to move the articulating deck sections of the hospital bed relative to each other. BACM 1018 is also coupled to a Break Not Set sensor 1056 and a Bed Not Down sensor 1058. When BACM 1018 receives an input signal from the network requesting movement of the bed to a predetermined position, the BACM 1018 first reads the position of the bed provided from position sense module 1026. If movement of a portion of the bed is necessary, BACM 1018 checks for a lockout signal from the left and right standard caregiver interface modules 1028 and 1030. If the lockouts are not set, BACM 1018 controls activation of the selected solenoid 1054 and then BACM 1018 turns on the hydraulic pump 1055 (gravity may also be used if appropriate) to actuate a selected cylinder if necessary.

Figure 50:
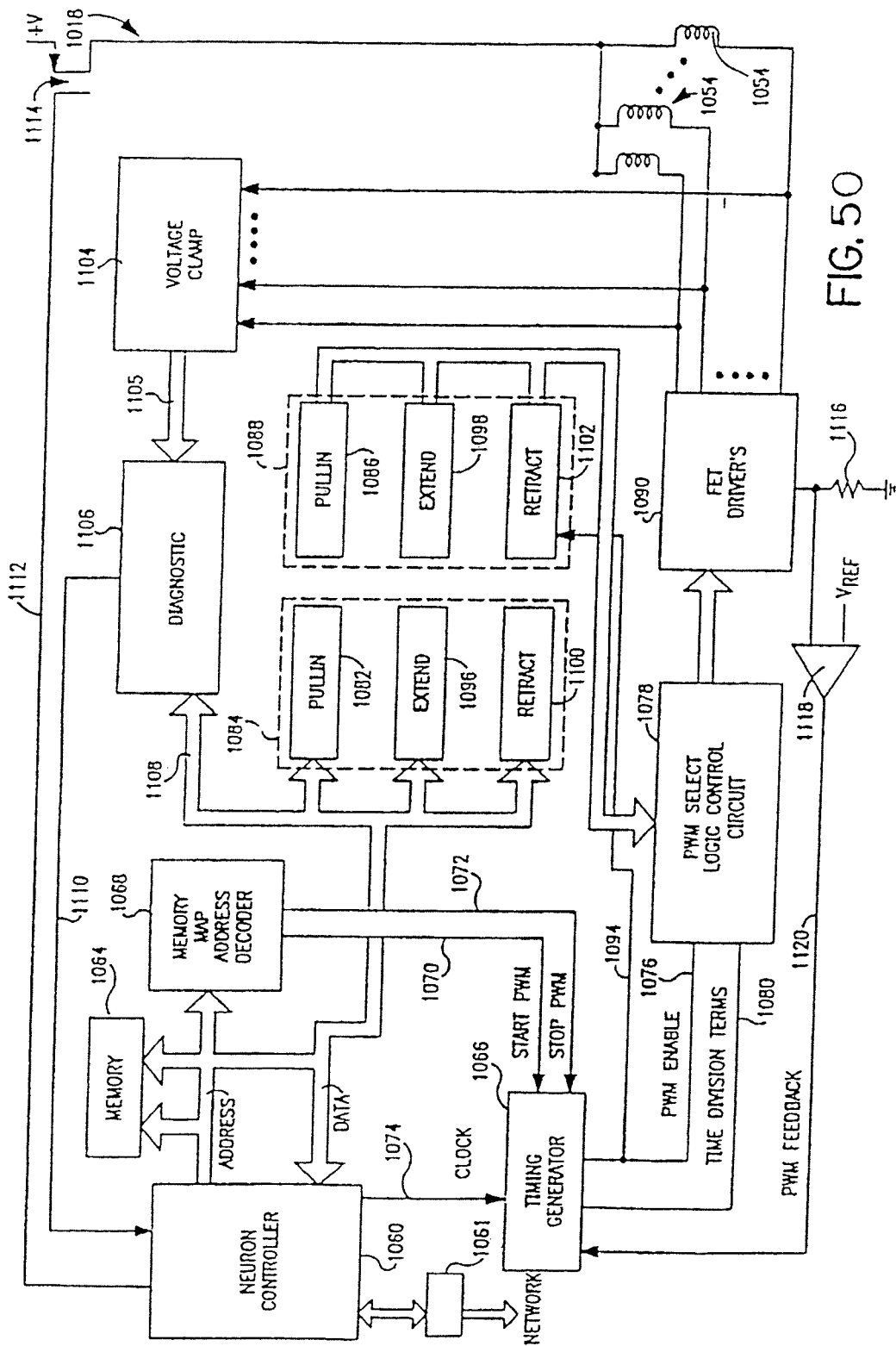
FIG. 50 is a schematic block diagram illustrating the electronic components of a bed articulation control module.

Details of the BACM 1018 are illustrated in FIG. 50. BACM 1018 includes a neuron controller 1060. Illustratively, neuron controller 1060 is a MC143150FU echelon neuron networking microprocessor available from Motorola. Controller 1060 is coupled to the network through an RS-485 transceiver 1061. BACM 1018 operates to move a plurality of solenoids 1054 in a hydraulic manifold to open and close control valves coupled to the hydraulic cylinders and articulate the bed based on various network commands received from the peer-to-peer network. Neuron controller 1060 receives commands from the right and left siderail standard caregiver interface modules 1028 and 1030, the graphic caregiver interface 1032, or from another input device to articulate the bed. Neuron controller 1060 also receives other information from the network regarding the position of the head, seat, thigh, and foot deck sections of the articulating deck of the bed. Therefore, neuron controller 1060 controls the solenoids and pump to stop articulating the bed as a limit is reached or when the particular bed section reaches its desired or selected position.

Both the articulating deck of the bed and the height of the deck are controlled by the BACM 1018. Upon receiving a bed function command from the network, the BACM 1018 energizes the appropriate solenoids and provides a control signal to the Power Supply/Battery Module 1062 illustrated in FIG. 48 to power the hydraulic pump, if necessary. BACM 1018 may use bed position information provided by the remotely mounted bed position transducers. Alternatively, the position of the various sections of the articulating deck may be supplied to BACM 1018 by the position sense module 1026. BACM 1018 also instructs air supply module 1014 and surface control module 1024 via the network to partially deflate a seat section and a foot section of the mattress when the bed moves to a chair position. BACM 1018 also receives lockout information from the siderail standard caregiver interface modules 1026 and 1028 to determine whether or not a particular section of the articulating deck should move.

Neuron controller 1060 executes code stored in EPROM 1064. Illustratively, EPROM 1064 is a 27C256-70 EPROM available from AMD. In order to conserve power, BACM 1018 uses a pulse width modulation (PWM) control system to minimize the current draw required to actuate the solenoids 1054. Conventional control systems simply turn the solenoid 1054 full on or full off and, as the voltage varies, current consumption goes up and down accordingly. With the PWM control design of the present invention, as the voltage varies BACM 1018 controls the power that is applied to the solenoid 1054 to maintain substantially the same current level to minimize power consumption. Neuron controller 1060 controls a timing generator 1066 through a memory map address decoder 1068. Memory map address decoder 1068 provides a signal to timing generator 1066 on line 1070 to start PWM and provides a signal on line 1072 to timing generator 1066 to stop PWM. Neuron controller 1060 provides a 5 or 10 MHz clock signal to timing generator 1066 on line 1074.

Timing generator 1066 provides six different time periods in which to actuate one of six pairs of solenoids 1054 used to control the valves of the hydraulic cylinders. Each time period is about 50 milliseconds. Only one solenoid 1054 can be pulled during any one time period. This minimizes the maximum current draw on the power supply or battery at any given time. It is understood that a different number of solenoid pairs may be controlled in accordance with the present invention. The number of time periods and the time period intervals may be changed, if desired. In the illustrated embodiment, six pairs of solenoids are controlled by the BACM 1018. One solenoid of each pair is used to open a first valve to control movement of a deck section in a first direction, and the other solenoid of each pair is used to open a second valve to control movement of the particular section in an opposite direction. Therefore, a pair of solenoids is provided for the head section cylinder, the foot section cylinder, the foot Hi Lo cylinder, the head Hi Lo cylinder, the knee section cylinder, and the foot retracting section cylinder.

Timing generator 1066 supplies a PWM enable signal on line 1076 to a solenoid PWM select logic control circuit 1078. Timing generator 1066 also provides time division terms to PWM control circuit 1078 on line 1080.

Illustratively, there are twelve different solenoids 1054 powered by FET drivers 1090. Neuron controller 1060 can provide three separate commands for each solenoid. The commands include an extend command, a retract command, and a pull-in command. The extend command is used to select the correct solenoid which when energized will extend the appropriate cylinder. Steady-state control of the FET which powers the solenoids is pulsed ON and OFF at the PWM rate. The retract command is used to select the opposing solenoid which when energized retracts the cylinder. It too is turned ON and OFF at the PWM rate. When a solenoid is initially activated or turned on, it is desirable to actuate the selected solenoid at "full on" for a predetermined time. Therefore, the pull-in command overrides the PWM control circuit.

Data including the control commands (pull-in, extend, or retract) for a selected solenoid 1054 transmitted from the neuron controller 1060 is written to buffer register 1084. To synchronize the commands stored in the buffer register 1084 with the timing pulses from timing generator 1066, the commands are shifted into a holding register 1088. Therefore, asynchronous information is received in buffer register 1084. This asynchronous information is synchronized into the holding register 1088 using a timing generator pulse on line 1094. The timing signal 1094 synchronizes the pull-in latch 1082 in buffer register 1084 and the pull-in latch 1086 in the holding register 1088 with the timing generator 1066. Timing signal 1094 also synchronizes the solenoid "extend" latches 1096 and 1098 and the solenoid 1054 "retract" latches 1100 and 1102 with the timing generator 1066.

The PWM select logic control circuit 1078 receives commands from the holding register 1088 and provides signals to drive a discrete FET through FET drivers 1090 during each timing interval of the PWM timing generator 1066. Driver 1090 pulls the selected solenoid 1054 down to ground and applies a voltage across the selected solenoid 1054 to control the solenoid. A voltage clamp 1104 is coupled to each of the solenoids 1054. When power is removed from a particular FET an inductive signal is supplied to the solenoids 1054. Voltage clamp 1104 clamps the inductive signal to the voltage rail. Therefore, voltage clamp 1104 provides voltage spike suppression.

A diagnostic block 1106 also receives current signals related to each pair of solenoids 1054 from voltage clamp 1104 on line 1105. Only one solenoid 1054 in each pair can be controlled or actuated at any given time. Diagnostic block 1106 also receives a data command signal from neuron controller 1060 on line 1108 indicating the particular solenoids 1054 which are designated by the controller 1060 for activation. Therefore, diagnostic block 1106 compares the actual information received from the solenoid 1054 pairs to the data received on lines 1108. If the actual solenoid 1054 current does not match the desired solenoid 1054 activation data from controller 1060, diagnostic block 1106 sends a signal to neuron controller 1060 on line 1110. A signal on line 1110 actuates a signal on supervisory line 1112 coupled to a master FET 1114 to turn off the master FET 1114 and shut off power to all the solenoids 1054. The master FET 1114 is coupled in line with all twelve solenoids 1054. Therefore, supervisory FET must be turned on to provide power to any one of the solenoids 1054.

A current sense resister 116 is coupled to the FET drivers 1090. The current sense resister 116 is coupled to the first input terminal of a comparator 1118. A second input terminal of comparator 1118 is coupled to a reference voltage. The output of comparator 1118 provides PWM feedback signal to timing generator 1066 on line 1120. In order to provide PWM, the current must be measured in each solenoid 1054. Therefore, the current sense resister 116 measures the current in each of the six time slots used for controlling the solenoids 1054. Depending on the measured current, the signal on line 1120 adjusts the timing generator 1066 to control the pulse width of the driver signal. Therefore, if too much current is being drawn, then timing generator 1066 shortens the width of the driver pulse in order to bring the current down.

Referring again to FIG. 48, communications module 1020 provides an interface needed for bed-to-hospital or hospital-to-bed information transfer. Communications module 1020 is a gateway between the bed network and the hospital information/control network. Communications module 1020 is connected to a standard side-com interface 1122. Interface 1122 also provides direct hard wired links between the nurse call switches on the siderails of the bed and the hospital priority nurse call network. Signals from these nurse call switches can also be sent over the network. On beds without a scale, a switch input port is provided to accept a bed exit signal coming from a bed exit sensor.

Interface 1122 supports all existing discrete wire protocols. Interface 1124 will support newly defined serial protocols, both to hospital network and other hospital room equipment. Any other hospital room equipment can use the GCI module 1032 as its user interface control module.

Communications module 1020 also provides entertainment functions. Television, radio, or the like may be controlled by communications module 1020 based on input/output signals received/sent from the left or right siderail standard caregiver interface modules 1028 and 1030 over the network or via discrete connections.

Communications module 1020 is directly coupled to the hospital information electrical network to transmit and receive signals from a remote location. Communications module 1020 receives weight information from scale instrument module 1022. Communications module also receives surface setting information, including pressures and other parameters from surface instrument module 1024. Communications module 1020 also receives bed position information from position sensing module 1026. In addition, communications module 1020 can receive all information traveling on the network.

The hospital network can drive a display on the graphic caregiver interface 1032 using signals transmitted from the remote location through a remote information interface 1124, to communications module 1020, and then to graphic caregiver interface 1032 over the network. Therefore, communications module 1020 provides an interactive data link between the remote location and the graphic caregiver interface module 1032. Requests for weight acquisition can be automatically sent from a remote location through remote information interface 1124 and communications module 1020. Communications module 1020 then communicates with scale instrument 1022 to determine the weight and then transmits the weight to the remote location via the remote information interface 1124.

The scale instrument module 1022 receives input signals from load beams coupled to a weigh frame of the bed. Specifically, scale instrument module 1022 receives input signals from a left head load beam 1126, a right head load beam 1128, a right foot load beam 1130, and a left foot load beam 1132. The scale module 1022 transmits weight information and operation parameters to the GCI module 1032 and communications module 1020. Load beams 1126, 1128, 1130, and 1132 are bolted to the intermediate frame. The articulating deck and weigh frame module is then bolted to the load bearing ends of the load beams. Any item attached to or resting on the articulating deck and weigh frame will be weighed by the load beams. Scale instrument module 1022 receives information from the network via a nurse caregiver interface unit or a graphic caregiver interface module 1032. The scale acquires data from the load beam transducers 1126, 1128, 1130, and 1132 and automatically factors in the tare weight to calculate a patient weight. Scale module 1022 transmits an output signal to the network representing the patient weight. Scale module 1022 can detect bed exit and alert the hospital via the communications module 1020 and remote information interface 1124.

Scale module 1022 also provides a weight change alarm. Scale module 1022 accepts a set point weight from the network. Scale module 1022 detects if a patient's weight change has exceeded or dropped below a preset level from the initial set point weight. If a preset weight change has occurred, scale module 1022 provides an alarm message to the network. Scale module 1022 stores all data critical to the functioning of the scale in non-volatile memory. Scale module 1022 has built in diagnostic capability to detect hardware integrity and data integrity.

Figure 51:
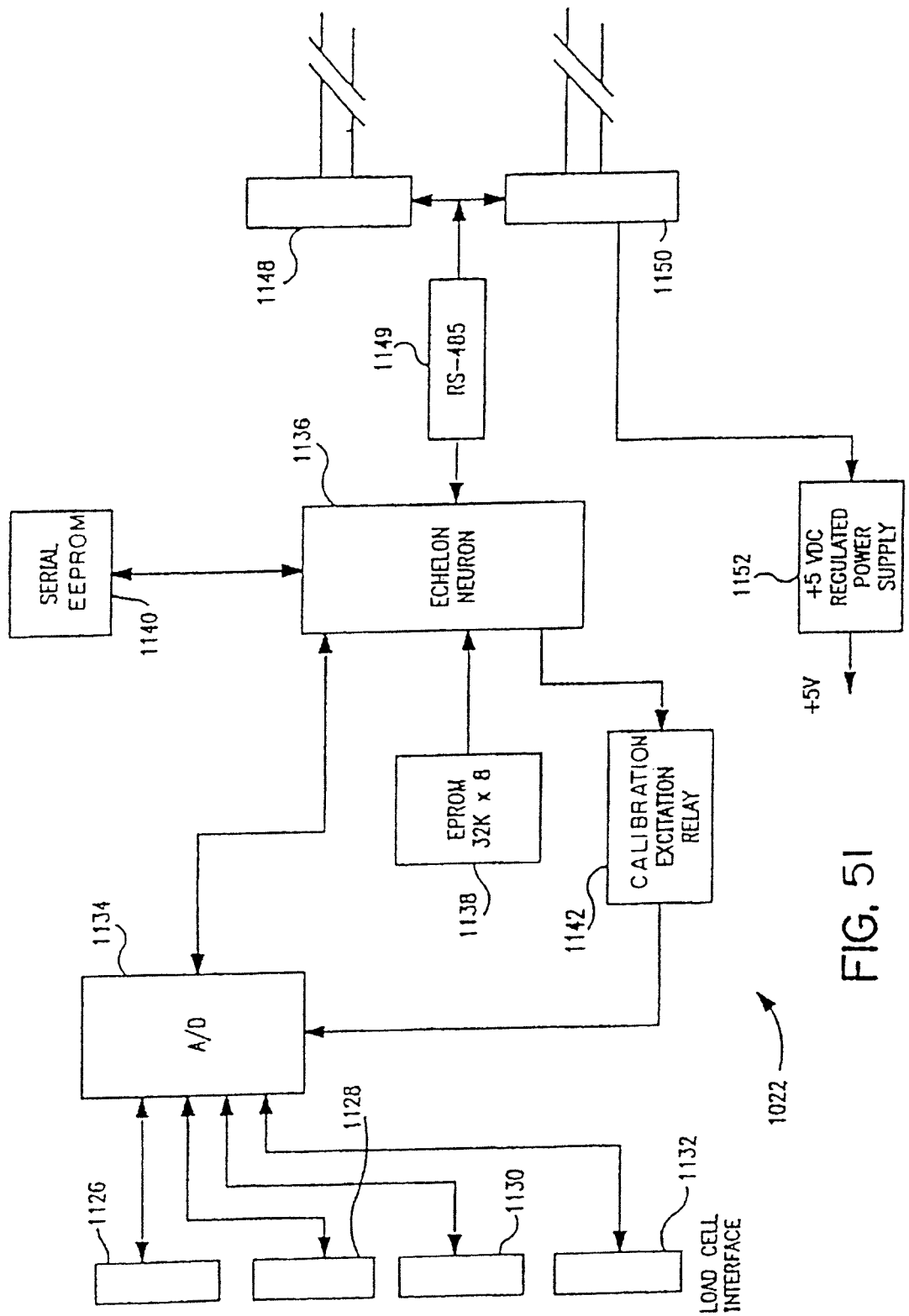
FIG. 51 is a schematic block diagram illustrating the electrical components of the scale instrument module.

Details of scale module 1022 are illustrated in FIG. 51. The four load cells 1126, 1128, 1130, and 1132 are coupled to a four channel analog to digital converter 134. Illustratively, analog to digital converter is a CS5516, 4 MHz analog to digital converter available from Crystal Semiconductor. Analog to digital converter 134 converts analog signals from the load cells 1126, 1128, 1130, and 1132 into digital signals and inputs the signals into the echelon neuron controller 1136. Neuron controller 1136 is a MC143150, 10 MHz networking microprocessor available from Motorola. Controller 1136 executes code stored in an EPROM 1138. Illustratively, EPROM 1138 is a 32K×8, model 27HC256 EPROM available from AMD.

Neuron controller 1136 stores calibration data related to each of the load cells 1126, 1128, 1130, and 1132 either in its internal memory or in external EEPROM 1140. Calibration data is necessary because each load beam 1126, 1128, 1130, and 1132 has slightly different gain or offset constant associated with it. Calibration/excitation relay 1142 transmits the calibration data from neuron controller 1136 to analog to digital converter 1134. Two connectors 1148 and 1150 are provided to couple scale module 1022 to the peer-to-peer communication network. Connector 1148 is hard wired to connector 1150. An RS-485 transceiver 1149 is coupled between connectors 1148 and 1150 and controller 1136. Transceiver 1149 takes logic inputs and outputs and converts them to RS-485 level signals for the network. For each of the modules on the peer-to-peer network, a connector such as connector 1148 is hard wired to another connector such as connector 1150 that goes onto the next node or module in a daisy chain configuration. Scale module 1022 also includes a +5VDC regulated power supply 1152.

Referring again to FIG. 48, the surface instrument module 1024 is provided for controlling operation of the mattress or support surface. Details of this module are discussed below with reference to the surface design (or in main application).

The bed includes position transducers mounted throughout the bed to sense any needed positions of individual bed sections for articulation and caregiver interface purposes. The position sense module 1026 also interfaces a Siderail Up Detect Sensor, and a Bed Exit Sensor.

Figure 52:
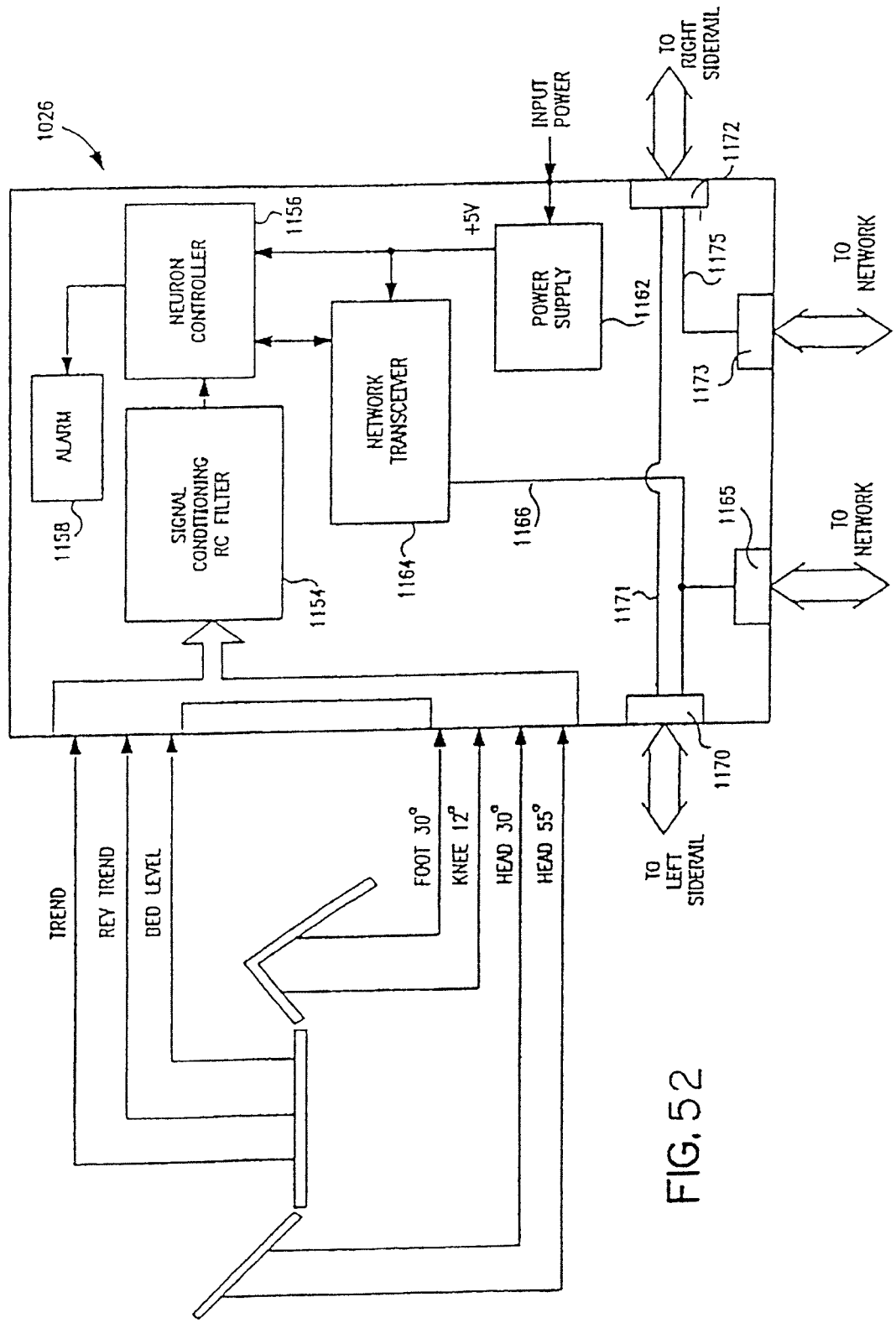
FIG. 52 is a schematic block diagram illustrating the mechanical and electrical components of the bed position sense and junction module.

Details of the position sense module 1026 are illustrated in FIG. 52. Illustratively, the position transducers are discrete tilt sensors on various deck sections of the bed. The sensors include a Trendelenburg limit sensor at 13° relative to earth, a reverse Trendelenburg sensor at −13° relative to earth, and a bed-level at 0° relative to earth. In addition, the articulating deck sections include position transducers which are also discrete tilt sensors. Illustratively, the tilt sensors are model A½ sensors available from AEC. The patient head limit sensor detects the head section at 55° relative to earth. The head contour limit sensor detects the head section at 30° relative to earth. The knee contour limit detects the knee section at 12° relative to earth. The patient foot limit detects the position of the foot section at 30° relative to earth.

The sensor inputs are coupled to the position sense module 1026. The sensor input signals are signed conditioned using a RC filter 1154. The output of RC filter 1154 is coupled to a neuron controller networking microprocessor 1156. An output from controller 1156 drives a local alarm 1158. Input power on line 1160 is coupled to a regulated power supply 1162 which produces a +5V output. The output from power supply 1162 is coupled to neuron controller 1156 and to a network transceiver 1164. The position transducers illustratively switch from a logic high to a logic low upon detection of the particular angle relative to earth.

Controller 1156 transmits and receives network information through transceiver 1164. Network transceiver 1164 is coupled to a first network connector 1165 via lines 1166. Position sense module 1126 also provides the connection points to the network for the left and right standard caregiver interface modules 1028 and 1030. Network connector 1165 also coupled to a left siderail network connector 1170 which is coupled to the left siderail standard caregiver interface module 1128. Left siderail connector 1170 is coupled to a right siderail connector 1172 by lines 1171. Connector 1172 is coupled to a right siderail standard caregiver interface module 1030. Connector 1172 is also coupled to a second network connector 1173 by lines 1175. Therefore, position sense module 1026 is also a junction module for connection to the left and right siderail standard care giver interface modules 1028 and 1030.

During operation, neuron controller 1156 interprets the sensor signals received from RC filter 1154 and sends an output signal indicative of the state of each sensor to the network through network transceiver 1164. Network transceiver 1164 is a RS-485 protocol transceiver. Alarm 1158 contains a piezo device so that any alarms on the bed that are transmitted through the network turn on the piezo alarm on the position sense module 1026. These alarms may include bed exit, patient weight gain, weight loss, surface pressure loss, or other desired alarms. Alarm 1158 can also be used to alert an operator when catastrophic failures are detected in the bed by the diagnostic tools.

The left and right standard caregiver interface modules 1028 and 1030 are substantially identical. The left standard caregiver interface module 1028 is coupled to patient controls including an articulation and entertainment interface in the left siderail as illustrated at block 1154 of FIG. 48. Standard caregiver interface module 1028 is also coupled to a surface patient interface on the left siderail as illustrated at block 1156. The standard caregiver interface module 1030 for the right side is coupled to articulation and entertainment patient interface module on the right siderail as illustrated at block 1158. The right standard caregiver interface module 1030 is also coupled to a surface patient interface caregiver interface on the right siderail as illustrated at block 1160.

Figure 53:
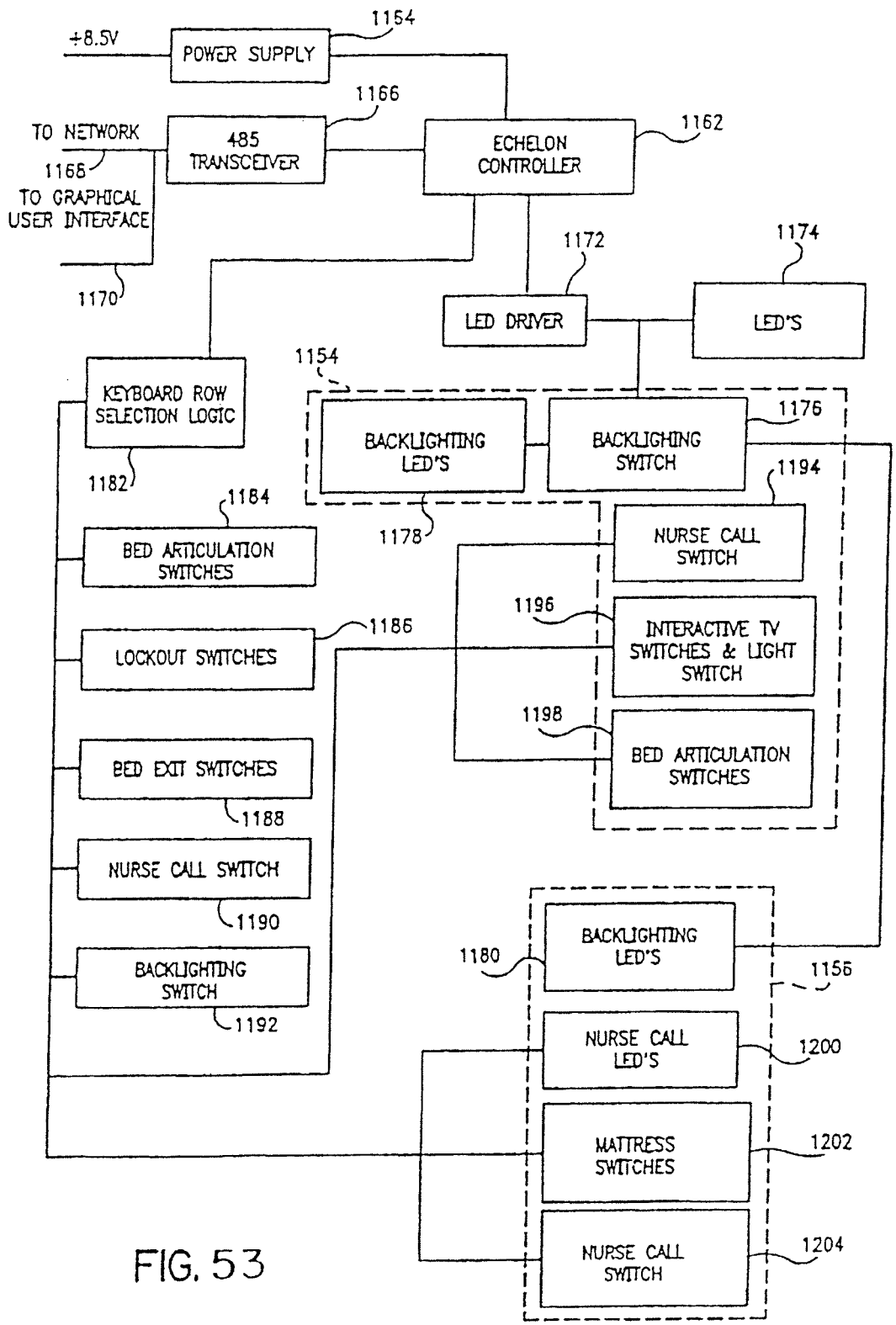
FIG. 53 is a schematic block diagram illustrating the components of the left and right standard caregiver interface module for either the left siderail or the right siderail.

Details of the left standard caregiver interface module 1028 is illustrated in FIG. 53. The standard caregiver interface module includes an echelon controller 1162 which is a networking microprocessor. Echelon controller 1162 is coupled to a +5.0V supply voltage from power supply 1164. Echelon controller 1162 is also coupled to a network transceiver 1166. Transceiver 1166 is an RS-485 protocol transceiver. Transceiver 1166 couples controller 1162 to the peer-to-peer communication network as illustrated at line 1168. A network connection for the graphic caregiver interface module 1032 is provided at line 1170 for both the left and right standard caregiver interface modules 1128 and 1030. Graphic caregiver interface module 1032 can be connected on either the left or right side of the bed. Echelon controller 1162 interprets the network messages. Network controller 1162 also detects switch activation from the articulation and entertainment patient interface 1154 and the surface patient interface 1156 and transmits output signals to the network on line 1168. The switches can be dead function switches, lockout switches, bed exit switches, nurse call backlit switches, and so on. Controller 1162 drives a LED driver 1172 to light indicator LEDS 1174 related to various bed status functions, such as bed-not-down, brake-not-set, battery low, and service required.

The LED driver 1172 is also coupled to a backlighting switch 1176 of the articulation and entertainment patient interface 1154. Backlighting switch 1176 is coupled to backlighting LEDs 1178. Backlighting switch 1176 is also coupled to backlighting LEDs 1180 on the surface patient interface 1156.

The standard caregiver modules 1028 and 1030 connect all the caregiver interfaces switches in a row/column type architecture to provide a 4×10 matrix. A keyboard row selection logic circuit is used to detect switch presses as illustrated at block 1182.

The standard caregiver interface (SCI) modules 1028 and 1030 include the network circuitry for interfacing all caregiver and patient siderail caregiver interfaces to the communication network. The patient caregiver interfaces are separated into modules which can be connected to the SCI module 1028 or 1030 in a modular fashion.

Each SCI module 1028 and 1030 includes bed articulation switches 1184. These include head up, head down, knee up, knee down, foot up, foot down, bed up, bed down, chair in, chair out, Trendelenburg, and reverse Trendelenburg. In the case of a switch closure, a signal is periodically output to the network until the opening of the switch occurs. The SCI modules 1028 and 1030 further include lockout switches 1186 as discussed below, bed exit switches 1188, nurse call switches 1190, and backlighting switches 1192. Control buttons for the switches 1184, 1186, 1188, 1190, and 1192 are typically on an outside portion of the siderail for use by a nurse.

The articulation and entertainment patient interface 1154 also includes a nurse call switch 1194, interactive TV switches and a light switch 1196, and bed articulation switches 1198. Surface patient interface 1156 includes nurse call LEDs 1200, mattress switches 1202, and a nurse call switch 1204.

Figure 54:
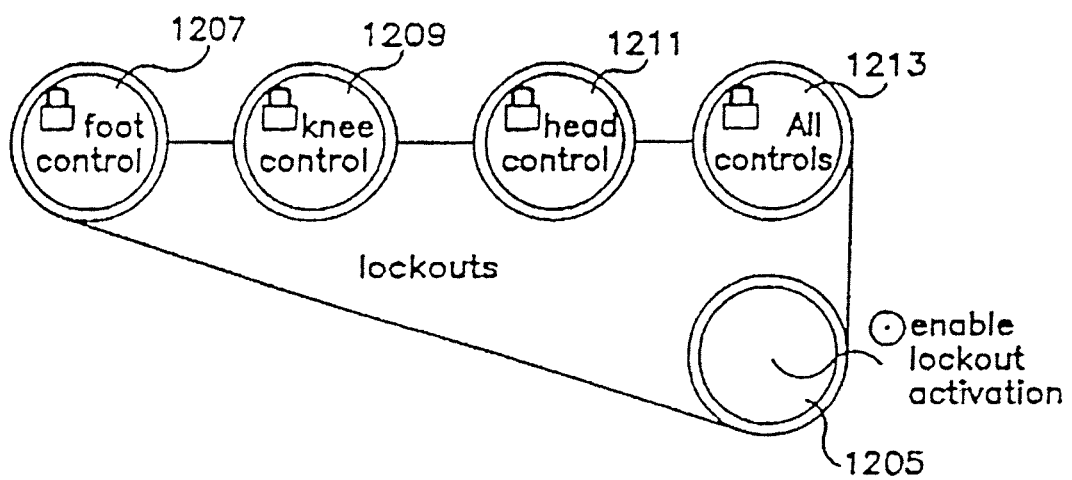
FIG. 54 is a diagrammatical view of the lockout switches on the siderail control panel to prevent movement of selected sections of the bed.

As discussed above, the lockout control switches are located on the left and right siderail control interfaces. As illustrated in FIG. 54, the lockout control includes a global enable lockout activation switch 1205 which must be pressed in order to activate any of the other lockout toggle switches for the foot control lockout 1207, the knee control lockout 1209, the head control lockout 1211, or the lockout for all controls at 1213. This double lockout activation reduces the likelihood of the accidental deactivation of one of the lockout control switches. Therefore, the global enable switch 1205 must be pressed in order to turn any of the other lockout controls on or off. The global enable switch 1205 automatically deactivates after about 5 seconds of inactivity. After the global enable is deactivated, the lockout status cannot be changed. Since the caregiver controls are within reach of a patient, the global enable switch may be used to enable and disable both the patient and caregiver bed articulation control switches.

Figure 55:
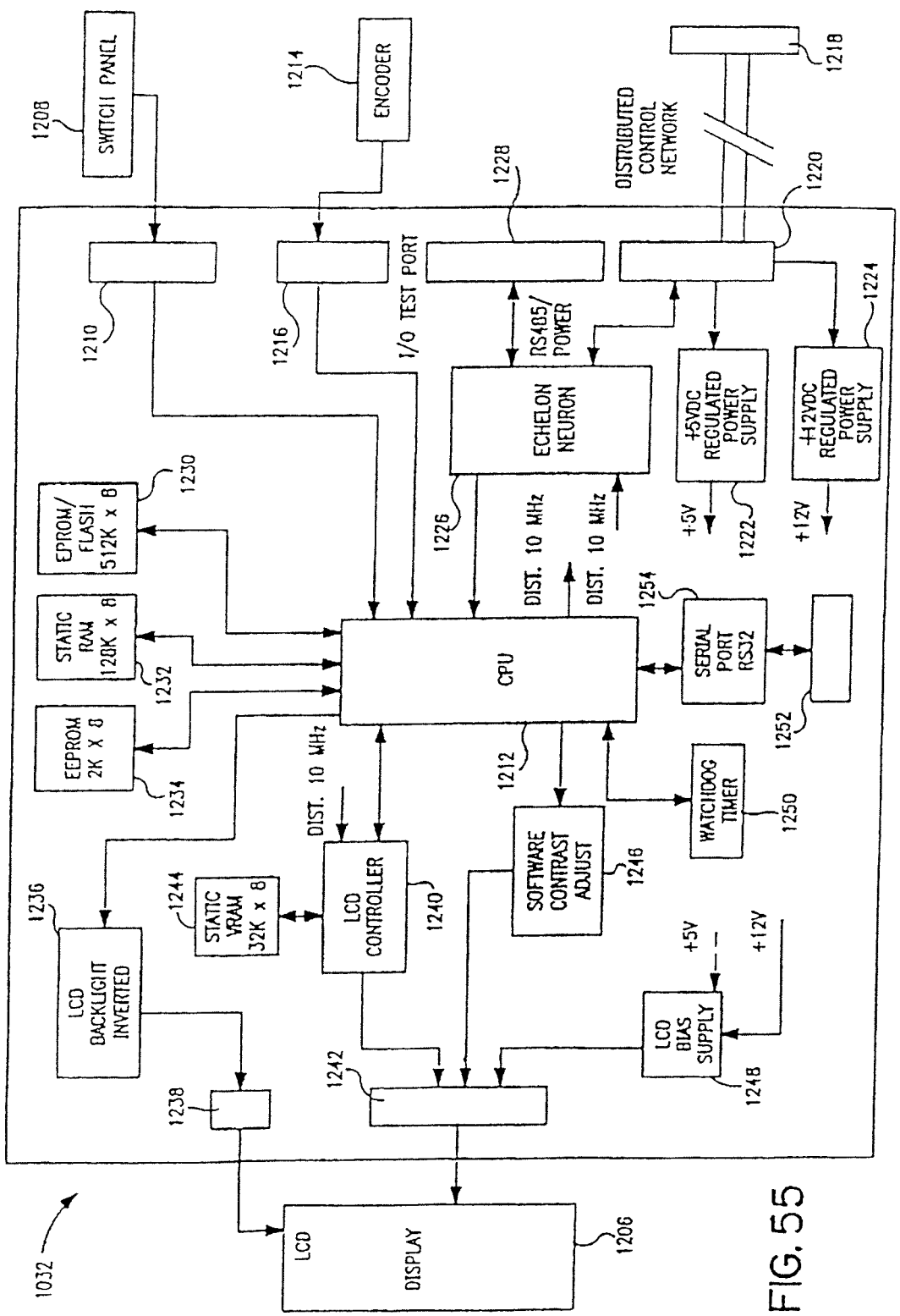
FIG. 55 is a schematic block diagram illustrating the mechanical and electrical components of the graphical caregiver interface module.

A graphic caregiver interface (GCI) module 1032 is illustrated in detail in FIG. 55. The GCI module 1032 provides an enhanced menu-driven caregiver input and output for bed articulation, scale, surface caregiver interface, and sequential compression device controller, and all other modules needing this type of user interface. The GCI module 1032 includes a LCD display 1206, which is illustratively a 320×240, model DMF 50081 available from Optrex. Display 1206 may also be a 320×240, model G321EX available from Seiko. Display 1206 outputs graphical information to the caregiver. A switch panel 1208 permits the caregiver to input information into the GCI module 1032. Switch panel 1208 may be a series of discrete switches or an alpha/numeric keypad. Switch panel 1208 is coupled to a connector 1210. Connector 1210 is coupled to an input of CPU 1212. CPU 1212 is illustratively an 80C188XL, 10 MHz CPU available from Intel. The input device for the caregiver may also be an encoder 1214 which is coupled to a connector 1216. Connector 1216 is coupled to CPU 1212. Illustratively, encoder 1214 is a rotary encoder.

Connection to the peer-to-peer communication network is provided at terminal 1218. The network connection is made to a RS-485 transceiver 1220. Transceiver 1220 is coupled to a +5 VDC regulated power supply 1222. Transceiver 1220 is also coupled to a +12VDC regulated power supply 1224. Transceiver 1220 is coupled to an echelon neuron controller networking microprocessor 1226. Controller 1226 is illustratively an AMC143120, 10 MHz networking microprocessor available from Motorola. Neuron controller 1226 is coupled to an I/O test port 1228. Controller 1226 is also coupled to CPU 1212. Software code for operating CPU 1212 is stored in an EPROM memory 1230. Illustratively, memory 1230 is a 512K×8 flash EPROM memory. Data is stored in static RAM memory 1232. Illustratively, memory 1232 is a 128K×8 memory chip. Additional memory is provided in a 2K×8 EEPROM 1234. An output from CPU 1212 is coupled to a LCD backlight inverter 1236. Backlight inverter 1236 is coupled to LCD display 1206 by connector 1238. Backlight inverter facilitates viewing of display 1206 in all types of room lighting. Inverter 1236 is configured to match the particular display 1206 selected.

CPU 1212 is also coupled to a LCD controller 1240. LCD controller 1240 drives the display 1206 through a connector 1242. Controller 1240 is coupled to a 32K×8 static video RAM 1244. As the CPU 1212 writes an image to LDC controller 1240, the controller 1240 stores the image in VRAM 1244 and then continuously refreshes the display screen 1206 with the image stored in the VRAM 1244.

Contrast of the display 1206 is controlled by software contrast adjustment as illustrated at block 1246. A LCD bias supply voltage at block 1248 is coupled to connector 1242. Supply 1248 converts a +5V input or a +12V input into a −22V output. An external watchdog timer 1250 monitors CPU 1212. If the CPU 1212 does not pulse the particular line on a periodic basis, timer 1250 resets the system.

GCI module 1032 also includes a diagnostic port 1252. Diagnostic port 1252 is coupled to CPU 1212 through a serial port 1254. Serial port 1254 is a RS-232 UART. Therefore, a laptop may be connected at port 1252 to interrogate the CPU 1212. CPU 1212 can access and send information to the network through controller 1226.

The GCI module 1032 provides an enhanced menu-driven caregiver input and output control for bed articulation, scale, surfaces, sequential compression devices, and all other modules needing this user interface capability. The GCI module 1032 is intended to be a drop in replacement for Scale/Surface Nurse Control Unit. GCI module 1032 interacts with scale module 1022. Specifically, GCI module 1032 can transmit a request for patient weight to the scale module 1022. In addition, the GCI module 1032 can also zero the scale and perform other scale module functions.

GCI module 1032 stores predetermined graphics data and caregiver interface data in memory 1230. This predetermined graphics data is stored in the GCI module 1032 at the time of production. Additionally, other modules on the peer-to-peer communication network can download screen formats to the GCI module into static RAM 1232. The GCI module then retrieves the stored graphic screen formats either from memory 1230 or static RAM 1232 and displays the output on display 1206. By providing stored built-in graphics in memory 1230, the GCI module 1032 can support products or other modules that may later be connected to the peer-to-peer communication network. By providing the stored predetermined graphic formats, the GCI module 1032 does not have to be updated each time a new module is added to the system. If the desired graphics format is not present in memory 1230, then the newly added module must download the desired graphic formats into RAM 1232 at run time.

The specific graphic formats stored in the GCI module 1032 can include charting formats such as bar graphs, X-Y graphs, pie charts, etc., icons or pictures representing each of the modules in the communication network, or any other type of graphical format desired. Graphic formats for use by the modules are stored in two different ways in the GCI module 1032. Typically, these various graphic formats are stored in EPROM 1230 at the time of manufacture. In other words, these graphical formats are typically designed into the GCI module 1032. If a particular GCI module 1032 does not include the desired graphic format stored in memory 1230, then the particular graphic format for the new module added to the system is downloaded into the static RAM 1232 of GCI module 1032 after the bed is powered up. For instance, if GCI module 1032 does not include a X-Y graphic format in memory 1230, this graphic format can be downloaded into RAM 1232 after the bed is powered up. Once a particular graphic format is stored in GCI module 1032, in either memory 1230 or RAM 1232, the new module transmits only data to the GCI module 1032 during operation. The GCI module 1032 uses the received data and the stored graphic format to produce an appropriate screen output on display 1206. For instance, after the X-Y graphic format is stored in either memory 1230 or RAM 1232, the particular module transmits only the X-Y data to the GCI module 1032 over the network. The GCI module 1032 then uses this data along with the stored X-Y graphic format to provide an output to display 1206. Each new module will also download a particular icon representative of the new module for the menu-driven display 1206 of GCI module 1032 as discussed below.

Updating of the graphic formats and menu information of the GCI module 1032 can be accomplished in one of three ways. The particular graphic format and menu information can be downloaded into static RAM 1232 at power up of the bed. The graphic format and menu information can also be downloaded to EEPROM 1234 during installation of a new module. Finally, EPROM 1232 can be changed to include the new graphic format and menu information at the time the new module is installed.

Figure 56:
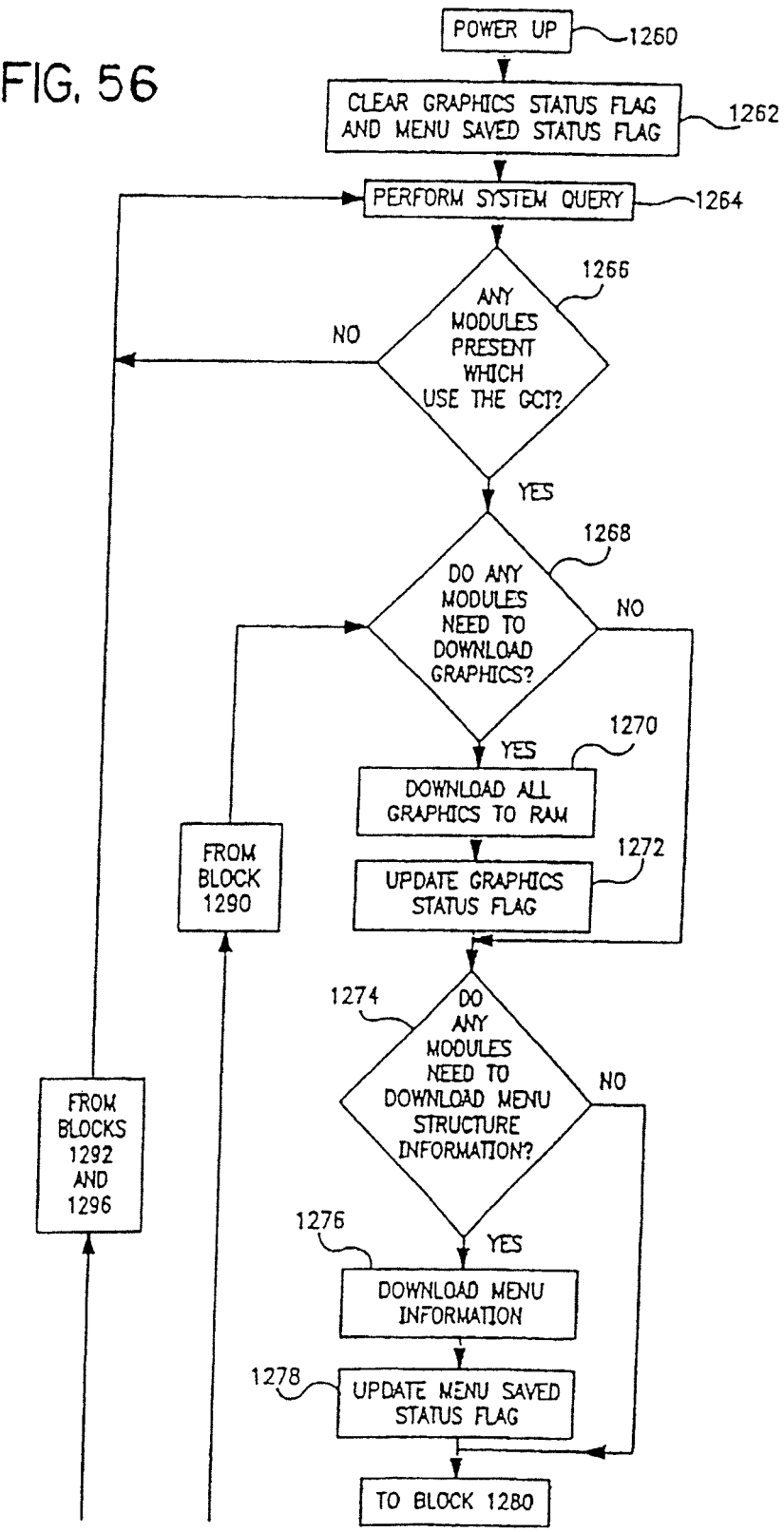
FIGS. 56 and 57 are flow charts illustrating details of the automatic module recognition feature of the graphical caregiver interface module.
Figure 57:
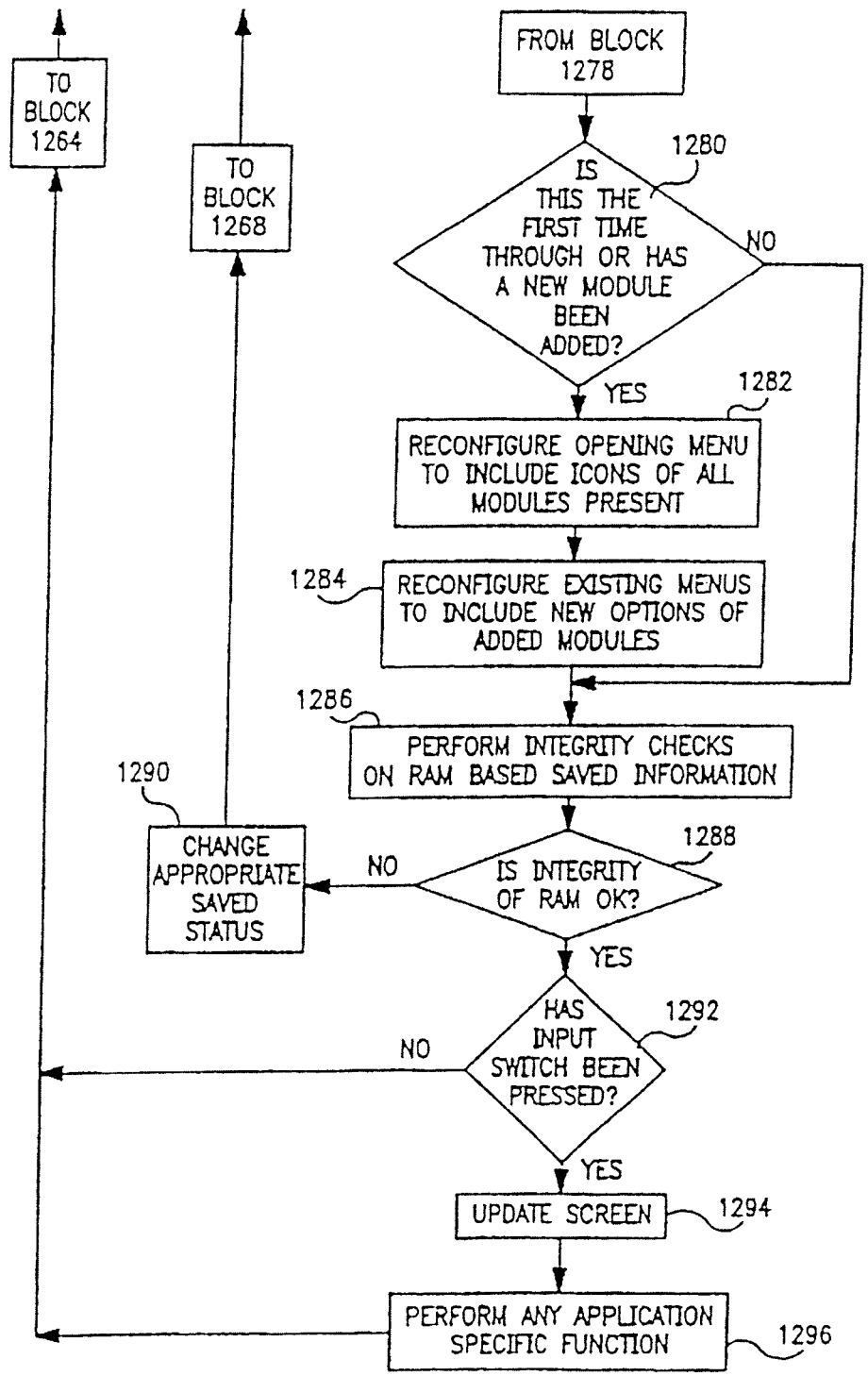

Details of the operation of GCI module 1032 for automatically recognizing and controlling newly added modules on the communication network are illustrated in FIGS. 56 and 57. Bed power up is illustrated at block 1260. A graphics status flag and a menu saved status flag are both cleared at block 1262. These flags provide an indication of whether a particular graphic format or menu information for the module must be downloaded to the GCI module 1032. For each module on the network, menu screens will be provided on display 1206. Therefore, if a particular module is selected using the GCI module 1032, control options for that module will appear as menu items on display 1206. Once a particular control option is selected, additional menu items for the selected control option may appear, and so on.

GCI module 1032 performs a system query at block 1264. GCI module 1032 first determines whether any modules are present on the communication network which use the GCI module 1032 as illustrated at block 1266. If no modules are present on the network which use the GCI module 1032, the GCI module 1032 returns to block 1264. The system query is carried out at predetermined time intervals.

If modules are present which use the GCI module 1032 at block 1266, the GCI module 1032 determines whether any of the modules need to download graphic formats to the GCI module 1032 as indicated at block 1268. If no modules need to download graphic information, GCI module 1032 advances to block 1274. If any of the modules need to download graphic formats, the graphic formats are downloaded to static RAM 1232 of GCI module 1032 as illustrated at block 1270. The graphics status flag for the module is then updated as illustrated at block 1272. The graphics status flag is initially generated at block 1266 during detection of any modules which use the GCI module. Therefore, after step 1270 the status flag 1272 indicates that all the graphic format data for the particular module is now stored on the GCI module 1032.

GCI module 1032 next determines whether any of the modules need to download menu structure information to the GCI module. If not, GCI module 1032 advances to block 1280 in FIG. 57. If any of the modules need to download menu structure information, the appropriate menu structure information is downloaded to the static RAM 1232 of GCI module 1032. This menu structure information provides the appropriate menu-driven control for each module. For instance, once the module icon is selected using the switch panel 1208 or encoder 1214 of the GCI module 1032, the GCI module 1032 automatically displays a menu screen of options on display 1206 associated with the particular module. Once a particular option is selected, another menu screen may be provided to display 1206 giving further options. Button sizes and text fonts are included in the graphics format data stored in the GCI module 1032. The menu structure information provides the actual textural material to be included with the menu-screen buttons.

The GCI module 1032 next updates a menu saved status flag at block 1278. This status flag provides an indication that all the menu structure information for the particular module has been downloaded. GCI module 1032 then proceeds to block 1280 of FIG. 57.

GCI module determines whether this particular loop is the first time through after power up or if a new module has been added as illustrated at block 1280. If not, GCI module 1032 proceeds to block 1286. If it is the first time through or a new module has been added, GCI module 1032 reconfigures an opening menu to include icons of all the modules present as illustrated at block 1282. In other words, the main menu initial display screen of display 1206 is updated to include an icon representing each of the controllable modules. GCI module 1032 then reconfigures existing menus to include the new options of added modules as illustrated at block 1284. The code stored in the GCI module 1032 is altered, in real time, to merge new menu information for the newly added modules with existing menu information of the previous modules.

GCI module 1032 then performs an integrity check on RAM 1232 based saved information as illustrated at block 1286 (i.e. checksum). If the integrity of the stored information in RAM 1232 is not correct at block 1288, GCI module 1032 changes an appropriate saved status flag at block 1290. GCI module 1032 then proceeds back to block 1268 to download the appropriate graphical format information or menu structure information for the particular module again.

If the integrity of the information saved in RAM 1232 is correct at block 1288, GCI module 1032 determines whether an input switch from switch panel 1208 or encoder 1214 has been pressed at block 1292. If no input has been pressed, GCI module returns to block 1264 of FIG. 56 to perform another system query at the next predetermined time interval.

If an input switch has been pressed at block 1292, GCI module 1032 updates the display screen 1206 as illustrated at block 1294. The GCI module 1032 then transmits an appropriate network command to the particular module to perform any selected application or specific function as illustrated at block 1296. For instance, GCI module 1032 can transmit a signal to scale module 1022 to weigh a patient, to surface instrument module 1024 and air supply module 1014 to adjust the pressure within a particular bladder of the bed surface, or to perform any other module function.

It is understood that the hospital network can use the GCI module 1032 in an identical way to the other network modules. The hospital network can send menu driven control options to the GCI if desired. Either the patient or the caregiver can use the GCI module 1032 to control bed functions and interact with the hospital network or another remote location.

Figure 58:
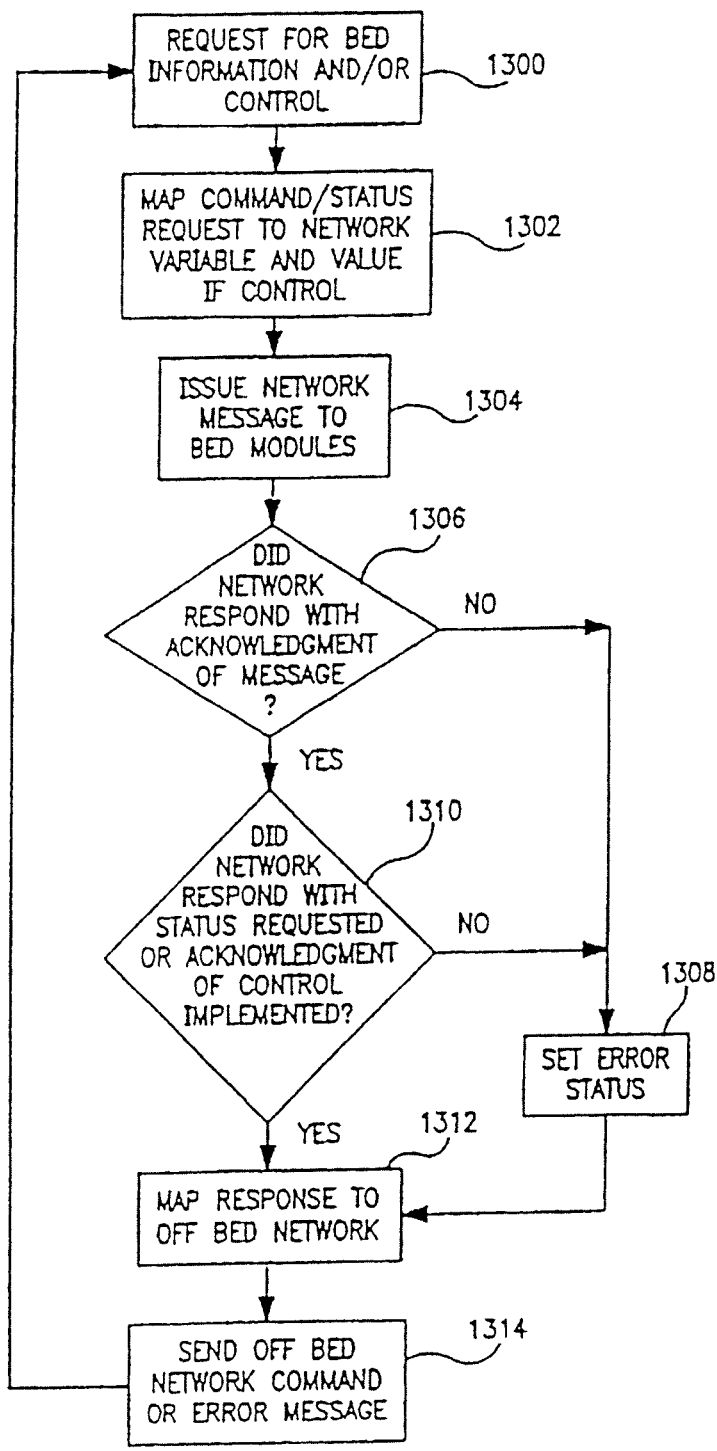
FIG. 58 is a flow chart illustrating the steps performed by the communications module for automated data collection from the other modules connected to the communication network of the bed.

The automated data collection feature of communications module 1020 is illustrated in further detail in FIG. 58. A request for bed information and/or bed control is received as illustrated at block 1300. The request is either from the hospital information network or from a remote data acquisition system. In other words, the hospital bed may be connected to the hospital network through wiring in a wall as discussed above. In addition, the bed may be connected to another piece of equipment in the room which can be connected to a remote location through the hospital network, a modem, or other data link. Finally, the request for information and/or control can be from an on-board bed data acquisition system.

The particular command or status request is then mapped to a network variable or value as illustrated at block 1302. In other words, the received request or command is changed to a usable network format at block 1302. Illustratively, a table is used to transform the received request for information and/or control to an appropriate and understandable network command.

A message is then issued to the bed modules over the communication network as illustrated at block 1304. Communications module 1020 determines whether the particular module responded over the network with an acknowledgment of the message at block 1306. Once a particular module receives a message, an acknowledgment of the message is transmitted back over the network before the particular function is carried out by the module. If the acknowledgment is not received, the communication module 1020 sets an error status indicator as illustrated at block 1308. If the acknowledgment is received at block 1306, communications module 1020 next determines whether the module responds over the network with a particular status that was requested or with an acknowledgment that a particular control has been implemented as illustrated at block 1310. If not, communications module 1020 sets the error status indicator as illustrated at block 1308. If the module did respond over the network with the particular status requested or with the acknowledgment that the control was implemented, the network response is mapped to the off bed network as illustrated at block 1310. The communications module 1020 transforms the response received from the bed network format to the off-bed network format for transmission at block 1312. The communications module 1020 then sends the off-bed network command or an error message to the remote network as illustrated at block 1314. An error message sent to the hospital network or other remote location provides an indication that something went wrong with the particular request for status information or control. This request can then be retransmitted. A persistent error message indicates problems with one of the modules. Therefore, corrective action to repair the module can be implemented.

Each of the modules on the hospital bed can store specific status information related to operation and control of the bed or related to the module functions in an internal memory present on each module. For instance, the BACM 1018 can store all bed articulations and positions in a memory of the BACM 1018. In addition, the surface instrument module 1024 can store all surface positions and settings or therapy module usages in memory on the surface instrument module 1024. This information can be retrieved using the automated data collection feature discussed above to indicate patient activity. The standard caregiver interface modules 1028 and 1030 can store all entertainment patient control interactions in memory. These interactions can be retrieved via the automated data collection feature for billing or other monitoring purposes. Each module has a capability of storing all patient interaction with controls on the module. This stored information is available to the GCI module 1032 and to the off bed information system via the automated data collection feature.

As discussed above, the hospital network can retrieve status information through the communications module 1020. In addition, status information can be retrieved from a remote location through a data link coupled to accessory port module 1016. This status information may be bed status information stored in any of the modules. Each module can store status information related to switch presses, and specific movements, controls, or functions performed by the module.

Figure 59:
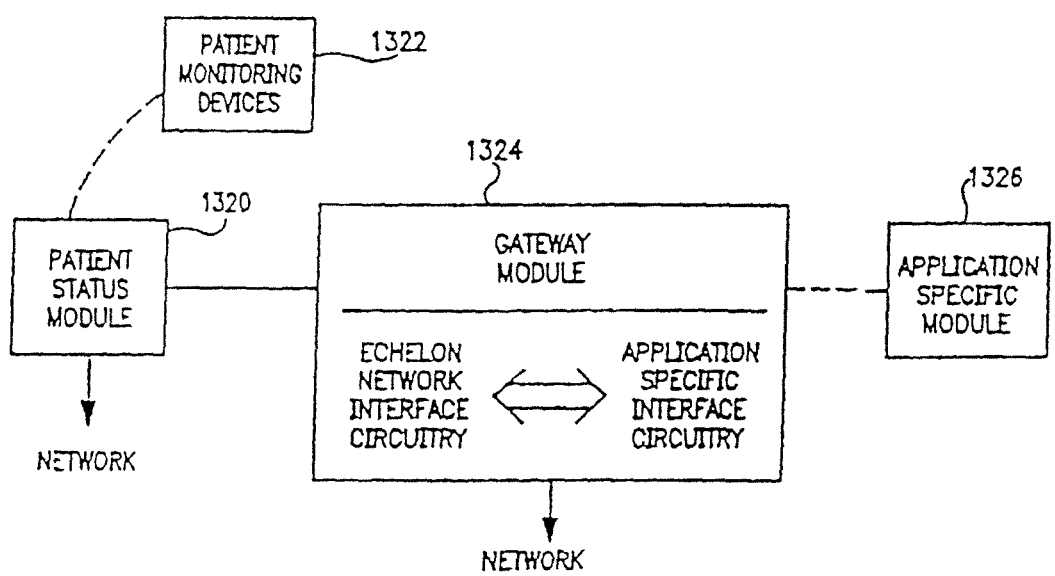
FIG. 59 is a diagrammatical view illustrating a patient status module and a gateway module of the present invention.

Another module which can be coupled to the peer-to-peer communication network is a patient status module 1320. This patient status module 1320 is illustrated in FIG. 59. The patient status module 1320 monitors and records vital statistics from the patient received from a selected patient monitoring device 1322. Such body monitors may include, for example, temperature sensors, blood pressure detectors, heart rate monitors, or any other body monitor. Data from these monitors 1322 is stored in memory of the patient status module 1320 and can be transmitted over the network to the hospital network or to a remote location through a data link coupled to accessory port 1016. Patient monitoring devices 1322 are discretely coupled to the patient status module 1320.

Another module coupled to the bed peer-to-peer communication network is a gateway module 1324. The gateway module 1324 provides an interface to the network for an application specific module 1326. Specifically, gateway module 1324 provides echelon network interface circuitry for communicating with the peer-to-peer network of the hospital bed. Gateway module 1324 also includes application specific interface circuitry for communicating with the application specific module 1326 for performing a dedicated function on the bed or elsewhere. Therefore, gateway module 1324 provides a format change for the data so that understandable information and commands are transmitted and received by both the bed network and the application specific module 1326.

Another feature of the present invention is that each of the bed modules can be upgraded over the network using a data link through accessory port 1016 or using communications module 1020. Upgrade information can be transmitted from the remote location to the peer-to-peer network. In other words, a remote location can be used to download new software to all the modules connected to the communication network of the bed. This permits an operator to reprogram the bed modules from a remote location over the peer-to-peer communication network.

Yet another feature of the present invention is that each module is able to perform internal diagnostics. After a module performs its dedicated function, a diagnostic check can be performed to make sure that the module is functioning correctly. If an error is detected, an error message can be transmitted over the network to another module or to a remote location through communications module 1020 or accessory port 1016.

Figure 60:
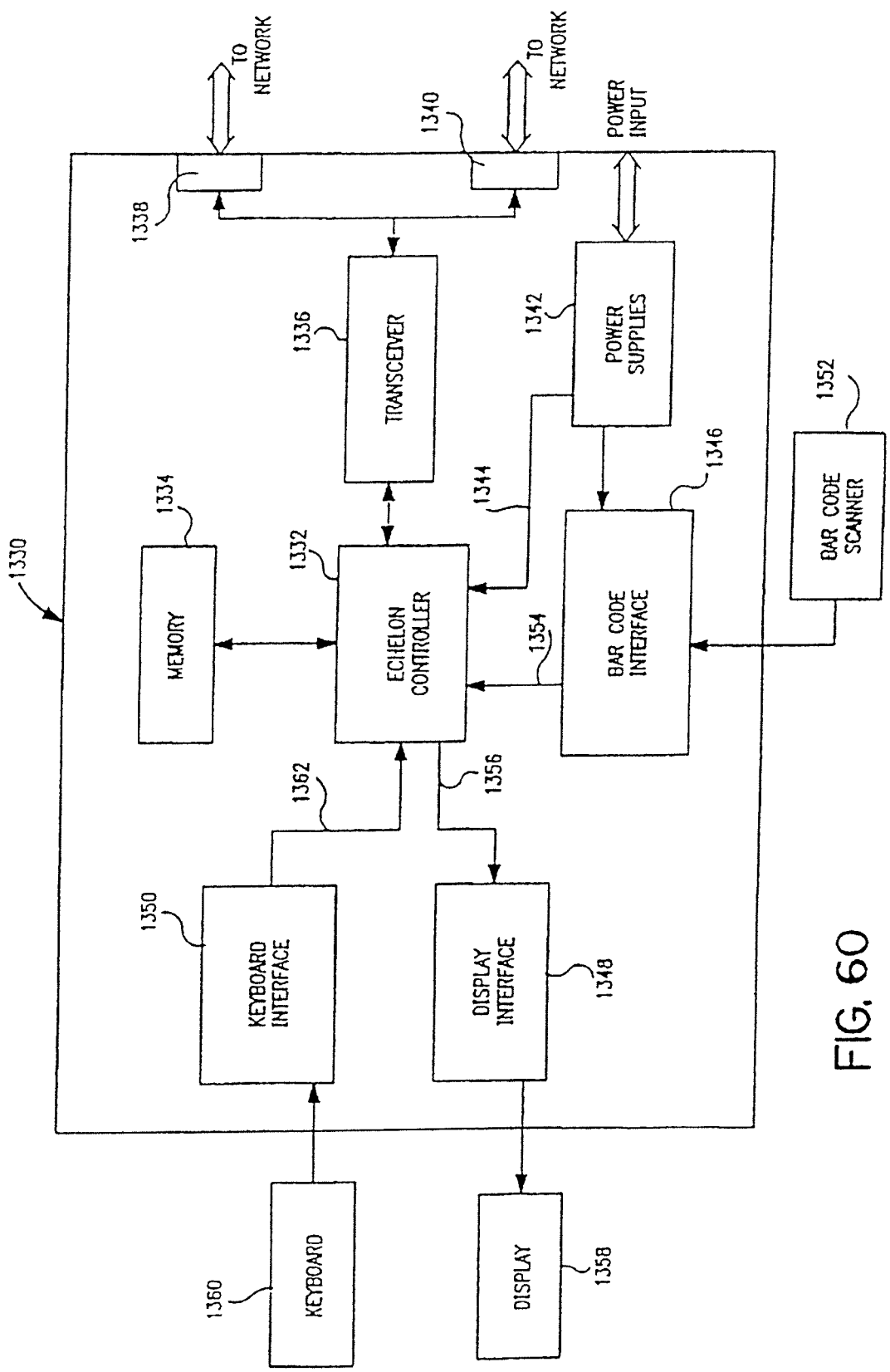
FIG. 60 is a diagrammatical view illustrating details of a patient charting module of the present invention.

Another module of the present invention is illustrated in FIG. 60. FIG. 60 illustrates an automatic charting module 1330. The automatic charting module 1330 includes an echelon controller 1332 which is a networking microprocessor. Controller 1332 accesses memory 1334. Memory 1334 includes an EEPROM, and EPROM, and a static RAM. Controller 1332 is coupled to a RS-485 transceiver 1336. Transceiver 1336 is coupled to first and second network connectors 1338 and 1340. Module 1330 includes an internal power supply 1342 coupled to a power input. Illustratively, power supply 1342 supplies a +5V supply voltage to controller 1332 on line 1344. Power supply 1342 also supplies power to a bar code interface 1346, a display interface 1348, and a keyboard interface 1350. Display interface 1348 and keyboard interface 1350 are optional elements of charting module 1330.

Bar code interface 1346 receives an input from bar code scanner 1352. An output of bar code interface 1346 is coupled to controller 1332 on line 1354. Controller supplies information to display interface 1348 on line 1356. An output from display interface 1348 is coupled to a suitable display 1358. Keyboard interface 1350 receives an input from a keyboard 1360. An output of keyboard interface 1350 is coupled to controller 1332 by line 1362.

Charting module 1330 provides an apparatus for automatically charting patient information. Bar code scanner 1352 and keyboard 1360 provide input devices for inputting information into charting module 1330. It is understood that any type of input device can be used in connection with the present invention. The patient or caregiver can input information to the network using the bar code scanner 1352 or keyboard 1360. This information can remain locally on the peer-to-peer communication network of the hospital bed. In addition, the information can be sent to the hospital network through transceiver 1336 and communication module 1020 or to another remote location via accessory module 1016.

An output device such as display 1358 is provided to display information to the user. The display 1359 can be a series of LEDS or a display panel, such as a LCD display.

The memory of 1334 of charting module 1330 is loaded in a manner similar to the GCI module 1032 discussed above. Memory 1334 contains code that translates raw bar code scanner information and keyboard input information from keyboard 1360 into specific network commands, either for local on-bed use or for hospital network off-bed use. For instance, the nurse can scan bar codes directly from prescription medicine or input various information into keyboard 1360 related to the patient. This input is used to generate an internal chart of the medical history of the patient for use on the hospital bed. This chart data can be displayed on display 1358. In addition, this chart can be transmitted over the hospital network or transmitted to a remote location using a data link coupled to accessory port 1016.

It is understood that the GCI module 1032 discussed above may be modified to include an input interface such as bar code interface 1346. The functionality of charting module 1330 is similar to the GCI module 1032 except for the scanning device 1352 and the bar code interface 1346.

Another use of charting module 1330 is for inputting a control sequence used to control a module to perform a dedicated function on the bed. For instance, a doctor can prescribe a certain surface therapy for pulmonary or other type of treatment of the patient on the bed. This treatment prescription can specify a period of time for percussion and vibration therapy or for rotational therapy of the patient on the bed. The prescription can include a specific period of time for the therapy with varying rates of rotation or a varying frequency of percussion and vibration. This specific control sequence or prescription is encoded onto a bar code or other appropriate input scanning device format and scanned or otherwise input into charting module 1330. Charting module 1330 then automatically executes the prescribed control sequence by transmitting appropriate commands at appropriate times through transceiver 1336 to the network and to the selected modules to control the selected modules in the prescribed control sequence.

As discussed above, each of the network modules includes a echelon neuron networking microprocessor or controller. Each of the networking controllers has a unique serial number which is different from the serial number on any other controller. At manufacturing time, a data base is created to associate each unique serial number with the module type and manufacturing date. Any other desired information related to the particular module may also be stored in the data base. Therefore, the hospital bed of the present invention provides an inventory control feature both in the plant prior to shipment of the beds and in the field at remote customer locations. A diagnostic tool coupled to accessory port module 1016 through a data link or the hospital network coupled to communications module 1020 can instantly query a bed over the peer-to-peer communication network to retrieve the unique serial number associated with all the modules on the network of the bed. Therefore, an operator has access to an instantaneous inventory of all the modules and associated features of a particular bed from a remote location for maintenance, repairs, recalls, upgrades, etc. An operator at a remote location can quickly determine the exact modules on the bed at any time.

The apparatus of the present invention can automatically poll beds at a remote location over the network by providing a query to all modules and retrieving all the serial numbers over the network. Therefore, by using the stored data base, an operator can determine an inventory of all bed modules present in a hospital or other remote location.

Figure 61:
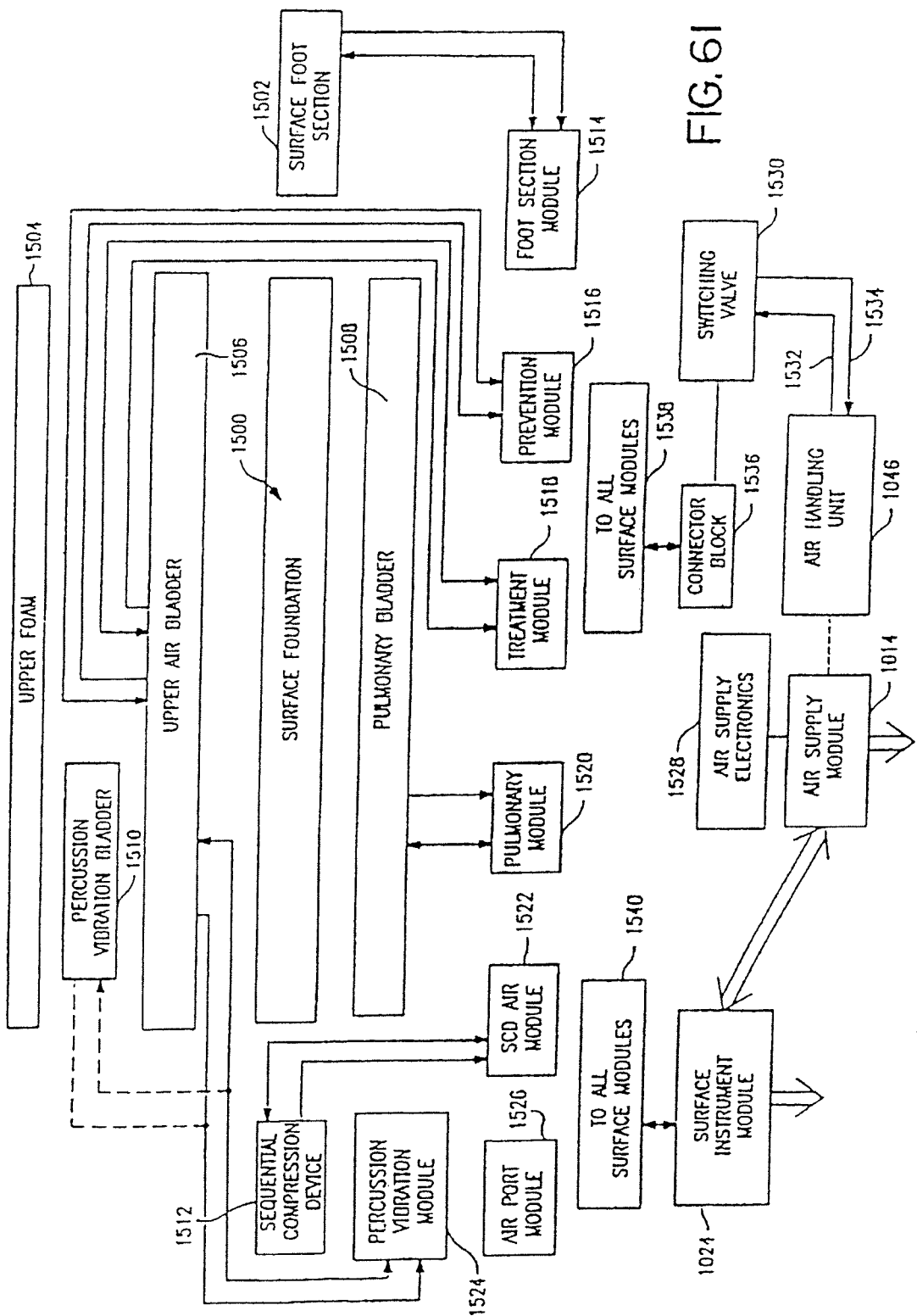
FIG. 61 is a block diagram illustrating the modular therapy and support surface system of the present invention including a plurality of control modules for controlling various air therapy devices and surface sections of a support surface and illustrating an air supply module for controlling an air handling unit and a switching valve to selectively supply air pressure and a vacuum to the various therapy devices and surface sections.

Details of the modular therapy and support surface apparatus of the present invention are illustrated in FIG. 61. The support surface of the present invention is configured to be positioned over a bed deck 1596 of a hospital bed. The support surface includes a surface foundation 1500 located on the bed deck. An inflatable and deflatable surface foot section 1502 is located adjacent surface foundation 1500. For certain applications, an upper foam support surface 1504 is located on foundation 1500. Upper foam support 1504 is typically used for short hospital stays. An upper air bladder 1506 can also be positioned over surface foundation 1500. A rotation bladder 1508 is located between the surface foundation and the bed deck. An optional percussion bladder 1510 may be inserted in place of a section of upper air bladder 1506. A sequential compression device 1512 for venous compression therapy of a patient is also provided.

A plurality of separate treatment and surface control modules are provided for interconnecting the various treatment devices and support surface bladders to the communication network of the bed and to on-board air handling unit 1046. Specifically, the present invention includes a foot section control module 1014, a decubitus prevention control module 1516, and a decubitus treatment control module 1518. The modular therapy apparatus further includes a pulmonary rotation control module 1520, a sequential compression device air control module 1522, and a pulmonary percussion and vibration control module 1524. An auxiliary air port control module 1526 is also provided. The air port control module 1526 provides for auxiliary air output for manual filling of auxiliary bladder systems for positioning, safety barriers, clinical treatments such as burn contractures, and other purposes.

Each of the modules is designed to physically and functionally connect the various bladders and treatment devices to both the communication network of the hospital bed through the surface instrument module 1024 and to the air handling unit 1046 which is controlled by air supply module 1014. Air supply module 1014 is coupled to the peer-to-peer communication network. Air supply electronics 1528 are connected to air supply module 1014 for controlling air handling unit 1046 and switching valve 1530 based on network commands for controlling the various surface and treatment modules illustrated in FIG. 61.

Air handling unit 1046 is configured to supply air under pressure to switching valve 1530 on line 1532. Air handling unit 1046 also applies a vacuum to switching valve 1530 through line 1534. An output of switching valve 1530 is coupled to a connector block 1536. Connector block 1536 provides an air and vacuum supply line to each of the surface control and treatment control modules as illustrated in block 1538 of FIG. 61. It is understood that dual control lines for both air and vacuum can be supplied to each of the surface control and treatment control modules of FIG. 61. This dual control allows each module to apply pressure and vacuum simultaneously to different zones of a bladder or treatment device.

The surface instrument module 1024 which is also coupled to the peer-to-peer communication network is electrically coupled to each of the surface control modules and treatment control modules as illustrated in block 1540 of FIG. 61. This network connection permits all the modules to receive input commands from other network modules and to output information to the network.

Figure 62:
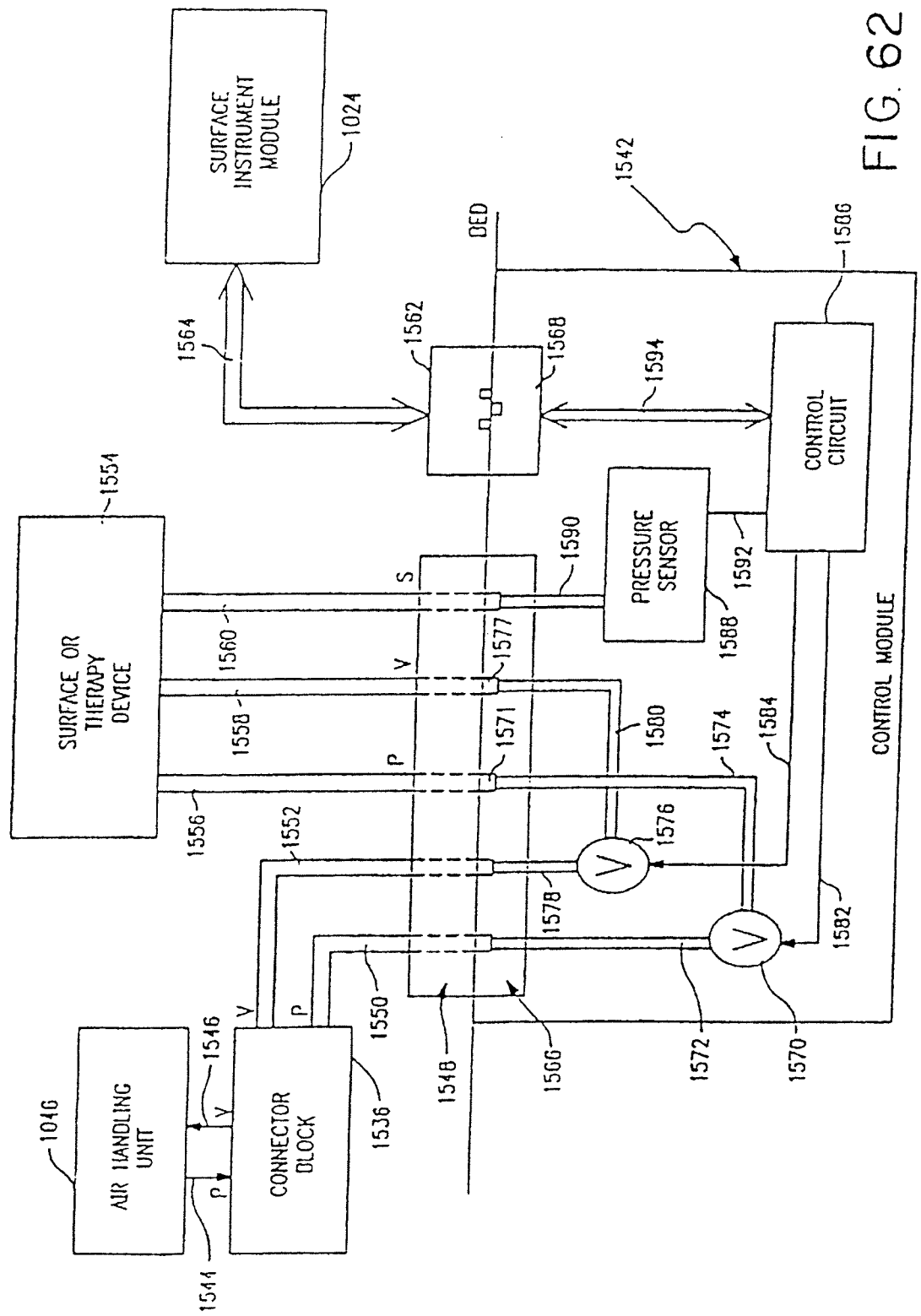
FIG. 62 is a diagrammatical illustration of the configuration of an air therapy control module.

Details of a therapy or support surface control module 1542 are illustrated in FIG. 62. It is understood that the details of foot section module 1514, prevention module 1516, treatment module 1518, pulmonary rotation module 1520, SCD air module 1522, pulmonary percussion/vibration module 1524, and air port module 1526 include the same or similar structural components as module 1542 illustrated in FIG. 62. The FIG. 62 embodiment illustrates the air handling unit 1046 coupled directly to connector block 1536 by both an air pressure supply line 1544 and a vacuum supply line 1546. As discussed above, lines 1549 and 1546 from air handling unit may be coupled to a switching valve 1530 and only a single pressure/vacuum tube may be coupled to connector block 1536 as illustrated in FIG. 61.

The connector block 1536 is coupled to module connector 1548 located on the hospital bed. Specifically, connector block 1536 is coupled to module connector 1548 by a pressure supply line 1550 and a vacuum supply line 1552. It is understood that a single supply line for both pressure and vacuum could also be used.

Module connector 1548 is also coupled to one of the surface or therapy devices as illustrated by a block 1554 by a pressure supply line 1556, a vacuum supply line 1558, and a sensor supply line 1560. Depending upon the particular surface or therapy device, more than one pressure, vacuum, and sensor lines may be connected between the connector block 1548 and the surface or therapy device 1554. Typically, each separate air zone of the surface or therapy device will have its own pressure, vacuum, and sensor lines. For illustration purposes, however, only a single set of supply lines will be discussed.

The bed also includes an electrical connector 1562 coupled to surface instrument module 1024 of the peer-to-peer communication network of the bed by suitable cable 1564. The therapy or surface control module 1542 illustrated in FIG. 62 is designed to facilitate coupling of the control module 1542 to the bed. Each of the surface and treatment options illustrated in FIG. 61 is provided in the bed with a pneumatic connector such as connector 1548 and an electrical connector such as connector 1562 provided for each of the surface and therapy devices. The module 1542 is easily installed by coupling connector 1548 on the bed to a mating connector 1566 of module 1542. In addition, a mating electrical connector 1568 is provided on module 1542 for coupling to electrical connector 1562 on the hospital bed. The configuration of module 1542 permits a simple "slide in" connection to be used to install the module 1542 and activate the surface of therapy device 1554.

An air pressure input from pneumatic connector 1566 is coupled to an electrically controlled valve 1570 by a supply line 1572. An output of valve 1570 is coupled to a pressure output port 1571 by line 1574. Port 1571 is coupled to the surface or therapy device 1554 by pressure supply line 1556.

The vacuum supply line 1552 from connector block 1536 is coupled to an electrically controlled valve 1576 by line 1578 of control module 1542. An output of valve 1576 is coupled to a vacuum port 1577 of connector 1566 by line 1580. Vacuum port 1577 is coupled to the surface or therapy device 1554 by the vacuum supply line 1558. The electrically controlled valves 1570 and 1576 are controlled by output signals on lines 1582 and 1584, respectively, from a control circuit 1586 of module 1542. Control circuit includes a microprocessor or other controller for selectively opening and closing valves 1570 and 1576 to control surface or treatment device 1554.

It is understood that several valves may be used for each surface or treatment device. For instance, the upper air bladder 1506 may have a plurality of different air zones which are independently controlled. In this instance, separate pressure and vacuum and sensor lines are coupled to each zone of the air bladder. A electrically controlled valve is provided for each pressure and sensor line in each zone to provide independent controls for each zone.

Module 1542 also includes a pressure sensor 1588. Pressure sensor 1588 is coupled to sensor supply line 1560 by line 1590. Pressure sensor 1588 generates an output signal indicative of the pressure in the particular zone of the surface or therapy device 1554. This output signal from pressure sensor 1588 is coupled to the control circuit 1586 by line 1592.

Control circuit 1586 is also coupled to an electrical connector 1568 by a suitable connection 1594 to couple the control circuit 1586 of module 1542 to the surface instrument module 1024. Therefore, control circuit 1586 can receive instructions from the other modules coupled to the peer-to-peer communications network illustrated in FIG. 48. Control circuit 1586 can also output information related to the particular surface or therapy device 1554 to the network. Specifically, the graphical interactive display 1664 or the graphic caregiver interface module 1032 is coupled to the electrical communication network for transmitting command signals for the plurality of air therapy devices over the electrical communication network to control operation of the plurality of air therapy devices. The graphical interactive display includes a display and a user input. Each control module transmits display commands to the display related to the corresponding air therapy device. The display commands from the control modules provide a menu driven list of options to the display to permit selection of control options for the plurality of air therapy devices from the user input.

Figure 63:
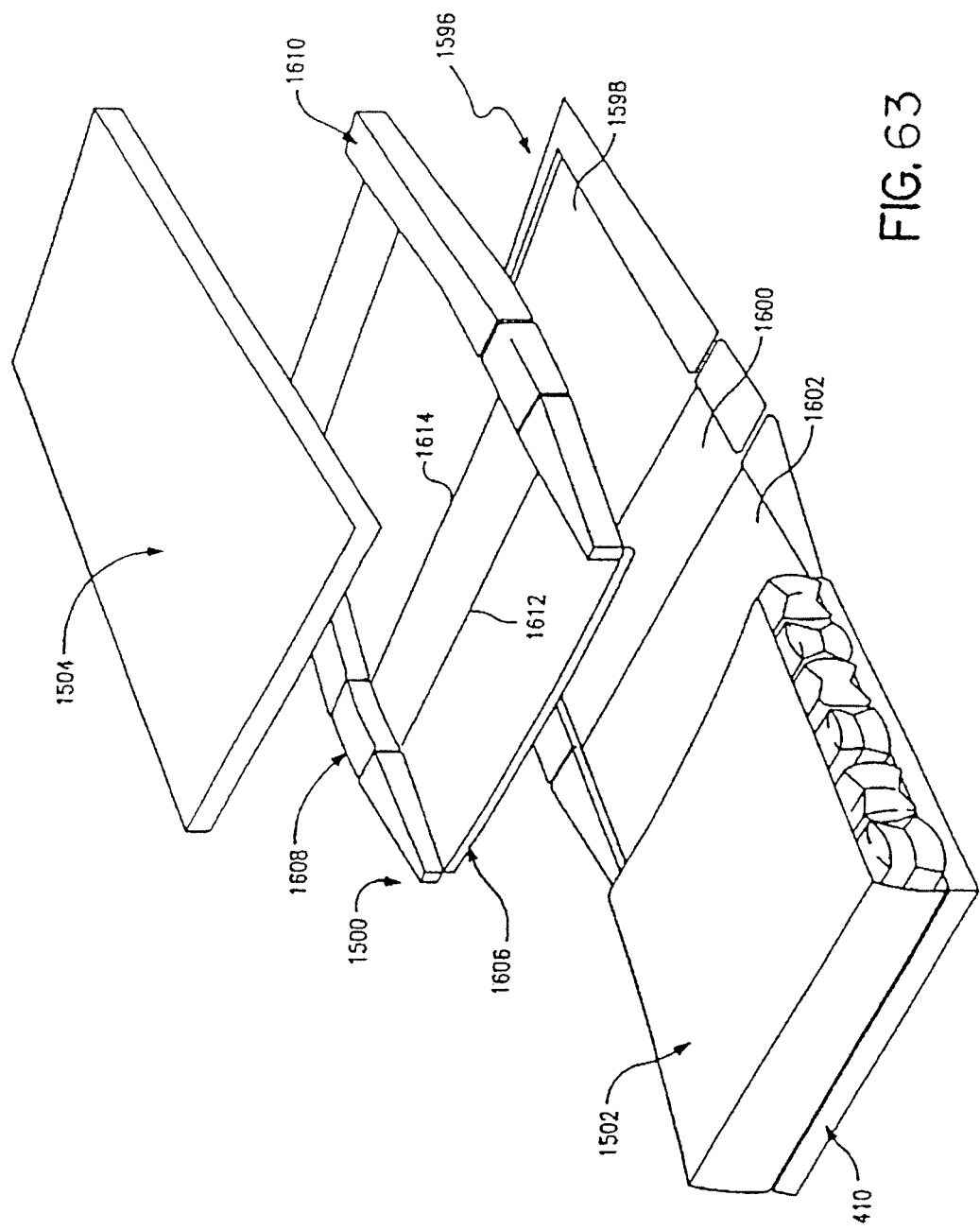
FIG. 63 is an exploded perspective view illustrating a foam surface foundation with side bolsters configured to be positioned on a deck of the bed, an upper foam support surface, and an inflatable and deflatable surface foot section.
Figure 64:
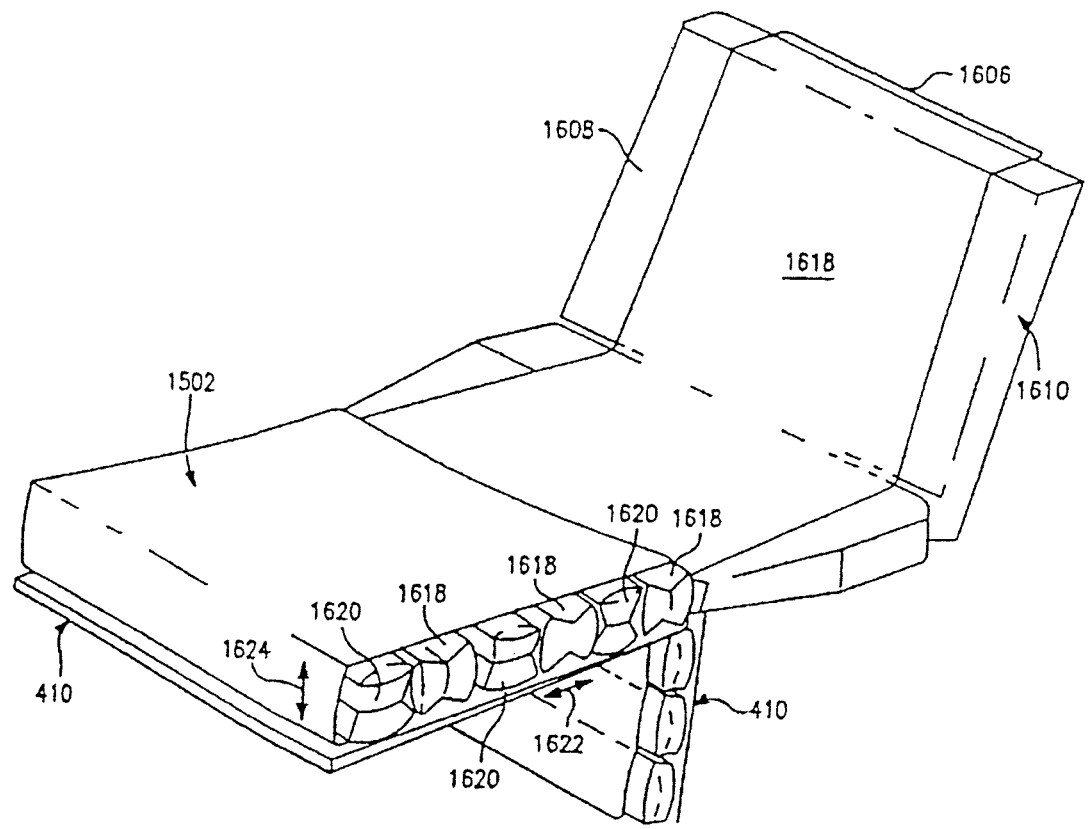
FIG. 64 is a perspective view illustrating the surface foot section in an inflated configuration when the bed is in a normal bed position and illustrating the surface foot section in a retracted and collapsed configuration when the bed is in a chair position.

Details of the structural features of the modular therapy and support surface are illustrated in FIGS. 63-72. FIG. 63 illustrates a deck portion 1596 of a hospital bed. Illustratively, deck portion 1596 is a step deck having a cross-sectional shape best illustrated in FIGS. 69-71. Illustratively, deck 1596 includes a head section 1598, a seat section 1600, and a thigh section 1602. Sections 1598, 1600, and 1602 are all articulatable relative to each other.

The modular therapy and support surface system of the present invention includes surface foundation 1500 including a foundation base 1606 and side bolsters 1608 and 1610. Preferably, side bolsters 1608 and 1610 are coupled to opposite sides of foundation base 1606. Foundation base 1606 includes foldable sections 1612 and 1614 to permit the foundation 1500 to move when the step deck 1596 articulates.

The hospital bed also includes an expanding and retracting foot section 410 to facilitate movement of the hospital bed to the chair position. Surface foot section 1502 is located over the retracting mechanical foot portion 410. Surface foot section 1502 is described in detail below with reference to FIGS. 64-67.

The FIG. 63 embodiment includes an upper foam surface insert 1504 configured to the positioned on the foam foundation base 1606 between side bolsters 1608 and 1610. Foam surface 1504 provides a suitable support surface for a patient who is mobile and whose length of stay is expected to be less than about two days.

The surface foot section 1502 is particularly designed for use with the chair bed of the present invention. The foot section 1502 includes a first set of air bladders 1618 and a second set of air bladders 1620 alternately positioned with air bladders 1618. Air bladders 1618 and 1620 are configured to collapse to a near zero dimension when air is withdrawn from the bladders 1618 and 1620. The first set of bladders 1618 are oriented to collapse in a first direction which is generally parallel to the foot section 410 of the bed deck as illustrated by double headed arrow 1622. The second set of bladders 1620 are configured to collapse in a second direction generally perpendicular to the foot deck section 410 as illustrated by double headed arrow 1624. This orientation of bladders 1618 and 1620 in foot section 1502 causes the foot section 1502 to retract or shorten and to collapses or thin as the bladders 1618 and 1620 are deflated by the foot section control module 1514 as the hospital bed moves from a bed orientation to a chair orientation. In the chair orientation, the foot deck section 410 and surface foot section 1502 move from a generally horizontal position to a generally vertical, downwardly extending position. Preferably, the foot deck section 410 moves from a retracted position to an extended position to shorten the foot deck section as the articulating deck of the bed moves to a chair configuration.

Figure 65:
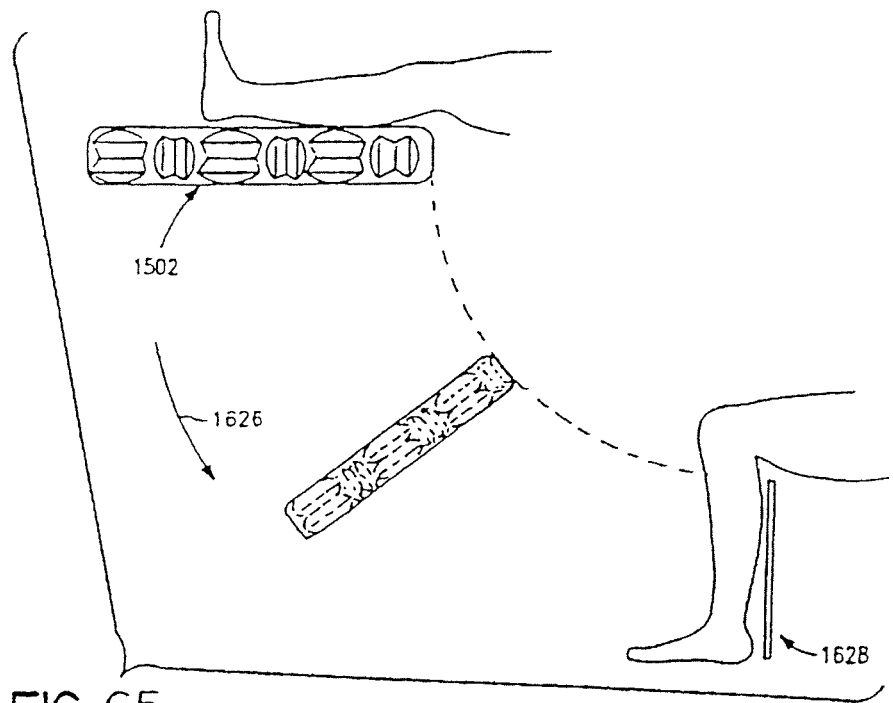
FIG. 65 is a diagrammatical view further illustrating how the surface foot section retracts or shortens and collapses or thins as the bed moves from the bed position to the chair position.

The minimizing foot section 1504 is further illustrated in FIG. 65. The surface foot section 1502 deflates as it moves from the bed position to the chair position in the direction of arrow 1626. In the bed position, the surface foot section 1502 has a length of about 27 inches (68.6 cm) and a thickness of about 5 inches (12.7 cm) when the bladders 1618 and 1620 are fully inflated. When in the downwardly extended chair position illustrated at location 1628 in FIG. 65, the surface foot section is fully deflated and has a length of about 14 inches (35.6 cm) and a thickness of preferably less than one inch (2.54 cm). The length of the surface foot section is preferably reduced by at least 40% and the thickness of the surface foot section is preferably reduced by at least 80% as the bed moves to the chair configuration. The width of the surface foot section 1502 remains substantially the same in both the bed orientation and the chair orientation.

Figure 66:
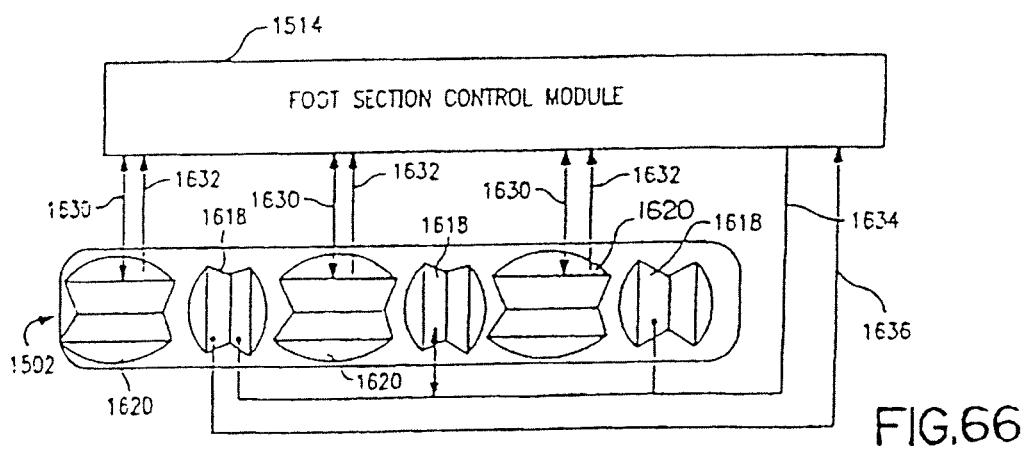
FIG. 66 is a diagrammatical view of the control module and bladder configuration of the surface foot section.

Pressure control in the surface foot section 1502 is illustrated diagrammatically in FIG. 66. Each of the vertically collapsible bladders 1620 are separately coupled to foot section control module 1514 by pressure/vacuum supply lines 1630 and sensor lines 1632. Therefore, each of the three bladders 1620 are independently coupled to and controlled by foot section control module 1514. Each of the three horizontally collapsing bladders 1618 are commonly connected to a common pressure/vacuum source of the foot section control module as illustrated line 1634. A single sensor line 1636 is used to determine the pressure in the common zone of the interconnected bladders 1618. The control configuration illustrated in FIG. 66 permits independent inflation and deflation of bladders 1620 to provide heel pressure relief in foot section 1502. Details of the heel pressure management apparatus are illustrated in copending U.S. Pat. No. 5,666,681, filed Jan. 3, 1995, owned by the assignee of the present application, the disclosure of which is hereby expressly incorporated by reference into the present application.

Figure 67:
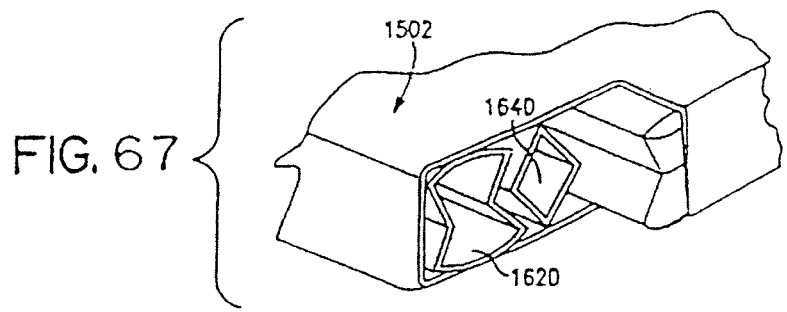
FIG. 67 is a partial perspective view with portions broken away illustrating another embodiment of the surface foot section.

Another embodiment of the foot section 1502 is illustrated in FIG. 67. In this embodiment, bladders 1618 have been replaced by diamond shaped bladders 1640. It is understood that any shape which collapses in a specified direction upon deflation may be used in foot section 1502 of the present invention to provide the shortening or retracting and thinning or collapsing features discussed above.

Figure 68:
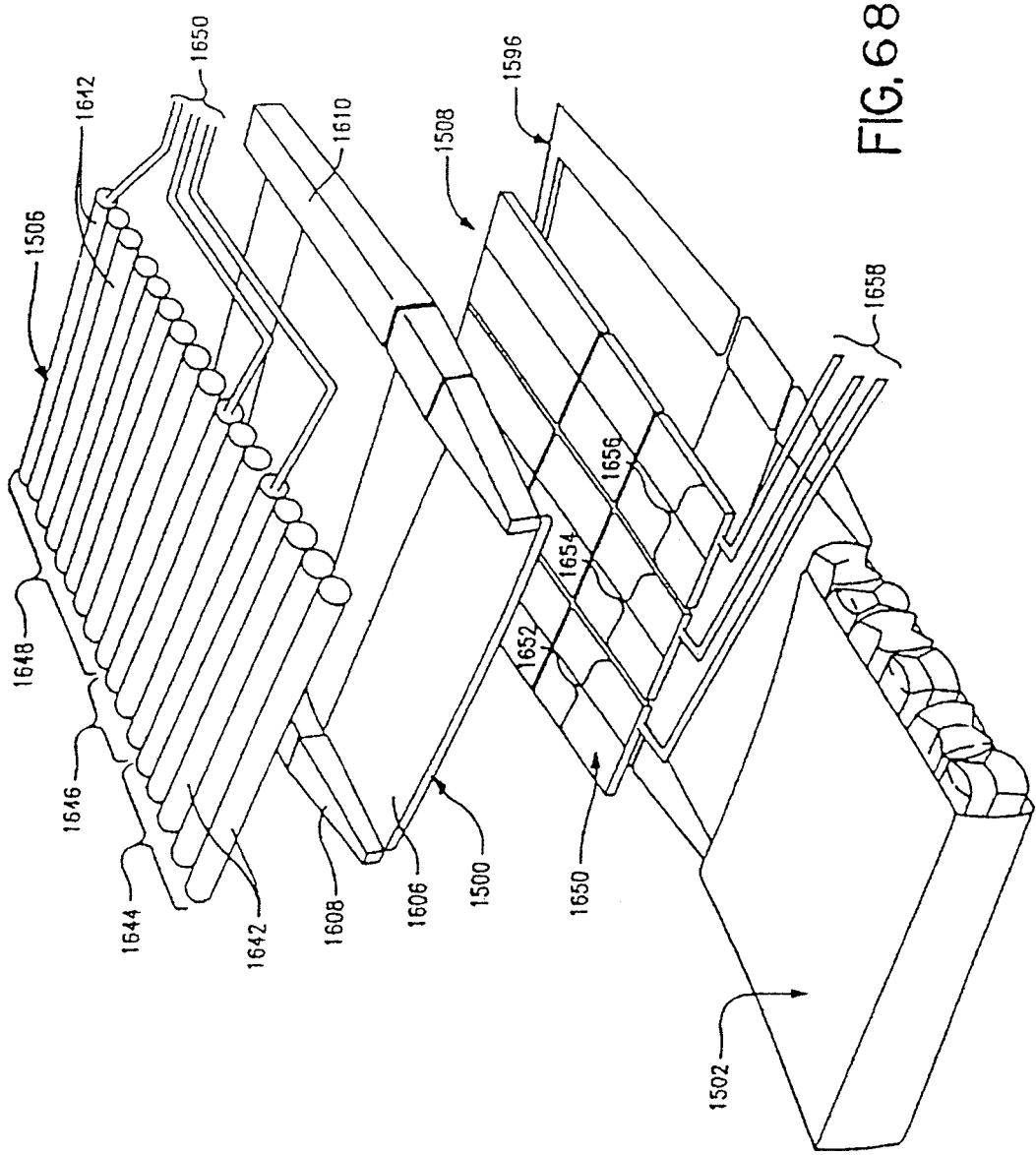
FIG. 68 is an exploded perspective view of another embodiment of the present invention illustrating a pulmonary therapy rotational bladder located between a deck of the bed and the surface foundation and illustrating an upper air bladder support surface located above the surface foundation in place of the upper foam support surface of FIG. 61.

Additional surface and treatment options of the modular air therapy and support surface apparatus are illustrated in FIG. 68. In FIG. 68, an upper air bladder 1506 is located on foam foundation base 1606 between side bolsters 1608 and 1610. Upper air bladder 1506 includes a plurality of adjacent air tubes or bladders 1642 oriented transverse to a longitudinal axis of the bed. Illustratively, bladders 1642 are connected in three commonly controlled zones 1644, 1646, and 1648. It is understood that more zones may be provided. If desired, each bladder 1642 may be controlled independently.

The surface instrument module 1024 receives commands from the BACM 1018 and the position sense module 1026 to reduce the pressure in a seat section defined by zone 1644 of the upper air bladder 1506 as the bed moves to the chair configuration in order to distribute a patient's weight. A thigh section of the deck is angled upwardly to help maintain the patient in a proper position on the seat when the bed is in the chair configuration.

For the upper surface decubitus prevention, the three supply tubes 1650 of upper air bladder 1506 are all connected to a common pressure source through prevention module 1516. For the upper surface decubitus treatment, the three supply lines 1650 are coupled to three separate valves in treatment module 1518 to control each of the zones 1644, 1646, and 1648 of upper air bladder 1506 independently.

A pulmonary rotation bladder 1508 is located between foundation base 1606 and step deck 1596. It is understood that rotation bladder 1508 may be positioned between foundation base 1606 and upper air bladder 1506 if desired. Rotation bladder 1508 includes separate bladders 1650 which are oriented to run parallel to a longitudinal axis of the hospital bed. Illustratively, three separate pressure zones 1652, 1654, and 1656 are provided in rotation bladder 1508. In the illustrated embodiment, each of the pressure zones 1652, 1654, and 1656 are independently controlled by pressure supply lines 1658. Each pressure supply line is coupled to a separate valve in pulmonary control module 1520 illustrated in FIG. 61. A separate sensor line (not shown) for each zone 1652, 1654, and 1656 is also coupled to pulmonary rotation control module 1520.

Figure 69:
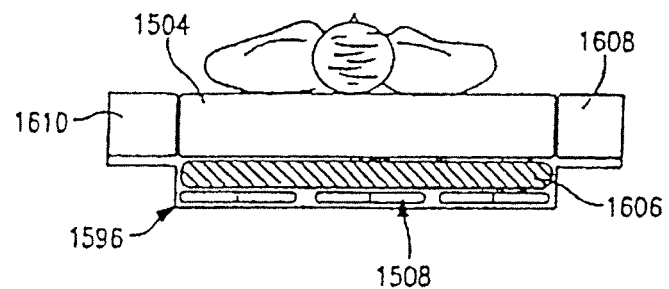
FIG. 69 is a diagrammatical end view illustrating the configuration of the modular therapy and support surface of the present invention when the pulmonary bladders are all deflated.

Pulmonary rotation bladder 1508 is stored in a deflated position within the bed until it is desired to treat the patient with rotational therapy. In this embodiment, the rotation bladder 1508 does not provide a support surface for the patient. The support surface is provided by either upper foam mattress 1504 or upper air bladder 1506. Therefore, rotation bladder 1508 can be stored flat in the bed during normal operation of the bed as illustrated in FIG. 69. It is understood that in another embodiment of the invention, the rotation bladder 1508 may be normally inflated to provide a support surface for the patient.

When it is desired to provide rotational treatment to the patient, a pulmonary rotation control module 1520 is coupled to the bed. The graphical interactive display 1664 of the bed or the graphic caregiver interface module 1032 automatically recognizes that the pulmonary rotation control module 1520 is attached to the bed. Therefore, controls for the pulmonary rotation therapy device can be actuated from the graphical interactive display 1664 or the graphic caregiver interface 1032.

FIG. 69 illustrates the configuration of rotation bladder 1508 in its deflated position during normal operation of the bed with the upper foam mattress 1504 in place of upper air bladder 1506. In FIG. 69, all three zones 1652, 1654, and 1656 of rotation bladder 1508 are deflated or flat.

Figure 70:
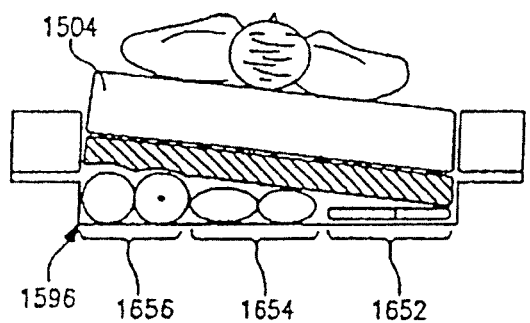
FIG. 70 is a diagrammatical view similar to FIG. 66 illustrating inflation of left side pulmonary bladders to rotate a patient to the right.
Figure 71:
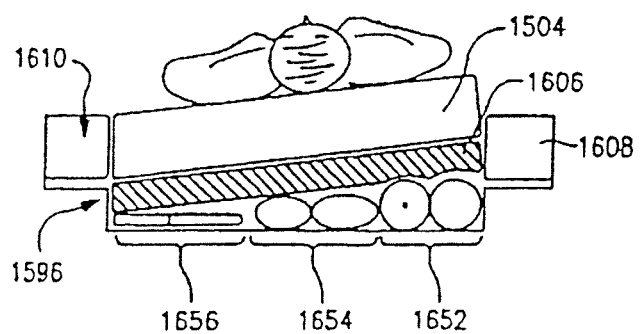
FIG. 71 is a diagrammatical view similar to FIGS. 66 and 67 illustrating inflation of the right side pulmonary bladders to rotate the patient to the left.

FIG. 70 illustrates actuation of the rotation bladder 1508 to rotate a patient situated on foam mattress 1504 to the right. Pulmonary rotation control module 1520 controls airflow to fully inflate zone 1656 to partially inflate zone 1654, and to deflate zone 1652 of rotation bladder 1508. FIG. 71 illustrates actuation of the rotation bladder 1508 to rotate the patient to the left. Pulmonary rotation control module 1520 fully inflates zone 1652, partially inflates zone 1656, and deflates zone 1654 to rotate the patient.

Figure 72:
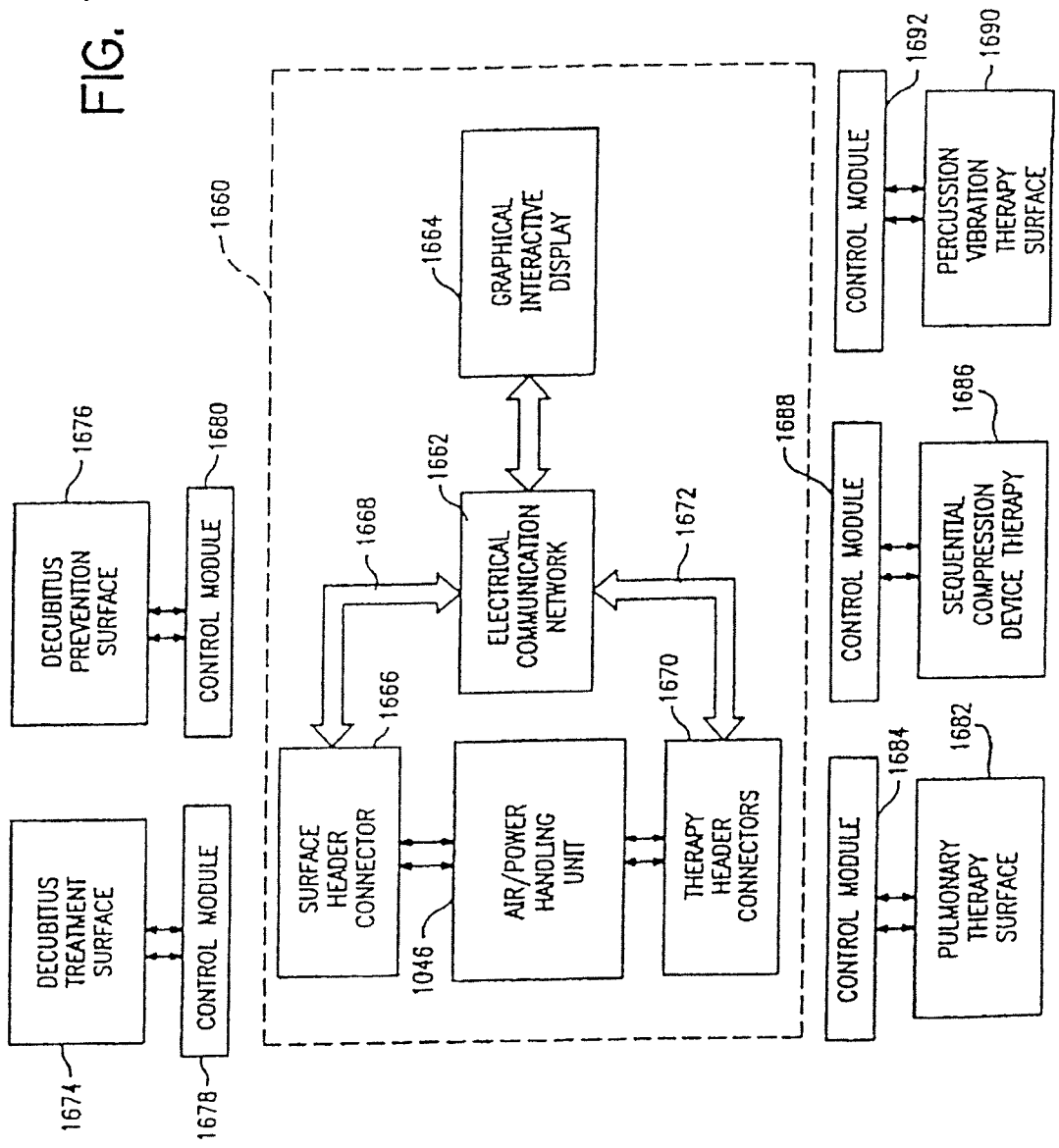
FIG. 72 is a block diagram illustrating another embodiment of the present invention illustrating separate exchangeable surfaces or therapy devices which are each coupled to a control module including pneumatic control valves and sensors, an electrical connection, and a processor for communicating with an air and power handling unit on the bed and with a graphical interface display on the bed through the electrical communication network of the bed.

Another embodiment of the modular therapy and support surface invention is illustrated in FIG. 72. In this embodiment, separate exchangeable surfaces are provided. The bed is illustrated by dotted line 1660. As discussed above, the bed includes a peer-to-peer communication network 1662 which is coupled to a graphical interactive display 1664. It is understood that graphical interactive display 1664 may be the graphic caregiver interface module 1032 discussed above. In addition, graphical interface display 1664 may be a display with control switches embedded in a foot board or at another location of the bed to provide a user control for all therapy and surface options. As discussed above, the network 1662 automatically recognizes when a specific therapy module is connected to the bed 1660 and automatically provides control options to the graphical interactive display 1664. The open architecture of the electrical communication network 1662 allows interaction between the added module and the graphical interactive display 1664 without redesigning the system. Bed 1660 includes a surface header connector 1664 coupled to the air handling unit 1046 and to the electrical communication network 1662 by line 1668. In addition, bed 1660 includes therapy header connectors illustrated at block 1670 which are connected to the air and power handling unit 1046 and to the electrical communication network 1662 as illustrated by line 1672.

In this embodiment of the present invention, separate surfaces are provided, including a decubitus treatment surface 1674 and a separate decubitus prevention surface 1676. The decubitus treatment surface 1674 has its own attached control module 1678 for connecting to surface header 1666. Decubitus prevention surface 1676 has its own control module 1680 configured to be coupled to surface header connector 1666. Header connector 1666 is connected to modules 1678 or 1680 in a manner similar to module 1542 in FIG. 62.

Separate therapy modules are also provided. A pulmonary rotation therapy surface 1682 can be added to bed 1660. Rotation therapy surface 1682 is coupled to its own control module 1684 which is configured to be connected to therapy header connector 1670. A sequential compression therapy device 1686 is also provided. Sequential compression device 1686 is coupled to its own control module 1688 which is configured to be connected to therapy header connector 1670. The present invention permits the sequential compression device to use an on board air handling unit 1046 and control system. This eliminates the requirement for a separate air pump and control panel which takes up valuable floor space near the bed and makes the bed difficult to move.

A separate pulmonary percussion and vibration therapy surface 1690 is also provided. Pulmonary percussion and vibration therapy surface is added to bed 1660 in place of a portion of the support surface of the bed. Pulmonary percussion and vibration therapy surface 1690 is coupled to its own control module 1692. Control module 1692 is configured to be coupled to a therapy header connector 1670.

The separate control modules are used to control power and air distribution, and to control user options displayed on the graphical interactive display 1664 for each therapy or surface option. As discussed above in detail with reference to FIG. 62, each control module 1678, 1680, 1684, 1688 and 1692 contain valves, sensors, and electronic control circuits specific to the particular surface or therapy application. All control features are implemented as a menu driven interactive control for the selected therapy or surface module of the present invention on the graphical interface display 1664 or on the graphic care giver interface 1023.

All surface related parameters can be transmitted from surface instrument module 1024 to communications module 1020 and then to a remote location via the hospital network. Surface instrument 1024 can be interrogated by a diagnostic tool coupled to accessory port 1016 if desired. Information related to the surface modules can also be received via modem from a remote location through accessory port 1016.

Figure 73:
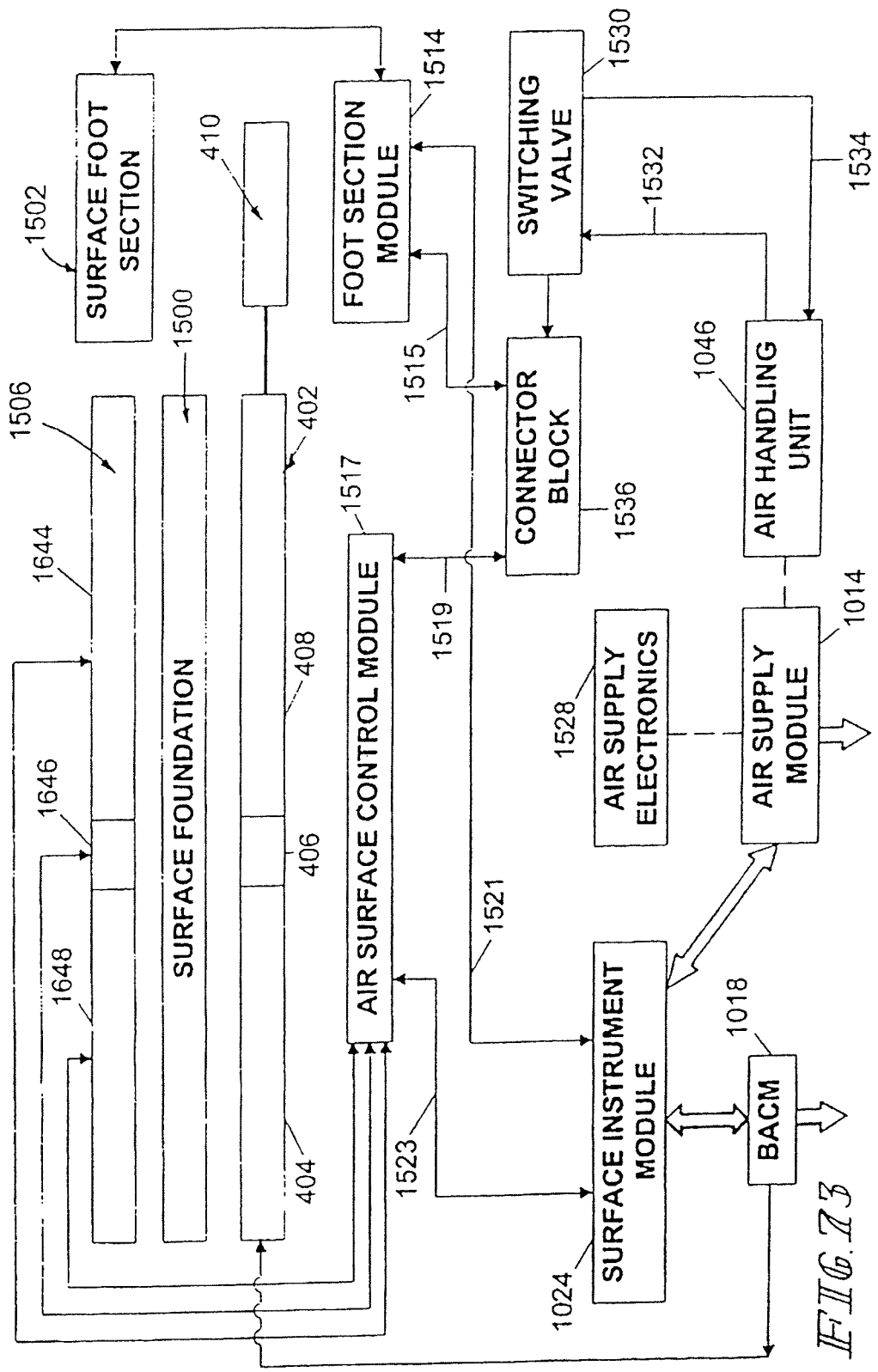
FIG. 73 is a block diagram illustrating the support surface system of the present invention including a plurality of a bed articulation control module controlling movement of the articulating deck sections and illustrating a surface instrument module and an air supply module for controlling an air handling unit and a switching valve to selectively supply air pressure and a vacuum to control inflation and deflation of zones of the support surface.

Further details of the air support surfaces, the articulating deck, and the control modules of the present invention are illustrated in FIG. 73. The support surface of the present invention is configured to be positioned over a bed deck 402 of a hospital bed. The support surface includes a surface foundation 1500 located on the bed deck 402. An inflatable and deflatable surface foot section 1502 is located adjacent surface foundation 1500. An upper air bladder 1506 is positioned over surface foundation 1500.

As discussed above, the articulating deck includes separate, independently movable deck sections. Specifically, deck 402 includes a head deck section 404, a seat deck section 406, a thigh deck section 408, and a foot deck section 410. Upper air bladder 1506 includes a plurality of separate air bladders. The air bladders are preferably connected in three independently controlled air zones corresponding to the different sections of deck 402. Specifically, air bladder 1506 is divided into a head air zone 1648, a seat air zone 1646, and a air thigh zone 1644. The separate surface foot section 1502 which overlies foot deck section 410 is also independently controlled.

An air surface control module 1517 is provided for selectively coupling the various air zones 1644, 1646, and 1648 to the air handling unit 1046. Air surface control module 1517 includes separate valves and pressure sensors for each air zone 1644, 1646, and 1648 of air bladder 1506. When a command to move the bed deck is transmitted to the network from a user input control on one of the standard caregiver interface modules 1028 and 1030, the graphic caregiver interface module 1032, or from another control device, the BACM 1018 actuates appropriate cylinders to articulate the deck 402. The BACM 1018 also provides signals to surface instrument module 1024 and air supply module 1014 for controlling inflation and deflation of the surface foot section 1502 and the independent air zones 1644, 1646, and 1648 of upper air bladder 1506 automatically as the bed articulates.

The surface instrument module 1024 sends signals to a controller inside the air surface control module 1517 to open and close valves at predetermined intervals to control inflation and deflation of the air zones 1649, 1646, and 1648. The surface instrument module 1024 and the air supply module 1014 also receive signals over the network from the position sense module 1026 to indicate the position of the articulating deck sections 409, 406, 408 and 410.

As discussed above, the surface foot section 1502 is deflated as the deck 402 moves to the chair position. In addition, seat air zone 1646 and thigh air zone 1644 are partially deflated to distribute the weight of the person in the chair. When in the chair position, the surface thigh bladder 1644 and the thigh deck section 408 support most of a patient's weight. This partial deflation of the chair seat section is controlled automatically by surface instrument module 1024, air supply module 1014, and air surface control module 1517 as the bed deck moves from the bed position of FIG. 1 to the chair position of FIG. 2. In some instances, a single air bladder may be provided for seat air zone 1646 and thigh air zone 1644. In other instances, a plurality of individual air zones may be all separately controlled. In other words, each of the air zones of air bladder 1506 may have several independently controlled air bladders 1642.

Separate valves and pressure sensors in air surface control module 1517 are provided for interconnecting the various air zones 1644, 1646, and 1648 to the communication network of the bed and to on-board air handling unit 1046. The present invention also includes a foot section control module 1514 which includes valves and pressure sensors for each air zone of the surface foot section 1502.

Each of the control modules 1514, 1517 is designed to physically and functionally connect the various air zone bladders and to both the communication network of the hospital bed through the surface instrument module 1024 and to the air handling unit 1046 which is controlled by air supply module 1014. Air supply module 1014 is coupled to the peer-to-peer communication network. Air supply electronics 1528 are connected to air supply module 1014 for controlling air handling unit 1046 and switching valve 1530 based on network commands for controlling the various surface and treatment modules illustrated in FIG. 73.

Air handling unit 1046 is configured to supply air under pressure to switching valve 1530 on line 1532. Air handling unit 1046 also applies a vacuum to switching valve 1530 through line 1534. An output of switching valve 1530 is coupled to a connector block 1536. Connector block 1536 provides an air and vacuum supply line 1515 to the foot section control module 1514 and provides an air and vacuum supply line 1519 to the air surface control module 1517. It is understood that dual control lines for both air and vacuum can be supplied to each of the foot section control module 1514 and the air surface control module 1517. This dual control allows each module to apply pressure and vacuum simultaneously to different zones of a bladder or treatment device.

The surface instrument module 1024 receives commands from the BACM 1018 and the position sense module 1026 to control the air surface control module 1517 to reduce the pressure in a seat section defined by zones 1644 and 1646 of the upper air bladder 1506 automatically as the bed moves to the chair configuration in order to distribute a patient's weight. An end of the thigh deck section 408 closest to foot end 54 is angled upwardly automatically as illustrated in FIG. 8 to help maintain the patient in a proper position on the seat when the bed is in the chair configuration.

Although the invention has been described in detail with reference to preferred embodiments, variations and modifications exist within the scope and spirit of the invention as described and defined in the following claims.

The invention claimed is:

1. A person support apparatus comprising:
  a base,
  a frame supported by the base, the frame having a head end and a foot end longitudinally spaced from the head end,
  a deck supported by the frame, the deck including movable sections configurable for the deck to assume at least a bed position and a chair position, the movable sections including at least a head section and a foot section spaced from the head section, a footboard coupled to the foot end of the frame, the footboard movable between a first position in which egress of a person from the foot end is obstructed by the footboard to a second position in which egress of a person from the foot end is not obstructed by the footboard, wherein the footboard comprises a pair of foot gates, and a grip handle coupled to at least one of the foot gates.

2. The person support apparatus of claim 1, wherein the footboard closes the foot end in the first position and opens the foot end in the second position.

3. The person support apparatus of claim 1, wherein the footboard is pivotably coupled to the frame.

4. The person support apparatus of claim 1, wherein a portion of the footboard is usable as a handle by a person egressing the person support apparatus from the foot end when the footboard is in the second position.

5. The person support apparatus of claim 1, wherein the footboard is movable to the first position when the person support apparatus is in the bed position.

6. The person support apparatus of claim 1, wherein the footboard is movable to the second position when the person support apparatus is in the bed position or the chair position.

7. The person support apparatus of claim 1, wherein each of the foot gates is pivotably coupled to the frame.

8. The person support apparatus of claim 1, wherein each of the foot gates is substantially parallel to the foot end in the first position and substantially perpendicular to the foot end in the second position.

9. A person support apparatus comprising:

a base, a frame supported by the base, the frame having a head end and a foot end longitudinally spaced from the head end, a deck supported by the frame, the deck including movable sections configurable for the deck to assume at least a bed position and a chair position, the movable sections including at least a head section and a foot section spaced from the head section, a footboard coupled to the foot end of the frame, the footboard movable between a first position in which egress of a person from the foot end is obstructed by the footboard to a second position in which egress of a person from the foot end is not obstructed by the footboard, and a mattress supported by the deck, wherein the mattress comprises a foot section supported by the foot section of the deck and the foot section of the mattress has an adjustable thickness.

10. The person support apparatus of claim 9, wherein the foot section of the mattress has a first thickness when the foot section of the deck is in the up position and a second thickness when the foot section of the deck is in the down position, and the second thickness is less than the first thickness.

11. The person support apparatus of claim 1, comprising a control system comprising controls operable by a caregiver to move the person support apparatus to the chair position while a person is supported by the person support apparatus.

12. A person support apparatus comprising:

a base, a frame supported by the base, the frame having a head end and a foot end longitudinally spaced from the head end, a deck supported by the frame, the deck including movable sections configurable for the deck to assume at least a bed position and a chair position, the movable sections including at least a head section and a foot section spaced from the head section, a footboard coupled to the foot end of the frame, the footboard movable between a first position in which egress of a person from the foot end is obstructed by the footboard to a second position in which egress of a person from the foot end is not obstructed by the footboard, and a mattress supported by the deck, wherein the mattress comprises at least one bladder configured to provide at least one therapy to a person supported by the person support apparatus.

13. A person support apparatus comprising:

a base, a frame supported by the base, the frame having a head end and a foot end longitudinally spaced from the head end, a deck supported by the frame, the deck including movable sections configurable for the deck to assume at least a bed position and a chair position, the movable sections including at least a head section and a foot section spaced from the head section, a footboard coupled to the foot end of the frame, the footboard movable between a first position in which egress of a person from the foot end is obstructed by the footboard to a second position in which egress of a person from the foot end is not obstructed by the footboard, and a mattress supported by the deck, wherein the mattress comprises an inflatable seat portion which is partially deflatable when the foot section of the deck is in the down position.

14. The person support apparatus of claim 1, comprising a seat section that is lowerable to a low position of in the range of about 15 inches or less above the floor when the person support apparatus is in the chair position.

15. The person support apparatus of claim 1, wherein the head section is configured to substantially simultaneously translate toward the head end and pivot upwardly as the head section moves to an elevated position.

16. A person support apparatus comprising:

a base, a frame supported by the base, the frame having a head end and a foot end longitudinally spaced from the head end, a deck supported by the frame, the deck including movable sections configurable for the deck to assume at least a bed position and a chair position, the movable sections including at least a head section and a foot section spaced from the head section, a footboard coupled to the foot end of the frame, the footboard movable between a first position in which egress of a person from the foot end is obstructed by the footboard to a second position in which egress of a person from the foot end is not obstructed by the footboard, and a communication network and an air supply and a graphical caregiver interface coupled to the communication network and configured to enable a caregiver to initiate an air therapy for a person supported by the person support apparatus without moving the person from the person support apparatus.

17. A person support apparatus comprising:

a base, a frame supported by the base, the frame having a head end and a foot end longitudinally spaced from the head end, a deck supported by the frame, the deck including movable sections configurable for the deck to assume at least a bed position and a chair position, the movable sections including at least a head section and a foot section spaced from the head section, a footboard coupled to the foot end of the frame, the footboard movable between a first position in which egress of a person from the foot end is obstructed by the footboard to a second position in which egress of a person from the foot end is not obstructed by the footboard, and a lift mechanism configured to raise and lower the frame relative to the base.

18. A person support apparatus comprising:

a base, a frame supported by the base, the frame having a head end and a foot end longitudinally spaced from the head end, a deck supported by the frame, the deck including movable sections configurable for the deck to assume at least a bed position and a chair position, the movable sections including at least a head section and a foot section spaced from the head section, a footboard coupled to the foot end of the frame, the footboard movable between a first position in which egress of a person from the foot end is obstructed by the footboard to a second position in which egress of a person from the foot end is not obstructed by the footboard, and at least one of a modular surface, an in-bed weighing apparatus, a movable thigh section, a radiolucent window, an electronic or manual Trendelenburg mechanism, a reduced-shear pivot mechanism, a one-handed siderail release mechanism, a breakaway siderail mechanism, a CPR foot pedal mechanism, a battery, an in-bed x-ray apparatus, a four-wheel braking mechanism, a seat section pressure reducing mechanism, and a plurality of siderails coupled to the frame, wherein the siderails are movable to a tucked position at least partially underneath the frame.

\* \* \* \* \*